US010654850B2

(12) United States Patent
Ledeboer et al.

(10) Patent No.: US 10,654,850 B2
(45) Date of Patent: May 19, 2020

(54) PYRIDAZINONES AND METHODS OF USE THEREOF

(71) Applicant: Goldfinch Bio, Inc., Cambridge, MA (US)

(72) Inventors: Mark W. Ledeboer, Acton, MA (US); Matthew H. Daniels, Somerville, MA (US); Maolin Yu, Brookfield, CT (US); Jean-Christophe P. Harmange, Andover, MA (US)

(73) Assignee: Goldfinch Bio, Inc., Cambridge, MA (US)

( * ) Notice: Subject to any disclaimer, the term of this patent is extended or adjusted under 35 U.S.C. 154(b) by 0 days.

(21) Appl. No.: 16/575,161

(22) Filed: Sep. 18, 2019

(65) Prior Publication Data

US 2020/0102301 A1     Apr. 2, 2020

Related U.S. Application Data

(60) Provisional application No. 62/780,553, filed on Dec. 17, 2018, provisional application No. 62/732,728, filed on Sep. 18, 2018.

(51) Int. Cl.
| | | |
|---|---|---|
| *C07D 471/04* | (2006.01) | |
| *A61K 31/519* | (2006.01) | |
| *A61P 13/12* | (2006.01) | |

(52) U.S. Cl.
CPC ............ *C07D 471/04* (2013.01); *A61P 13/12* (2018.01)

(58) Field of Classification Search
CPC .................................................. C07D 471/04
See application file for complete search history.

(56) References Cited

U.S. PATENT DOCUMENTS

| | | |
|---|---|---|
| 9,139,573 B2 | 9/2015 | Chong et al. |
| 2005/0176722 A1 | 8/2005 | Bono et al. |
| 2007/0287686 A1 | 12/2007 | Burgey et al. |
| 2008/0027041 A1 | 1/2008 | Hudkins et al. |
| 2016/0046624 A1 | 2/2016 | Chenard et al. |
| 2019/0127370 A1 | 5/2019 | Kc et al. |

FOREIGN PATENT DOCUMENTS

| | | |
|---|---|---|
| WO | WO-2008/115385 A2 | 9/2008 |
| WO | WO-2014/058747 A1 | 4/2014 |
| WO | WO-2017/197051 A1 | 11/2017 |
| WO | WO-2019/055966 A2 | 3/2019 |

OTHER PUBLICATIONS

Minard et al. Cells 2018, 7, 52; pp. 1-20. (Year: 2018).*
Castle et al., "Pyridazines. III. The synthesis of substituted pyridazines," Journal of Heterocyclic Chemistry, 2:463-472 (1965).
International Search Report and Written Opinion for International Application No. PCI/US18/51465 dated Feb. 27, 2019.
Pubmed Compound Summary for CID 45834084, "4-Chloro-4[4-(4-methoxyphenoxy)piperidin-1-yl]-2,3-dihydropyridazin-3-one," https://pubchem.ncbi.nlm.nih.gov/compound/45834084, (2015).
Pubmed Compound Summary for CID 75420213, "4-Chloro-2-phenyl-5-{5H,6H,7H,8H-pyrido[3,4-d]pyrimidin-7-yl}-2,3-dihydropropyridazin-3-one," https://pubchem.ncbi.nlm.nih.gov/compound/75420213 (2014).
Pubmed Compound Summary for CID 86805598, "NRUODMAEBORIK-UHFFFAOYSA-N," https://pubchem.ncbi.nlm.nih.gov/compound/86805598, (2015).
Pubmed Compound Summary for CID 86942850, "YDHFXQRLHBDRHD-UHFFFAOYSA-N," https://pubchem.ncbi.nlm.nih.gov/compound/86942850 (2015).
International Search Report and Written Opinion for International Application No. PCT/US19/51680 dated Jan. 9, 2020.
Miller et al., "Identification of ML204, a Novel Potent Antagonist That Selectively Modulates Native TRPC4/C5 Ion Channels," Journal of Biological Chemistry, 286(38):33436-33446 (2011).
Strappaghetti et al., "Adenosine receptors: synthesis, structure-activity relationships and biological activity of new 6-amino purine derivatives," European Journal of Medicinal Chemistry, 33(6):501-508 (1998).

* cited by examiner

*Primary Examiner* — Emily A Bernhardt
(74) *Attorney, Agent, or Firm* — Dana M. Gordon; Foley Hoag LLP

(57) ABSTRACT

Disclosed are compounds according to Formula (I), and related pharmaceutical compositions. Also disclosed are therapeutic methods, e.g., of treating kidney diseases, using the compounds of Formula (I).

4 Claims, 3 Drawing Sheets
Specification includes a Sequence Listing.

PYRIDAZINONES AND METHODS OF USE THEREOF

CROSS-REFERENCE TO RELATED APPLICATIONS

This application claims the benefit of priority to U.S. Provisional Patent Application No. 62/732,728, filed Sep. 18, 2018; and U.S. Provisional Patent Application No. 62/780,553, filed Dec. 17, 2018.

INCORPORATION-BY-REFERENCE OF SEQUENCE LISTING

The contents of the sequence listing text file named "GFX-01101_SL_20191216.txt", which was created on Dec. 16, 2019 and is 22,939 bytes in size, is hereby incorporated by reference in its entirety.

BACKGROUND

Proteinuria is a condition in which an excessive amount of protein in the blood leaks into the urine. Proteinuria can progress from a loss of 30 mg of protein in the urine over a 24-hour period (called microalbuminuria) to >300 mg/day (called macroalbuminuria), before reaching levels of 3.5 grams of protein or more over a 24-hour period, or 25 times the normal amount. Proteinuria occurs when there is a malfunction in the kidney's glomeruli, causing fluid to accumulate in the body (edema). Prolonged protein leakage has been shown to result in kidney failure. Nephrotic Syndrome (NS) disease accounts for approximately 12% of prevalent end stage renal disease cases at an annual cost in the United States of more than $3 billion. Approximately 5 out of every 100,000 children are diagnosed with NS every year and 15 out of every 100,000 children are living with it today. For patients who respond positively to treatment, the relapse frequency is extremely high. Ninety % of children with Nephrotic Syndrome will respond to treatment, however, an estimated 75% will relapse. There is a need for more effective methods of treating, or reducing risk of developing, kidney disease, e.g., proteinuria.

Mammalian TRP channel proteins form six-transmembrane cation-permeable channels that may be grouped into six subfamilies on the basis of amino acid sequence homology (TRPC, TRPV, TRPM, TRPA, TRPP, and TRPML). Recent studies of TRP channels indicate that they are involved in numerous fundamental cell functions and are considered to play an important role in the pathophysiology of many diseases. Many TRPs are expressed in kidney along different parts of the nephron and growing evidence suggest that these channels are involved in hereditary, as well as acquired kidney disorders. TRPC6, TRPM6, and TRPP2 have been implicated in hereditary focal segmental glomerulosclerosis (FSGS), hypomagnesemia with secondary hypocalcemia (HSH), and polycystic kidney disease (PKD), respectively.

TRPC5 has also been reported to contribute to the mechanisms underlying regulation of innate fear responses. (J Neurosci. 2014 Mar. 5; 34(10): 3653-3667).

Hence, there is a need for additional inhibitors of TRPC5 or TRPC4 or both.

SUMMARY

This invention is based, at least in part, on the discovery that Transient Receptor Potential Cation Channel, subfamily C, member 5 (TRPC5), activity abolishes actin stress fibers and diminishes focal adhesion formation, rendering a motile, migratory podocyte phenotype.

One aspect of the invention is compounds that are antagonists of TRPC5 or TRPC4 or both. In some embodiments, the compound of the invention is a compound of structural formula I:

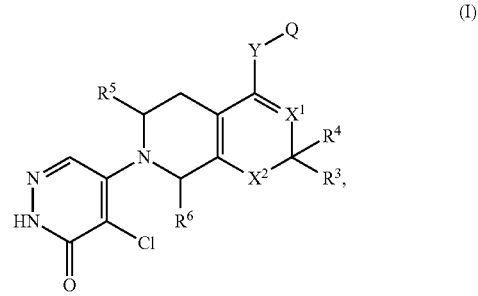

(I)

or a pharmaceutically acceptable salt thereof;
wherein:
"---" is a single bond or a double bond
$X^1$ is CH or N;
when "---" is a double bond, $X^2$ is CH or N;
when "---" is a single bond, $X^2$ is $N(CH_3)$,
when $X^1$ is CH, $X^2$ is N or $N(CH_3)$;
Y is —O—, —N($CH_3$)—, —N($CH_2CH_2OH$)—, cyclopropan-1,1-diyl, or —CH($CH_3$)—;
Q is 2-trifluoromethyl-4-fluorophenyl, 2-difluoromethyl-4-fluorophenyl, 2-trifluoromethylphenyl, 2-methyl-4-fluorophenyl, 2-chloro-4-fluorophenyl, 2-chlorophenyl, 1-(benzyl)-4-methylpiperidin-3-yl, 4-trifluoromethylpyridin-3-yl, 2-trifluoromethyl-6-fluorophenyl, 2-trifluoromethyl-3-cyanophenyl, 2-ethyl-3-fluorophenyl, 2-chloro-3-cyanophenyl, 2-trifluoromethyl-5-fluorophenyl, or 2-difluoromethylphenyl;
$R^3$ is hydrogen, —$CH_2OH$, —CH(OH)—$CH_2OH$, —$NH_2$, —CH(OH)$CH_3$, —$OCH_3$, or —NH—($CH_2$)$_2$OH; and when "---" is a double bond, $R^4$ is absent;
and when "---" is a single bond, $R^3$ and $R^4$ are taken together to form =O; and
each of $R^5$ and $R^6$ is independently hydrogen or —$CH_3$, provided that if $X^1$ is N, $X^2$ is N, Y is —O— or —N($CH_3$)—, and Q is 2-trifluoromethylphenyl, then at least one of $R^3$, $R^5$, and $R^6$ is not hydrogen.

In some embodiments, the compound of the invention is represented by structural formula II:

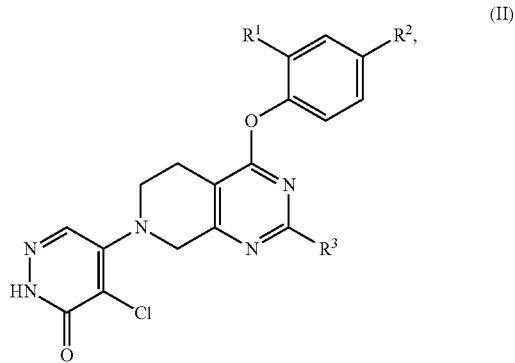

(II)

or a pharmaceutically acceptable salt thereof; wherein:
$R^1$ is chloro, —$CF_3$, —$CHF_2$, or —$CH_3$;
$R^2$ is hydrogen or fluoro; and
$R^3$ is hydrogen, —$NH_2$, —$CH_2OH$, or $CH(OH)$—$CH_2OH$.

In one aspect, the invention features a pharmaceutical composition comprising a compound of the invention and a pharmaceutically acceptable carrier.

In one aspect, the invention relates to methods of treating, or reducing the risk of developing, a disease or condition selected from kidney disease, pulmonary arterial hypertension, anxiety, depression, cancer, diabetic retinopathy, or pain, comprising administering to a subject in need thereof a therapeutically effective amount of the compound or the composition. In some embodiments, the disease is kidney disease, anxiety, depression, cancer, or diabetic retinopathy. In some embodiments, the disease or condition is kidney disease selected from Focal Segmental Glomerulosclerosis (FSGS), Diabetic nephropathy, Alport syndrome, hypertensive kidney disease, nephrotic syndrome, steroid-resistant nephrotic syndrome, minimal change disease, membranous nephropathy, idiopathic membranous nephropathy, membranoproliferative glomerulonephritis (MPGN), immune complex-mediated MPGN, complement-mediated MPGN, Lupus nephritis, postinfectious glomerulonephritis, thin basement membrane disease, mesangial proliferative glomerulonephritis, amyloidosis (primary), c1q nephropathy, rapidly progressive GN, anti-GBM disease, C3 glomerulonephritis, hypertensive nephrosclerosis, or IgA nephropathy. In some embodiments, the kidney disease is proteinuric kidney disease. In some embodiments, the kidney disease is microalbuminuria or macroalbuminuria kidney disease. In some embodiments, the disease or condition to be treated is pulmonary arterial hypertension. In some embodiments, the disease or condition to be treated is pain selected from neuropathic pain and visceral pain.

In some embodiments, the disease or condition is cancer selected from chemoresistant breast carcinoma, adriamycin-resistant breast cancer, chemoresistant colorectal cancer, medulloblastoma, and tumor angiogenesis.

In some embodiments, the disease or condition to be treated is transplant-related FSGS, transplant-related nephrotic syndrome, transplant-related proteinuria, cholestatic liver disease, polycystic kidney disease, autosomal dominant polycystic kidney disease (ADPKD), obesity, insulin resistance, Type II diabetes, prediabetes, metabolic syndrome, non-alcoholic fatty liver disease (NAFLD), or non-alcoholic steatohepatitis (NASH).

The methods are effective for a variety of subjects including mammals, e.g., humans and other animals, such as laboratory animals, e.g., mice, rats, rabbits, or monkeys, or domesticated and farm animals, e.g., cats, dogs, goats, sheep, pigs, cows, or horses.

The invention provides several advantages. The prophylactic and therapeutic methods described herein are effective in treating kidney disease, e.g., proteinuria, and have minimal, if any, side effects. Further, methods described herein are effective to identify compounds that treat or reduce risk of developing a kidney disease, anxiety, depression, or cancer.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the detailed description, and from the claims.

DETAILED DESCRIPTION

Definitions

Figure 1:
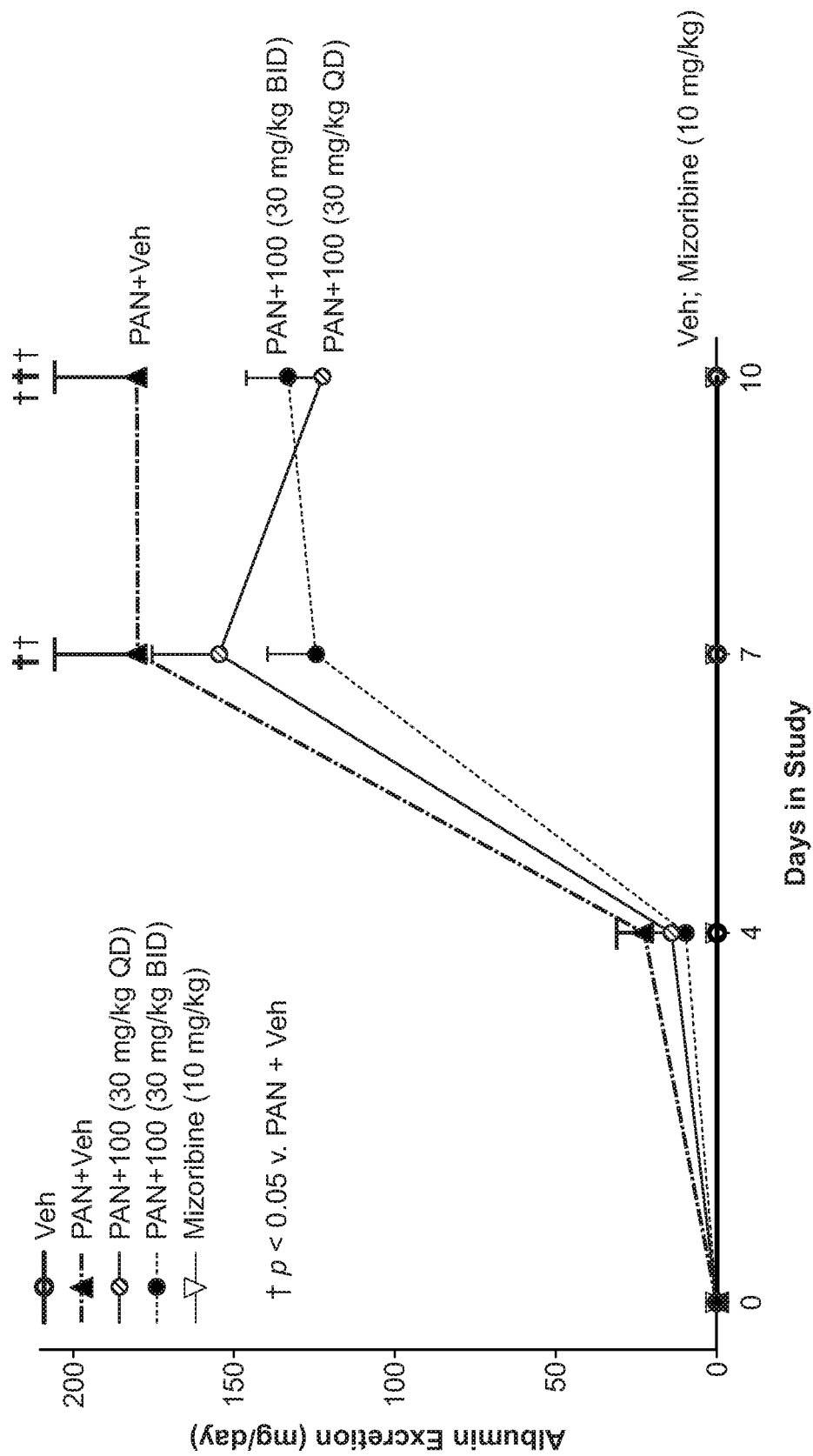
FIG. 1 shows albumin excretion in PAN-injured rats treated with compound 100 or mizoribine.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, trifluoromethoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen (e.g., fluoro), a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

Unless otherwise specified, "alkylene" by itself or as part of another substituent refers to a saturated straight-chain or branched divalent group having the stated number of carbon atoms and derived from the removal of two hydrogen atoms from the corresponding alkane. Examples of straight chained and branched alkylene groups include —$CH_2$— (methylene), —$CH_2$—$CH_2$— (ethylene), —$CH_2$—$CH_2$—$CH_2$— (propylene), —$C(CH_3)_2$—, —$CH_2$—$CH(CH_3)$—, —$CH_2$—$CH_2$—$CH_2$—$CH_2$—, —$CH_2$—$CH_2$—$CH_2$—$CH_2$—$CH_2$— (pentylene), —$CH_2$—$CH(CH_3)$—$CH_2$—, and —$CH_2$—$C(CH_3)_2$—$CH_2$—.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. $C_0$ alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

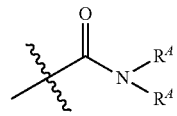

wherein each $R^A$ independently represent a hydrogen or hydrocarbyl group, or two $R^A$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

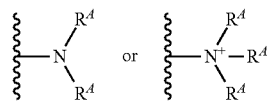

wherein each $R^A$ independently represents a hydrogen or a hydrocarbyl group, or two $R^A$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 6- or 10-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, aryls, heteroaryls, and/or heterocyclyls. Aryl groups include benzene, naphthalene, phenanthrene, phenol, aniline, and the like.

The term "carbamate" is art-recognized and refers to a group

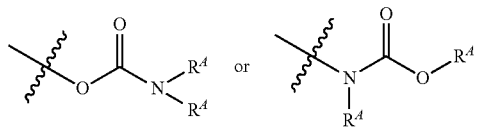

wherein each $R^A$ independently represent hydrogen or a hydrocarbyl group, such as an alkyl group, or both $R^A$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^A$, wherein R$^A$ represents a hydrocarbyl group.

The term "carboxy", as used herein, refers to a group represented by the formula —CO$_2$H.

The term "ester", as used herein, refers to a group —C(O)OR$^A$ wherein R$^A$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, aryls, heteroaryls, and/or heterocyclyls. Heterocyclyl groups include, for example, piperidine, piperazine, pyrrolidine, tetrahydropyran, tetrahydrofuran, morpholine, lactones, lactams, and the like.

The term "heterocyclylalkyl" or "heterocycloalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —$OSO_3H$, or a pharmaceutically acceptable salt thereof.

The term "sulfonamide" is art-recognized and refers to the group represented by the general formulae

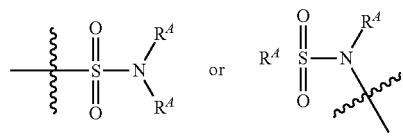

wherein each $R^A$ independently represents hydrogen or hydrocarbyl, such as alkyl, or both $R^A$ taken together with the intervening atom(s) complete a heterocycle having from 4 to 8 atoms in the ring structure.

The term "sulfoxide" is art-recognized and refers to the group —S(O)—$R^A$, wherein $R^A$ represents a hydrocarbyl.

The term "sulfonate" is art-recognized and refers to the group $SO_3H$, or a pharmaceutically acceptable salt thereof.

The term "sulfone" is art-recognized and refers to the group —$S(O)_2$—$R^A$, wherein $R^A$ represents a hydrocarbyl.

The term "thioalkyl", as used herein, refers to an alkyl group substituted with a thiol group.

The term "thioester", as used herein, refers to a group —$C(O)SR^A$ or —$SC(O)R^A$ wherein $R^A$ represents a hydrocarbyl.

The term "thioether", as used herein, is equivalent to an ether, wherein the oxygen is replaced with a sulfur.

The term "urea" is art-recognized and may be represented by the general formula

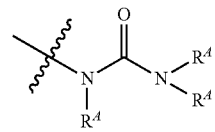

wherein each $R^A$ independently represents hydrogen or a hydrocarbyl, such as alkyl, or any occurrence of $R^A$ taken together with another and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" or "reduces the risk of developing" a disease, disorder, or condition refers to a compound that, in a statistical sample, reduces the occurrence of the disease, disorder, or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The phrases "conjoint administration" and "administered conjointly" refer to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

The term "prodrug" is intended to encompass compounds which, under physiologic conditions, are converted into the therapeutically active agents of the present invention. A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of the invention in a formulation represented above can be replaced with the corresponding suitable prodrug, e.g., wherein a hydroxyl in the parent compound is presented as an ester or a carbonate or carboxylic acid present in the parent compound is presented as an ester.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

In some embodiments, a "small molecule" refers to an organic, inorganic, or organometallic compound typically having a molecular weight of less than about 1000. In some embodiments, a small molecule is an organic compound, with a size on the order of 1 nm. In some embodiments, small molecule drugs of the invention encompass oligopeptides and other biomolecules having a molecular weight of less than about 1000.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

COMPOUNDS OF THE INVENTION

One aspect of the invention provides small molecule inhibitors of TRPC5.

In some embodiments, the compound of the invention is a compound of structural formula I:

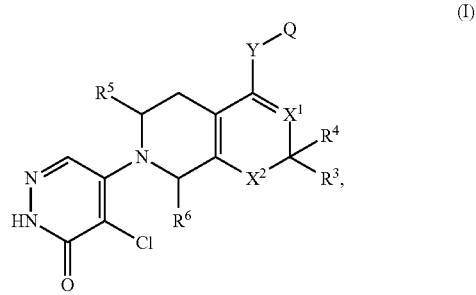

or a pharmaceutically acceptable salt thereof;
wherein:
"---" is a single bond or a double bond
$X^1$ is CH or N;
when "---" is a double bond, $X^2$ is CH or N;
when "---" is a single bond, $X^2$ is $N(CH_3)$,
when $X^1$ is CH, $X^2$ is N or $N(CH_3)$;
Y is —O—, —$N(CH_3)$—, —$N(CH_2CH_2OH)$—, cyclopropan-1,1-diyl, or —$CH(CH_3)$—;
Q is 2-trifluoromethyl-4-fluorophenyl, 2-difluoromethyl-4-fluorophenyl, 2-trifluoromethylphenyl, 2-methyl-4-fluorophenyl, 2-chloro-4-fluorophenyl, 2-chlorophenyl, 1-(benzyl)-4-methylpiperidin-3-yl, 4-trifluoromethylpyridin-3-yl, 2-trifluoromethyl-6-fluorophenyl, 2-trifluoromethyl-3-cyanophenyl, 2-ethyl-3-fluorophenyl, 2-chloro-3-cyanophenyl, 2-trifluoromethyl-5-fluorophenyl, or 2-difluoromethylphenyl;
$R^3$ is hydrogen, —$CH_2OH$, —$CH(OH)$—$CH_2OH$, —$NH_2$, —$CH(OH)CH_3$, —$OCH_3$, or —NH—$(CH_2)_2OH$;
and when "---" is a double bond, $R^4$ is absent;
and when "---" is a single bond, $R^3$ and $R^4$ are taken together to form =O; and
each of $R^5$ and $R^6$ is independently hydrogen or —$CH_3$, provided that if $X^1$ is N, $X^2$ is N, Y is —O— or —$N(CH_3)$—, and Q is 2-trifluoromethylphenyl, then at least one of $R^3$, $R^5$, and $R^6$ is not hydrogen.

In some embodiments, the compound of the invention is a compound represented by structural formula II:

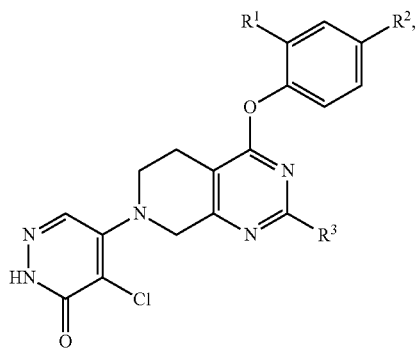

(II)

or a pharmaceutically acceptable salt thereof; wherein:

R$^1$ is chloro, —CF$_3$, —CHF$_2$, or —CH$_3$;

R$^2$ is hydrogen or fluoro; and

R$^3$ is hydrogen, —NH$_2$, —CH$_2$OH, or CH(OH)—CH$_2$OH.

In some embodiments, when R$^1$ is —CHF$_2$, R$^2$ is not hydrogen.

In some embodiments, the compound of the invention is selected from any one of the following compounds, or a pharmaceutically acceptable salt thereof:

| Compound | Structure |
|---|---|
| 100 | 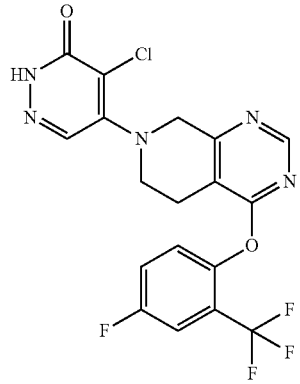 [SMILES: O=c1[nH]ncc(N2CCc3c(ncnc3Oc3ccc(F)cc3C(F)(F)F)C2)c1Cl] |
| 101 | 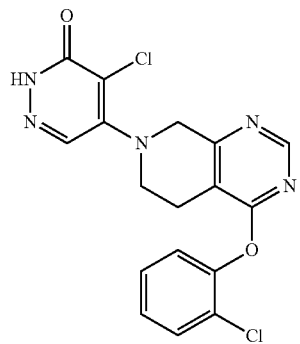 [SMILES: O=c1[nH]ncc(N2CCc3c(ncnc3Oc3ccccc3Cl)C2)c1Cl] |
| 102 | 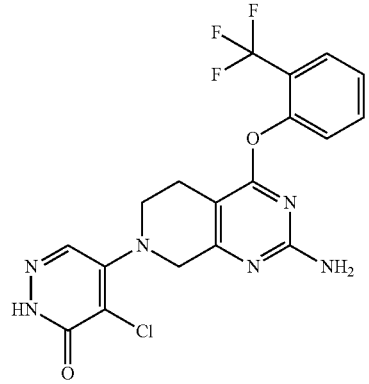 [SMILES: Nc1nc2c(c(Oc3ccccc3C(F)(F)F)n1)CCN(c1cn[nH]c(=O)c1Cl)C2] |
| 103 | 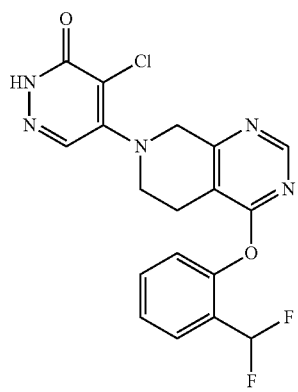 |
| 104 | 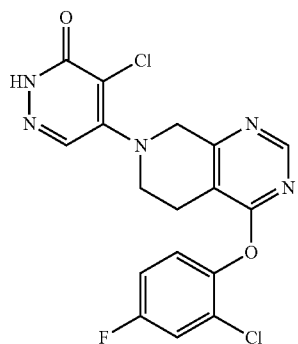 [SMILES: O=c1[nH]ncc(N2CCc3c(ncnc3Oc3ccc(F)cc3Cl)C2)c1Cl] |
| 105 | 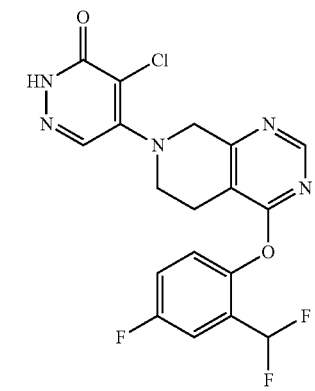 |

| Compound | Structure |
|---|---|
| 106 | 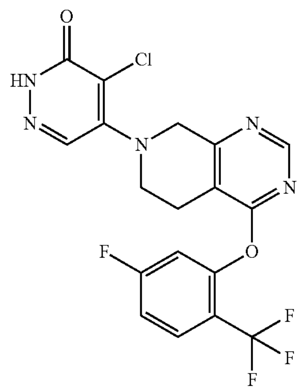 [SMILES: O=c1[nH]ncc(N2CCc3c(ncnc3Oc3cc(F)ccc3C(F)(F)F)C2)c1Cl] |
| 107 | 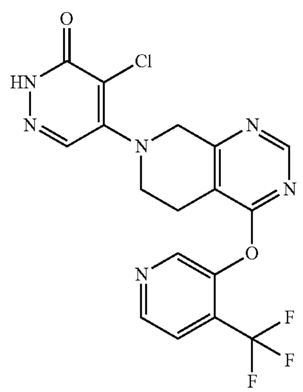 [SMILES: O=c1[nH]ncc(N2CCc3c(ncnc3Oc3cnccc3C(F)(F)F)C2)c1Cl] |
| 108 | 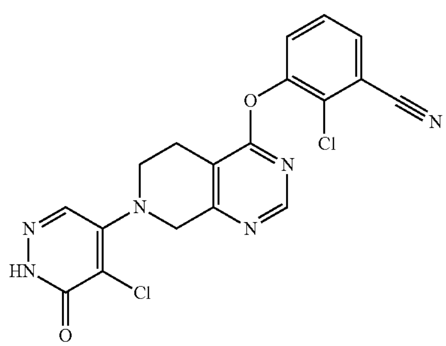 [SMILES: N#Cc1cccc(Oc2ncnc3c2CCN(c2cn[nH]c(=O)c2Cl)C3)c1Cl] |
| 109 | 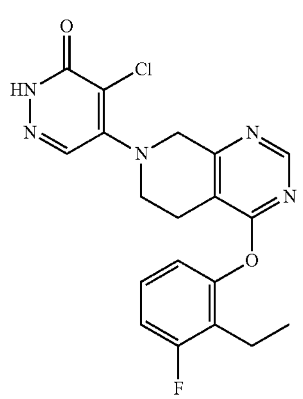 [SMILES: CCc1c(F)cccc1Oc1ncnc2c1CCN(c1cn[nH]c(=O)c1Cl)C2] |
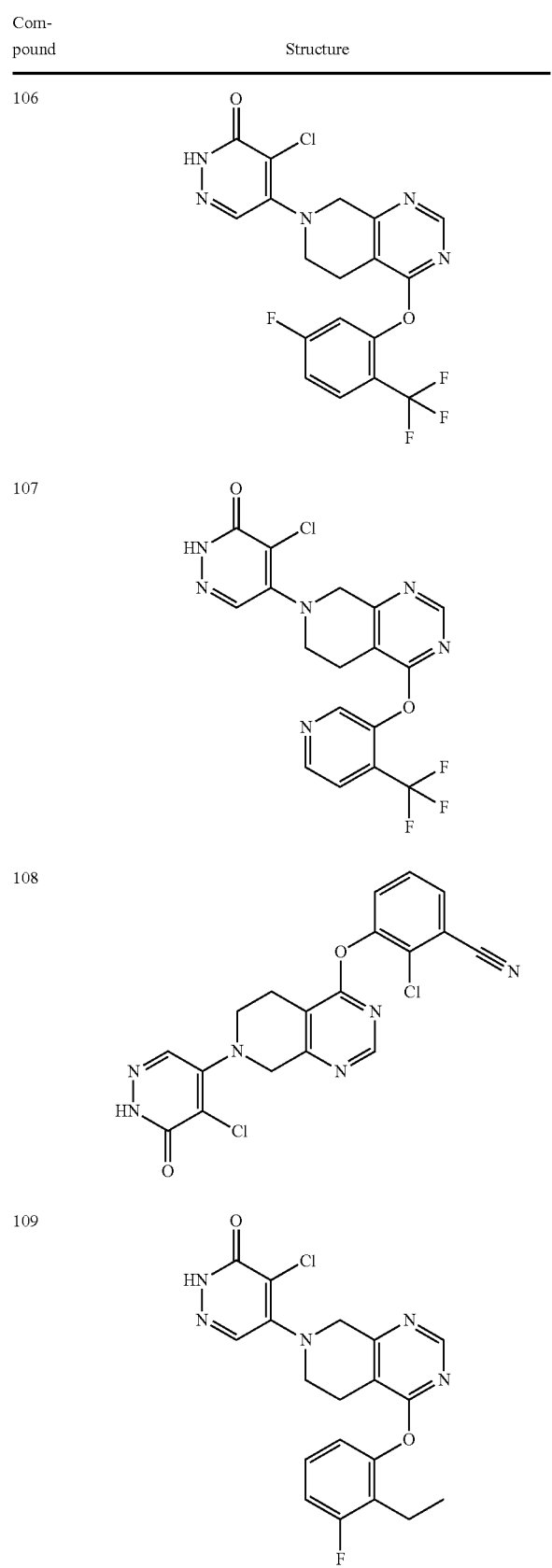
| Compound | Structure |
|---|---|
| 110 | |
| 111 | |
| 112 | |
| 113 | |
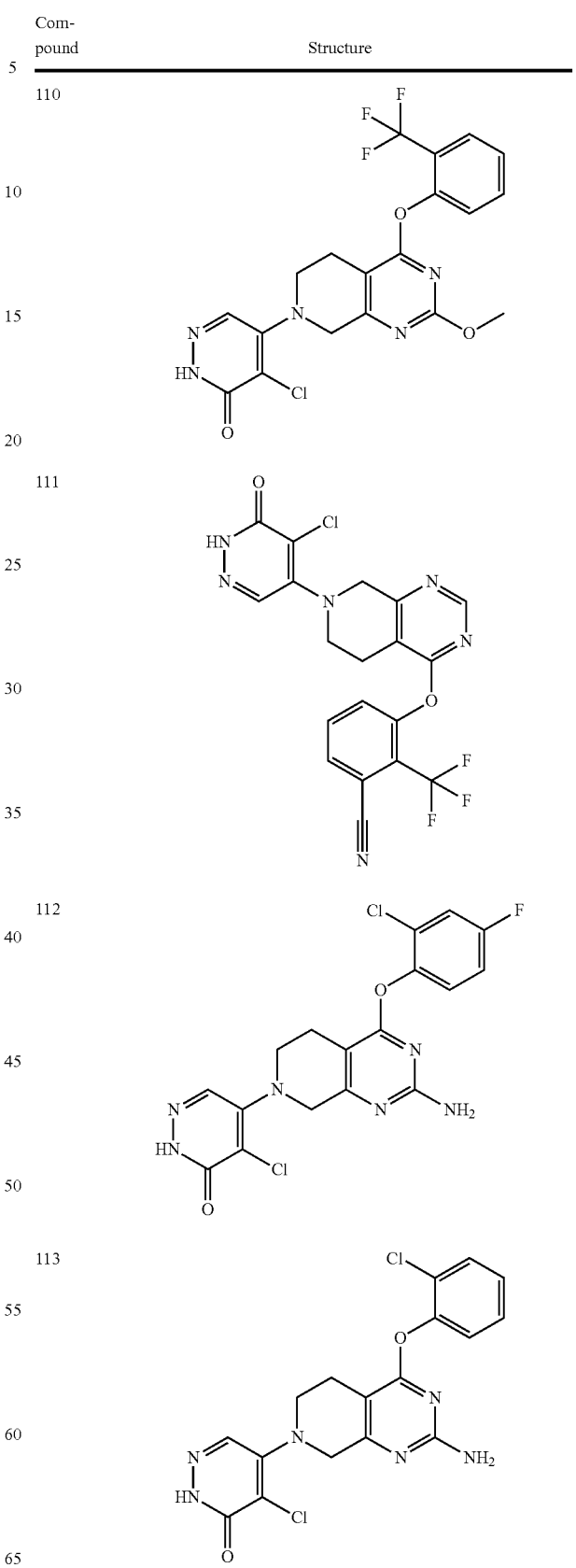

-continued

| Compound | Structure |
|---|---|
| 114 | (chemical structure) |
| 115 | (chemical structure) |
| 116 | (chemical structure) |
| 117 | (chemical structure) |
| 117a | (chemical structure) |
| 118 | (chemical structure) |
| 119 | (chemical structure) |
| 120 | (chemical structure) |

| Compound | Structure |
|---|---|
| 121 | 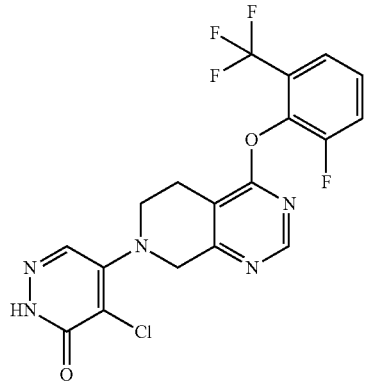 [SMILES: O=c1[nH]ncc(N2CCc3c(ncnc3Oc3c(F)cccc3C(F)(F)F)C2)c1Cl] |
| 122 | 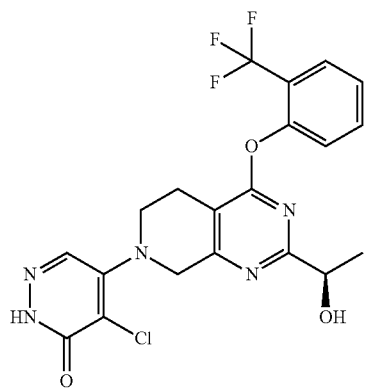 [SMILES: C[C@@H](O)c1nc2c(c(Oc3ccccc3C(F)(F)F)n1)CCN(c1cn[nH]c(=O)c1Cl)C2] |
| 123 | 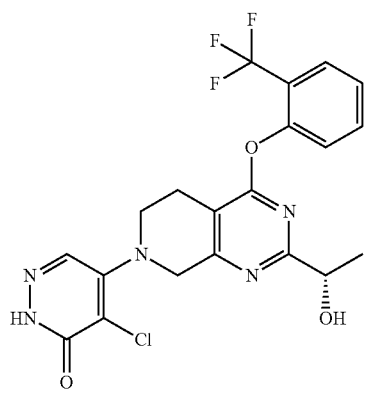 [SMILES: C[C@H](O)c1nc2c(c(Oc3ccccc3C(F)(F)F)n1)CCN(c1cn[nH]c(=O)c1Cl)C2] |
| 124 | 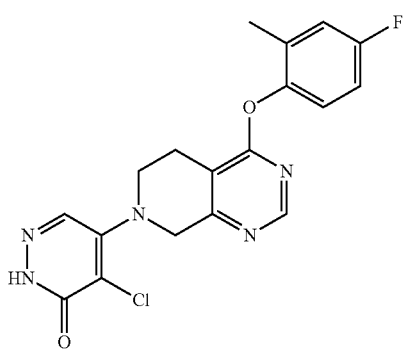 [SMILES: Cc1cc(F)ccc1Oc1ncnc2c1CCN(c1cn[nH]c(=O)c1Cl)C2] |
| 125 | 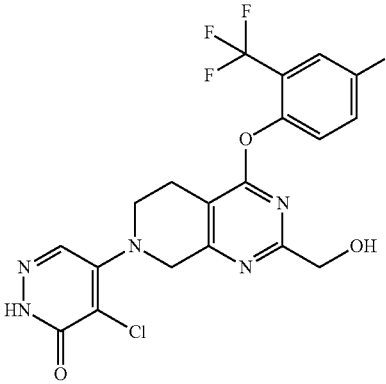 |
| 126 | 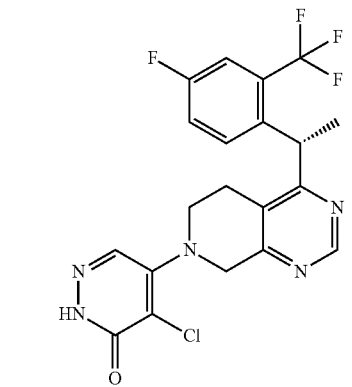 [SMILES: C[C@@H](c1ccc(F)cc1C(F)(F)F)c1ncnc2c1CCN(c1cn[nH]c(=O)c1Cl)C2] |
| 126a | 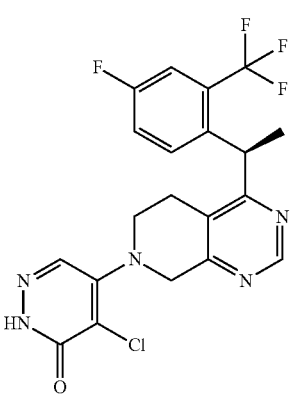 [SMILES: C[C@H](c1ccc(F)cc1C(F)(F)F)c1ncnc2c1CCN(c1cn[nH]c(=O)c1Cl)C2] |
| 127 | 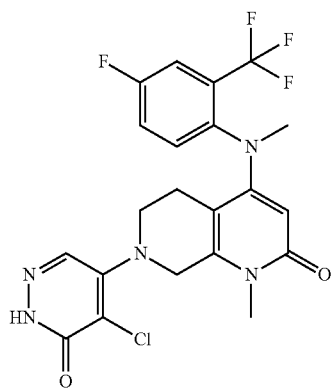 |

| Compound | Structure |
|---|---|
| 128 | 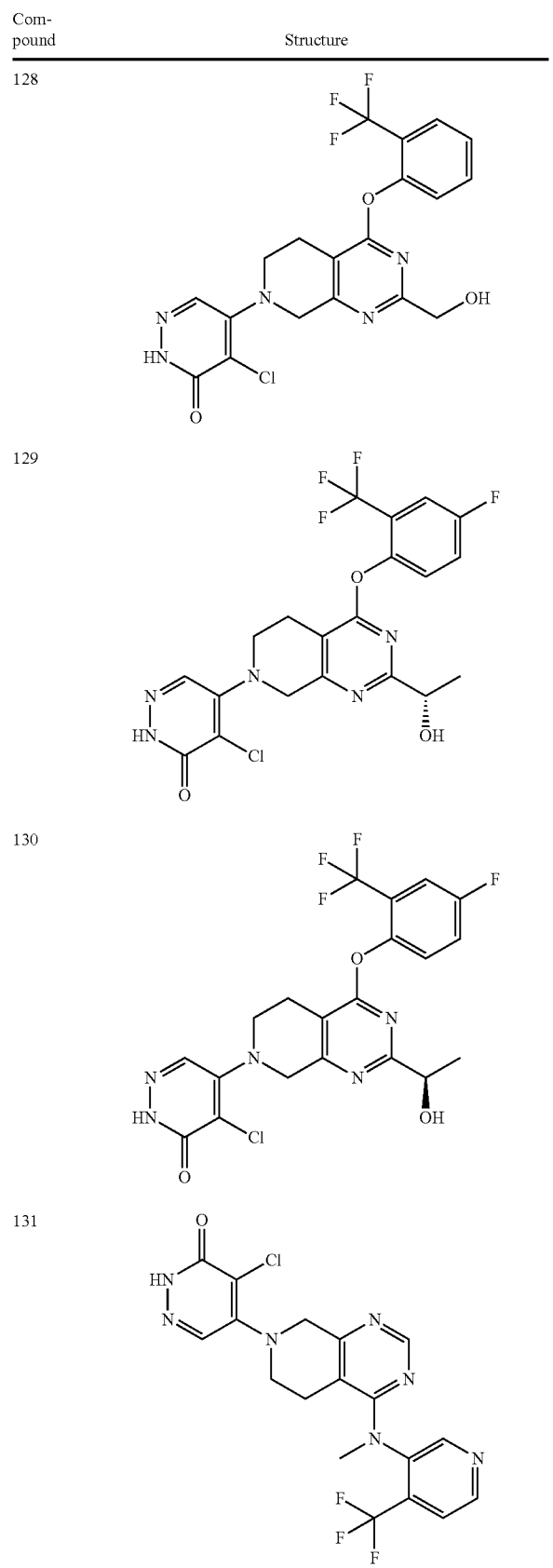 |
| 129 | |
| 130 | |
| 131 | |
| Compound | Structure |
|---|---|
| 132 | 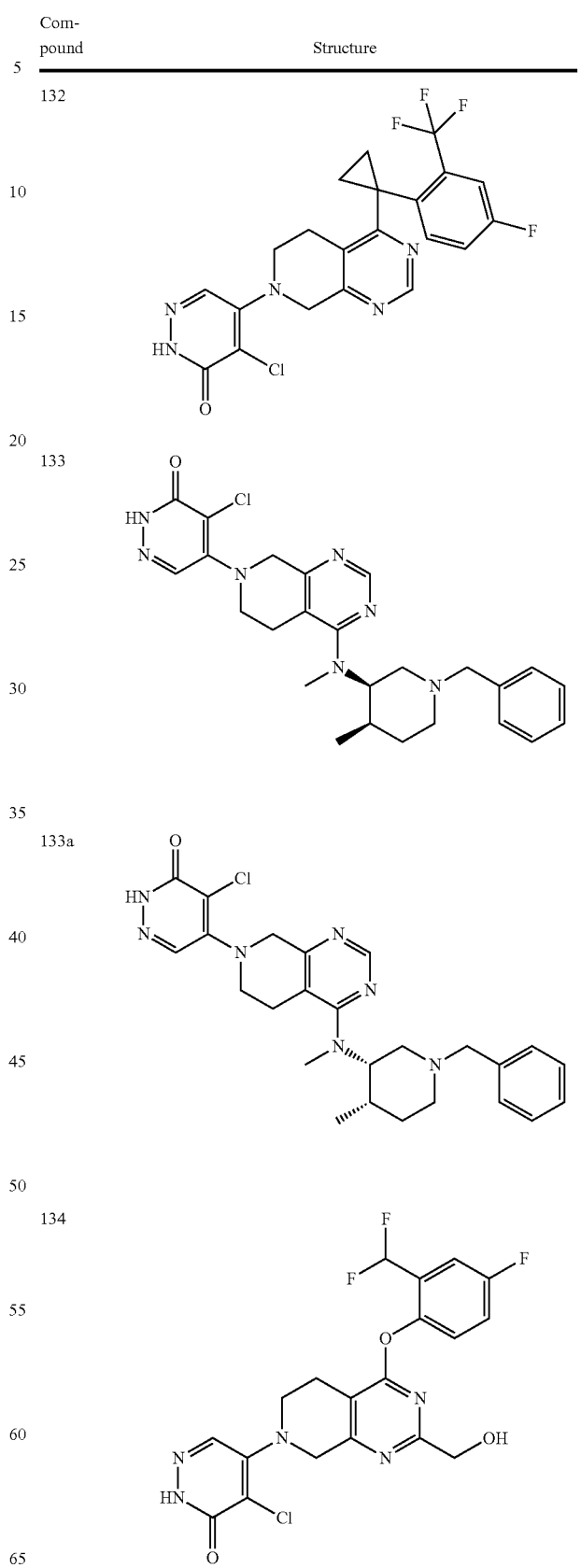 |
| 133 | |
| 133a | |
| 134 | |

| Compound | Structure |
|---|---|
| 135 | 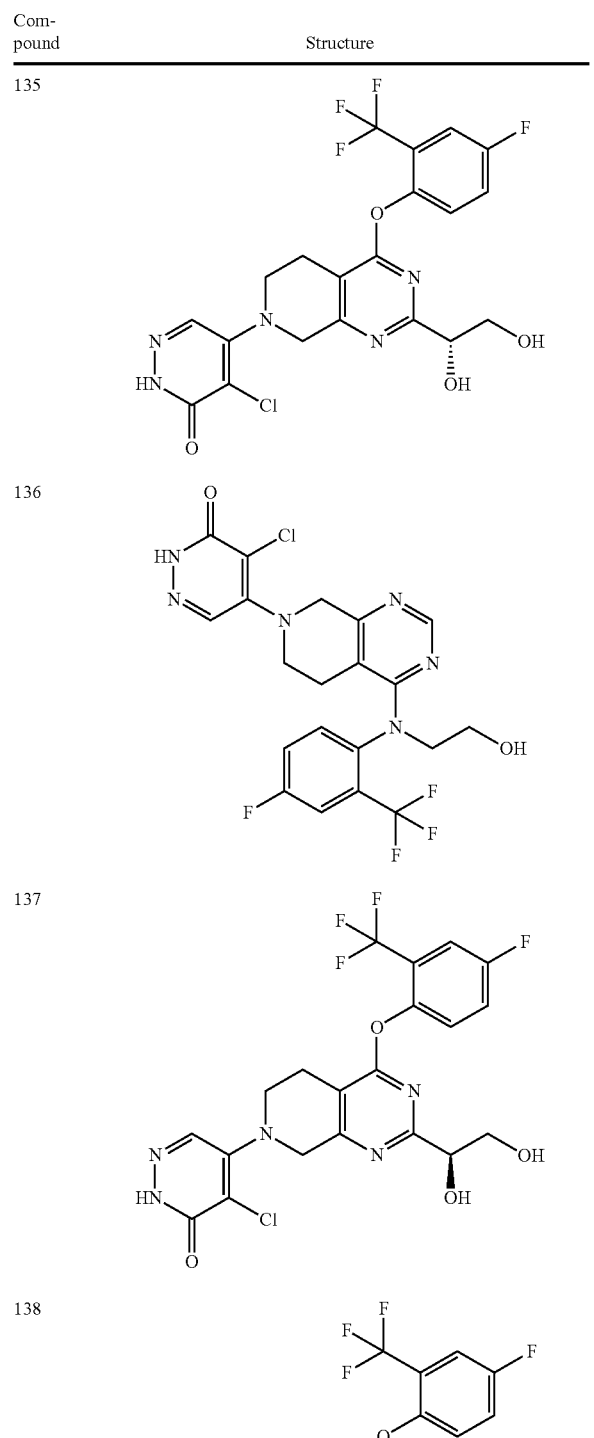 |
| 136 | |
| 137 | |
| 138 | |
| Compound | Structure |
|---|---|
| 139 | 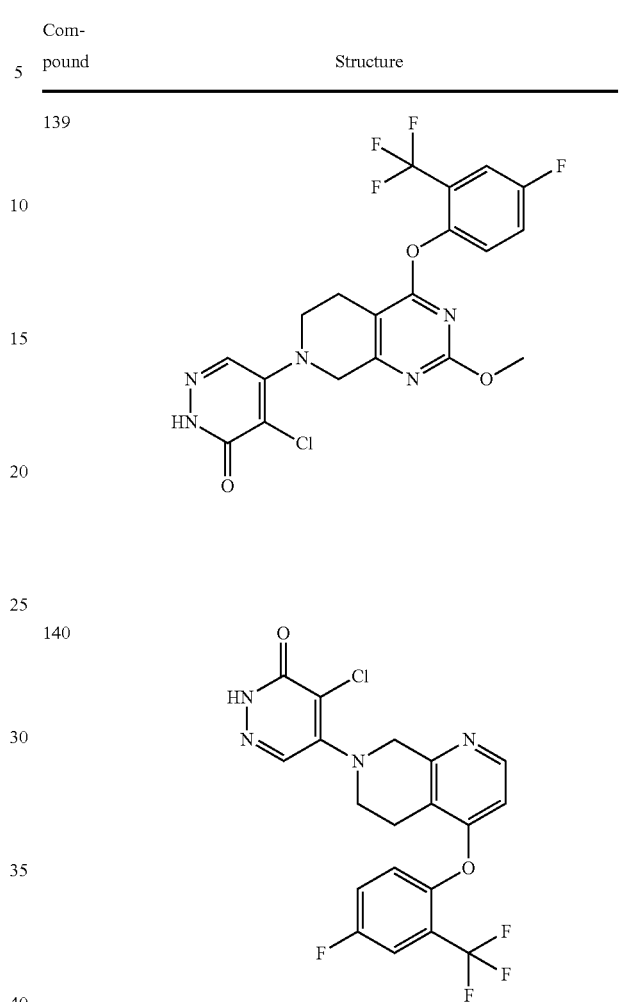 |
| 140 | |
In some embodiments, the compound of the invention is selected from any one of the following compounds, or a pharmaceutically acceptable salt thereof:
| Compound | Structure |
|---|---|
| 100 | 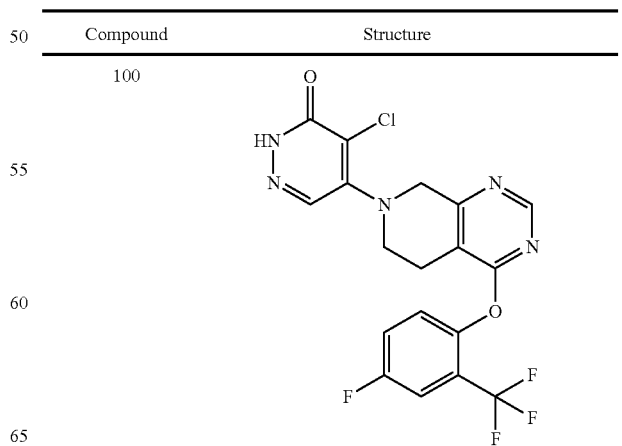 |

| Compound | Structure |
|---|---|
| 101 | 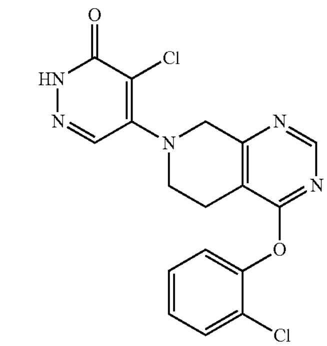 [SMILES: O=c1[nH]ncc(N2CCc3c(ncnc3Oc3ccccc3Cl)C2)c1Cl] |
| 102 | 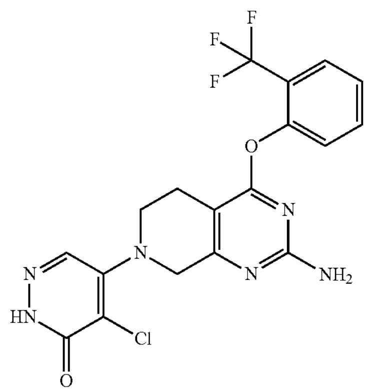 [SMILES: Nc1nc2c(c(Oc3ccccc3C(F)(F)F)n1)CCN(c1cn[nH]c(=O)c1Cl)C2] |
| 104 | 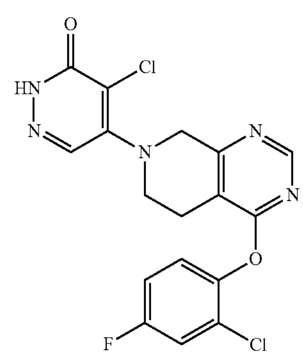 [SMILES: O=c1[nH]ncc(N2CCc3c(ncnc3Oc3ccc(F)cc3Cl)C2)c1Cl] |
| 105 | 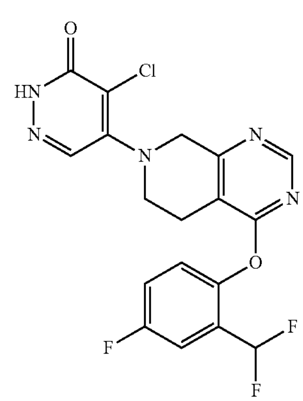 [SMILES: O=c1[nH]ncc(N2CCc3c(ncnc3Oc3ccc(F)cc3C(F)F)C2)c1Cl] |
| 112 | |
| 113 | |
| 114 | |
| 116 | |

-continued
| Compound | Structure |
|---|---|
| 124 | 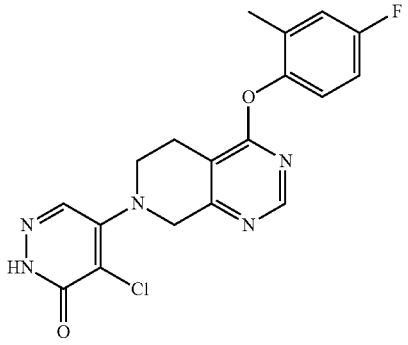 |
| 125 | 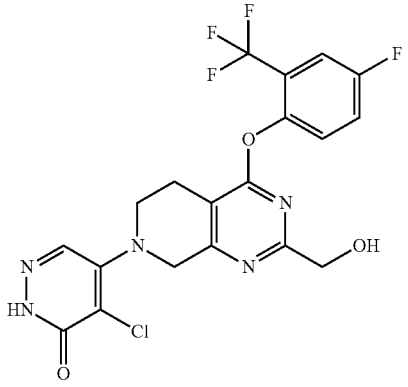 [SMILES: O=c1[nH]ncc(N2CCc3c(nc(CO)nc3Oc3ccc(F)cc3C(F)(F)F)C2)c1Cl] |
| 128 | 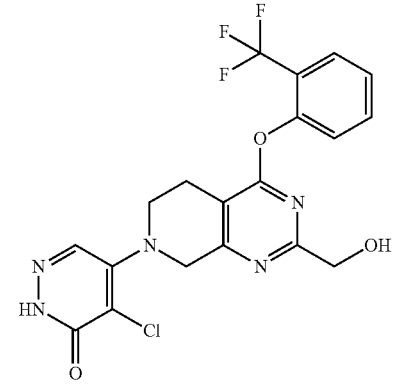 [SMILES: O=c1[nH]ncc(N2CCc3c(nc(CO)nc3Oc3ccccc3C(F)(F)F)C2)c1Cl] |
| 134 | 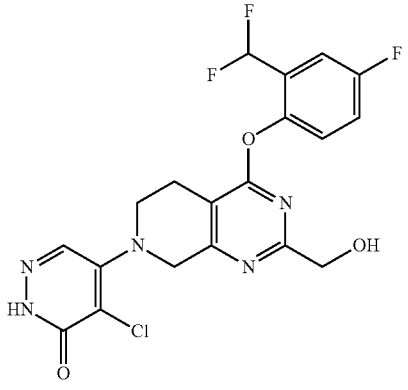 [SMILES: O=c1[nH]ncc(N2CCc3c(nc(CO)nc3Oc3ccc(F)cc3C(F)F)C2)c1Cl] |
-continued
| Compound | Structure |
|---|---|
| 135 | 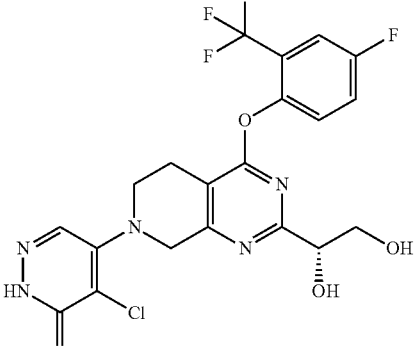 |
| 137 | 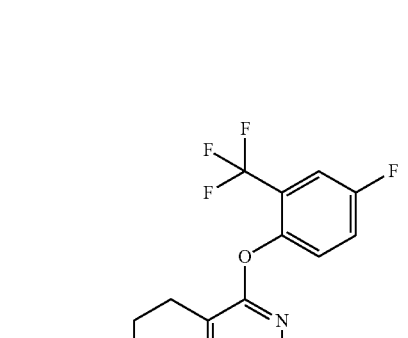 |
In some embodiments, the compound of the invention is selected from any one of the following compounds, or a pharmaceutically acceptable salt thereof:
| Compound | Structure |
|---|---|
| 100 | 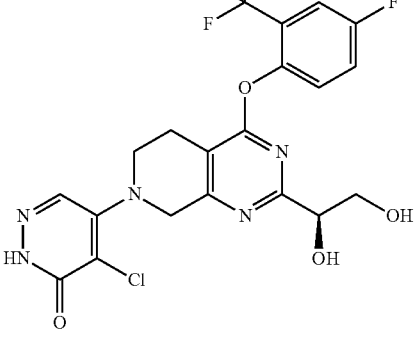 |

| Compound | Structure |
|---|---|
| 101 | 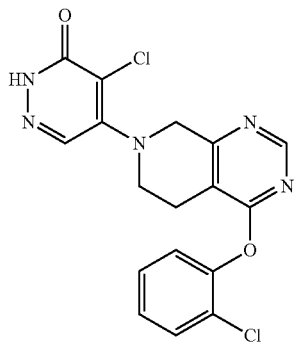 [SMILES: O=c1[nH]ncc(N2CCc3c(ncnc3Oc3ccccc3Cl)C2)c1Cl] |
| 102 | 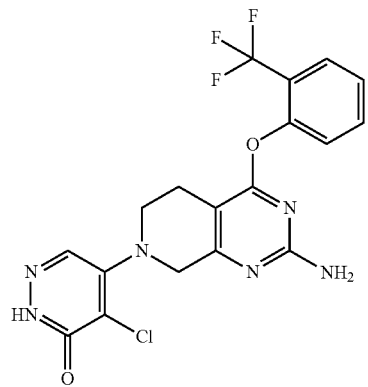 |
| 104 | 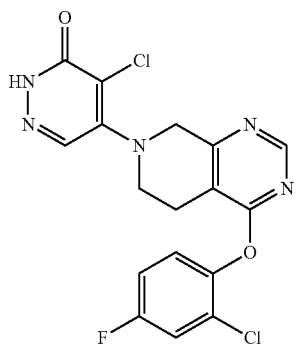 [SMILES: O=c1[nH]ncc(N2CCc3c(ncnc3Oc3ccc(F)cc3Cl)C2)c1Cl] |
| 105 | 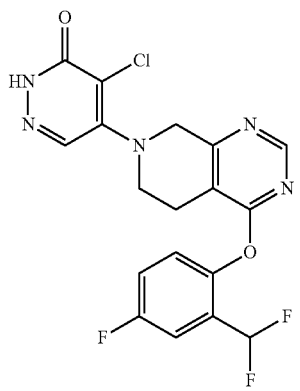 [SMILES: O=c1[nH]ncc(N2CCc3c(ncnc3Oc3ccc(F)cc3C(F)F)C2)c1Cl] |
| 114 | 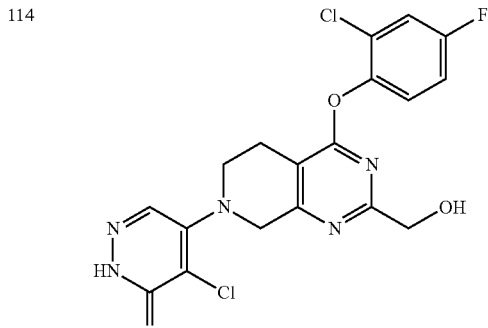 |
| 116 | 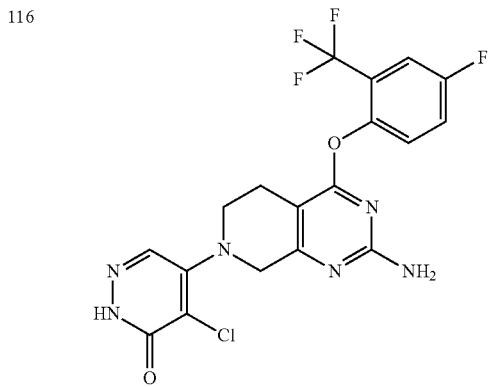 |
| 124 | 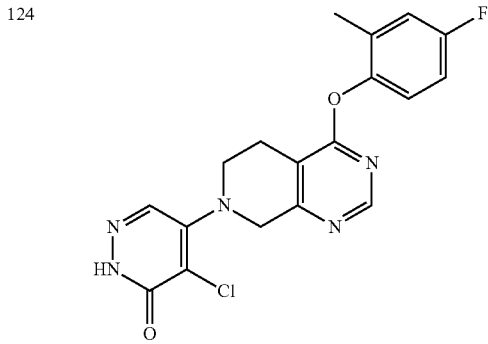 |
| 125 | 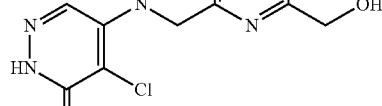 |

| Compound | Structure |
|---|---|
| 128 | (structure) |
| 134 | (structure) |
| 135 | (structure) |
| 137 | (structure) |

In certain embodiments, the compounds of the invention may be racemic. In certain embodiments, the compounds of the invention may be enriched in one enantiomer. For example, a compound of the invention may have greater than 30% ee, 40% ee, 50% ee, 60% ee, 70% ee, 80% ee, 90% ee, or even 95% or greater ee.

The compounds of the invention have more than one stereocenter. Accordingly, the compounds of the invention may be enriched in one or more diastereomers. For example, a compound of the invention may have greater than 30% de, 40% de, 50% de, 60% de, 70% de, 80% de, 90% de, or even 95% or greater de. In certain embodiments, the compounds of the invention have substantially one isomeric configuration at one or more stereogenic centers, and have multiple isomeric configurations at the remaining stereogenic centers.

In certain embodiments, the enantiomeric excess of the stereocenter is at least 40% ee, 50% ee, 60% ee, 70% ee, 80% ee, 90% ee, 92% ee, 94% ee, 95% ee, 96% ee, 98% ee or greater ee.

As used herein, single bonds drawn without stereochemistry do not indicate the stereochemistry of the compound.

As used herein, hashed or bolded non-wedge bonds indicate relative, but not absolute, stereochemical configuration (e.g., do not distinguish between enantiomers of a given diastereomer).

As used herein, hashed or bolded wedge bonds indicate absolute stereochemical configuration.

In some embodiments, the invention relates to pharmaceutical composition comprising a compound of the invention and a pharmaceutically acceptable carrier. In certain embodiments, a therapeutic preparation or pharmaceutical composition of the compound of the invention may be enriched to provide predominantly one enantiomer of a compound. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, a therapeutic preparation or pharmaceutical composition may be enriched to provide predominantly one diastereomer of the compound of the invention. A diastereomerically enriched mixture may comprise, for example, at least 60 mol percent of one diastereomer, or more preferably at least 75, 90, 95, or even 99 mol percent.

Methods of Treatment

The non-selective $Ca^{2+}$-permeable Transient Receptor Potential (TRP) channels act as sensors that transduce extracellular cues to the intracellular environment in diverse cellular processes, including actin remodeling and cell migration (Greka et al., Nat Neurosci 6, 837-845, 2003; Ramsey et al., Annu Rev Physiol 68, 619-647, 2006; Montell, Pflugers Arch 451, 19-28, 2005, Clapham, Nature 426, 517-524, 2003). Dynamic rearrangement of the actin cytoskeleton relies on spatiotemporally regulated $Ca^{2+}$ influx (Zheng and Poo, Annu Rev Cell Dev Biol 23, 375-404, 2007); Brandman and Meyer, Science 322, 390-395, 2008); Collins and Meyer, Dev Cell 16, 160-161, 2009) and the small GTPases RhoA and Rac1 serve as key modulators of these changes (Etienne-Manneville and Hall, Nature 420, 629-635, 2002); Raftopoulou and Hall, Dev Biol 265, 23-32, 2004). RhoA induces stress fiber and focal adhesion formation, while Rac1 mediates lamellipodia formation (Etienne-Manneville and Hall, Nature 420, 629-635, 2002). The Transient Receptor Potential Cation Channel, subfamily C, member 5 (TRPC5) acts in concert with TRPC6 to regulate Ca2+ influx, actin remodeling, and cell motility in kidney podocytes and fibroblasts. TRPC5-mediated $Ca^{2+}$ influx increases Rac1 activity, whereas TRPC6-mediated Ca2+ influx promotes RhoA activity. Gene silencing of TRPC6 channels abolishes stress fibers and diminishes focal contacts, rendering a motile, migratory cell phenotype. In contrast, gene silencing of TRPC5 channels rescues stress fiber formation, rendering a contractile cell phenotype. The results described herein unveil a conserved signaling mechanism whereby TRPC5 and TRPC6 channels control a tightly regulated balance of cytoskeletal dynamics through differential coupling to Rac1 and RhoA.

$Ca^{2+}$-dependent remodeling of the actin cytoskeleton is a dynamic process that drives cell migration (Wei et al., Nature 457, 901-905, 2009). RhoA and Rac1 act as switches responsible for cytoskeletal rearrangements in migrating cells (Etienne-Manneville and Hall, Nature 420, 629-635, 2002); Raftopoulou and Hall, Dev Biol 265, 23-32, 2004). Activation of Rac1 mediates a motile cell phenotype, whereas RhoA activity promotes a contractile phenotype (Etienne-Manneville and Hall, Nature 420, 629-635, 2002). $Ca^{2+}$ plays a central role in small GTPase regulation (Aspenstrom et al., Biochem J 377, 327-337, 2004). Spatially and temporally restricted flickers of $Ca^{2+}$ are enriched near the leading edge of migrating cells (Wei et al., Nature 457, 901-905, 2009). Ca2+microdomains have thus joined local bursts in Rac1 activity (Gardiner et al., Curr Biol 12, 2029-2034, 2002; Machacek et al., Nature 461, 99-103, 2009) as critical events at the leading edge. To date, the sources of Ca2+influx responsible for GTPase regulation remain largely elusive. TRP (Transient Receptor Potential) channels generate time and space-limited $Ca^{2+}$ signals linked to cell migration in fibroblasts and neuronal growth cones0. Specifically, TRPC5 channels are known regulators of neuronal growth cone guidance 1 and their activity in neurons is dependent on PI3K and Rac1 activity (Bezzerides et al., Nat Cell Biol 6, 709-720, 2004).

Podocytes are neuronal-like cells that originate from the metanephric mesenchyme of the kidney glomerulus and are essential to the formation of the kidney filtration apparatus (Somlo and Mundel, Nat Genet. 24, 333-335, 2000; Fukasawa et al., J Am Soc Nephrol 20, 1491-1503, 2009). Podocytes possess an exquisitely refined repertoire of cytoskeletal adaptations to environmental cues (Somlo and Mundel, Nat Genet 24, 333-335, 2000; Garg et al., Mol Cell Biol 27, 8698-8712, 2007; Verma et al., J Clin Invest 116, 1346-1359, 2006; Verma et al., J Biol Chem 278, 20716-20723, 2003; Barletta et al., J Biol Chem 278, 19266-19271, 2003; Holzman et al., Kidney Int 56, 1481-1491, 1999; Ahola et al., Am J Pathol 155, 907-913, 1999; Tryggvason and Wartiovaara, N Engl J Med 354, 1387-1401, 2006; Schnabel and Farquhar, J Cell Biol 111, 1255-1263, 1990; Kurihara et al., Proc Natl Acad Sci USA 89, 7075-7079, 1992). Early events of podocyte injury are characterized by dysregulation of the actin cytoskeleton (Faul et al., Trends Cell Biol 17, 428-437, 2007, Takeda et al., J Clin Invest 108, 289-301, 2001; Asanuma et al., Nat Cell Biol 8, 485-491, 2006) and Ca2+ homeostasis (Hunt et al., J Am Soc Nephrol 16, 1593-1602, 2005; Faul et al., Nat Med 14, 931-938, 2008). These changes are associated with the onset of proteinuria, the loss of albumin into the urinary space, and ultimately kidney failure (Tryggvason and Wartiovaara, N Engl J Med 354, 1387-1401, 2006). The vasoactive hormone Angiotensin II induces $Ca^{2+}$ influx in podocytes, and prolonged treatment results in loss of stress fibers (Hsu et al., J Mol Med 86, 1379-1394, 2008). While there is a recognized link between Ca2+ influx and cytoskeletal reorganization, the mechanisms by which the podocyte senses and transduces extracellular cues that modulate cell shape and motility remain elusive. TRP Canonical 6 (TRPC6) channel mutations have been linked to podocyte injury (Winn et al., Science 308, 1801-1804, 2005; Reiser et al., Nat Genet 37, 739-744, 2005; Moller et al., J Am Soc Nephrol 18, 29-36, 2007; Hsu et al., Biochim Biophys Acta 1772, 928-936, 2007), but little is known about the specific pathways that regulate this process. Moreover, TRPC6 shares close homology with six other members of the TRPC channel family (Ramsey et al., Annu Rev Physiol 68, 619-647, 2006; Clapham, Nature 426, 517-524, 2003). TRPC5 channels antagonize TRPC6 channel activity to control a tightly regulated balance of cytoskeletal dynamics through differential coupling to distinct small GTPases.

Proteinuria

Proteinuria is a pathological condition wherein protein is present in the urine. Albuminuria is a type of proteinuria. Microalbuminuria occurs when the kidney leaks small amounts of albumin into the urine. In a properly functioning body, albumin is not normally present in urine because it is retained in the bloodstream by the kidneys. Microalbuminuria is diagnosed either from a 24-hour urine collection (20 to 200 µg/min) or, more commonly, from elevated concentrations (30 to 300 mg/L) on at least two occasions. Microalbuminuria can be a forerunner of diabetic nephropathy. An albumin level above these values is called macroalbuminuria. Subjects with certain conditions, e.g., diabetic nephropathy, can progress from microalbuminuria to macroalbuminuria and reach a nephrotic range (>3.5 g/24 hours) as kidney disease reaches advanced stages.

Causes of Proteinuria

Proteinuria can be associated with a number of conditions, including focal segmental glomerulosclerosis, IgA nephropathy, diabetic nephropathy, lupus nephritis, membranoproliferative glomerulonephritis, progressive (crescentic) glomerulonephritis, and membranous glomerulonephritis.

A. Focal Segmental Glomerulosclerosis (FSGS)

Focal Segmental Glomerulosclerosis (FSGS) is a disease that attacks the kidney's filtering system (glomeruli) causing serious scarring. FSGS is one of the many causes of a disease known as Nephrotic Syndrome, which occurs when protein in the blood leaks into the urine (proteinuria).

Very few treatments are available for patients with FSGS. Many patients are treated with steroid regimens, most of which have very harsh side effects. Some patients have shown to respond positively to immunosuppressive drugs as well as blood pressure drugs which have shown to lower the level of protein in the urine. To date, there is no commonly accepted effective treatment or cure and there are no FDA approved drugs to treat FSGS. Therefore, more effective methods to reduce or inhibit proteinuria are desirable.

B. IgA Nephropathy

IgA nephropathy (also known as IgA nephritis, IgAN, Berger's disease, and synpharyngitic glomerulonephritis) is a form of glomerulonephritis (inflammation of the glomeruli of the kidney). IgA nephropathy is the most common glomerulonephritis throughout the world. Primary IgA nephropathy is characterized by deposition of the IgA antibody in the glomerulus. There are other diseases associated with glomerular IgA deposits, the most common being Henoch-Schönlein purpura (HSP), which is considered by many to be a systemic form of IgA nephropathy. Henoch-Schönlein purpura presents with a characteristic purpuric skin rash, arthritis, and abdominal pain and occurs more commonly in young adults (16-35 yrs old). HSP is associated with a more benign prognosis than IgA nephropathy. In IgA nephropathy there is a slow progression to chronic renal failure in 25-30% of cases during a period of 20 years.

C. Diabetic Nephropathy

Diabetic nephropathy, also known as Kimmelstiel-Wilson syndrome and intercapillary glomerulonephritis, is a progressive kidney disease caused by angiopathy of capillaries in the kidney glomeruli. It is characterized by nephrotic syndrome and diffuse glomerulosclerosis. It is due to long-standing diabetes mellitus and is a prime cause for dialysis. The earliest detectable change in the course of diabetic nephropathy is a thickening in the glomerulus. At this stage, the kidney may start allowing more serum albumin than normal in the urine. As diabetic nephropathy progresses, increasing numbers of glomeruli are destroyed by nodular glomerulosclerosis and the amount of albumin excreted in the urine increases.

D. Lupus Nephritis

Lupus nephritis is a kidney disorder that is a complication of systemic lupus erythematosus. Lupus nephritis occurs when antibodies and complement build up in the kidneys, causing inflammation. It often causes proteinuria and may progress rapidly to renal failure. Nitrogen waste products build up in the bloodstream. Systemic lupus erythematosus causes various disorders of the internal structures of the kidney, including interstitial nephritis. Lupus nephritis affects approximately 3 out of 10,000 people.

E. Membranoproliferative Glomerulonephritis I/II/III

Membranoproliferative glomerulonephritis is a type of glomerulonephritis caused by deposits in the kidney glomerular mesangium and basement membrane thickening, activating complement and damaging the glomeruli. There are three types of membranoproliferative glomerulonephritis. Type I is caused by immune complexes depositing in the kidney and is believed to be associated with the classical complement pathway. Type II is similar to Type I, however, it is believed to be associated with the alternative complement pathway. Type III is very rare and it is characterized by a mixture of subepithelial deposits and the typical pathological findings of Type I disease.

F. Progressive (Crescentic) Glomerulonephritis

Progressive (crescentic) glomerulonephritis (PG) is a syndrome of the kidney that, if left untreated, rapidly progresses into acute renal failure and death within months. In 50% of cases, PG is associated with an underlying disease such as Goodpasture's syndrome, systemic lupus erythematosus, or Wegener granulomatosis; the remaining cases are idiopathic. Regardless of the underlying cause, PG involves severe injury to the kidney's glomeruli, with many of the glomeruli containing characteristic crescent-shaped scars. Patients with PG have hematuria, proteinuria, and occasionally, hypertension and edema. The clinical picture is consistent with nephritic syndrome, although the degree of proteinuria may occasionally exceed 3 g/24 hours, a range associated with nephrotic syndrome. Untreated disease may progress to decreased urinary volume (oliguria), which is associated with poor kidney function.

G. Membranous Glomerulonephritis

Membranous glomerulonephritis (MGN) is a slowly progressive disease of the kidney affecting mostly patients between ages of 30 and 50 years, usually Caucasian. It can develop into nephrotic syndrome. MGN is caused by circulating immune complex. Current research indicates that the majority of the immune complexes are formed via binding of antibodies to antigens in situ to the glomerular basement membrane. The said antigens may be endogenous to the basement membrane, or deposited from systemic circulation.

Measurement of Urine Protein Levels

Protein levels in urine can be measured using methods known in the art. Until recently, an accurate protein measurement required a 24-hour urine collection. In a 24-hour collection, the patient urinates into a container, which is kept refrigerated between trips to the bathroom. The patient is instructed to begin collecting urine after the first trip to the bathroom in the morning. Every drop of urine for the rest of the day is to be collected in the container. The next morning, the patient adds the first urination after waking and the collection is complete.

More recently, researchers have found that a single urine sample can provide the needed information. In the newer technique, the amount of albumin in the urine sample is compared with the amount of creatinine, a waste product of normal muscle breakdown. The measurement is called a urine albumin-to-creatinine ratio (UACR). A urine sample containing more than 30 milligrams of albumin for each gram of creatinine (30 mg/g) is a warning that there may be a problem. If the laboratory test exceeds 30 mg/g, another UACR test should be performed 1 to 2 weeks later. If the second test also shows high levels of protein, the person has persistent proteinuria, a sign of declining kidney function, and should have additional tests to evaluate kidney function.

Tests that measure the amount of creatinine in the blood will also show whether a subject's kidneys are removing wastes efficiently. Too much creatinine in the blood is a sign that a person has kidney damage. A physician can use the creatinine measurement to estimate how efficiently the kidneys are filtering the blood. This calculation is called the estimated glomerular filtration rate, or eGFR. Chronic kidney disease is present when the eGFR is less than 60 milliliters per minute (mL/min).

TRPC5

TRPC is a family of transient receptor potential cation channels in animals. TRPC5 is subtype of the TRPC family of mammalian transient receptor potential ion channels. Three examples of TRPC5 are highlighted below in Table 1.

TABLE 1

The TRPC5 orthologs from three different species along with their GenBank Ref Seq Accession Numbers.

| Species | Nucleic Acid | Amino Acid | GeneID |
|---|---|---|---|
| Homo sapiens | NM_012471.2 | NP_036603.1 | 7224 |
| Mus musculus | NM_009428.2 | NP_033454.1 | 22067 |
| Rattus norvegicus | NM_080898.2 | NP_543174.1 | 140933 |

Accordingly, in certain embodiments, the invention provides methods for treating, or the reducing risk of developing, a disease or condition selected from kidney disease, pulmonary arterial hypertension, anxiety, depression, cancer, diabetic retinopathy, or pain, comprising administering to a subject in need thereof a therapeutically effective amount of a compound of the invention (e.g., a compound of structural formula I) or a pharmaceutical composition comprising said compound.

In some embodiments, the disease is kidney disease, anxiety, depression, cancer, or diabetic retinopathy.

In some embodiments, the disease or condition is kidney disease selected from Focal Segmental Glomerulosclerosis (FSGS), Diabetic nephropathy, Alport syndrome, hypertensive kidney disease, nephrotic syndrome, steroid-resistant nephrotic syndrome, minimal change disease, membranous nephropathy, idiopathic membranous nephropathy, membranoproliferative glomerulonephritis (MPGN), immune complex-mediated MPGN, complement-mediated MPGN, Lupus nephritis, postinfectious glomerulonephritis, thin basement membrane disease, mesangial proliferative glomerulonephritis, amyloidosis (primary), c1q nephropathy, rapidly progressive GN, anti-GBM disease, C3 glomerulonephritis, hypertensive nephrosclerosis, or IgA nephropathy. In some embodiments, the kidney disease is proteinuric kidney disease. In some embodiments, the kidney disease is microalbuminuria or macroalbuminuria kidney disease.

In some embodiments, the disease or condition to be treated is pulmonary arterial hypertension.

In some embodiments, the disease or condition to be treated is pain selected from neuropathic pain and visceral pain.

In some embodiments, the disease or condition is cancer selected from chemoresistant breast carcinoma, adriamycin-resistant breast cancer, chemoresistant colorectal cancer, medulloblastoma, and tumor angiogenesis.

The invention also provides methods of treating, or the reducing risk of developing, anxiety, or depression, or cancer, comprising administering to a subject in need thereof a therapeutically effective amount of a compound of the invention (e.g., a compound of Formula I), or a pharmaceutical composition comprising said compound.

In some embodiments, the disease or condition to be treated is transplant-related FSGS, transplant-related nephrotic syndrome, transplant-related proteinuria, cholestatic liver disease, polycystic kidney disease, autosomal dominant polycystic kidney disease (ADPKD), obesity, insulin resistance, Type II diabetes, prediabetes, metabolic syndrome, non-alcoholic fatty liver disease (NAFLD), or non-alcoholic steatohepatitis (NASH).

Subjects to be Treated

In one aspect of the invention, a subject is selected on the basis that they have, or are at risk of developing, a kidney disease, pulmonary arterial hypertension, anxiety, depression, cancer, diabetic retinopathy, or pain. In another aspect, a subject is selected on the basis that they have, or are at risk of developing, kidney disease, anxiety, depression, cancer, or diabetic retinopathy. In another aspect of the invention, a subject is selected on the basis that they have, or are at risk of developing, pain, neuropathic pain, visceral pain, transplant-related FSGS, transplant-related nephrotic syndrome, transplant-related proteinuria, cholestatic liver disease, polycystic kidney disease, autosomal dominant polycystic kidney disease (ADPKD), obesity, insulin resistance, Type II diabetes, prediabetes, metabolic syndrome, non-alcoholic fatty liver disease (NAFLD), or non-alcoholic steatohepatitis (NASH).

Subjects that have, or are at risk of developing, proteinuria include those with diabetes, hypertension, or certain family backgrounds. In the United States, diabetes is the leading cause of end-stage renal disease (ESRD). In both type 1 and type 2 diabetes, albumin in the urine is one of the first signs of deteriorating kidney function. As kidney function declines, the amount of albumin in the urine increases. Another risk factor for developing proteinuria is hypertension. Proteinuria in a person with high blood pressure is an indicator of declining kidney function. If the hypertension is not controlled, the person can progress to full kidney failure. African Americans are more likely than Caucasians to have high blood pressure and to develop kidney problems from it, even when their blood pressure is only mildly elevated. Other groups at risk for proteinuria are American Indians, Hispanics/Latinos, Pacific Islander Americans, older adults, and overweight subjects.

In one aspect of the invention, a subject is selected on the basis that they have, or are at risk of developing proteinuria. A subject that has, or is at risk of developing, proteinuria is one having one or more symptoms of the condition. Symptoms of proteinuria are known to those of skill in the art and include, without limitation, large amounts of protein in the urine, which may cause it to look foamy in the toilet. Loss of large amounts of protein may result in edema, where swelling in the hands, feet, abdomen, or face may occur. These are signs of large protein loss and indicate that kidney disease has progressed. Laboratory testing is the only way to find out whether protein is in a subject's urine before extensive kidney damage occurs.

The methods are effective for a variety of subjects including mammals, e.g., humans and other animals, such as laboratory animals, e.g., mice, rats, rabbits, or monkeys, or domesticated and farm animals, e.g., cats, dogs, goats, sheep, pigs, cows, or horses. In some embodiments, the subject is a mammal. In some embodiments, the subject is a human.

EXAMPLES

The invention is further described in the following examples, which do not limit the scope of the invention described in the claims.

Example 1. Synthesis of Compound 100

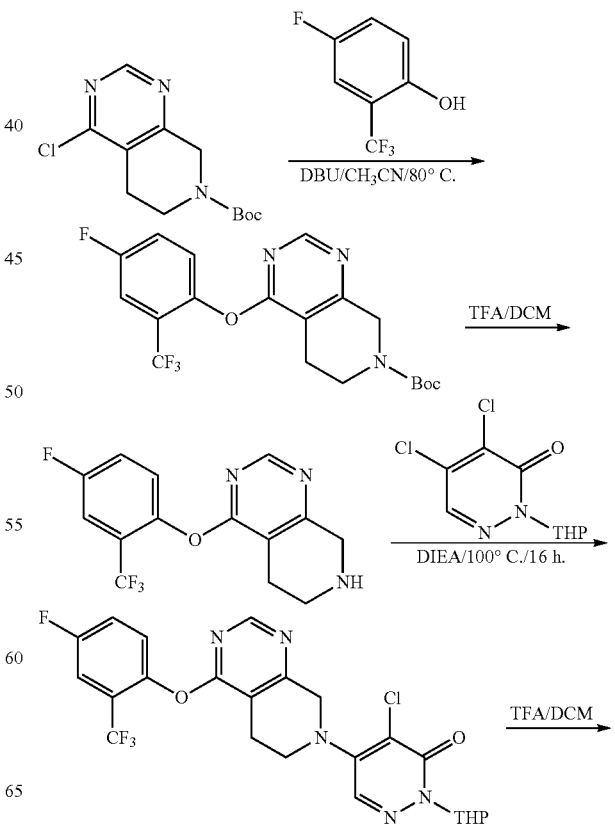

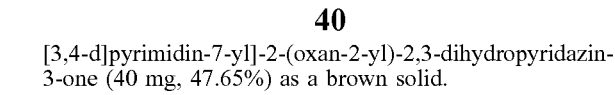

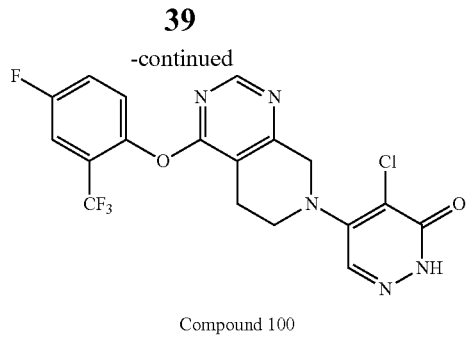

Compound 100 tert-butyl 4-[4-fluoro-2-(trifluoromethyl)phenoxy]-5H,6H,7H,8H-pyrido[3,4-d]pyrimidine-7-carboxylate To a stirred solution of tert-butyl 4-chloro-5H,6H,7H,8H-pyrido[3,4-d]pyrimidine-7-carboxylate (400 mg, 1.48 mmol, 1 equiv.) and 4-fluoro-2-(trifluoromethyl)phenol (400.6 mg, 2.22 mmol, 1.5 equiv.) in acetonitrile (10 mL) was added DBU (451.5 mg, 2.97 mmol, 2.00 equiv.) at room temperature. The resulting mixture was stirred for 2 h at 80° C. The reaction was monitored by LCMS. The mixture was allowed to cool down to room temperature. The resulting mixture was concentrated under reduced pressure. The resulting mixture was extracted with DCM (3×100 mL). The combined organic layers were washed with brine (3×100 mL), dried over anhydrous $Na_2SO_4$. After filtration, the filtrate was concentrated under reduced pressure. The residue was purified by Prep-TLC (PE/EtOAc 2:1) to afford tert-butyl 4-[4-fluoro-2-(trifluoromethyl)phenoxy]-5H,6H,7H,8H-pyrido[3,4-d]pyrimidine-7-carboxylate (110 mg, 17.94%) as a brown solid.

4-[4-fluoro-2-(trifluoromethyl)phenoxy]-5H,6H,7H,8H-pyrido[3,4-d]pyrimidine

To a stirred solution of tert-butyl 4-[4-fluoro-2-(trifluoromethyl)phenoxy]-5H,6H,7H,8H-pyrido[3,4-d]pyrimidine-7-carboxylate (110 mg, 0.27 mmol, 1 equiv.) in DCM (4 mL) was added TFA (1 mL, 13.46 mmol, 50.59 equiv.) at room temperature. The resulting mixture was stirred for 1 h at room temperature. The reaction was monitored by LCMS. The resulting mixture was concentrated under reduced pressure. The mixture was basified to pH 8 with saturated $NaHCO_3$ (aq.). The resulting mixture was concentrated under reduced pressure. The residue was purified by Prep-TLC (DCM/MeOH 12:1) to afford 4-[4-fluoro-2-(trifluoromethyl)phenoxy]-5H,6H,7H,8H-pyrido[3,4-d]pyrimidine (50 mg, 59.98%) as a brown solid.

4-chloro-5-[4-[4-fluoro-2-(trifluoromethyl)phenoxy]-5H,6H,7H,8H-pyrido[3,4-d]pyrimidin-7-yl]-2-(oxan-2-yl)-2,3-dihydropyridazin-3-one To a stirred solution of 4-[4-fluoro-2-(trifluoromethyl)phenoxy]-5H,6H,7H,8H-pyrido[3,4-d]pyrimidine (50 mg, 0.16 mmol, 1 equiv.) in DIEA (2 mL) was added 4,5-dichloro-2-(oxan-2-yl)-2,3-dihydropyridazin-3-one (47.5 mg, 0.19 mmol, 1.19 equiv.) at room temperature. The resulting mixture was stirred for 2 h at 100° C. The reaction was monitored by LCMS. The mixture was allowed to cool down to room temperature. The residue was purified by Prep-TLC (PE/EtOAc 2:1) to afford 4-chloro-5-[4-[4-fluoro-2-(trifluoromethyl)phenoxy]-5H,6H,7H,8H-pyrido[3,4-d]pyrimidin-7-yl]-2-(oxan-2-yl)-2,3-dihydropyridazin-3-one (40 mg, 47.65%) as a brown solid.

4-chloro-5-[4-[4-fluoro-2-(trifluoromethyl)phenoxy]-5H,6H,7H,8H-pyrido[3,4-d]pyrimidin-7-yl]-2,3-dihydropyridazin-3-one To a stirred solution of 4-chloro-5-[4-[4-fluoro-2-(trifluoromethyl)phenoxy]-5H,6H,7H,8H-pyrido[3,4-d]pyrimidin-7-yl]-2-(oxan-2-yl)-2,3-dihydropyridazin-3-one (40 mg, 0.08 mmol, 1 equiv.) in DCM (4 mL) was added TFA (1 mL, 13.46 mmol, 177.00 equiv.) dropwise at room temperature. The resulting mixture was stirred for 1 h at room temperature. The reaction was monitored by LCMS. The resulting mixture was concentrated under reduced pressure. The mixture was basified to pH 8 with saturated $NaHCO_3$ (aq.). The resulting mixture was concentrated under reduced pressure. The crude product (40 mg) was purified by Prep-HPLC with the following conditions (Column: XBridge Prep OBD C18 Column 30×150 mm 5 um; Mobile Phase A: Water (10 MMOL/L NH4HCO3), Mobile Phase B: acetonitrile; Flow rate: 60 mL/min; Gradient: 18% B to 47% B in 7 min; 220 nm; Rt: 6.22 min) to afford 4-chloro-5-[4-[4-fluoro-2-(trifluoromethyl)phenoxy]-5H,6H,7H,8H-pyrido[3,4-d]pyrimidin-7-yl]-2,3-dihydropyridazin-3-one (8.6 mg, 25.59%) as a white solid.

Example 2. Synthesis of Compound 140

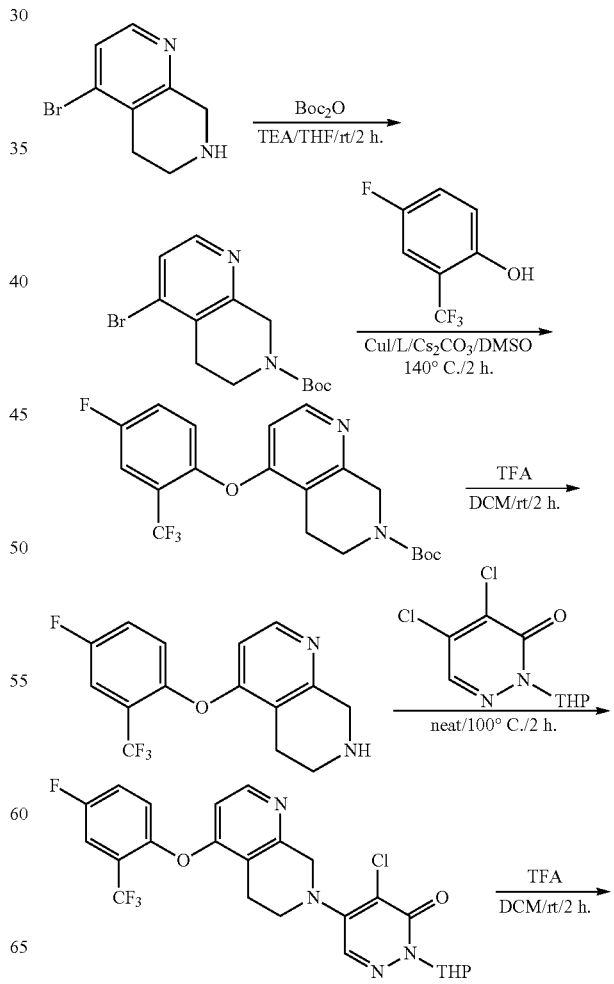

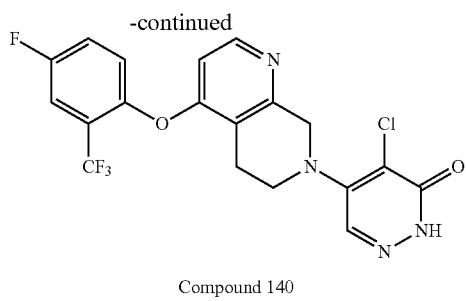

Compound 140

Tert-butyl 4-bromo-5,6,7,8-tetrahydro-1,7-naphthyridine-7-carboxylate

To a solution of 4-bromo-5,6,7,8-tetrahydro-1,7-naphthyridine (250 mg, 1.173 mmol, 1 equiv.) in THF (10 mL, 123.430 mmol, 105.20 equiv.) were added Boc$_2$O (512.13 mg, 2.347 mmol, 2.00 equiv.) and TEA (474.90 mg, 4.693 mmol, 4 equiv.) at 25° C. The solution was stirred at 25° C. for 2 hours. The resulting mixture was concentrated under reduced pressure. The residue was purified by Prep-TLC (PE/EA 5/1) to afford tert-butyl 4-bromo-5,6,7,8-tetrahydro-1,7-naphthyridine-7-carboxylate (210 mg, 57.15%) as a light yellow oil.

Tert-butyl 4-[4-fluoro-2-(trifluoromethyl)phenoxy]-5,6,7,8-tetrahydro-1,7-naphthyridine-7-carboxylate To a solution of tert-butyl 4-bromo-5,6,7,8-tetrahydro-1,7-naphthyridine-7-carboxylate (210 mg, 0.671 mmol, 1 equiv.) and 4-fluoro-2-(trifluoromethyl)phenol (241.52 mg, 1.341 mmol, 2 equiv.) in DMSO (10 mL) were added Cs$_2$CO$_3$ (873.86 mg, 2.682 mmol, 4 equiv), 2-(dimethylamino)acetic acid (41.46 mg, 0.402 mmol, 0.6 equiv.) and CuI (76.62 mg, 0.402 mmol, 0.60 equiv). After stirring for 4 hours at 120° C. under a nitrogen atmosphere, the resulting mixture was concentrated under reduced pressure. The residue was purified by Prep-TLC, eluted with PE/EA (5/1) to afford tert-butyl 4-[4-fluoro-2-(trifluoromethyl)phenoxy]-5,6,7,8-tetrahydro-1,7-naphthyridine-7-carboxylate (100 mg, 36.17%) as a light yellow solid.

4-[4-fluoro-2-(trifluoromethyl)phenoxy]-5,6,7,8-tetrahydro-1,7-naphthyridine To a solution of tert-butyl 4-[4-fluoro-2-(trifluoromethyl)phenoxy]-5,6,7,8-tetrahydro-1,7-naphthyridine-7-carboxylate (150 mg, 0.364 mmol, 1 equiv.) in DCM (10 mL, 157.300 mmol, 432.46 equiv.) was added TFA (414.75 mg, 3.637 mmol, 10 equiv.) at 25° C. The solution was stirred at 25° C. for 2 hours. The resulting mixture was concentrated under reduced pressure. The residue was used the next step.

4-chloro-5-[4-[4-fluoro-2-(trifluoromethyl)phenoxy]-5,6,7,8-tetrahydro-1,7-naphthyridin-7-yl]-2-(oxan-2-yl)-2,3-dihydropyridazin-3-one A mixture of 4-[4-fluoro-2-(trifluoromethyl)phenoxy]-5,6,7,8-tetrahydro-1,7-naphthyridine (60 mg, 0.192 mmol, 1 equiv.) and 4,5-dichloro-2-(oxan-2-yl)-2,3-dihydropyridazin-3-one (47.86 mg, 0.192 mmol, 1.00 equiv.) in DIEA (49.67 mg, 0.384 mmol, 2 equiv.) was stirred for 2 hours at 100° C. under N$_2$ atmosphere. The residue was purified by Prep-TLC (PE/EA 1/1) to afford 4-chloro-5-[4-[4-fluoro-2-(trifluoromethyl)phenoxy]-5,6,7,8-tetrahydro-1,7-naphthyridin-7-yl]-2-(oxan-2-yl)-2,3-dihydropyridazin-3-one (100 mg, 99.15%) as a light yellow solid.

4-chloro-5-[4-[4-fluoro-2-(trifluoromethyl)phenoxy]-5,6,7,8-tetrahydro-1,7-naphthyridin-7-yl]-2,3-dihydropyridazin-3-one To a solution of 4-chloro-5-[4-[4-fluoro-2-(trifluoromethyl)phenoxy]-5,6,7,8-tetrahydro-1,7-naphthyridin-7-yl]-2-(oxan-2-yl)-2,3-dihydropyridazin-3-one (100 mg, 0.191 mmol, 1 equiv.) in DCM (10 mL, 157.300 mmol, 825.67 equiv.) was added TFA (217.23 mg, 1.905 mmol, 10.00 equiv.) at 25° C. The solution was stirred at 25° C. for 2 hours. The crude product (150 mg) was purified by Prep-HPLC with the following conditions (Column: XBridge Shield RP18 OBD Column 30*150 mm, 5 um; Mobile Phase A: Water (10 mM NH$_4$HCO$_3$), Mobile Phase B: acetonitrile; Flow rate: 60 mL/min; Gradient: 20% B to 40% B in 7 min; 220 nm; Rt: 6.63 min) to afford 4-chloro-5-[4-[4-fluoro-2-(trifluoromethyl)phenoxy]-5,6,7,8-tetrahydro-1,7-naphthyridin-7-yl]-2,3-dihydropyridazin-3-one (42.9 mg, 51.09%) as a white solid.

Example 3. Synthesis of Compound 120

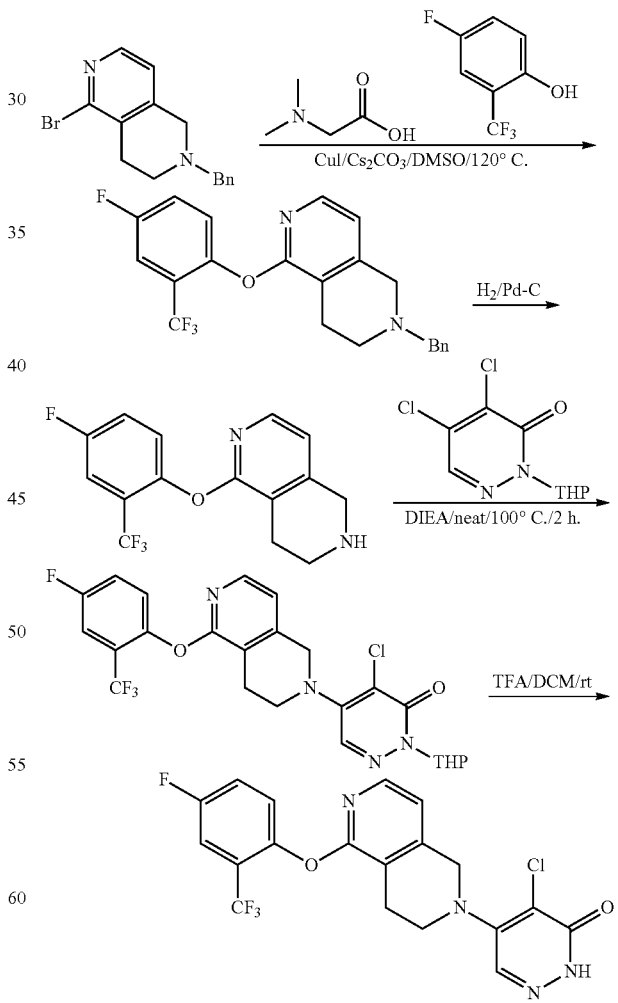

Compound 120

2-Benzyl-5-[4-fluoro-2-(trifluoromethyl)phenoxy]-1,2,3,4-tetrahydro-2,6-naphthyridine To a stirred mixture of 2-benzyl-5-bromo-1,2,3,4-tetrahydro-2,6-naphthyridine (250 mg, 0.825 mmol, 1 equiv.) and 2-(dimethylamino)acetic acid (170.05 mg, 1.649 mmol, 2.00 equiv.) in DMSO (5 mL) were added 4-fluoro-2-(trifluoromethyl)phenol (89.10 mg, 0.495 mmol, 0.6 equiv.) and CuI (94.22 mg, 0.495 mmol, 0.6 equiv.) at room temperature. Then $Cs_2CO_3$ (1074.59 mg, 3.298 mmol, 4 equiv.) was added at room temperature. The final reaction mixture was irradiated with microwave radiation for 1 hours at 120° C. The reaction was monitored by LCMS. The mixture was allowed to cool down to room temperature. The crude product was purified by reverse phase flash with the following conditions (Column: XBridge Prep OBD C18 Column 30×150 mm 5 um; Mobile Phase A: Water (10 mM $NH_4HCO_3$), Mobile Phase B: acetonitrile; Flow rate: 60 mL/min; Gradient: 18% B to 35% B in 8 min; 220 nm; Rt: 7.12 min) to afford 2-benzyl-5-[4-fluoro-2-(trifluoromethyl)phenoxy]-1,2,3,4-tetrahydro-2,6-naphthyridine (180 mg, 54.25%) as a brown solid.

5-[4-fluoro-2-(trifluoromethyl)phenoxy]-1,2,3,4-tetrahydro-2,6-naphthyridine To a stirred solution of 2-benzyl-5-[4-fluoro-2-(trifluoromethyl)phenoxy]-1,2,3,4-tetrahydro-2,6-naphthyridine (180 mg) in MeOH (10 mL) was added Pd/C (20 mg) at room temperature under nitrogen atmosphere. The resulting mixture was stirred for 5 hours at room temperature under hydrogen atmosphere. The reaction was monitored by LCMS. The resulting mixture was concentrated under reduced pressure. The residue was purified by Prep-TLC (DCM/MeOH 12:1) to afford 5-[4-fluoro-2-(trifluoromethyl)phenoxy]-1,2,3,4-tetrahydro-2,6-naphthyridine (100 mg) as a brown solid.

4-chloro-5-[5-[4-fluoro-2-(trifluoromethyl)phenoxy]-1,2,3,4-tetrahydro-2,6-naphthyridin-2-yl]-2-(oxan-2-yl)-2,3-dihydropyridazin-3-one To a stirred solution of 5-[4-fluoro-2-(trifluoromethyl)phenoxy]-1,2,3,4-tetrahydro-2,6-naphthyridine (100 mg, 0.320 mmol, 1 equiv.) in DIEA (0.1 mL) was added 4,5-dichloro-2-(oxan-2-yl)-2,3-dihydropyridazin-3-one (63.81 mg, 0.256 mmol, 0.8 equiv.) at room temperature. The resulting mixture was stirred for 1 hours at 90° C. The reaction was monitored by LCMS. The mixture was allowed to cool down to room temperature. The residue was purified by Prep-TLC (DCM/MeOH; 12:1) to afford 4-chloro-5-[5-[4-fluoro-2-(trifluoromethyl)phenoxy]-1,2,3,4-tetrahydro-2,6-naphthyridin-2-yl]-2-(oxan-2-yl)-2,3-dihydropyridazin-3-one (130 mg, 77.34%) as a white solid.

4-chloro-5-[5-[4-fluoro-2-(trifluoromethyl)phenoxy]-1,2,3,4-tetrahydro-2,6-naphthyridin-2-yl]-2,3-dihydropyridazin-3-one To a stirred solution of 4-chloro-5-[5-[4-fluoro-2-(trifluoromethyl)phenoxy]-1,2,3,4-tetrahydro-2,6-naphthyridin-2-yl]-2-(oxan-2-yl)-2,3-dihydropyridazin-3-one (107 mg, 0.204 mmol, 1 equiv.) in DCM (4 mL) was added TFA (1 mL) at room temperature. The resulting mixture was stirred for 1 hours at room temperature. The reaction was monitored by LCMS. The mixture was basified to pH 7 with saturated $NaHCO_3$ (aq.). The resulting mixture was concentrated under reduced pressure. The crude product (50 mg) was purified by Prep-HPLC with the following conditions (Column: XBridge Prep OBD C18 Column 30×150 mm 5 um; Mobile Phase A: Water (10 mM $NH_4HCO_3$), Mobile Phase B: acetonitrile; Flow rate: 60 mL/min; Gradient: 30% B to 50% B in 8 min; 220 nm; Rt: 7.55 min) to afford 4-chloro-5-[5-[4-fluoro-2-(trifluoromethyl)phenoxy]-1,2,3,4-tetrahydro-2,6-naphthyridin-2-yl]-2,3-dihydropyridazin-3-one (60 mg, 66.78%) as a white solid.

Example 4. Synthesis of Compound 118

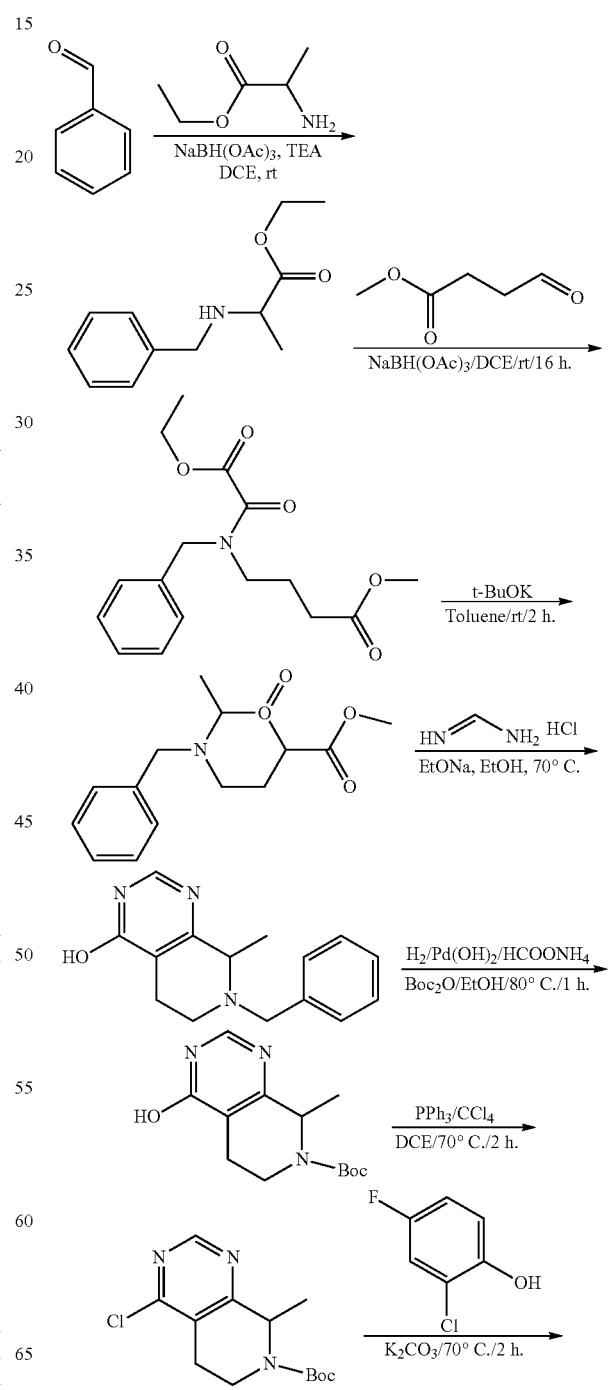

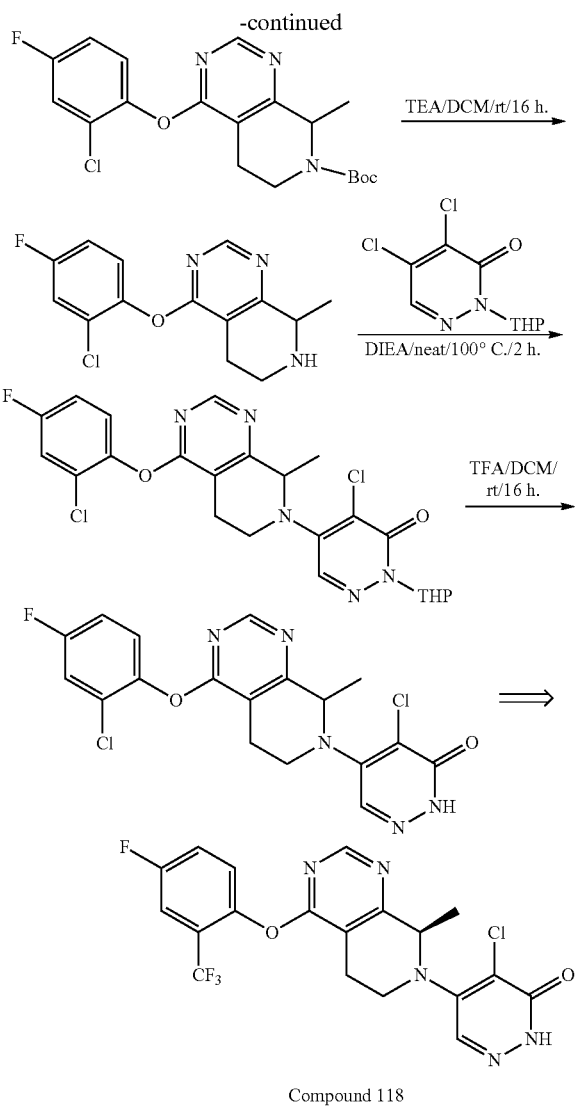

Compound 118

Ethyl 2-(benzylamino)propanoate

To a stirred solution of benzaldehyde (8 g, 75.384 mmol, 1 equiv.) and TEA (7.63 g, 75.384 mmol, 1 equiv.) in DCE (100 mL, 1263.149 mmol, 16.76 equiv.) was added TEA (7.63 g, 75.384 mmol, 1 equiv.) and NaBH(OAc)$_3$ (31.95 g, 150.767 mmol, 2 equiv.) in portions at room temperature under nitrogen atmosphere. The mixture was stirred at rt overnight. Desired product could be detected by LCMS. The resulting mixture was extracted with DCM (2×150 mL). The combined organic layers were washed with brine (1×90 mL), dried over anhydrous Na$_2$SO$_4$. After filtration, the filtrate was concentrated under reduced pressure to afford ethyl 2-(benzylamino)propanoate (12 g, 76.80%) as colorless oil.

Methyl 4-[benzyl(1-ethoxy-1-oxopropan-2-yl)amino]butanoate

To a stirred solution of ethyl 2-(benzylamino)propanoate (8 g, 38.596 mmol, 1 equiv.) and methyl 4-oxobutanoate (4.48 g, 38.596 mmol, 1.00 equiv.) in DCE (120 mL, 1515.779 mmol, 39.27 equiv.) was added TEA (3.91 g, 38.596 mmol, 1 equiv.) and NaBH(OAc)$_3$ (16.36 g, 77.193 mmol, 2 equiv.) in portions at room temperature under nitrogen atmosphere. The mixture was stirred at rt overnight. Desired product could be detected by LCMS. The resulting mixture was extracted with DCM (2×150 mL). The combined organic layers were washed with brine (1×90 mL), dried over anhydrous Na$_2$SO$_4$. After filtration, the filtrate was concentrated under reduced pressure to afford methyl 4-[benzyl(1-ethoxy-1-oxopropan-2-yl)amino]butanoate (10 g, 84.29%) as colorless oil.

Methyl 1-benzyl-2-methyl-3-oxopiperidine-4-carboxylate

To a stirred solution of methyl 4-[benzyl(1-ethoxy-1-oxopropan-2-yl)amino]butanoate (8 g, 26.026 mmol, 1 equiv.) in Toluene (100 mL) was added t-BuOK (5.00 g, 52.051 mmol, 2 equiv.) in portions at room temperature under nitrogen atmosphere. The mixture was stirred at 80° C. for 2 hours. Desired product was detected by LCMS. The resulting mixture was concentrated under vacuum. The residue was purified by silica gel column chromatography, eluted with PE/EtOAc (5:1 to 2:1) to afford methyl 1-benzyl-2-methyl-3-oxopiperidine-4-carboxylate (6.5 g, 95.57%) as a white solid.

7-Benzyl-8-methyl-5H,6H,7H,8H-pyrido[3,4-d]pyrimidin-4-ol

To a stirred solution of methyl 1-benzyl-2-methyl-3-oxopiperidine-4-carboxylate (6 g, 22.960 mmol, 1 equiv.) in EtOH (80 mL, 1377.083 mmol, 59.98 equiv.) was added t-BuONa (4.41 g, 45.921 mmol, 2 equiv.) and methanimidamide hydrochloride (3.70 g, 45.921 mmol, 2.00 equiv.) in portions at room temperature under nitrogen atmosphere. The mixture was stirred at 80° C. for 2 h. Desired product could be detected by LCMS. The resulting mixture was concentrated under vacuum. The residue was purified by silica gel column chromatography, eluted with PE/EtOAc (3:1 to 2:1) to afford 7-benzyl-8-methyl-5H,6H,7H,8H-pyrido[3,4-d]pyrimidin-4-ol (5 g, 85.29%) as a white solid.

Tert-Butyl 4-hydroxy-8-methyl-5H,6H,7H,8H-pyrido[3,4-d]pyrimidine-7-carboxylate To a solution of 7-benzyl-8-methyl-5H,6H,7H,8H-pyrido[3,4-d]pyrimidin-4-ol (5 g, 19.583 mmol, 1 equiv.) in EtOH (60 mL, 1032.812 mmol, 52.74 equiv.) was added Boc$_2$O (8.55 g, 39.166 mmol, 2 equiv), CH$_3$COONa (1.81 g, 23.500 mmol, 1.2 equiv), Pd(OH)$_2$/C (275.01 mg, 1.958 mmol, 0.1 equiv.) under nitrogen atmosphere. The mixture was hydrogenated at room temperature for 2 h under hydrogen atmosphere, filtered through a Celite pad and concentrated under reduced pressure to afford tert-butyl 4-hydroxy-8-methyl-5H,6H,7H,8H-pyrido[3,4-d]pyrimidine-7-carboxylate (4.5 g, 86.61%) as white solid.

Tert-butyl 4-chloro-8-methyl-5H,6H,7H,8H-pyrido[3,4-d]pyrimidine-7-carboxylate

To a stirred solution of tert-butyl 4-hydroxy-8-methyl-5H,6H,7H,8H-pyrido[3,4-d]pyrimidine-7-carboxylate (4.5 g, 16.961 mmol, 1 equiv.) and PPh$_3$ (6.67 g, 25.442 mmol, 1.5 equiv.) in DCE (60 mL, 0.606 mmol, 0.04 equiv.) was added CCl$_4$ (5.22 g, 33.922 mmol, 2 equiv.) in portions at room temperature under nitrogen atmosphere. The mixture was stirred at 70° C. for 2 hours. Desired product could be detected by LCMS. The resulting mixture was concentrated under vacuum. The residue was purified by silica gel column chromatography, eluted with PE/EtOAc (7:1) to afford tert-butyl 4-chloro-8-methyl-5H,6H,7H,8H-pyrido[3,4-d]pyrimidine-7-carboxylate (4 g, 83.11%) as a white solid.

Tert-butyl 4-(2-chloro-4-fluorophenoxy)-8-methyl-5H,6H,7H,8H-pyrido[3,4-d]pyrimidine-7-carboxylate To a stirred solution of tert-butyl 4-chloro-8-methyl-5H,6H,7H,8H-pyrido[3,4-d]pyrimidine-7-carboxylate (4 g, 14.096 mmol, 1 equiv.) and 2-chloro-4-fluorophenol (2.07 g, 14.096 mmol, 1 equiv.) in DMF (50 mL) was added K₂CO₃ (3.90 g, 28.193 mmol, 2 equiv.) in portions at room temperature under nitrogen atmosphere. The mixture was stirred at 70 for 1 h. Desired product could be detected by LCMS. The resulting mixture was concentrated under vacuum. The residue was purified by silica gel column chromatography, eluted with PE/EtOAc (1:1) to afford tert-butyl 4-(2-chloro-4-fluorophenoxy)-8-methyl-5H,6H,7H,8H-pyrido[3,4-d]pyrimidine-7-carboxylate (4 g, 72.05%) as a white solid.

4-(2-Chloro-4-fluorophenoxy)-8-methyl-5H,6H,7H,8H-pyrido[3,4-d]pyrimidine

To a stirred solution of tert-butyl 4-(2-chloro-4-fluorophenoxy)-8-methyl-5H,6H,7H,8H-pyrido[3,4-d]pyrimidine-7-carboxylate (4 g, 1 equiv.) in DCM (20 mL) was added TFA (4 mL) dropwise/in portions at room temperature under nitrogen atmosphere. The mixture was stirred at rt for 2 h. Desired product could be detected by LCMS. The resulting mixture was concentrated under reduced pressure to afford 4-(2-chloro-4-fluorophenoxy)-8-methyl-5H,6H,7H,8H-pyrido[3,4-d]pyrimidine (2.7 g, 90.51%) as off-white solid.

4-chloro-5-[4-(2-chloro-4-fluorophenoxy)-8-methyl-5H,6H,7H,8H-pyrido[3,4-d]pyrimidin-7-yl]-2-(oxan-2-yl)-2,3-dihydropyridazin-3-one To a stirred solution of 4-(2-chloro-4-fluorophenoxy)-8-methyl-5H,6H,7H,8H-pyrido[3,4-d]pyrimidine (1 g, 3.404 mmol, 1 equiv.) in DIEA (1 mL) was added 4,5-dichloro-2-(oxan-2-yl)-2,3-dihydropyridazin-3-one (0.85 g, 3.404 mmol, 1 equiv.) in portions at room temperature under nitrogen atmosphere. The mixture was stirred at 100° C. overnight. The desired product could be detected by LCMS. The residue was purified by silica gel column chromatography, eluted with PE/EtOAc (1:1 to 1:2) to afford 4-chloro-5-[4-(2-chloro-4-fluorophenoxy)-8-methyl-5H,6H,7H,8H-pyrido[3,4-d]pyrimidin-7-yl]-2-(oxan-2-yl)-2,3-dihydropyridazin-3-one (1 g, 58.01%) as a white solid.

4-chloro-5-[4-(2-chloro-4-fluorophenoxy)-8-methyl-5H,6H,7H,8H-pyrido[3,4-d]pyrimidin-7-yl]-2,3-dihydropyridazin-3-one To a stirred solution of 4-chloro-5-[4-(2-chloro-4-fluorophenoxy)-8-methyl-5H,6H,7H,8H-pyrido[3,4-d]pyrimidin-7-yl]-2-(oxan-2-yl)-2,3-dihydropyridazin-3-one (1 g, 1 equiv.) in DCM (10 mL) was added TFA (2 mL) dropwise at room temperature under nitrogen atmosphere. The mixture was stirred at rt for 1 h. Desired product could be detected by LCMS. The resulting mixture was concentrated under reduced pressure to afford 4-chloro-5-[4-(2-chloro-4-fluorophenoxy)-8-methyl-5H,6H,7H,8H-pyrido[3,4-d]pyrimidin-7-yl]-2,3-dihydropyridazin-3-one (600 mg, 71.95%) as white solid.

4-chloro-5-[(8R)-4-(2-chloro-4-fluorophenoxy)-8-methyl-5H,6H,7H,8H-pyrido[3,4-d]pyrimidin-7-yl]-2,3-dihydropyridazin-3-one 4-chloro-5-[4-(2-chloro-4-fluorophenoxy)-8-methyl-5H,6H,7H,8H-pyrido[3,4-d]pyrimidin-7-yl]-2,3-dihydropyridazin-3-one (250 mg, 1 equiv.) was separated by prep chiral-HPLC (Column: CHIRALPAK IG, 20*250 mm, 5 um; Mobile Phase A: Hex:DCM=3:1 (0.1% FA)-HPLC, Mobile Phase B: EtOH-HPLC; Flow rate: 20 mL/min; Gradient: 15 B to 15 B in 19 min; 220/254 nm; RT1:13.016; RT2:16.004) to afford 4-chloro-5-[(8R)-4-(2-chloro-4-fluorophenoxy)-8-methyl-5H,6H,7H,8H-pyrido[3,4-d]pyrimidin-7-yl]-2,3-dihydropyridazin-3-one (144 mg, 57.60%) as white solid.

Example 5. Synthesis of Compound 103

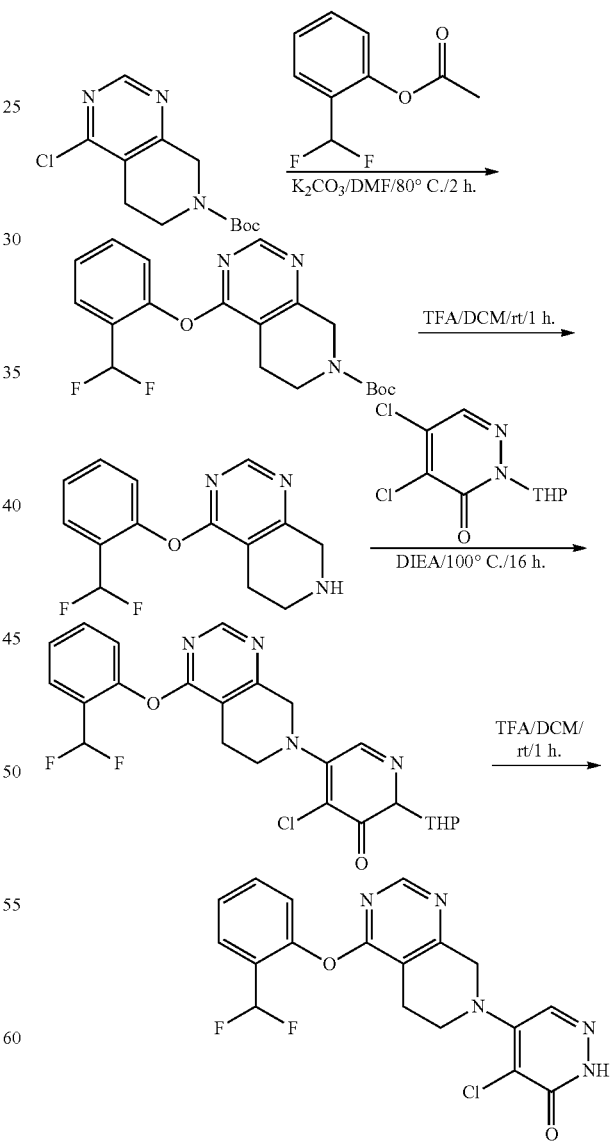

Compound 103

Tert-Butyl 4-[2-(difluoromethyl)phenoxy]-5H,6H,7H,8H-pyrido[3,4-d]pyrimidine-7-carboxylate To a stirred solution of tert-butyl 4-chloro-5H,6H,7H,8H-pyrido[3,4-d]pyrimidine-7-carboxylate (800 mg, 2.966 mmol, 1 equiv.) and 2-(difluoromethyl)phenyl acetate (1104.26 mg, 5.932 mmol, 2.00 equiv.) in DMF (20 mL) were added $K_2CO_3$ (1229.72 mg, 8.898 mmol, 3 equiv.) in portions at 80° C. under nitrogen atmosphere. The mixture was stirred for 2 hours. The reaction was monitored by LCMS. The reaction was quenched with Water at room temperature. The mixture was extracted with EtOAc (3×50 mL). The combined organic layers were washed with brine (3×100 mL), dried over anhydrous $Na_2SO_4$. After filtration, the filtrate was concentrated under reduced pressure. The residue was purified by reverse flash chromatography with the following conditions: column, C18 silica gel; mobile phase, MeOH in water, 10% to 50% gradient in 10 min; detector, UV 254 nm. to afford tert-butyl 4-[2-(difluoromethyl)phenoxy]-5H,6H,7H,8H-pyrido[3,4-d]pyrimidine-7-carboxylate (900 mg, 80.41%) as off-white solid.

4-[2-(Difluoromethyl)phenoxy]-5H,6H,7H,8H-pyrido[3,4-d]pyrimidine

To a stirred solution of tert-butyl 4-[2-(difluoromethyl)phenoxy]-5H,6H,7H,8H-pyrido[3,4-d]pyrimidine-7-carboxylate (900 mg, 2.385 mmol, 1 equiv.) in DCM was added 3,3,3-trifluoropropanoic acid (3 mL, 6.00 equiv.) dropwise at room temperature. The mixture was stirred for 1.5 hours. The reaction was monitored by TLC (PE/EtOAc 10:1). The residue was basified to pH 8 with saturated NaHCO3 (aq.). The mixture was concentrated under reduced pressure. The crude product (100 mg) was purified by Prep-HPLC with the following conditions to afford 4-[2-(difluoromethyl)phenoxy]-5H,6H,7H,8H-pyrido[3,4-d]pyrimidine (329 mg, 49.75%) as off-white solid.

4-Chloro-5-[4-[2-(difluoromethyl)phenoxy]-5H,6H,7H,8H-pyrido[3,4-d]pyrimidin-7-yl]-2-(oxan-2-yl)-2,3-dihydropyridazin-3-one To a stirred solution of 4-[2-(difluoromethyl)phenoxy]-5H,6H,7H,8H-pyrido[3,4-d]pyrimidine (328 mg, 1.183 mmol, 1 equiv.) and 4,5-dichloro-2-(oxan-2-yl)-2,3-dihydropyridazin-3-one (169.05 mg, 0.679 mmol, 1.00 equiv.) were added DIEA (175.43 mg, 1.357 mmol, 2.00 equiv.) in portions at 70° C. The mixture was stirred for 2 hours at 70° C. The residue was purified by reverse flash chromatography with the following conditions: column, C18 silica gel; mobile phase, MeOH in water, 10% to 50% gradient in 10 min; detector, UV 254 nm. to afford 4-chloro-5-[4-[2-(difluoromethyl)phenoxy]-5H,6H,7H,8H-pyrido[3,4-d]pyrimidin-7-yl]-2-(oxan-2-yl)-2,3-dihydropyridazin-3-one (328 mg, 56.60%) as off-white solid.

4-Chloro-5-[4-[2-(difluoromethyl)phenoxy]-5H,6H,7H,8H-pyrido[3,4-d]pyrimidin-7-yl]-2,3-dihydropyridazin-3-one To a stirred solution of 4-chloro-5-[4-[2-(difluoromethyl)phenoxy]-5H,6H,7H,8H-pyrido[3,4-d]pyrimidin-7-yl]-2-(oxan-2-yl)-2,3-dihydropyridazin-3-one (328 mg, 0.670 mmol, 1 equiv.) in DCM (10 mL) was added trifluoroacetic acid (3 mL) dropwise at room temperature. The mixture was concentrated under vacuum. The product was purified by Prep-HPLC to afford 4-chloro-5-[4-[2-(difluoromethyl)phenoxy]-5H,6H,7H,8H-pyrido[3,4-d]pyrimidin-7-yl]-2,3-dihydropyridazin-3-one (256.4 mg, 94.38%) as off-white solid.

Example 6. Synthesis of Compound 117 and 117a

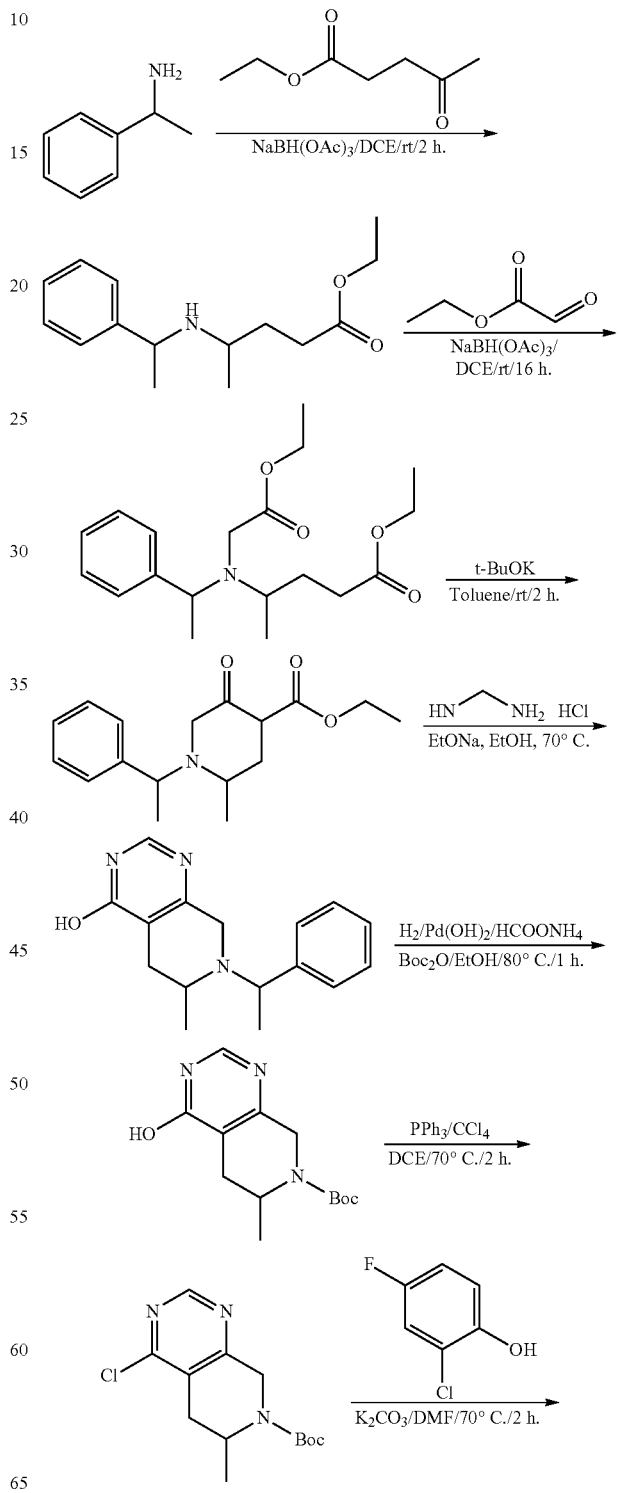

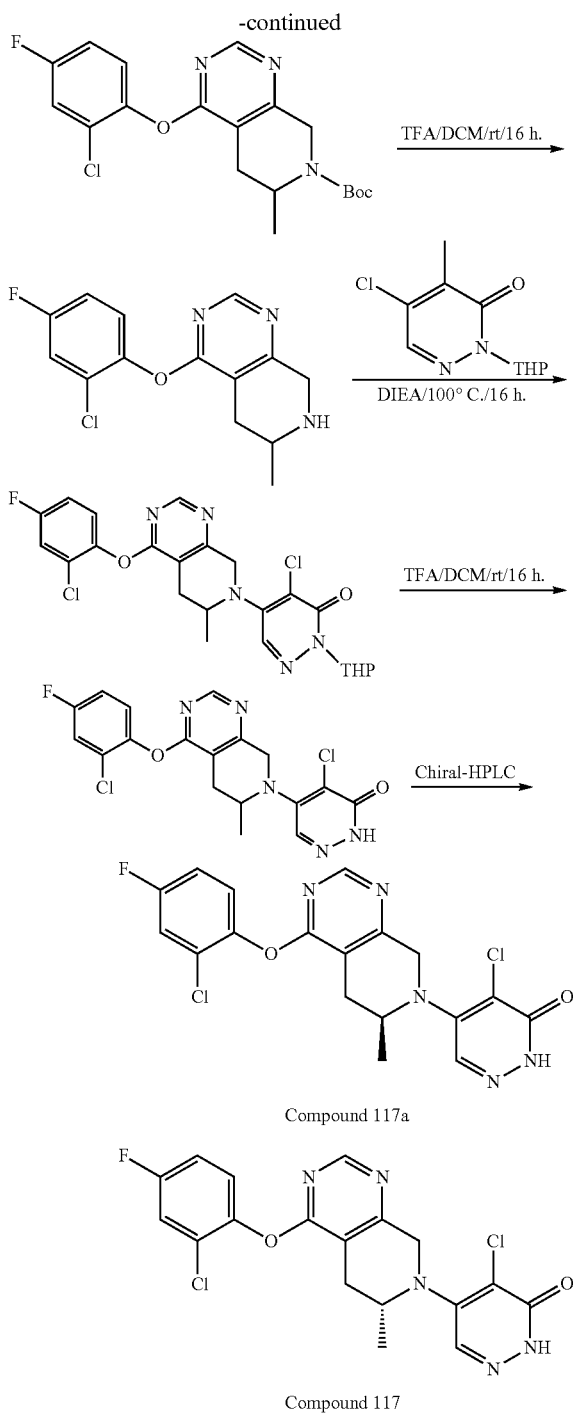

Compound 117a

Compound 117

Ethyl 4-[(1-phenylethyl)amino]pentanoate

To a stirred solution of 1-phenylethan-1-amine (25 g, 206.300 mmol, 1 equiv.) and ethyl 4-oxopentanoate (29.74 g, 206.300 mmol, 1 equiv.) in DCE (400 mL, 5052.598 mmol, 24.49 equiv.) was added NaBH(OAc)$_3$ (65.59 g, 309.449 mmol, 1.5 equiv.) in portions at 25° C. under nitrogen atmosphere. The solution was stirred at 25° C. for 2 hours. The reaction was quenched by the addition of H$_2$O (400 mL) at 0° C. The resulting mixture was extracted with DCM (3×200 mL). The combined organic layers were washed with saturated NaCl (aq.) (3×200 mL), dried over anhydrous Na$_2$SO$_4$. After filtration, the filtrate was concentrated under reduced pressure. The crude product was used to the next step.

Ethyl 4-[(2-ethoxy-2-oxoethyl)(1-phenylethyl)amino]pentanoate

To a stirred solution of ethyl 4-[(1-phenylethyl)amino]pentanoate (49 g, 196.508 mmol, 1 equiv.) and ethyl 2-oxoacetate (40.12 g, 392.990 mmol, 2.00 equiv.) in DCE (500 mL, 6315.747 mmol, 32.14 equiv.) was added NaBH(OAc)$_3$ (62.47 g, 294.762 mmol, 1.5 equiv.) in portions at 25° C. under nitrogen atmosphere. The solution was stirred at 25° C. for 2 hours. The reaction was quenched by the addition of H$_2$O (400 mL) at 0° C. The resulting mixture was extracted with DCM (3×200 mL). The combined organic layers were washed with saturated NaCl (aq.) (3×200 mL), dried over anhydrous Na$_2$SO$_4$. After filtration, the filtrate was concentrated under reduced pressure. The crude product ethyl 4-[(2-ethoxy-2-oxoethyl)(1-phenylethyl)amino]pentanoate (57 g, 86.47%) was used to the next step.

Ethyl 2-methyl-5-oxo-1-(1-phenylethyl)piperidine-4-carboxylate

To a solution of ethyl 4-[(2-ethoxy-2-oxoethyl)(1-phenylethyl)amino]pentanoate (57 g, 169.924 mmol, 1 equiv.) in Toluene (500 mL, 4699.452 mmol, 27.66 equiv.) was added t-BuOK (47.67 g, 424.810 mmol, 2.5 equiv.) in ports at 0° C. The mixture was stirred at 25° C. for 2 hours. The resulting mixture was concentrated under reduced pressure. The residue was purified by silica gel column chromatography, eluted with PE/EA (50/1 to 10/1) to afford ethyl 2-methyl-5-oxo-1-(1-phenylethyl)piperidine-4-carboxylate (29 g, 58.98%) as a yellow oil

7-(1-cyclohexylethyl)-6-methyl-decahydropyrido[3,4-d]pyrimidin-4-ol

To a solution of ethyl 2-methyl-5-oxo-1-(1-phenylethyl)piperidine-4-carboxylate (10 g, 34.557 mmol, 1 equiv.) and methanimidamide hydrochloride (4.17 g, 51.836 mmol, 1.50 equiv.) in EtOH (100 mL, 1721.353 mmol, 49.81 equiv.) was added EtONa (5.88 g, 86.393 mmol, 2.50 equiv.) in ports at 25° C. The mixture was stirred at 90° C. for 2 hours. The residue was purified by silica gel column chromatography, eluted with DCM/MeOH (20/1 to 10/1) to afford 7-(1-cyclohexylethyl)-6-methyl-decahydropyrido[3,4-d]pyrimidin-4-ol (3.4 g, 34.96%) as a yellow solid.

Tert-Butyl 4-hydroxy-6-methyl-5H,6H,7H,8H-pyrido[3,4-d]pyrimidine-7-carboxylate To a solution of 6-methyl-7-(1-phenylethyl)-5H,6H,7H,8H-pyrido[3,4-d]pyrimidin-4-ol (3.5 g, 12.994 mmol, 1 equiv), HCOONH$_4$ (4.10 g, 65.022 mmol, 5.00 equiv.) and Boc$_2$O (8.51 g, 38.983 mmol, 3 equiv.) in EtOH (50 mL, 860.677 mmol, 66.23 equiv.) was added Pd(OH)$_2$/C (0.36 g, 2.599 mmol, 0.2 equiv.) under nitrogen atmosphere. The mixture was hydrogenated at 70° C. for 2 hours under hydrogen atmosphere using a hydrogen balloon, filtered through a Celite pad and concentrated under reduced pressure. To afford tert-butyl 4-hydroxy-6-methyl-5H,6H,7H,8H-pyrido[3,4-d]pyrimidine-7-carboxylate (1.8 g, 52.21%) as a yellow solid.

Tert-Butyl 4-chloro-6-methyl-5H,6H,7H,8H-pyrido[3,4-d]pyrimidine-7-carboxylate To a solution of tert-butyl 4-hydroxy-6-methyl-5H,6H,7H,8H-pyrido[3,4-d]pyrimidine-7-carboxylate (1.8 g, 6.784 mmol, 1 equiv.) and PPh$_3$ (3.56 g, 13.569 mmol, 2 equiv.) in DCE (20 mL, 252.630 mmol, 37.24 equiv.) was added CCl$_4$ (3.13 g, 20.353 mmol, 3 equiv.) at 25° C. The mixture was stirred at 70° C. for 3 hours. The resulting mixture was concentrated under reduced pressure. The residue was purified by silica gel column chromatography, eluted with PE/EA (10/1 to 1/1) to afford tert-butyl 4-chloro-6-methyl-5H,6H,7H,8H-pyrido[3,4-d]pyrimidine-7-carboxylate (1.1 g, 57.14%) as a yellow solid.

Tert-Butyl 4-(2-chloro-4-fluorophenoxy)-6-methyl-5H,6H,7H,8H-pyrido[3,4-d]pyrimidine-7-carboxylate To a solution of tert-butyl 4-chloro-6-methyl-5H,6H,7H,8H-pyrido[3,4-d]pyrimidine-7-carboxylate (1.1 g, 3.877 mmol, 1 equiv.) and 2-chloro-4-fluorophenol (0.85 g, 5.800 mmol, 1.50 equiv.) in DMF (15 mL, 193.826 mmol, 50.00 equiv.) was added K$_2$CO$_3$ (1.07 g, 7.753 mmol, 2 equiv.) at 25° C. The mixture was stirred at 70° C. for 1 hour. The resulting mixture was concentrated under reduced pressure. The residue was purified by silica gel column chromatography, eluted with PE/EA (10/1 to 5/1) to afford tert-butyl 4-(2-chloro-4-fluorophenoxy)-6-methyl-5H,6H,7H,8H-pyrido[3,4-d]pyrimidine-7-carboxylate (1.2 g, 78.60%) as a yellow solid.

4-Chloro-5-[4-(2-chloro-4-fluorophenoxy)-6-methyl-5H,6H,7H,8H-pyrido[3,4-d]pyrimidin-7-yl]-2-(oxan-2-yl)-2,3-dihydropyridazin-3-one A mixture of 4-(2-chloro-4-fluorophenoxy)-6-methyl-5H,6H,7H,8H-pyrido[3,4-d]pyrimidine (800 mg, 2.724 mmol, 1 equiv.) and 4,5-dichloro-2-(oxan-2-yl)-2,3-dihydropyridazin-3-one (678.42 mg, 2.724 mmol, 1.00 equiv.) in DIEA (704.01 mg, 5.447 mmol, 2 equiv.) was stirred for 16 hours at 100° C. under nitrogen atmosphere. The residue was purified by Prep-TLC (PE/EA 1/1) to afford 4-chloro-5-[4-(2-chloro-4-fluorophenoxy)-6-methyl-5H,6H,7H,8H-pyrido[3,4-d]pyrimidin-7-yl]-2-(oxan-2-yl)-2,3-dihydropyridazin-3-one (530 mg, 38.43%) as a light yellow solid.

4-chloro-5-[(6R)-4-(2-chloro-4-fluorophenoxy)-6-methyl-5H,6H,7H,8H-pyrido[3,4-d]pyrimidin-7-yl]-2,3-dihydropyridazin-3-one To a solution of 4-chloro-5-[4-(2-chloro-4-fluorophenoxy)-6-methyl-5H,6H,7H,8H-pyrido[3,4-d]pyrimidin-7-yl]-2-(oxan-2-yl)-2,3-dihydropyridazin-3-one (530 mg, 1.047 mmol, 1 equiv.) in DCM (20 mL, 314.601 mmol, 300.57 equiv.) was added TFA (1193.47 mg, 10.467 mmol, 10 equiv.) at 25° C. The solution was stirred at 25° C. for 2 hours. The resulting mixture was concentrated under reduced pressure. The crude product (600 mg) was purified by Prep-HPLC with the following conditions (Column: XBridge Shield RP18 OBD Column 30*150 mm, 5 um; Mobile Phase A: Water (10 mM NH4HCO3), Mobile Phase B: acetonitrile; Flow rate: 60 mL/min; Gradient: 20% B to 40% B in 7 min; 220 nm; Rt: 6.63 min) to afford the racemate (200 mg). The residue (200 mg) was purified by Chiral-Prep-HPLC with the following conditions: Column: CHIRALPAK IE, 2*25 cm, 5 um; Mobile Phase A: MTBE (0.1% FA)-HPLC, Mobile Phase B: IPA-HPLC; Flow rate: 18 mL/min; Gradient: 20 B to 20 B in 15 min; 220/254 nm. Although the two isomers were separated by this technique, the absolute orientation was not determined. The compound designated as 4-chloro-5-[(6S)-4-(2-chloro-4-fluorophenoxy)-6-methyl-5H,6H,7H,8H-pyrido[3,4-d]pyrimidin-7-yl]-2,3-dihydropyridazin-3-one (60.9 mg, 13.78%) was obtained at 9.688 min as a white solid. The compound designated as 4-chloro-5-[(6R)-4-(2-chloro-4-fluorophenoxy)-6-methyl-5H,6H,7H,8H-pyrido[3,4-d]pyrimidin-7-yl]-2,3-dihydropyridazin-3-one (61.5 mg, 13.92%) was obtained at 11.813 min as a white solid.

Example 7. Synthesis of Compound 134

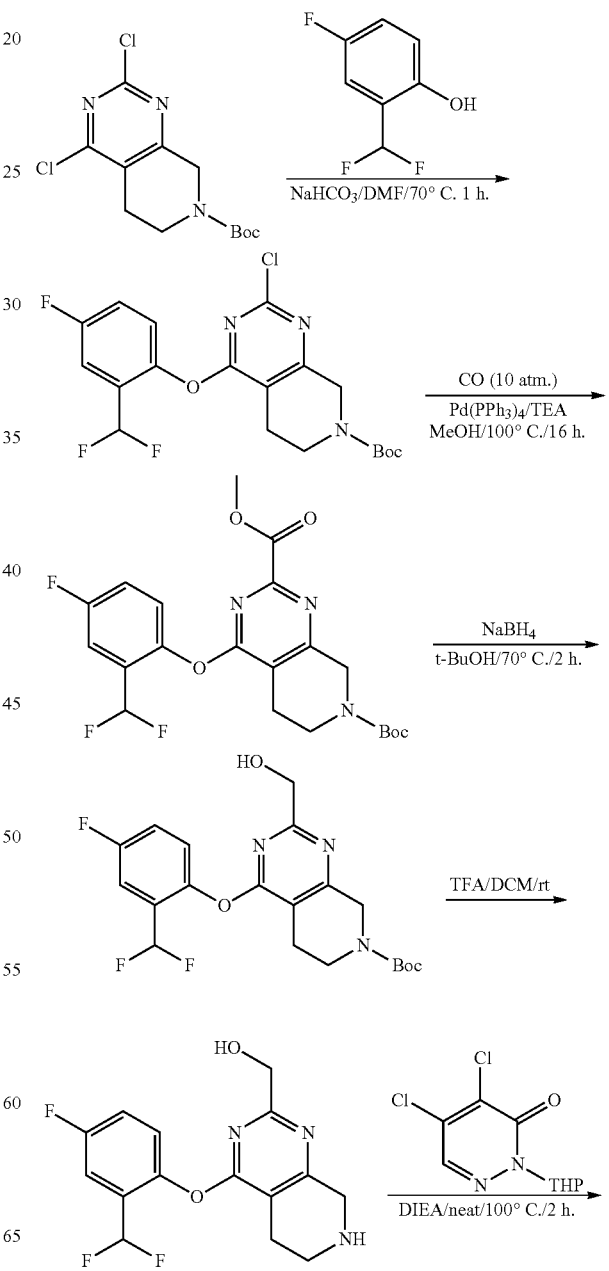

-continued

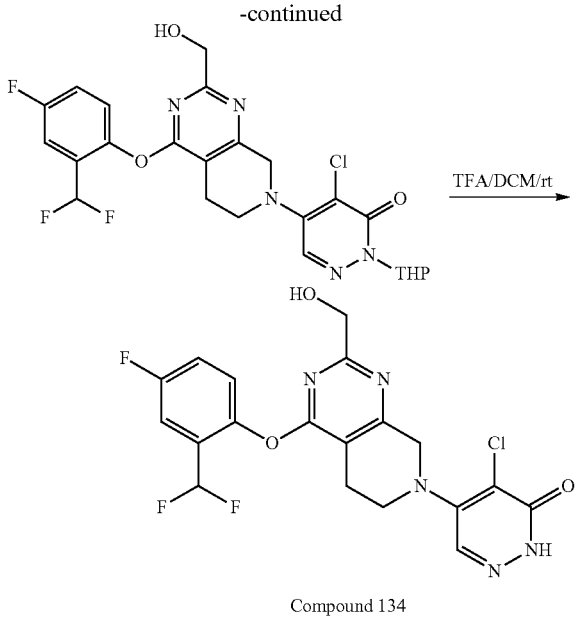

Compound 134

Tert-butyl 2-chloro-4-[2-(difluoromethyl)-4-fluorophenoxy]-5H,6H,7H,8H-pyrido[3,4-d]pyrimidine-7-carboxylate To a stirred solution of 2-(difluoromethyl)-4-fluorophenol (5.33 g, 32.879 mmol, 2.00 equiv.) and tert-butyl 2,4-dichloro-5H,6H,7H,8H-pyrido[3,4-d]pyrimidine-7-carboxylate (5 g, 16.438 mmol, 1 equiv.) in DMF (30 mL) was added NaHCO3 (4.14 g, 49.282 mmol, 3.00 equiv.) at room temperature. The solution was stirred at 70° C. for 0.5 hours. The mixture was concentrated under reduced pressure. The residue was purified by reverse phase flash chromatography with the following conditions: Column: Spherical C18, 20-40 um, 330 g; Mobile Phase A: Water (plus 10 mM NH4HCO3); Mobile Phase B: acetonitrile; Flow rate: 80 mL/min; Gradient: 5%-5% B, 10 min, 70% B-95% B gradient in 100 min; Detector: 254 nm. The fractions containing the desired product were collected at 92% B and concentrated under reduced pressure to afford tert-butyl 2-chloro-4-[2-(difluoromethyl)-4-fluorophenoxy]-5H,6H,7H,8H-pyrido[3,4-d]pyrimidine-7-carboxylate (2.100 g) as off-white solid.

7-tert-Butyl 2-methyl 4-[2-(difluoromethyl)-4-fluorophenoxy]-5H,6H,7H,8H-pyrido[3,4-d]pyrimidine-2,7-dicarboxylate To a solution of tert-butyl 2-chloro-4-[2-(difluoromethyl)-4-fluorophenoxy]-5H,6H,7H,8H-pyrido[3,4-d]pyrimidine-7-carboxylate (400 mg, 0.931 mmol, 1 equiv.) and TEA (188.34 mg, 1.861 mmol, 2 equiv.) in MeOH (15 mL, 370.484 mmol, 398.10 equiv.) was added Pd(PPh3)4 (107.54 mg, 0.093 mmol, 0.1 equiv.) in a pressure tank. The mixture was purged with nitrogen for 1 hours and then was pressurized to 10 atm with carbon monoxide at 100° C. for 16 hours. The reaction mixture was cooled to room temperature and filtered to remove insoluble solids. The residue was purified by reverse phase flash chromatography with the following conditions: Column: Spherical C$_{18}$, 20-40 um, 330 g; Mobile Phase A: Water (plus 10 mM NH4HCO3); Mobile Phase B: acetonitrile; Flow rate: 80 mL/min; Gradient: 5%-5% B, 10 min, 35% B-65% B gradient in 20 min; Detector: 254 nm. The fractions containing the desired product were collected at 62% B and concentrated under reduced pressure to afford 7-tert-butyl 2-methyl 4-[2-(difluoromethyl)-4-fluorophenoxy]-5H,6H,7H,8H-pyrido[3,4-d]pyrimidine-2,7-dicarboxylate (100 mg, 23.70%) as colorless oil.

Tert-butyl 4-[2-(difluoromethyl)-4-fluorophenoxy]-2-(hydroxymethyl)-5H,6H,7H,8H-pyrido[3,4-d]pyrimidine-7-carboxylate To a stirred solution of 7-tert-butyl 2-methyl 4-[2-(difluoromethyl)-4-fluorophenoxy]-5H,6H,7H,8H-pyrido[3,4-d]pyrimidine-2,7-dicarboxylate (100 mg, 0.221 mmol, 1 equiv.) in t-BuOH (6 mL, 63.139 mmol, 286.29 equiv.) was added NaBH$_4$ (16.69 mg, 0.441 mmol, 2 equiv.) at room temperature. The solution was stirred at 70° C. for 3 hours. To the mixture was added water (3 mL). The residue was purified by reverse phase flash chromatography with the following conditions: Column: Spherical C18, 20-40 um, 330 g; Mobile Phase A: Water (plus 10 mM NH$_4$HCO3); Mobile Phase B: acetonitrile; Flow rate: 80 mL/min; Gradient: 5%-5% B, 10 min, 45% B-80% B gradient in 20 min; Detector: 254 nm. The fractions containing the desired product were collected at 74% B and concentrated under reduced pressure to afford tert-butyl 4-[2-(difluoromethyl)-4-fluorophenoxy]-2-(hydroxymethyl)-5H,6H,7H,8H-pyrido[3,4-d]pyrimidine-7-carboxylate (35 mg, 37.30%) as colorless oil.

[4-[2-(difluoromethyl)-4-fluorophenoxy]-5H,6H,7H,8H-pyrido[3,4-d]pyrimidin-2-yl]methanol To a stirred solution of tert-butyl 4-[2-(difluoromethyl)-4-fluorophenoxy]-2-(hydroxymethyl)-5H,6H,7H,8H-pyrido[3,4-d]pyrimidine-7-carboxylate (35 mg) in DCM (6 mg) was added TFA (1 mg) at room temperature. The solution was stirred at rt for 2 hours. The mixture was concentrated under reduced pressure. The residue was purified by reverse phase flash chromatography with the following conditions: Column: Spherical C18, 20-40 um, 330 g; Mobile Phase A: Water (plus 10 mM NH$_4$HCO3); Mobile Phase B: acetonitrile; Flow rate: 80 mL/min; Gradient: 5%-5% B, 10 min, 25% B-55% B gradient in 20 min; Detector: 254 nm. The fractions containing the desired product were collected at 41% B and concentrated under reduced pressure to afford as [4-[2-(difluoromethyl)-4-fluorophenoxy]-5H,6H,7H,8H-pyrido[3,4-d]pyrimidin-2-yl]methanol (20 mg) as colorless oil.

4-chloro-5-[4-[2-(difluoromethyl)-4-fluorophenoxy]-2-(hydroxymethyl)-5H,6H,7H,8H-pyrido[3,4-d]pyrimidin-7-yl]-2-(oxan-2-yl)-2,3-dihydropyridazin-3-one Into a 25 mL round-bottom flask were added [4-[2-(difluoromethyl)-4-fluorophenoxy]-5H,6H,7H,8H-pyrido[3,4-d]pyrimidin-2-yl]methanol (20 mg, 0.061 mmol, 1 equiv.) and 4,5-dichloro-2-(oxan-2-yl)-2,3-dihydropyridazin-3-one (15.31 mg, 0.061 mmol, 1 equiv.) at room temperature. To the mixture was added DIEA (15.89 mg, 0.123 mmol, 2 equiv.) at rt. The mixture was stirred at 90° C. for 2 hours. The residue was purified by reverse phase flash chromatography with the following conditions: Column: Spherical C18, 20-40 um, 330 g; Mobile Phase A: Water (plus 10 mM NH$_4$HCO3); Mobile Phase B: acetonitrile; Flow rate: 80 mL/min; Gradient: 5%-5% B, 10 min, 35% B-70% B gradient in 20 min; Detector: 254 nm. The fractions containing the desired product were collected at 65% B and concentrated under reduced pressure to afford 4-chloro-5-[4-[2-(difluoromethyl)-4-fluorophenoxy]-2-(hydroxymethyl)-5H,6H,7H,8H-pyrido[3,4-d]pyrimidin-7-yl]-2-(oxan-2-yl)-2,3-dihydropyridazin-3-one (30 mg, 90.71%) as colorless oil.

4-chloro-5-[4-[2-(difluoromethyl)-4-fluorophenoxy]-2-(hydroxymethyl)-5H,6H,7H,8H-pyrido[3,4-d]pyrimidin-7-yl]-2,3-dihydropyridazin-3-one To a stirred solution of 4-chloro-5-[4-[2-(difluoromethyl)-4-fluorophenoxy]-2-(hydroxymethyl)-5H,6H,7H,8H-pyrido[3,4-d]pyrimidin-7-yl]-2-(oxan-2-yl)-2,3-dihydropyridazin-3-one (30 mg) in DCM (5 mL) was added TFA (1 mL) at room temperature. The solution was stirred at rt for 2 hours. The mixture was concentrated under reduced pressure. The crude product (30 mg) was purified by Prep-HPLC with the following conditions (Column: XBridge Prep OBD C18 Column 30×150 mm 5 um; Mobile Phase A: undefined, Mobile Phase B: undefined; Flow rate: 60 mL/min; Gradient: 20% B to 40% B in 8 min; 220 nm; Rt: 7.22 min) to afford 4-chloro-5-[4-[2-(difluoromethyl)-4-fluorophenoxy]-2-(hydroxymethyl)-5H,6H,7H,8H-pyrido[3,4-d]pyrimidin-7-yl]-2,3-dihydropyridazin-3-one (8.7 mg) as a white solid.

Compounds 128, 125, 114 were prepared by the methods and scheme described in this Example by using 2-trifluoromethylphenol, 4-fluoro-2-trifluoromethylphenol and 4-fluoro-2-chlorophenol respectively, in place of 2-(difluoromethyl)-4-fluorophenol in the first step of the synthesis.

Example 8. Synthesis of Compound 112

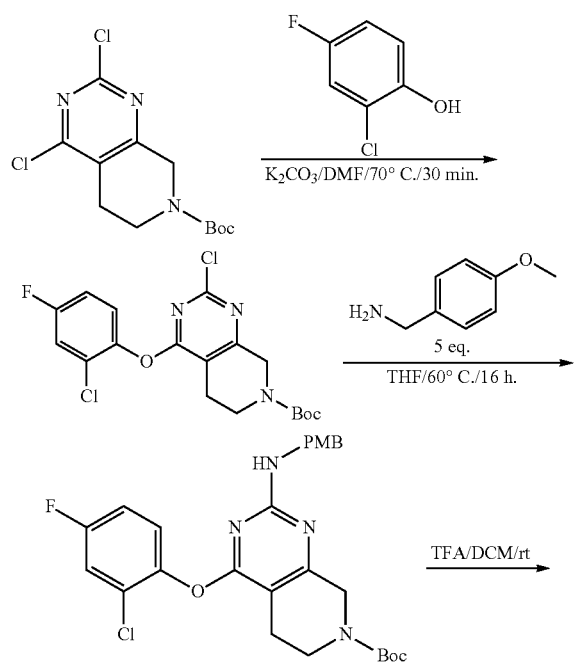

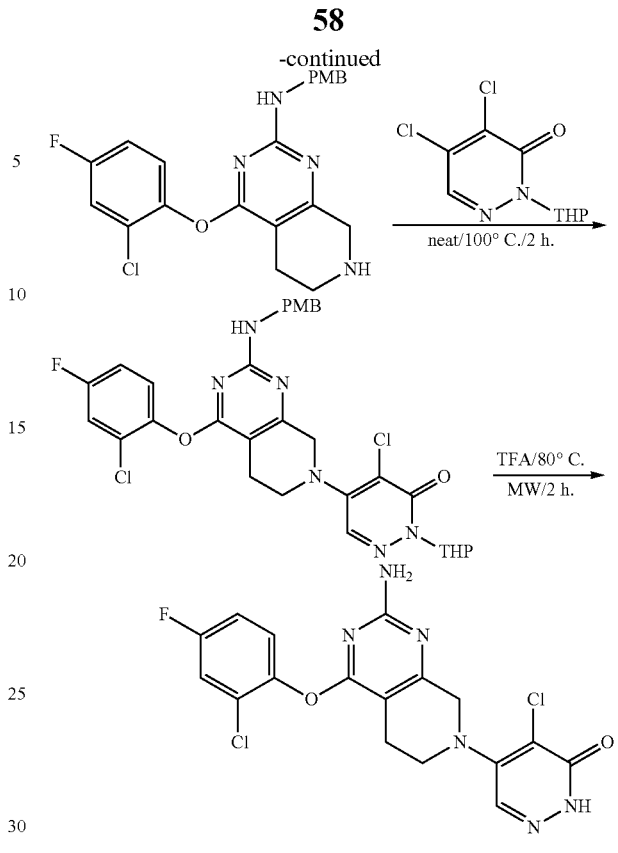

Compound 112

Tert-butyl 2-chloro-4-(2-chloro-4-fluorophenoxy)-5H,6H,7H,8H-pyrido[3,4-d]pyrimidine-7-carboxylate To a stirred mixture of tert-butyl 2,4-dichloro-5H,6H,7H,8H-pyrido[3,4-d]pyrimidine-7-carboxylate (800 mg, 2.630 mmol, 1 equiv.) and 2-chloro-4-fluorophenol (578.16 mg, 3.945 mmol, 1.50 equiv.) in DMF (15 mL) was added $K_2CO_3$ (726.99 mg, 5.260 mmol, 2.00 equiv.) in portions at rt under nitrogen atmosphere. The resulting mixture was stirred for 0.5 hours at 70° C. under nitrogen atmosphere. The reaction was monitored by LCMS. The mixture was allowed to cool down to rt. The resulting mixture was concentrated under reduced pressure. The resulting mixture was extracted with EtOAc (3×200 mL). The combined organic layers were washed with brine (2×100 mL), dried over anhydrous $Na_2SO_4$. After filtration, the filtrate was concentrated under reduced pressure. The residue was purified by silica gel column chromatography, eluted with PE/EtOAc (30/1 to 10/1) to afford tert-butyl 2-chloro-4-(2-chloro-4-fluorophenoxy)-5H,6H,7H,8H-pyrido[3,4-d]pyrimidine-7-carboxylate (1 g, 91.78%) as a yellow oil.

Tert-Butyl 4-(2-chloro-4-fluorophenoxy)-2-[[(4-methoxyphenyl)methyl]amino]-5H,6H,7H,8H-pyrido[3,4-d]pyrimidine-7-carboxylate To a stirred mixture of tert-butyl 2-chloro-4-(2-chloro-4-fluorophenoxy)-5H,6H,7H,8H-pyrido[3,4-d]pyrimidine-7-carboxylate (700 mg, 1.690 mmol, 1 equiv.) in THF (30 mL) was added 1-(4-methoxyphenyl)methanamine (1159.02 mg, 8.449 mmol, 5.00 equiv.) in portions at rt under nitrogen atmosphere. The resulting mixture was stirred for 16 hours at 60° C. under nitrogen atmosphere. The reaction was monitored by LCMS. The mixture was allowed to cool down to rt. The resulting mixture was concentrated under reduced pressure. The resulting mixture was extracted with EtOAc (3×200 mL). The combined organic layers were washed with brine (2×100 mL), dried over anhydrous Na$_2$SO$_4$. After filtration, the filtrate was concentrated under reduced pressure. The residue was purified by reverse flash chromatography with the following conditions (Column, C18 silica gel; mobile phase, acetonitrile in water, 60% to 95% gradient in 20 min; detector, UV 220 nm) to afford tert-butyl 4-(2-chloro-4-fluorophenoxy)-2-[[(4-methoxyphenyl)methyl]amino]-5H,6H,7H,8H-pyrido[3,4-d]pyrimidine-7-carboxylate (350 mg, 40.22%) as a yellow oil.

4-(2-chloro-4-fluorophenoxy)-N-[(4-methoxyphenyl)methyl]-5H,6H,7H,8H-pyrido[3,4-d]pyrimidin-2-amine To a stirred solution of tert-butyl 4-(2-chloro-4-fluorophenoxy)-2-[[(4-methoxyphenyl)methyl]amino]-5H,6H,7H,8H-pyrido[3,4-d]pyrimidine-7-carboxylate (350 mg, 1 equiv.) in DCM (10 mL) was added TFA (1 mL) dropwise at rt. The reaction mixture was stirred for 2 hours at rt. The reaction was monitored by LCMS. The resulting mixture was concentrated under reduced pressure. The residue was basified to pH=8 with saturated NH$_4$HCO$_3$ (aq.). The resulting mixture was extracted with DCM (3×100 mL). The combined organic layers were washed with brine (1×100 mL), dried over anhydrous Na$_2$SO$_4$. After filtration, the filtrate was concentrated under reduced pressure. The residue was purified by Prep-HPLC with the following conditions (Column: XBridge Shield RP18 OBD Column, 5 um, 19*150 mm; Mobile Phase A: Water (10 mM NH$_4$HCO$_3$), Mobile Phase B: acetonitrile; Flow rate: 25 mL/min; Gradient: 2% B to 32% B in 1 min; 220/254 nm; Rt: 7.08 min) to afford 4-(2-chloro-4-fluorophenoxy)-N-[(4-methoxyphenyl)methyl]-5H,6H,7H,8H-pyrido[3,4-d]pyrimidin-2-amine (260 mg) as a yellow oil.

4-chloro-5-[4-(2-chloro-4-fluorophenoxy)-2-[[(4-methoxyphenyl)methyl]amino]-5H,6H,7H,8H-pyrido[3,4-d]pyrimidin-7-yl]-2-(oxan-2-yl)-2,3-dihydropyridazin-3-one Into a 50 mL round-bottom flask were added 4-(2-chloro-4-fluorophenoxy)-N-[(4-methoxyphenyl)methyl]-5H,6H,7H,8H-pyrido[3,4-d]pyrimidin-2-amine (260 mg, 0.627 mmol, 1 equiv), 4,5-dichloro-2-(oxan-2-yl)-2,3-dihydropyridazin-3-one (156.11 mg, 0.627 mmol, 1.00 equiv.) and DIEA (242.99 mg, 1.880 mmol, 3.00 equiv.) at rt under nitrogen atmosphere. The resulting mixture was stirred for 2 hours at 90° C. under nitrogen atmosphere. The residue was purified by reverse flash chromatography with the following conditions (Column, C18 silica gel; mobile phase, acetonitrile in water, 50% to 85% gradient in 25 min; detector, UV 220 nm) to afford 4-chloro-5-[4-(2-chloro-4-fluorophenoxy)-2-[[(4-methoxyphenyl)methyl]amino]-5H,6H,7H,8H-pyrido[3,4-d]pyrimidin-7-yl]-2-(oxan-2-yl)-2,3-dihydropyridazin-3-one (350 mg, 89.00%) as a yellow solid.

5-[2-amino-4-(2-chloro-4-fluorophenoxy)-5H,6H,7H,8H-pyrido[3,4-d]pyrimidin-7-yl]-4-chloro-2,3-dihydropyridazin-3-one To a stirred solution of 4-chloro-5-[4-(2-chloro-4-fluorophenoxy)-2-[[(4-methoxyphenyl)methyl]amino]-5H,6H,7H,8H-pyrido[3,4-d]pyrimidin-7-yl]-2-(oxan-2-yl)-2,3-dihydropyridazin-3-one (200 mg) in TFA (8 mL, 107.704 mmol, 328.23 equiv). The final reaction mixture was irradiated with microwave radiation for 2 hours at 80° C. The reaction was monitored by LCMS. The resulting mixture was concentrated under reduced pressure. The residue was basified to pH=8 with saturated NH$_4$HCO$_3$ (aq.). The resulting mixture was extracted with DCM (2×100 mL). The combined organic layers were washed with brine (1×100 mL), dried over anhydrous Na$_2$SO$_4$. After filtration, the filtrate was concentrated under reduced pressure. The residue was purified by Prep-HPLC with the following conditions (Column: XBridge Prep OBD C18 Column 30×150 mm 5 um; Mobile Phase A: Water (10 mM NH4HCO3), Mobile Phase B: acetonitrile; Flow rate: 60 mL/min; Gradient: 25% B to 40% B in 8 min; 220 nm; Rt: 7.35 min) to afford 5-[2-amino-4-(2-chloro-4-fluorophenoxy)-5H,6H,7H,8H-pyrido[3,4-d]pyrimidin-7-yl]-4-chloro-2,3-dihydropyridazin-3-one (52.4 mg) as a yellow solid.

Compounds 113, 116, and 102 were prepared by the methods and scheme described in this Example by using 2-chlorophenol, 4-fluoro-2-trifluoromethylphenol, 2-trifluorophenol respectively, in place of 2-chloro-4-fluorophenol in the first step of the synthesis.

Example 9. Synthesis of Compounds 129 and 130

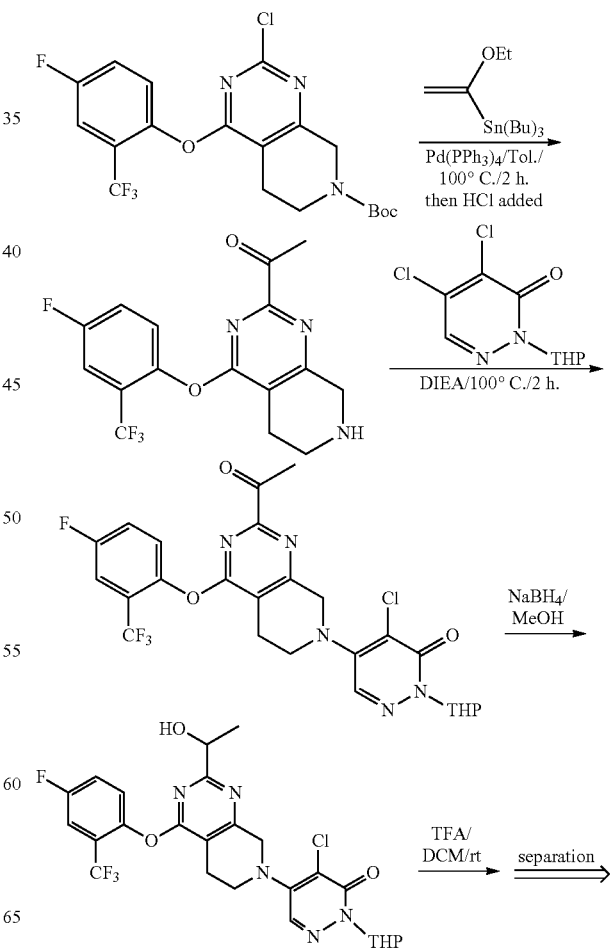

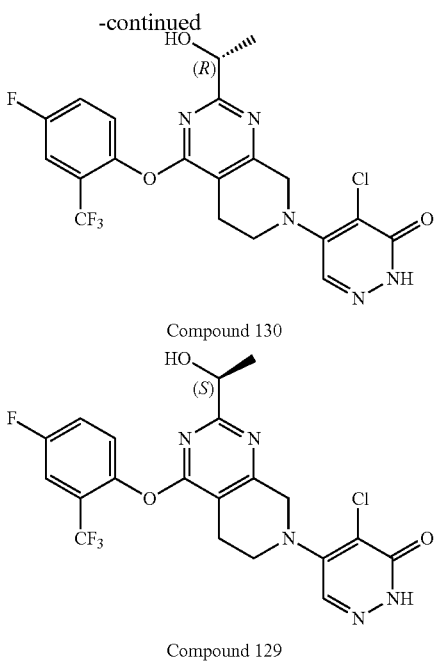

Compound 130

Compound 129

1-[4-[4-fluoro-2-(trifluoromethyl)phenoxy]-5H,6H, 7H,8H-pyrido[3,4-d]pyrimidin-2-yl]ethan-1-one To a mixture of tert-butyl 2-chloro-4-[4-fluoro-2-(trifluoromethyl)phenoxy]-5H,6H,7H,8H-pyrido[3,4-d]pyrimidine-7-carboxylate (600 mg, 1.340 mmol, 1 equiv.) and tributyl (1-ethoxyethenyl)stannane (967.80 mg, 2.680 mmol, 2.00 equiv.) in Toluene (10 mL) was added Pd(PPh$_3$)$_4$ (77.41 mg, 0.067 mmol, 0.05 equiv.) at room temperature under nitrogen atmosphere. The resulting mixture was stirred for 4 hours at 110° C. The reaction was monitored by LCMS. This resulted in tert-butyl 2-(1-ethoxyethenyl)-4-[4-fluoro-2-(trifluoromethyl)phenoxy]-5H,6H,7H,8H-pyrido [3,4-d]pyrimidine-7-carboxylate (700 mg, 108.06%) as a yellow oil. The crude resulting mixture was used in the next step directly without further purification. To a stirred solution of tert-butyl 2-(1-ethoxyethenyl)-4-[4-fluoro-2-(trifluoromethyl)phenoxy]-5H,6H,7H,8H-pyrido[3,4-d]pyrimidine-7-carboxylate (1 g, 2.068 mmol, 1 equiv.) in DCM (5 mL) was added TFA (3.33 mL, 29.239 mmol, 21.70 equiv.) at room temperature. The resulting mixture was stirred for 2 hours at room temperature. The reaction was monitored by LCMS. The resulting mixture was concentrated under reduced pressure. The mixture/residue was basified to pH 8 with saturated NaHCO$_3$ (aq.). The resulting mixture was concentrated under reduced pressure. The residue was purified by reverse phase flash chromatography with the following conditions: Column: Spherical C18, 20-40 um, 330 g; Mobile Phase A: Water (plus 5 mM NH$_4$HCO$_3$); Mobile Phase B: acetonitrile; Flow rate: 80 mL/min; Gradient: 5%-5% B, 10 min, 43% B-55% B gradient in 20 min; Detector: 220 nm. The fractions containing the desired product were collected at 50% B and concentrated under reduced pressure to afford 1-[4-[4-fluoro-2-(trifluoromethyl) phenoxy]-5H,6H,7H,8H-pyrido[3,4-d]pyrimidin-2-yl] ethan-1-one (750 mg, 102.06%) as a light yellow solid.

5-[2-Acetyl-4-[4-fluoro-2-(trifluoromethyl)phenoxy]-5H,6H,7H,8H-pyrido[3,4d]pyrimidin-7-yl]-4-chloro-2-(oxan-2-yl)-2,3-dihydropyridazin-3-one Into a 50 mL round-bottom flask were added 1-[4-[4-fluoro-2-(trifluoromethyl)phenoxy]-5H,6H,7H,8H-pyrido [3,4-d]pyrimidin-2-yl]ethan-1-one (750 mg, 2.111 mmol, 1 equiv.) and 4,5-dichloro-2-(oxan-2-yl)-2,3-dihydropyridazin-3-one (525.81 mg, 2.111 mmol, 1.00 equiv.) at room temperature. To the above mixture was added DIEA (818.47 mg, 6.333 mmol, 3.00 equiv). The resulting mixture was stirred for 2 hours at 100° C. The reaction was monitored by LCMS. The mixture was allowed to cool down to room temperature. The residue was purified by reverse phase flash chromatography with the following conditions: Column: Spherical C18, 20-40 um, 330 g; Mobile Phase A: Water (plus 5 mM NH$_4$HCO$_3$); Mobile Phase B: acetonitrile; Flow rate: 80 mL/min; Gradient: 5%-5% B, 10 min, 60% B-85% B gradient in 20 min; Detector: 220 nm. The fractions containing the desired product were collected at 80% B and concentrated under reduced pressure to afford 5-[2-acetyl-4-[4-fluoro-2-(trifluoromethyl)phenoxy]-5H, 6H,7H,8H-pyrido[3,4-d]pyrimidin-7-yl]-4-chloro-2-(oxan-2-yl)-2,3-dihydropyridazin-3-one (230 mg, 19.18%) as a light yellow oil.

4-Chloro-5-[4-[4-fluoro-2-(trifluoromethyl)phenoxyl-2-(1-hydroxyethyl)-5H,6H,7H,8H-pyrido[3,4-d]]pyrimidin-7-yl]-2-(oxan-2-yl)-2,3-dihydropyridazin-3-one To a stirred solution of 5-[2-acetyl-4-[4-fluoro-2-(trifluoromethyl)phenoxy]-5H,6H,7H,8H-pyrido[3,4-d]pyrimidin-7-yl]-4-chloro-2-(oxan-2-yl)-2,3-dihydropyridazin-3-one (230 mg, 0.405 mmol, 1 equiv.) in MeOH (10 mL) was added NaBH$_4$ (30.64 mg, 0.810 mmol, 2.00 equiv.) in portions at 0° C. under nitrogen atmosphere. The resulting mixture was stirred for 2 hours at room temperature. The reaction was monitored by LCMS. The resulting mixture was concentrated under reduced pressure. The residue was purified by Prep-TLC (PE/EtOAc 1/1) to afford 4-chloro-5-[4-[4-fluoro-2-(trifluoromethyl)phenoxy]-2-(1-hydroxyethyl)-5H,6H,7H,8H-pyrido[3,4-d]pyrimidin-7-yl]-2-(oxan-2-yl)-2,3-dihydropyridazin-3-one (120 mg, 51.99%) as a light yellow oil.

4-Chloro-5-[4-[4-fluoro-2-(trifluoromethyl)phenoxy]-2-[(1 S)-1-hydroxyethyl]-5H,6H,7H,8H-pyrido[3,4-d]pyrimidin-7-yl]-2,3-dihydropyridazin-3-one and 4-chloro-5-[4-[4-fluoro-2-(trifluoromethyl)phenoxy]-2-[(1R)-1-hydroxyethyl]-5H,6H,7H,8H-pyrido[3,4-d]pyrimidin-7-yl]-2,3-dihydropyridazin-3-one To a stirred solution of 4-chloro-5-[4-[4-fluoro-2-(trifluoromethyl)phenoxy]-2-(1-hydroxyethyl)-5H,6H,7H,8H-pyrido[3,4-d]pyrimidin-7-yl]-2-(oxan-2-yl)-2,3-dihydropyridazin-3-one (120 mg, 0.211 mmol, 1 equiv.) in DCM (5 mL) was added TFA (2.00 mL, 17.541 mmol, 127.89 equiv.) dropwise at room temperature. The resulting mixture was stirred for 2 hours at room temperature. The reaction was monitored by LCMS. The residue was basified to pH 8 with saturated NaHCO3 (aq.). The resulting mixture was concentrated under reduced pressure. The residue was purified by reverse phase flash chromatography with the following conditions: Column: Spherical Cis, 20-40 um, 330 g; Mobile Phase A: Water (plus 5 mM NH$_4$HCO$_3$); Mobile Phase B:

acetonitrile; Flow rate: 80 mL/min; Gradient: 5%-5% B, 10 min, 40% B-80% B gradient in 25 min; Detector: 220 nm. The fractions containing the desired product were collected at 55% B and concentrated under reduced pressure. The crude product (50 mg) was purified by Chiral-Prep-HPLC with the following conditions (Column: CHIRALPAK IE, 2*25 cm, 5 um; Mobile Phase A: Hex (0.1% FA)-HPLC, Mobile Phase B: EtOH-HPLC; Flow rate: 16 mL/min; Gradient: 30 B to 30 B in 33 min; 220/254 nm; RT1:26.219; RT2:29.589). Although the two isomers were separated by this technique, the absolute orientation was not determined. The compound designated as 4-chloro-5-[4-[4-fluoro-2-(trifluoromethyl)phenoxy]-2-[(1 S)-1-hydroxyethyl]-5H,6H,7H,8H-pyrido[3,4-d]pyrimidin-7-yl]-2,3-dihydropyridazin-3-one (27.1 mg) was obtained at 29.589 min as an off-white solid. The compound designated as 4-chloro-5-[4-[4-fluoro-2-(trifluoromethyl)phenoxy]-2-[(1R)-1-hydroxyethyl]-5H,6H,7H,8H-pyrido[3,4-d]pyrimidin-7-yl]-2,3-dihydropyridazin-3-one (22.6 mg) was obtained at 26.219 min as an off-white solid.

Compound 119 was prepared by the methods and scheme described in this Example using tert-butyl 2-chloro-4-[4-fluoro-2-chlorophenoxy]-5H,6H,7H,8H-pyrido[3,4-d]pyrimidine-7-carboxylate as the starting material.

Compounds 122 and 123 were prepared by the methods and scheme described in this Example using tert-butyl 2-chloro-4-[2-(trifluoromethyl)phenoxy]-5H,6H,7H,8H-pyrido[3,4-d]pyrimidine-7-carboxylate as the starting material. Again, the absolute orientation of these separated isomers was not determined and the designation as (S) or (R) was arbitrary.

Example 10. Synthesis of Compound 115

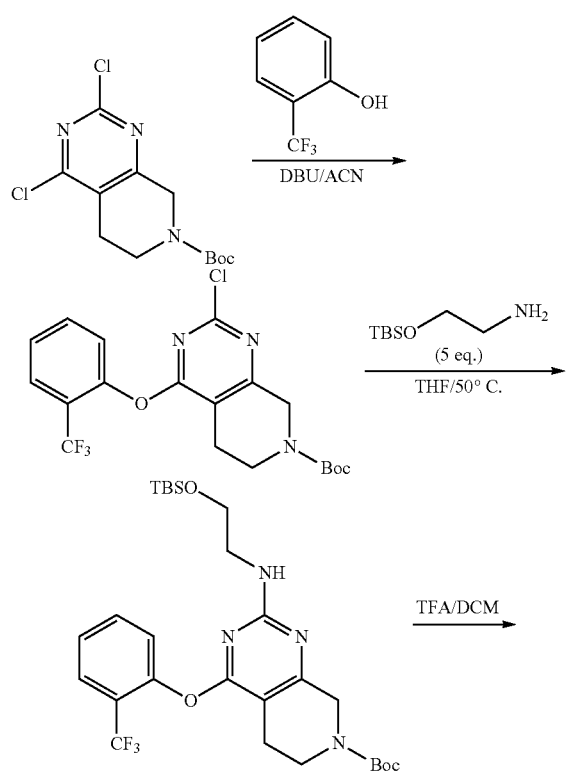

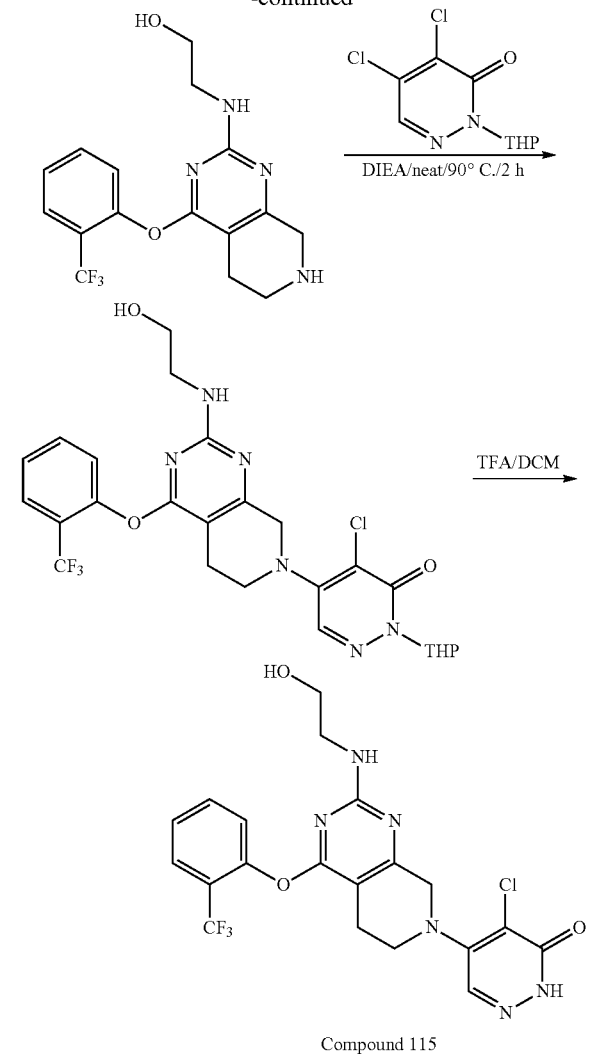

Compound 115 tert-Butyl 2-chloro-4-[2-(trifluoromethyl)phenoxy]-5H,6H,7H,8H-pyrido[3,4-d]pyrimidine-7-carboxylate To a stirred solution of tert-butyl 2,4-dichloro-5H,6H,7H,8H-pyrido[3,4-d]pyrimidine-7-carboxylate (2 g, 6.58 mmol, 1 equiv.) and 2-(trifluoromethyl)phenol (1.6 g, 9.86 mmol, 1.5 equiv.) in acetonitrile (20 mL) was added DBU (2.0 g, 13.15 mmol, 2 equiv.) at room temperature. The solution was stirred at rt for 4 hours. The mixture was concentrated under reduced pressure. The residue was purified by Prep-TLC (PE/EtOAc 10:1) to afford tert-butyl 2-chloro-4-[2-(trifluoromethyl)phenoxy]-5H,6H,7H,8H-pyrido[3,4-d]pyrimidine-7-carboxylate (700 mg, 24.77%) as colorless oil.

tert-butyl 2-([2-[(tert-butyldimethylsilyl)oxy]ethyl]amino)-4-[2-(trifluoromethyl)phenoxy]-5H,6H,7H,8H-pyrido[3,4-d]pyrimidine-7-carboxylate To a solution of tert-butyl 2-chloro-4-[2-(trifluoromethyl)phenoxy]-5H,6H,7H,8H-pyrido[3,4-d]pyrimidine-7-carboxylate (500 mg, 1.163 mmol, 1 equiv.) in THF (15 mL) was added (2-aminoethoxy)(tert-butyldimethylsilane (1019.89 mg, 5.816 mmol, 5.00 equiv.) at room temperature under nitrogen atmosphere. The resulting mixture was stirred for 16 h at 50° C. The reaction was monitored by LCMS. The resulting mixture was concentrated under reduced pressure. The residue was purified by Prep-TLC (PE/EtOAc 3/1) to afford tert-butyl 2-([2-[(tert-butyldimethylsilyl)oxy]ethyl]amino)-4-[2-(trifluoromethyl)phenoxy]-5H,6H,7H,8H-pyrido[3,4-d]pyrimidine-7-carboxylate (440 mg, 66.51%) as a light yellow oil.

2-([4-[2-(trifluoromethyl)phenoxy]-5H,6H,7H,8H-pyrido[3,4-d]pyrimidin-2-yl]amino)ethan-1-ol To a stirred solution of tert-butyl 2-([2-[(tert-butyldimethylsilyl)oxy]ethyl]amino)-4-[2-(trifluoromethyl)phenoxy]-5H,6H,7H,8H-pyrido[3,4-d]pyrimidine-7-carboxylate (440 mg, 0.774 mmol, 1 equiv.) in DCM (10 mL) was added TFA (3 mL, 40.389 mmol, 52.20 equiv.) at room temperature. The resulting mixture was stirred for 2 h at room temperature. The reaction was monitored by LCMS. The resulting mixture was concentrated under reduced pressure. The residue was purified by reverse flash chromatography with the following conditions: column, C18 silica gel; mobile phase, ACN in water, 40% to 60% gradient in 15 min; detector, UV 254 nm to afford 2-([4-[2-(trifluoromethyl)phenoxy]-5H,6H,7H,8H-pyrido[3,4-d]pyrimidin-2-yl]amino)ethan-1-ol (220 mg) as light yellow oil.

4-chloro-5-[2-[(2-hydroxyethyl)amino]-4-[2-(trifluoromethyl)phenoxy]-5H,6H,7H,8H-pyrido[3,4-d]pyrimidin-7-yl]-2-(oxan-2-yl)-2,3-dihydropyridazin-3-one Into a 50 mL round-bottom flask were added 2-([4-[2-(trifluoromethyl)phenoxy]-5H,6H,7H,8H-pyrido[3,4-d]pyrimidin-2-yl]amino)ethan-1-ol (220 mg, 0.621 mmol, 1 equiv.) and 4,5-dichloro-2-(oxan-2-yl)-2,3-dihydropyridazin-3-one (154.66 mg, 0.621 mmol, 1.00 equiv.) at room temperature. To the above mixture was added DIEA (240.74 mg, 1.863 mmol, 3.00 equiv). The resulting mixture was stirred for 2 h at 100 degrees C. The reaction was monitored by LCMS. The mixture was allowed to cool down to room temperature. The residue was purified by reverse phase flash chromatography with the following conditions: Column: Spherical C18, 20-40 um, 330 g; Mobile Phase A: Water (plus 5 mM NH$_4$HCO$_3$); Mobile Phase B: ACN; Flow rate: 80 mL/min; Gradient: 5%-5% B, 10 min, 45% B-60% B gradient in 20 min; Detector: 220 nm. The fractions containing the desired product were collected at 55% B and concentrated under reduced pressure to afford 4-chloro-5-[2-[(2-hydroxyethyl)amino]-4-[2-(trifluoromethyl)phenoxy]-5H,6H,7H,8H-pyrido[3,4-d]pyrimidin-7-yl]-2-(oxan-2-yl)-2,3-dihydropyridazin-3-one (210 mg, 59.66%) as a yellow solid.

4-chloro-5-[2-[(2-hydroxyethyl)amino]-4-[2-(trifluoromethyl)phenoxy]-5H,6H,7H,8H-pyrido[3,4-d]pyrimidin-7-yl]-2,3-dihydropyridazin-3-one To a stirred solution of 4-chloro-5-[2-[(2-hydroxyethyl)amino]-4-[2-(trifluoromethyl)phenoxy]-5H,6H,7H,8H-pyrido[3,4-d]pyrimidin-7-yl]-2-(oxan-2-yl)-2,3-dihydropyridazin-3-one (200 mg, 0.353 mmol, 1 equiv.) in DCM (5 mL) was added TFA (2 mL) at room temperature. The resulting mixture was stirred for 1 h at room temperature. The reaction was monitored by LCMS. The mixture was basified to pH 8 with saturated NaHCO$_3$ (aq.). The resulting mixture was concentrated under reduced pressure. The residue was purified by Prep-HPLC with the following conditions (Column: XBridge Prep OBD C18 Column 30×150 mm 5 um; Mobile Phase A: undefined, Mobile Phase B: undefined; Flow rate: 60 mL/min; Gradient: 25% B to 50% B in 8 min; 220 nm; Rt: 7.67 min) to afford 4-chloro-5-[2-[(2-hydroxyethyl)amino]-4-[2-(trifluoromethyl)phenoxy]-5H,6H,7H,8H-pyrido[3,4-d]pyrimidin-7-yl]-2,3-dihydropyridazin-3-one (106.3 mg) as a white solid.

Example 11. Synthesis of Compounds 138 and 139

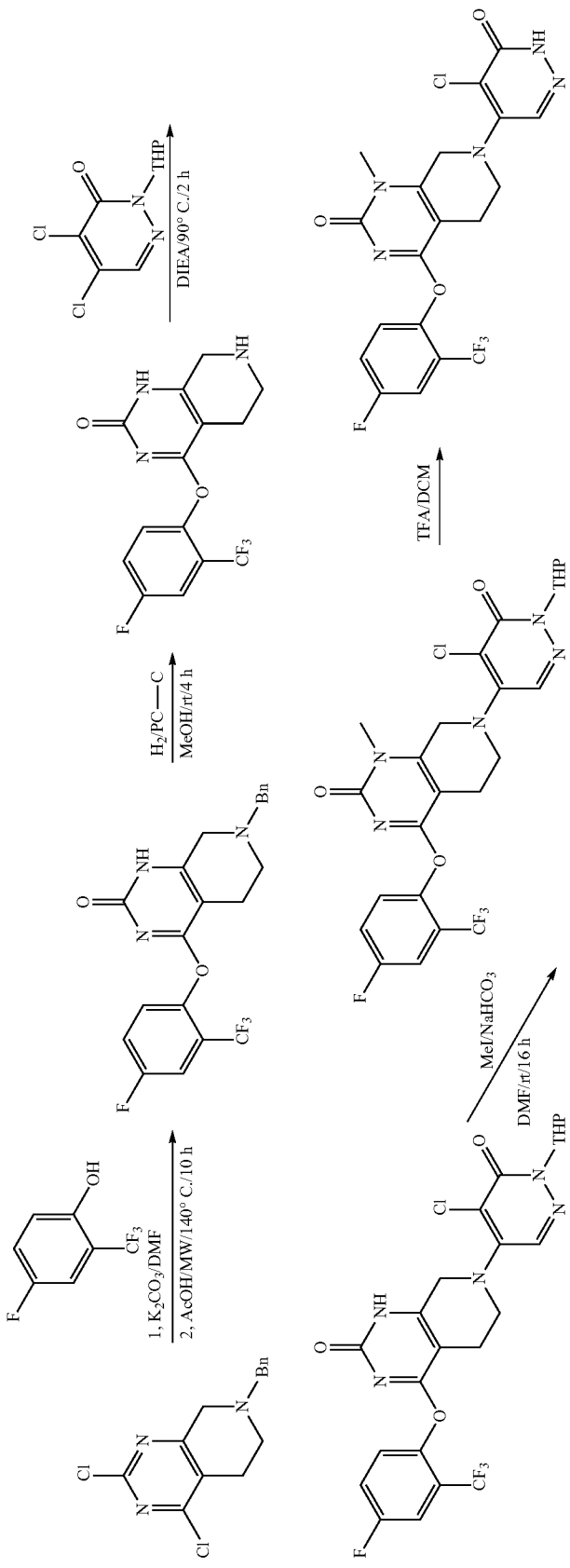

7-Benzyl-2-chloro-4-[4-fluoro-2-(trifluoromethyl) phenoxy]-5H,6H,7H,8H-pyrido[3,4-d]pyrimidine To a stirred solution of 4-fluoro-2-(trifluoromethyl)phenol (1469.32 mg, 8.158 mmol, 1.20 equiv.) and 7-benzyl-2,4-dichloro-5H,6H,7H,8H-pyrido[3,4-d]pyrimidine (2000 mg, 6.799 mmol, 1 equiv.) in DMF (20 mL) was added $K_2CO_3$ (1879.20 mg, 13.597 mmol, 2 equiv.) at room temperature. The solution was stirred at 70° C. for 0.5 hours. The mixture was concentrated under reduced pressure. The residue was purified by reverse phase flash chromatography with the following conditions: Column: Spherical C18, 20-40 um, 330 g; Mobile Phase A: Water (plus 5 mM TFA); Mobile Phase B: acetonitrile; Flow rate: 80 mL/min; Gradient: 5%-5% B, 10 min, 70% B-95% B gradient in 20 min; Detector: 254 nm. The fractions containing the desired product were collected at 95% B and concentrated under reduced pressure to afford 7-benzyl-2-chloro-4-[4-fluoro-2-(trifluoromethyl)phenoxy]-5H,6H,7H,8H-pyrido[3,4-d]pyrimidine (2331 mg, 78.31%) as an off-white solid.

7-Benzyl-4-[4-fluoro-2-(trifluoromethyl)phenoxy]-1H,2H,5H,6H,7H,8H-pyrido[3,4-d]pyrimidin-2-one A solution of 7-benzyl-2-chloro-4-[4-fluoro-2-(trifluoromethyl)phenoxy]-5H,6H,7H,8H-pyrido[3,4-d]pyrimidine (2 g, 4.568 mmol, 1 equiv.) in HAc (10 mL, 174.515 mmol, 38.20 equiv.) and H2O (1 mL, 55.508 mmol, 12.15 equiv.) was stirred for 10 hours at 140° C. under N2 atmosphere. The resulting mixture was concentrated under reduced pressure. The residue was purified by Prep-TLC (PE/EA 1/1) to afford 7-benzyl-4-[4-fluoro-2-(trifluoromethyl)phenoxy]-1H,2H,5H,6H,7H,8H-pyrido[3,4-d]pyrimidin-2-one (530 mg, 27.67%) as a light yellow solid.

4-[4-Fluoro-2-(trifluoromethyl)phenoxy]-1H,2H,5H,6H,7H,8H-pyrido[3,4-d]pyrimidin-2-one To a solution of 7-benzyl-4-[4-fluoro-2-(trifluoromethyl)phenoxy]-1H,2H,5H,6H,7H,8H-pyrido[3,4-d]pyrimidin-2-one (530 mg, 1.264 mmol, 1 equiv.) in MeOH (10 mL, 246.989 mmol, 195.44 equiv.) was added Pd/C (268.98 mg, 2.528 mmol, 2 equiv.) under nitrogen atmosphere. The mixture was hydrogenated at room temperature for 4 hours under hydrogen atmosphere using a hydrogen balloon, filtered through a Celite pad and concentrated under reduced pressure. To afford 4-[4-fluoro-2-(trifluoromethyl)phenoxy]-1H,2H,5H,6H,7H,8H-pyrido[3,4-d]pyrimidin-2-one (430 mg, 103.34%) as a light yellow solid.

4-Chloro-5-[4-[4-fluoro-2-(trifluoromethyl)phenoxy]-2-oxo-1H,2H,5H,6H,7H,8H-pyrido[3,4-d]pyrimidin-7-yl]-2-(oxan-2-yl)-2,3-dihydropyridazin-3-one A mixture of 4-[4-fluoro-2-(trifluoromethyl)phenoxy]-1H,2H,5H,6H,7H,8H-pyrido[3,4-d]pyrimidin-2-one (430 mg, 1.306 mmol, 1 equiv.) and 4,5-dichloro-2-(oxan-2-yl)-2,3-dihydropyridazin-3-one (357.84 mg, 1.437 mmol, 1.1 equiv.) in DIEA (337.58 mg, 2.612 mmol, 2.00 equiv.) was stirred for 2 hours at 100° C. under N2 atmosphere. The residue was purified by Prep-TLC (PE/EA 1/1) to afford 4-chloro-5-[4-[4-fluoro-2-(trifluoromethyl)phenoxy]-2-oxo-1H,2H,5H,6H,7H,8H-pyrido[3,4-d]pyrimidin-7-yl]-2-(oxan-2-yl)-2,3-dihydropyridazin-3-one (210 mg, 29.67%) as a light yellow solid.

4-Chloro-5-[4-[4-fluoro-2-(trifluoromethyl)phenoxy]-1-methyl-2-oxo-1H,2H,5H,6H,7H,8H-pyrido[3,4-d]pyrimidin-7-yl]-2-(oxan-2-yl)-2,3-dihydropyridazin-3-one and 4-chloro-5-[4-[4-fluoro-2-(trifluoromethyl)phenoxy]-2-methoxy-5H,6H,7H,8H-pyrido[3,4-d]pyrimidin-7-yl]-2-(oxan-2-yl)-2,3-dihydropyridazin-3-one To a solution of 4-chloro-5-[4-[4-fluoro-2-(trifluoromethyl)phenoxy]-2-oxo-1H,2H,5H,6H,7H,8H-pyrido[3,4-d]pyrimidin-7-yl]-2-(oxan-2-yl)-2,3-dihydropyridazin-3-one (90 mg, 0.166 mmol, 1 equiv.) and NaHCO3 (27.90 mg, 0.332 mmol, 2 equiv.) in DMF (10 mL, 129.218 mmol, 778.02 equiv.) was added $CH_3I$ (47.15 mg, 0.332 mmol, 2.00 equiv.) dropwise at 0° C. under nitrogen atmosphere. The mixture was stirred at 25° C. for 16 hours. The resulting mixture was concentrated under reduced pressure. The residue was purified by Prep-TLC (PE/EA 0/1) to afford 4-chloro-5-[4-[4-fluoro-2-(trifluoromethyl)phenoxy]-1-methyl-2-oxo-1H,2H,5H,6H,7H,8H-pyrido[3,4-d]pyrimidin-7-yl]-2-(oxan-2-yl)-2,3-dihydropyridazin-3-one (60 mg, 64.99%) and 4-chloro-5-[4-[4-fluoro-2-(trifluoromethyl)phenoxy]-2-methoxy-5H,6H,7H,8H-pyrido[3,4-d]pyrimidin-7-yl]-2-(oxan-2-yl)-2,3-dihydropyridazin-3-one (15 mg) as a light yellow solid.

4-Chloro-5-[4-[4-fluoro-2-(trifluoromethyl)phenoxy]-1-methyl-2-oxo-1H,2H,5H,6H,7H,8H-pyrido[3,4-d]pyrimidin-7-yl]-2,3-dihydropyridazin-3-one To a solution of 4-chloro-5-[4-[4-fluoro-2-(trifluoromethyl)phenoxy]-1-methyl-2-oxo-1H,2H,5H,6H,7H,8H-pyrido[3,4-d]pyrimidin-7-yl]-2-(oxan-2-yl)-2,3-dihydropyridazin-3-one (60 mg, 0.108 mmol, 1 equiv.) in DCM (10 mL, 157.300 mmol, 1457.41 equiv.) was added TFA (123.07 mg, 1.079 mmol, 10 equiv.) at 25° C. The resulting mixture was concentrated under reduced pressure. The crude product (100 mg) was purified by Prep-HPLC with the following conditions (Column: XBridge Shield RP18 OBD Column 30*150 mm, 5 um; Mobile Phase A: Water (10 mM $NH_4HCO_3$), Mobile Phase B: acetonitrile; Flow rate: 60 mL/min; Gradient: 20% B to 40% B in 7 min; 220 nm; Rt: 6.63 min) to afford 4-chloro-5-[4-[4-fluoro-2-(trifluoromethyl)phenoxy]-1-methyl-2-oxo-1H,2H,5H,6H,7H,8H-pyrido[3,4-d]pyrimidin-7-yl]-2,3-dihydropyridazin-3-one (29.3 mg, 57.54%) as a white solid.

4-Chloro-5-[4-[4-fluoro-2-(trifluoromethyl)phenoxy]-2-methoxy-5H,6H,7H,8H-pyrido[3,4-d]pyrimidin-7-yl]-2,3-dihydropyridazin-3-one To a solution of 4-chloro-5-[4-[4-fluoro-2-(trifluoromethyl)phenoxy]-2-methoxy-5H,6H,7H,8H-pyrido[3,4-d]pyrimidin-7-yl]-2-(oxan-2-yl)-2,3-dihydropyridazin-3-one (15 mg, 0.027 mmol, 1 equiv.) in DCM (5 mL, 78.650 mmol, 2914.83 equiv.) was added TFA (30.77 mg, 0.270 mmol, 10 equiv.) at 25° C. The resulting mixture was concentrated under reduced pressure. The crude product (20 mg) was purified by Prep-HPLC with the following conditions (Column: XBridge Shield RP18 OBD Column 30*150 mm, 5 um; Mobile Phase A: Water (10 mM $NH_4HCO_3$), Mobile Phase B: acetonitrile; Flow rate: 60 mL/min; Gradient: 20% B to 40% B in 7 min; 220 nm; Rt: 6.63 min) to afford 4-chloro-5-[4-[4-fluoro-2-(trifluoromethyl)phenoxy]-2-methoxy-5H,6H,7H,8H-pyrido[3,4-d]pyrimidin-7-yl]-2,3-dihydropyridazin-3-one (7.5 mg, 58.91%) as a white solid.

Example 12. Synthesis of Compound 110

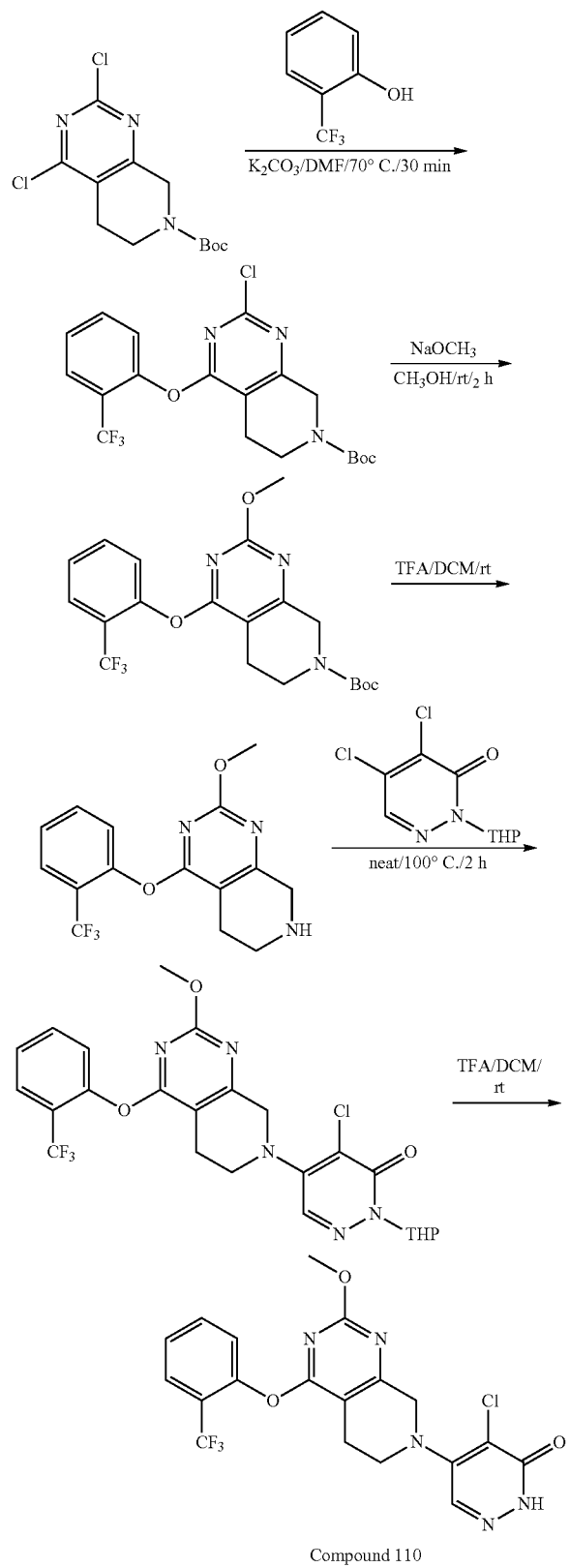

Compound 110

Tert-Butyl 2-chloro-4-[2-(trifluoromethyl)phenoxy]-5H,6H,7H,8H-pyrido[3,4-d]pyrimidine-7-carboxylate To a stirred solution of tert-butyl 2,4-dichloro-5H,6H,7H,8H-pyrido[3,4-d]pyrimidine-7-carboxylate (2 g, 6.58 mmol, 1 equiv.) and 2-(trifluoromethyl)phenol (1.6 g, 9.86 mmol, 1.5 equiv.) in acetonitrile (20 mL) was added DBU (2.0 g, 13.15 mmol, 2 equiv.) at room temperature. The solution was stirred at rt for 4 hours. The mixture was concentrated under reduced pressure. The residue was purified by Prep-TLC (PE/EtOAc 10:1) to afford tert-butyl 2-chloro-4-[2-(trifluoromethyl)phenoxy]-5H,6H,7H,8H-pyrido[3,4-d]pyrimidine-7-carboxylate (700 mg, 24.77%) as colorless oil.

Tert-Butyl 2-methoxy-4-[2-(trifluoromethyl)phenoxy]-5H,6H,7H,8H-pyrido[3,4-d]pyrimidine-7-carboxylate To a solution of tert-butyl 2-chloro-4-[2-(trifluoromethyl)phenoxy]-5H,6H,7H,8H-pyrido[3,4-d]pyrimidine-7-carboxylate (1 g, 2.327 mmol, 1 equiv.) in MeOH (20 mL, 493.978 mmol, 212.32 equiv.) was added NaOMe (0.25 g, 0.005 mmol, 2 equiv.) at 25° C. The mixture was stirred at 25° C. for 4 hours. The resulting mixture was concentrated under reduced pressure. The residue was purified by silica gel column chromatography, eluted with PE/EA (10/1 to 1/1) to afford tert-butyl 2-methoxy-4-[2-(trifluoromethyl)phenoxy]-5H,6H,7H,8H-pyrido[3,4-d]pyrimidine-7-carboxylate (100 mg, 10.10%) as a light yellow solid.

2-Methoxy-4-[2-(trifluoromethyl)phenoxy]-5H,6H,7H,8H-pyrido[3,4-d]pyrimidine To a solution of tert-butyl 2-methoxy-4-[2-(trifluoromethyl)phenoxy]-5H,6H,7H,8H-pyrido[3,4-d]pyrimidine-7-carboxylate (100 mg, 0.235 mmol, 1 equiv.) in DCM (10 mL) was added TFA (268.03 mg, 2.351 mmol, 10 equiv.) at 25° C. The solution was stirred at 25° C. for 4 hours. The resulting mixture was concentrated under reduced pressure. The crude product (150 mg) was purified by Prep-HPLC with the following conditions (Column: XBridge Shield RP18 OBD Column 30*150 mm, 5 um; Mobile Phase A: Water (10 mM $NH_4HCO_3$), Mobile Phase B: acetonitrile; Flow rate: 60 mL/min; Gradient: 20% B to 40% B in 7 min; 220 nm; Rt: 6.63 min) to afford 2-methoxy-4-[2-(trifluoromethyl)phenoxy]-5H,6H,7H,8H-pyrido[3,4-d]pyrimidine (80 mg, 104.62%) as a light yellow solid.

4-Chloro-5-[2-methoxy-4-[2-(trifluoromethyl)phenoxy]-5H,6H,7H,8H-pyrido[3,4-d]pyrimidin-7-yl]-2-(oxan-2-yl)-2,3-dihydropyridazin-3-one A solution of 2-methoxy-4-[2-(trifluoromethyl)phenoxy]-5H,6H,7H,8H-pyrido[3,4-d]pyrimidine (80 mg, 0.246 mmol, 1 equiv.) and 4,5-dichloro-2-(oxan-2-yl)-2,3-dihydropyridazin-3-one (61.26 mg, 0.246 mmol, 1 equiv.) in DIEA (63.57 mg, 0.492 mmol, 2.00 equiv.) was stirred for 2 hours at 100° C. under nitrogen atmosphere. The residue was purified by silica gel column chromatography, eluted with PE/EA (5/1 to 1/1) to afford 4-chloro-5-[2-methoxy-4-[2-(trifluoromethyl)phenoxy]-5H,6H,7H,8H-pyrido[3,4-d]

pyrimidin-7-yl]-2-(oxan-2-yl)-2,3-dihydropyridazin-3-one (120 mg, 90.71%) as a light yellow solid.

4-Chloro-5-[2-methoxy-4-[2-(trifluoromethyl)phenoxy]-5H,6H,7H,8H-pyrido[3,4-d]pyrimidin-7-yl]-2,3-dihydropyridazin-3-one To a solution of 4-chloro-5-[2-methoxy-4-[2-(trifluoromethyl)phenoxy]-5H,6H,7H,8H-pyrido[3,4-d]pyrimidin-7-yl]-2-(oxan-2-yl)-2,3-dihydropyridazin-3-one (120 mg, 0.223 mmol, 1 equiv.) in DCM (5 mL, 78.650 mmol, 352.56 equiv.) was added TFA (254.36 mg, 2.231 mmol, 10.00 equiv.) at 25° C. The resulting mixture was concentrated under reduced pressure. The crude product (150 mg) was purified by Prep-HPLC with the following conditions (Column: XBridge Shield RP18 OBD Column 30*150 mm, 5 um; Mobile Phase A: Water (10 mM NH4HCO3), Mobile Phase B: acetonitrile; Flow rate: 60 mL/min; Gradient: 20% B to 40% B in 7 min; 220 nm; Rt: 6.63 min) to afford 4-chloro-5-[2-methoxy-4-[2-(trifluoromethyl)phenoxy]-5H,6H,7H,8H-pyrido[3,4-d]pyrimidin-7-yl]-2,3-dihydropyridazin-3-one (24.1 mg, 23.81%) as a white solid.

Example 13. Synthesis of Compound 108

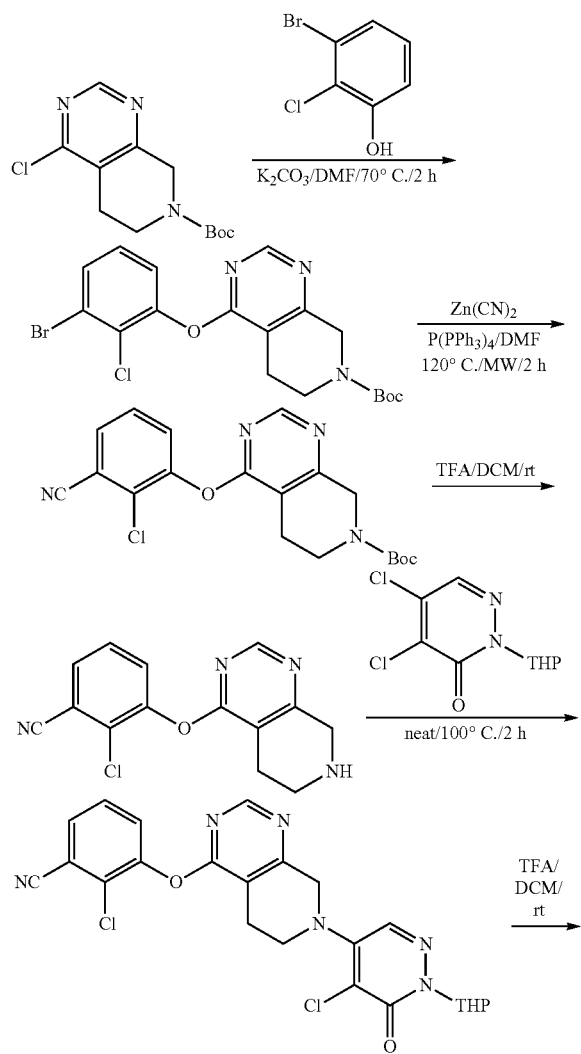

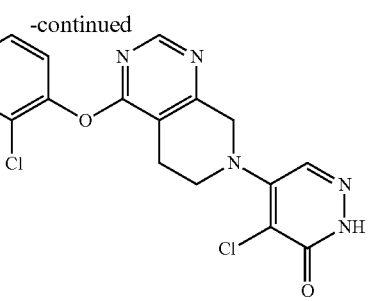

Compound 108

Tert-Butyl 4-(3-bromo-2-chlorophenoxy)-5H,6H,7H,8H-pyrido[3,4-d]pyrimidine-7-carboxylate To a stirred solution of tert-butyl 4-chloro-5H,6H,7H,8H-pyrido[3,4-d]pyrimidine-7-carboxylate (500 mg, 1.854 mmol, 1 equiv.) and 3-bromo-2-chlorophenol (461.46 mg, 2.224 mmol, 1.20 equiv.) in DMF (10 mL) was added K2CO3 (512.38 mg, 3.707 mmol, 2 equiv). The resulting mixture was stirred for 1 h at 70° C. The mixture was purified by reverse flash chromatography with the following conditions: Column: (spherical C18, 20-40 um, 330 g; Mobile Phase A: Water (5 mM NH4HCO3), Mobile Phase B: acetonitrile; Flow rate: 80 mL/min; Gradient: 20% B to 60% B in 55 min; 254 nm). The fractions containing the desired product were collected at 40% B and concentrated under reduced pressure. This resulted in tert-butyl 4-(3-bromo-2-chlorophenoxy)-5H,6H,7H,8H-pyrido[3,4-d]pyrimidine-7-carboxylate (300 mg, 36.72%) as an off-white solid.

Tert-Butyl 4-(2-chloro-3-cyanophenoxy)-5H,6H,7H,8H-pyrido[3,4-d]pyrimidine-7-carboxylate To a stirred solution of tert-butyl 4-(3-bromo-2-chlorophenoxy)-5H,6H,7H,8H-pyrido[3,4-d]pyrimidine-7-carboxylate (450 mg, 1.021 mmol, 1 equiv.) and zinc dicarbonitrile (143.87 mg, 1.225 mmol, 1.20 equiv.) in DMF (5 mL) was added Pd(PPh3)4 (117.99 mg, 0.102 mmol, 0.1 equiv). The resulting mixture was stirred for 2 hours at 120° C. under nitrogen atmosphere. The residue was purified by reverse flash chromatography with the following conditions: Column: spherical C18, 20-40 um, 180 g; Mobile Phase A: Water (5 mM NH4HCO3), Mobile Phase B: acetonitrile; Flow rate: 45 mL/min; Gradient: 10% B to 60% B in 55 min; 254 nm. The fractions containing the desired product were collected at 40% B and concentrated under reduced pressure. This resulted in tert-butyl 4-(2-chloro-3-cyanophenoxy)-5H,6H,7H,8H-pyrido[3,4-d]pyrimidine-7-carboxylate (280 mg, 70.89%) as a light yellow solid.

2-Chloro-3-[5H,6H,7H,8H-pyrido[3,4-d]pyrimidin-4-yloxy]benzonitrile

To a stirred solution of tert-butyl 4-(2-chloro-3-cyanophenoxy)-5H,6H,7H,8H-pyrido[3,4-d]pyrimidine-7-carboxylate (100 mg, 0.259 mmol, 1 equiv.) in DCM (3 mL) was added TFA (1 mL). The resulting mixture was stirred for 2 hours at room temperature under air atmosphere. The resulting mixture was concentrated under reduced pressure. The mixture was basified to pH 7 with saturated NH4HCO3 (aq.). The mixture was purified by reverse flash chromatography with the following conditions: Column: spherical C18, 20-40 um, 180 g; Mobile Phase A: Water (5 mM NH4HCO3), Mobile Phase B: acetonitrile; Flow rate: 45 mL/min; Gradient: 30% B to 60% B in 30 min; 254 nm). The fractions containing the desired product were collected at 45% B and concentrated under reduced pressure. This resulted in 2-chloro-3-[5H,6H,7H,8H-pyrido[3,4-d]pyrimidin-4-yloxy]benzonitrile (60 mg, 80.95%) as a light yellow oil.

2-Chloro-3-([7-[5-chloro-1-(oxan-2-yl)-6-oxo-1,6-dihydropyridazin-4-yl]-5H,6H,7H,8H-pyrido[3,4-d]pyrimidin-4-yl]oxy)benzonitrile To a stirred solution of tert-butyl 4-(2-chloro-3-cyanophenoxy)-5H,6H,7H,8H-pyrido[3,4-d]pyrimidine-7-carboxylate (60 mg, 0.155 mmol, 1 equiv.) and 4,5-dichloro-2-(oxan-2-yl)-2,3-dihydropyridazin-3-one (38.63 mg, 0.155 mmol, 1.00 equiv.) in DIEA (40.09 mg, 0.310 mmol, 2 equiv). The resulting mixture was stirred for hours at 100° C. under air atmosphere. The residue was purified by Prep-TLC (PE/EtOAc 1:1) to afford 2-chloro-3-([7-[5-chloro-1-(oxan-2-yl)-6-oxo-1,6-dihydropyridazin-4-yl]-5H,6H,7H,8H-pyrido[3,4-d]pyrimidin-4-yl]oxy)benzonitrile (50 mg, 64.56%) as a light yellow solid.

2-Chloro-3-[[7-(5-chloro-6-oxo-1,6-dihydropyridazin-4-yl)-5H,6H,7H,8H-pyrido[3,4-d]pyrimidin-4-yl]oxy]benzonitrile To a stirred solution of 2-chloro-3-([7-[5-chloro-1-(oxan-2-yl)-6-oxo-1,6-dihydropyridazin-4-yl]-5H,6H,7H,8H-pyrido[3,4-d]pyrimidin-4-yl]oxy)benzonitrile (50 mg, 0.100 mmol, 1 equiv.) in DCM (3 mL) was added TFA (1 mL). The resulting mixture was stirred for 2 hours at room temperature. The resulting mixture was concentrated under reduced pressure. The mixture was basified to pH 7 with saturated NH4CO3 (aq.). The crude product was purified by Prep-HPLC with the following conditions (Column: XBridge Prep OBD C18 Column 30×150 mm 5 um; Mobile Phase A: Water (10 mM NH4HCO3), Mobile Phase B: acetonitrile; Flow rate: 60 mL/min; Gradient: 20% B to 42% B in 8 min; 220 nm; Rt: 7.58 min) to afford 2-chloro-3-[[7-(5-chloro-6-oxo-1,6-dihydropyridazin-4-yl)-5H,6H,7H,8H-pyrido[3,4-d]pyrimidin-4-yl]oxy]benzonitrile (14.5 mg, 34.88%) as an off-white solid.

Example 14. Synthesis of Compound 111

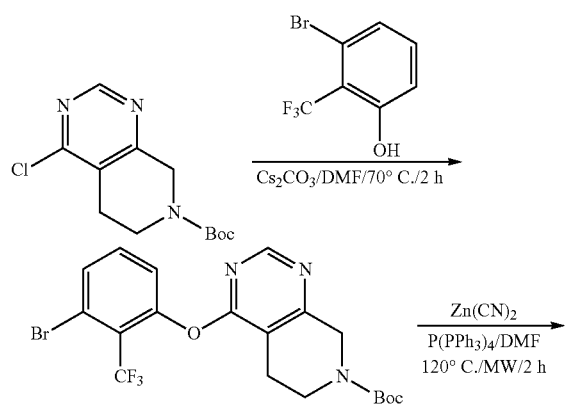

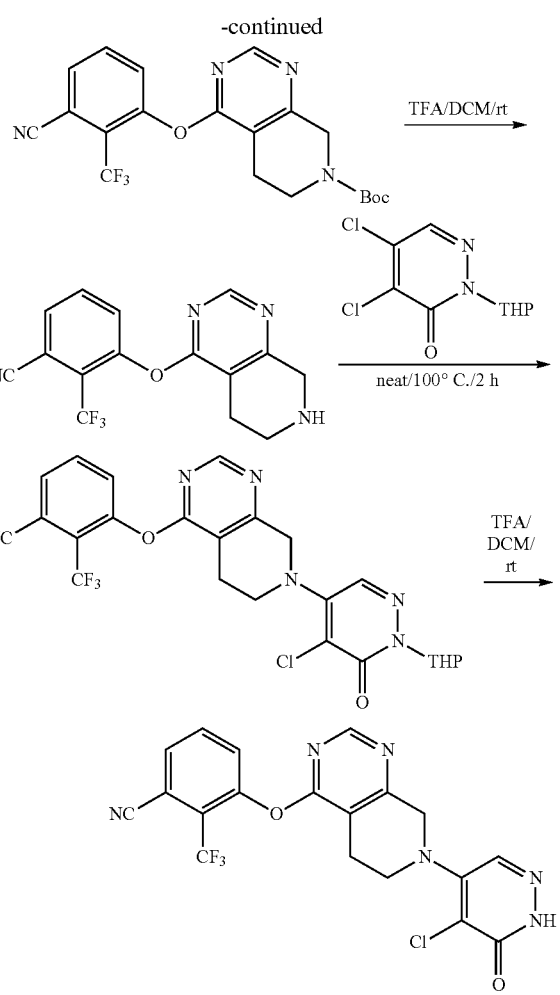

Compound 111

Tert-Butyl 4-[3-bromo-2-(trifluoromethyl)phenoxy]-5H,6H,7H,8H-pyrido[3,4-d]pyrimidine-7-carboxylate To a stirred mixture of tert-butyl 4-chloro-5H,6H,7H,8H-pyrido[3,4-d]pyrimidine-7-carboxylate (180 mg, 0.667 mmol, 1 equiv.) and 3-bromo-2-(trifluoromethyl)phenol (241.25 mg, 1.001 mmol, 1.50 equiv.) in DMF (10 mL) was added $Cs_2CO_3$ (434.86 mg, 1.335 mmol, 2.00 equiv.) in portions at rt under nitrogen atmosphere. The resulting mixture was stirred for 0.5 hours at 70° C. under nitrogen atmosphere. The reaction was monitored by LCMS. The mixture was allowed to cool down to rt. The resulting mixture was concentrated under reduced pressure. The resulting mixture was extracted with EtOAc (3×200 mL). The combined organic layers were washed with brine (2×100 mL), dried over anhydrous $Na_2SO_4$. After filtration, the filtrate was concentrated under reduced pressure. The residue was purified by reverse flash chromatography with the following conditions (Column, C18 silica gel; mobile phase, acetonitrile in water, 40% to 85% gradient in 30 min; detector, UV 220 nm) to afford tert-butyl 4-[3-bromo-2-(trifluoromethyl)phenoxy]-5H,6H,7H,8H-pyrido[3,4-d]pyrimidine-7-carboxylate (150 mg, 47.39%) as a yellow oil.

Tert-Butyl 4-[3-cyano-2-(trifluoromethyl)phenoxy]-5H,6H,7H,8H-pyrido[3,4-d]pyrimidine-7-carboxylate To a stirred mixture of tert-butyl 4-[3-bromo-2-(trifluoromethyl)phenoxy]-5H,6H,7H,8H-pyrido[3,4-d]pyrimidine-7-carboxylate (150 mg, 0.316 mmol, 1 equiv.) and Zn(CN)$_2$ (111.43 mg, 0.949 mmol, 3.00 equiv.) in DMF (8 mL) was added Pd(PPh3)4 (36.55 mg, 0.032 mmol, 0.1 equiv.) in portions at rt under nitrogen atmosphere. The final reaction mixture was irradiated with microwave radiation for 3 hours at 150° C. The reaction was monitored by LCMS. The residue was purified by reverse flash chromatography with the following conditions (Column, C18 silica gel; mobile phase, acetonitrile in water, 40% to 95% gradient in 30 min; detector, UV 220 nm) to afford tert-butyl 4-[3-cyano-2-(trifluoromethyl)phenoxy]-5H,6H,7H,8H-pyrido[3,4-d]pyrimidine-7-carboxylate (70 mg, 52.65%) as a yellow oil.

3-[5H,6H,7H,8H-pyrido[3,4-d]pyrimidin-4-yloxy]-2-(trifluoromethyl)benzonitrile To a stirred solution of tert-butyl 4-[3-cyano-2-(trifluoromethyl)phenoxy]-5H,6H,7H,8H-pyrido[3,4-d]pyrimidine-7-carboxylate (70 mg) in DCM (10 mL) was added TFA (1 mL) dropwise at rt. The reaction mixture was stirred for 2 hours at rt. The reaction was monitored by LCMS. The resulting mixture was concentrated under reduced pressure. The residue was basified to pH=8 with saturated NH$_4$HCO$_3$ (aq.). The resulting mixture was extracted with DCM (3×100 mL). The combined organic layers were washed with brine (1×100 mL), dried over anhydrous Na$_2$SO$_4$. After filtration, the filtrate was concentrated under reduced pressure. The residue was purified by reverse flash chromatography with the following conditions (Column, C18 silica gel; mobile phase, acetonitrile in water, 30% to 60% gradient in 20 min; detector, UV 220 nm) to afford 3-[5H,6H,7H,8H-pyrido[3,4-d]pyrimidin-4-yloxy]-2-(trifluoromethyl)benzonitrile (40 mg) as a yellow oil.

3-([7-[5-chloro-1-(oxan-2-yl)-6-oxo-1,6-dihydropyridazin-4-yl]-5H,6H,7H,8H-pyrido[3,4-d]pyrimidin-4-yl]oxy)-2-(trifluoromethyl)benzonitrile Into a 25 mL round-bottom flask were added 3-[5H,6H,7H,8H-pyrido[3,4-d]pyrimidin-4-yloxy]-2-(trifluoromethyl)benzonitrile (40 mg, 0.125 mmol, 1 equiv), 4,5-dichloro-2-(oxan-2-yl)-2,3-dihydropyridazin-3-one (62.22 mg, 0.250 mmol, 2.00 equiv.) and DIEA (48.42 mg, 0.375 mmol, 3.00 equiv.) at rt under nitrogen atmosphere. The resulting mixture was stirred for 16 hours at 90° C. under nitrogen atmosphere. The residue was purified by Prep-TLC (PE/EtOAc=5/1) to afford 3-([7-[5-chloro-1-(oxan-2-yl)-6-oxo-1,6-dihydropyridazin-4-yl]-5H,6H,7H,8H-pyrido[3,4-d]pyrimidin-4-yl]oxy)-2-(trifluoromethyl)benzonitrile (50 mg, 75.12%) as a yellow oil.

3-[[7-(5-Chloro-6-oxo-1,6-dihydropyridazin-4-yl)-5H,6H,7H,8H-pyrido[3,4-d]pyrimidin-4-yl]oxy]-2-(trifluoromethyl)benzonitrile To a stirred solution of 3-([7-[5-chloro-1-(oxan-2-yl)-6-oxo-1,6-dihydropyridazin-4-yl]-5H,6H,7H,8H-pyrido[3,4-d]pyrimidin-4-yl]oxy)-2-(trifluoromethyl)benzonitrile (50 mg) in DCM (10 mL) was added TFA (1 mL) dropwise at rt. The reaction mixture was stirred for 2 hours at rt. The reaction was monitored by LCMS. The resulting mixture was concentrated under reduced pressure. The residue was basified to pH=8 with saturated NH$_4$HCO$_3$ (aq.). The resulting mixture was extracted with DCM (3×100 mL). The combined organic layers were washed with brine (1×100 mL), dried over anhydrous Na$_2$SO$_4$. After filtration, the filtrate was concentrated under reduced pressure. The residue was purified by Prep-HPLC with the following conditions (Column: XBridge Prep OBD C18 Column 30×150 mm 5 um; Mobile Phase A: Water (10 mM NH$_4$HCO$_3$), Mobile Phase B: acetonitrile; Flow rate: 60 mL/min; Gradient: 25% B to 45% B in 8 min; 220 nm; Rt: 7.07 min) to afford 3-[[7-(5-chloro-6-oxo-1,6-dihydropyridazin-4-yl)-5H,6H,7H,8H-pyrido[3,4-d]pyrimidin-4-yl]oxy]-2-(trifluoromethyl)benzonitrile (10.8 mg) as a white solid.

Example 15. Synthesis of Compounds 126 and 126a

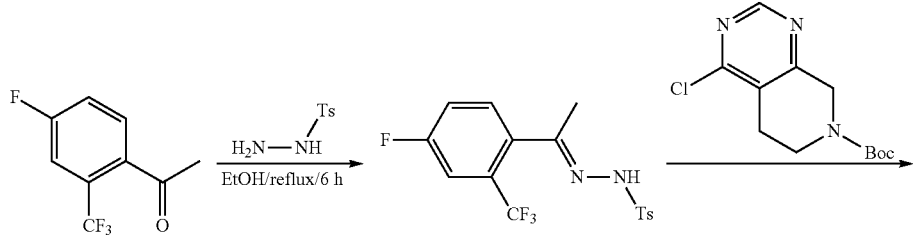

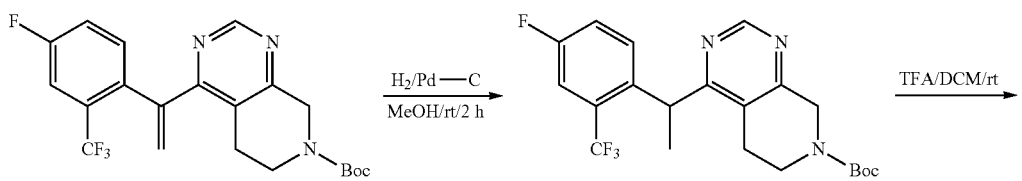

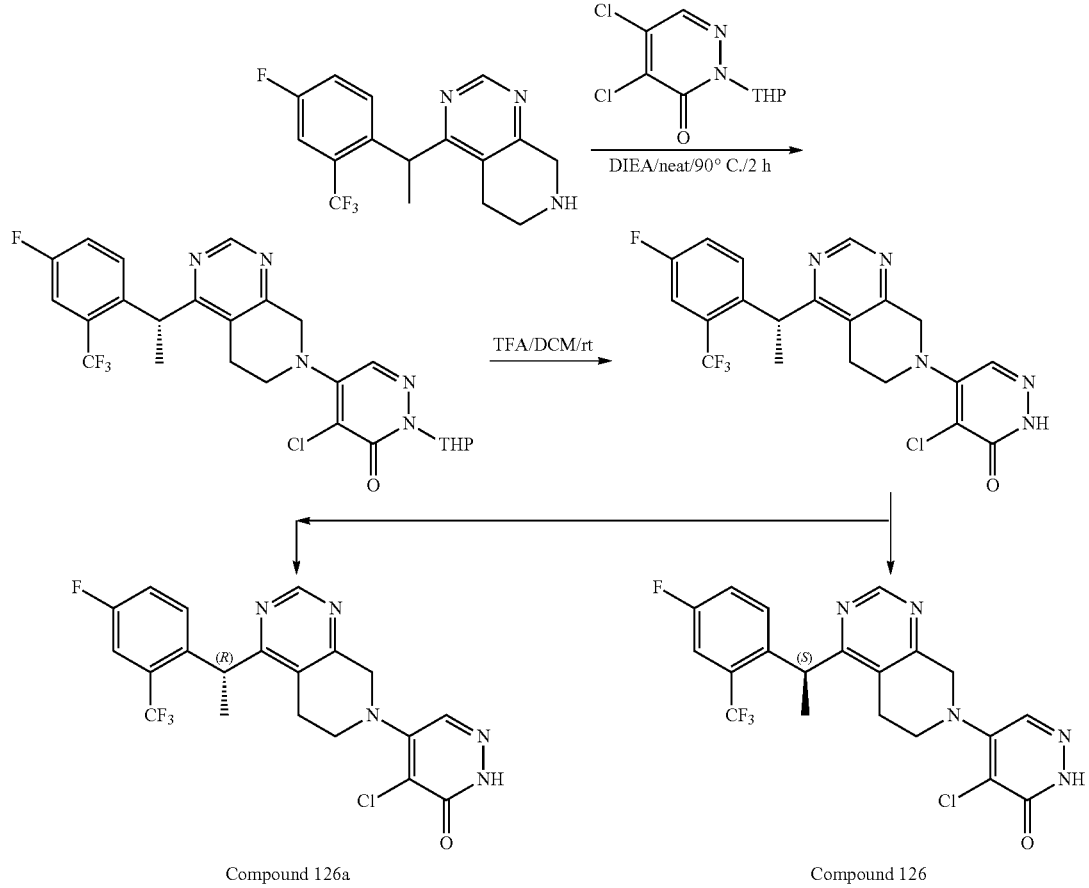

Compound 126a

Compound 126

N-[(1E)-1-[4-fluoro-2-(trifluoromethyl)phenyl]ethylidene]-4-methylbenzene-1-sulfonohydrazide To a stirred solution of 1-[4-fluoro-2-(trifluoromethyl)phenyl]ethan-1-one (2 g, 9.702 mmol, 1 equiv.) in EtOH (40 mL) was added 4-methylbenzene-1-sulfonohydrazide (1.81 g, 9.719 mmol, 1.00 equiv.) in portions at rt under nitrogen atmosphere. The resulting mixture was stirred for 6 hours at 90° C. under nitrogen atmosphere. The reaction was monitored by LCMS. The mixture was allowed to cool down to rt. The resulting mixture was concentrated under vacuum. The residue was purified by reverse phase flash chromatography with the following conditions: Column: Spherical C18, 20-40 um, 330 g; Mobile Phase A: Water (plus 5 mM AcOH); Mobile Phase B: acetonitrile; Flow rate: 80 mL/min; Gradient: 5%-5% B, 10 min, 45% B-70% B gradient in 20 min; Detector: 220 nm. The fractions containing the desired product were collected at 60% B and concentrated under reduced pressure to afford N-[(1E)-1-[4-fluoro-2-(trifluoromethyl)phenyl]ethylidene]-4-methylbenzene-1-sulfonohydrazide (2.5 g, 68.83%) as a white solid.

Tert-Butyl 4-[1-[4-fluoro-2-(trifluoromethyl)phenyl]ethenyl]-5H,6H,7H,8H-pyrido[3,4-d]pyrimidine-7-carboxylate To a stirred mixture of tert-butyl 4-chloro-5H,6H,7H,8H-pyrido[3,4-d]pyrimidine-7-carboxylate (750 mg, 2.781 mmol, 1 equiv.) and N-[(1E)-1-[4-fluoro-2-(trifluoromethyl)phenyl]ethylidene]-4-methylbenzene-1-sulfonohydrazide (2081.80 mg, 5.561 mmol, 2.00 equiv.) in 1,4-dioxane (20 mL) were added Pd(acetonitrile)$_2$Cl$_2$ (72.14 mg, 0.278 mmol, 0.10 equiv), Dppf (307.18 mg, 0.556 mmol, 0.2 equiv.) and t-BuOLi (489.71 mg, 6.117 mmol, 2.20 equiv.) in portions at rt under nitrogen atmosphere. The final reaction mixture was irradiated with microwave radiation for 2 hours at 100° C. The reaction was monitored by LCMS. The mixture was allowed to cool down to rt. The resulting mixture was filtered, the filter cake was washed with EtOAc (2×50 mL). The filtrate was concentrated under reduced pressure. The residue was purified by reverse phase flash chromatography with the following conditions: Column: Spherical C18, 20-40 um, 330 g; Mobile Phase A: Water (plus 5 mM AcOH); Mobile Phase B: acetonitrile; Flow rate: 80 mL/min; Gradient: 5%-5% B, 10 min, 50% B-90% B gradient in 30 min; Detector: 220 nm. The fractions containing the desired product were collected at 85% B and concentrated under reduced pressure to afford tert-butyl 4-[1-[4-fluoro-2-(trifluoromethyl)phenyl]ethenyl]-5H,6H,7H,8H-pyrido[3,4-d]pyrimidine-7-carboxylate (800 mg, 67.95%) as a brown oil.

Tert-Butyl 4-[1-[4-fluoro-2-(trifluoromethyl)phenyl]ethyl]-5H,6H,7H,8H-pyrido[3,4-d]pyrimidine-7-carboxylate To a solution of tert-butyl 4-[1-[4-fluoro-2-(trifluoromethyl)phenyl]ethenyl]-5H,6H,7H,8H-pyrido[3,4-d]pyrimidine-7-carboxylate (150 mg) in 30 mL MeOH was added Pd/C (10%, 30 mg) under nitrogen atmosphere in a 100 mL round-bottom flask. The mixture was hydrogenated at room temperature for 4 hours under hydrogen atmosphere using a hydrogen balloon, filtered through a celite pad and concentrated under reduced pressure. This resulted in tert-butyl 4-[1-[4-fluoro-2-(trifluoromethyl)phenyl]ethyl]-5H,6H,7H, 8H-pyrido[3,4-d]pyrimidine-7-carboxylate (150 mg) as a yellow oil.

4-[1-[4-Fluoro-2-(trifluoromethyl)phenyl]ethyl]-5H, 6H,7H,8H-pyrido[3,4-d]pyrimidine To a stirred solution of tert-butyl 4-[1-[4-fluoro-2-(trifluoromethyl)phenyl]ethyl]-5H,6H,7H,8H-pyrido[3,4-d]pyrimidine-7-carboxylate (150 mg) in DCM (10 mL) was added TFA (1 mL) dropwise at rt. The reaction mixture was stirred for 2 hours at rt. The reaction was monitored by LCMS. The resulting mixture was concentrated under reduced pressure. The residue was basified to pH=8 with saturated $NH_4HCO_3$ (aq.). The resulting mixture was extracted with DCM (3×50 mL). The combined organic layers were washed with brine (1×30 mL), dried over anhydrous $Na_2SO_4$. After filtration, the filtrate was concentrated under reduced pressure. The residue was purified by reverse phase flash chromatography with the following conditions: Column: Spherical C18, 20-40 um, 120 g; Mobile Phase A: Water (plus 5 mM AcOH); Mobile Phase B: acetonitrile; Flow rate: 45 mL/min; Gradient: 5%-5% B, 10 min, 40% B-58% B gradient in 15 min; Detector: 254 nm. The fractions containing the desired product were collected at 53% B and concentrated under reduced pressure to afford 4-[1-[4-fluoro-2-(trifluoromethyl)phenyl]ethyl]-5H,6H,7H, 8H-pyrido[3,4-d]pyrimidine (100 mg) as a yellow oil.

4-chloro-5-(4-[1-[4-fluoro-2-(trifluoromethyl)phenyl]ethyl]-5H,6H,7H,8H-pyrido[3,4-d]pyrimidin-7-yl)-2-(oxan-2-yl)-2,3-dihydropyridazin-3-one Into a 50 mL round-bottom flask were added 4-[1-[4-fluoro-2-(trifluoromethyl)phenyl]ethyl]-5H,6H,7H,8H-pyrido[3,4-d]pyrimidine (100 mg, 0.307 mmol, 1 equiv), 4,5-dichloro-2-(oxan-2-yl)-2,3-dihydropyridazin-3-one (91.88 mg, 0.369 mmol, 1.20 equiv.) and DIEA (119.19 mg, 0.922 mmol, 3.00 equiv.) at rt under nitrogen atmosphere. The resulting mixture was stirred for 2 hours at 90° C. under nitrogen atmosphere. The reaction was monitored by LCMS. The mixture was allowed to cool down to rt. The residue was purified by reverse phase flash chromatography with the following conditions: Column: Spherical C18, 20-40 um, 120 g; Mobile Phase A: Water (plus 5 mM AcOH); Mobile Phase B: acetonitrile; Flow rate: 45 mL/min; Gradient: 5%-5% B, 10 min, 40% B-60% B gradient in 15 min; Detector: 220 nm. The fractions containing the desired product were collected at 53% B and concentrated under reduced pressure to afford 4-chloro-5-(4-[1-[4-fluoro-2-(trifluoromethyl)phenyl]ethyl]-5H,6H,7H,8H-pyrido[3,4-d]pyrimidin-7-yl)-2-(oxan-2-yl)-2,3-dihydropyridazin-3-one (120 mg, 72.57%) as a yellow oil.

4-Chloro-5-[4-[(1S)-1-[4-fluoro-2-(trifluoromethyl) phenyl]ethyl]-5H,6H,7H,8H-pyrido[3,4-d]pyrimidin-7-yl]-2,3-dihydropyridazin-3-one and 4-chloro-5-[4-[(1R)-1-[4-fluoro-2-(trifluoromethyl)phenyl]ethyl]-5H,6H,7H,8H-pyrido[3,4-d]pyrimidin-7-yl]-2,3-dihydropyridazin-3-one To a stirred solution of 4-chloro-5-(4-[1-[4-fluoro-2-(trifluoromethyl)phenyl]ethyl]-5H,6H,7H,8H-pyrido[3,4-d]pyrimidin-7-yl)-2-(oxan-2-yl)-2,3-dihydropyridazin-3-one (200 mg) in DCM (10 mL) was added TFA (1 mL) dropwise at rt. The reaction mixture was stirred for 4 hours at rt. The reaction was monitored by LCMS. The resulting mixture was concentrated under reduced pressure. The residue was basified to pH=8 with saturated NH4HCO3 (aq.). The resulting mixture was extracted with DCM (3×100 mL). The combined organic layers were washed with brine (1×100 mL), dried over anhydrous $Na_2SO_4$. After filtration, the filtrate was concentrated under reduced pressure. The residue was purified by Chiral-Prep-HPLC with the following conditions (Column: XBridge Prep Phenyl OBD Column 19×150 mm 5 um 13 nm; Mobile Phase A: Mobile Phase B: Flow rate: 60 mL/min; Gradient: 20% B to 37% B in 8 min; 220 nm; Rt: 7.97 min). Although the two isomers were separated by this technique, the absolute orientation was not determined. The compound designated as 4-chloro-5-[4-[(1S)-1-[4-fluoro-2-(trifluoromethyl)phenyl]ethyl]-5H,6H, 7H,8H-pyrido[3,4-d]pyrimidin-7-yl]-2,3-dihydropyridazin-3-one (11.8 mg) was obtained at 1.819 min as an off-white solid. The compound designated as 4-chloro-5-[4-[(1R)-1-[4-fluoro-2-(trifluoromethyl)phenyl]ethyl]-5H,6H,7H,8H-pyrido[3,4-d]pyrimidin-7-yl]-2,3-dihydropyridazin-3-one (13.5 mg) was obtained at 2.470 min as a white solid.

Example 16. Synthesis of Compound 133

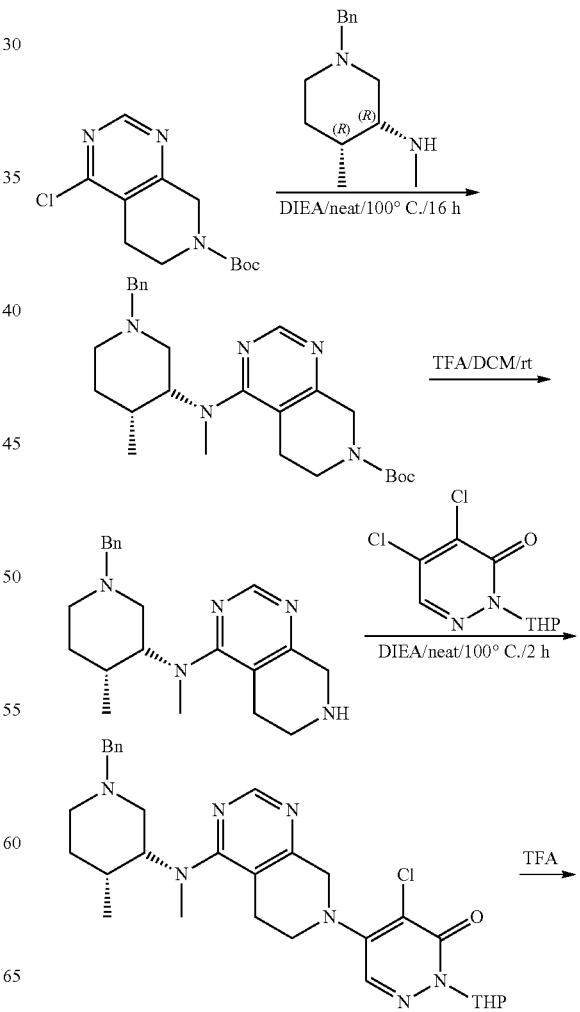

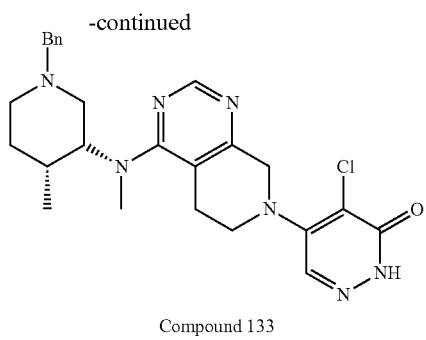

Compound 133 tert-Butyl 4-[methyl[(3R,4R)-4-methylpiperidin-3-yl]amino]-5H,6H,7H,8H-pyrido[3,4-d]pyrimidine-7-carboxylate Into a 25 mL round-bottom flask were added (3R,4R)-1-benzyl-N,4-dimethylpiperidin-3-amine (2.43 g, 0.011 mmol, 1.50 equiv.) and tert-butyl 4-chloro-5H,6H,7H,8H-pyrido[3,4-d]pyrimidine-7-carboxylate (2 g, 0.007 mmol, 1 equiv.) at room temperature. To the mixture was added DIEA (1.92 g, 0.015 mmol, 2.00 equiv.) at rt. The mixture was stirred at 100° C. for 2 hours. The residue was purified by Prep-TLC (PE/EtOAc 1:1) to afford tert-butyl 4-[methyl[(3R,4R)-4-methylpiperidin-3-yl]amino]-5H,6H,7H,8H-pyrido[3,4-d]pyrimidine-7-carboxylate (670 mg, 25.00%) as an off-white solid.

(3R,4R)-1-Benzyl-N,4-dimethyl-N-[5H,6H,7H,8H-pyrido[3,4-d]pyrimidin-4-yl]piperidin-3-amine To a stirred solution of tert-butyl 4-[[(3R,4R)-1-benzyl-4-methylpiperidin-3-yl](methyl)amino]-5H,6H,7H,8H-pyrido[3,4-d]pyrimidine-7-carboxylate (413 mg, 0.914 mmol, 1 equiv.) in DCM (10 mL) was added trifluoroacetic acid (3 mL, 0.026 mmol, 6.00 equiv.) dropwise at 0° C. The mixture was stirred for 2 hours at room temperature. The reaction was monitored by LCMS. The solution was concentrated under reduced pressure. The crude product (362 mg) was purified by Prep-HPLC with the following conditions (Column: XBridge Shield RP18 OBD Column, 5 um, 19*150 mm; Mobile Phase A: Water (10 mM NH4HCO3), Mobile Phase B: acetonitrile; Flow rate: 80 mL/min; Gradient: 30% B to 80% B in 25 min; 220 nm; Rt: 21.65 min) to afford (3R,4R)-1-benzyl-N,4-dimethyl-N-[5H,6H,7H,8H-pyrido[3,4-d]pyrimidin-4-yl]piperidin-3-amine (250 mg, 77.77%) as red oil.

5-(4-[[(3R,4R)-1-Benzyl-4-methylpiperidin-3-yl](methyl)amino]-5H,6H,7H,8H-pyrido[3,4-d]pyrimidin-7-yl)-4-chloro-2-(oxan-2-yl)-2,3-dihydropyridazin-3-one Into a 25 mL round-bottom flask were added (3R,4R)-1-benzyl-N,4-dimethyl-N-[5H,6H,7H,8H-pyrido[3,4-d]pyrimidin-4-yl]piperidin-3-amine (263 mg, 0.748 mmol, 1 equiv.) and 4,5-dichloro-2-(oxan-2-yl)-2,3-dihydropyridazin-3-one (186.38 mg, 0.748 mmol, 1.00 equiv.) at room temperature. To the mixture was added DIEA (193.41 mg, 1.261 mmol, 2 equiv.) at rt. The mixture was stirred for 2 hours at 100° C. The residue was purified by reverse phase flash chromatography with the following conditions: Column: Spherical C18, 20-40 um, 330 g; Mobile Phase A: Water (plus 5 mM NH4HCO3); Mobile Phase B: acetonitrile; Flow rate: 80 mL/min; Gradient: 5%-5% B, 10 min, 45% B-95% B gradient in 30 min; Detector: 254 nm. The fractions containing the desired product were collected at 85% B and concentrated under reduced pressure to afford 5-(4-[[(3R,4R)-1-benzyl-4-methylpiperidin-3-yl](methyl)amino]-5H,6H,7H,8H-pyrido[3,4-d]pyrimidin-7-yl)-4-chloro-2-(oxan-2-yl)-2,3-dihydropyridazin-3-one (245 mg, 58.04%) as an off-white solid.

5-(4-[[(3R,4R)-1-Benzyl-4-methylpiperidin-3-yl](methyl)amino]-5H,6H,7H,8H-pyrido[3,4-d]pyrimidin-7-yl)-4-chloro-2,3-dihydropyridazin-3-one To a stirred solution of 5-(4-[[(3R,4R)-1-benzyl-4-methylpiperidin-3-yl](methyl)amino]-5H,6H,7H,8H-pyrido[3,4-d]pyrimidin-7-yl)-4-chloro-2-(oxan-2-yl)-2,3-dihydropyridazin-3-one (88 mg, 1 equiv.) in DCM (10 mL) was added trifluoroacetic acid (3 mL, 0.026 mmol, 6.00 equiv.) dropwise at 0° C. The mixture was stirred for 2 hours at room temperature. The solution was concentrated under reduced pressure. The residue was purified by reverse phase flash chromatography with the following conditions: Column: Spherical C18, 20-40 um, 330 g; Mobile Phase A: Water (plus 5 mM TFA); Mobile Phase B: acetonitrile; Flow rate: 80 mL/min; Gradient: 5%-5% B, 10 min, 33% B-95% B gradient in 30 min; Detector: 254 nm. The fractions containing the desired product were collected at 90% B and concentrated under reduced pressure to afford 5-(4-[[(3R,4R)-1-benzyl-4-methylpiperidin-3-yl](methyl)amino]-5H,6H,7H,8H-pyrido[3,4-d]pyrimidin-7-yl)-4-chloro-2,3-dihydropyridazin-3-one (33.5 mg, 44.74%) as an off-white solid.

Compound 133a was prepared by the methods and scheme described in this example by using (3S,4S)-1-benzyl-N,4-dimethylpiperidin-3-amine in place of (3R,4R)-1-benzyl-N,4-dimethylpiperidin-3-amine.

Example 17. Synthesis of Compound 136

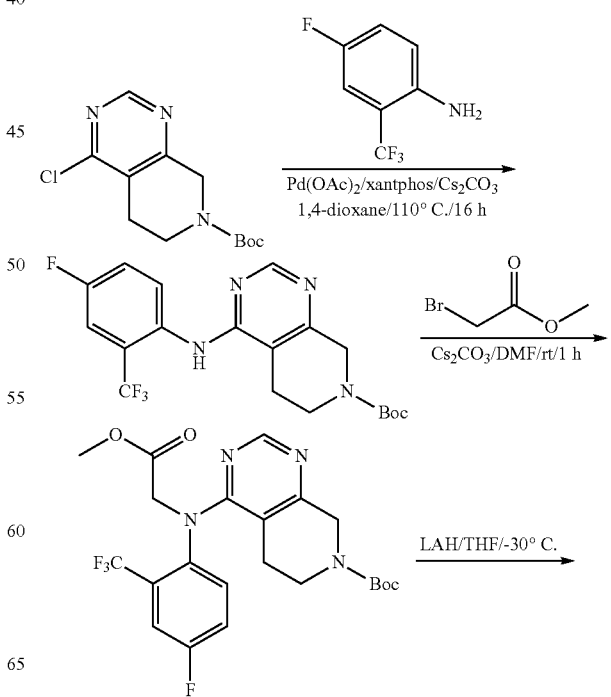

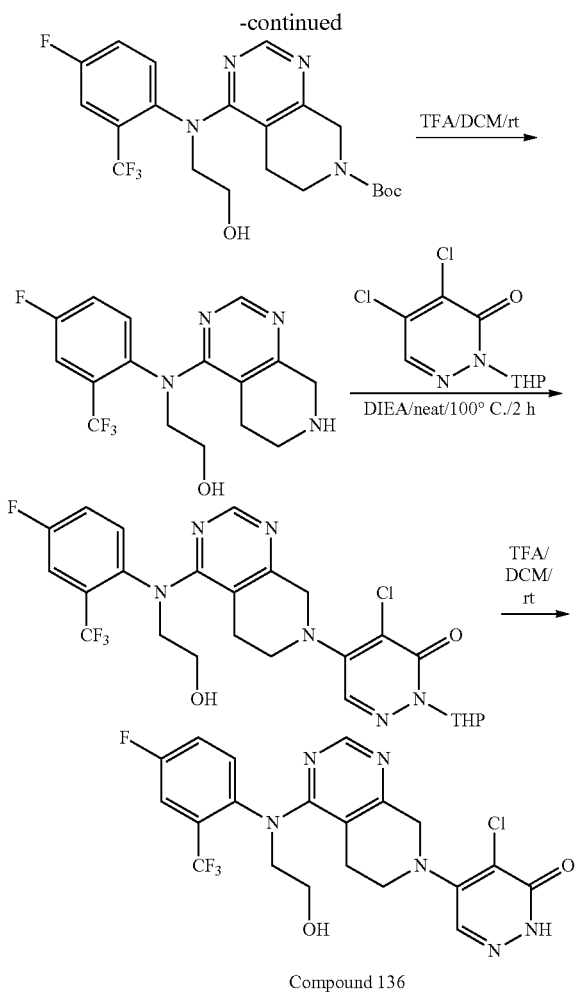

Compound 136

Tert-Butyl 4-[[4-fluoro-2-(trifluoromethyl)phenyl]amino]-5H,6H,7H,8H-pyrido[3,4-d]pyrimidine-7-carboxylate A mixture of 4-fluoro-2-(trifluoromethyl)aniline (6.64 g, 37.074 mmol, 2 equiv), tert-butyl 4-chloro-5H,6H,7H,8H-pyrido[3,4-d]pyrimidine-7-carboxylate (5 g, 18.537 mmol, 1 equiv), Pd(AcO)2 (0.83 g, 3.707 mmol, 0.2 equiv), XantPhos (4.29 g, 7.415 mmol, 0.4 equiv.) and Cs2CO3 (12.08 g, 37.074 mmol, 2 equiv.) in 1,4-dioxane (80 mL) was stirred at 110° C. for 16 hours. The reaction mixture was filtered and the filtrate was concentrated to give the crude product which was purified by silica gel column chromatography, eluted with PE:EA (20:1 to 1:2) to afford tert-butyl 4-[[4-fluoro-2-(trifluoromethyl)phenyl]amino]-5H,6H,7H,8H-pyrido[3,4-d]pyrimidine-7-carboxylate (5.6 g, 73.26%) as a white solid.

Tert-Butyl 4-[[4-fluoro-2-(trifluoromethyl)phenyl](2-methoxy-2-oxoethyl)amino]-5H,6H,7H,8H-pyrido[3,4-d]pyrimidine-7-carboxylate To a stirred mixture of tert-butyl 4-[[4-fluoro-2-(trifluoromethyl)phenyl]amino]-5H,6H,7H,8H-pyrido[3,4-d]pyrimidine-7-carboxylate (3 g, 7.275 mmol, 1 equiv.) and methyl 2-bromoacetate (2.23 g, 14.578 mmol, 2.00 equiv.) in DMF (30 mL) was added Cs$_2$CO$_3$ (4.74 g, 14.548 mmol, 2.00 equiv.) in portions at rt under nitrogen atmosphere. The resulting mixture was stirred for 2 hours at rt. The reaction was monitored by LCMS. The resulting mixture was extracted with EtOAc (3×400 mL). The combined organic layers were washed with brine (2×200 mL), dried over anhydrous Na$_2$SO$_4$. After filtration, the filtrate was concentrated under reduced pressure. The residue was purified by reverse phase flash chromatography with the following conditions: Column: Spherical C18, 20-40 um, 330 g; Mobile Phase A: Water (plus 5 mM TFA); Mobile Phase B: acetonitrile; Flow rate: 80 mL/min; Gradient: 5%-5% B, 10 min, 55% B-85% B gradient in 30 min; Detector: 220 nm. The fractions containing the desired product were collected at 79% B and concentrated under reduced pressure to afford tert-butyl 4-[[4-fluoro-2-(trifluoromethyl)phenyl](2-methoxy-2-oxoethyl)amino]-5H,6H,7H,8H-pyrido[3,4-d]pyrimidine-7-carboxylate (500 mg, 14.19%) as a yellow solid.

Tert-Butyl 4-[[4-fluoro-2-(trifluoromethyl)phenyl](2-hydroxyethyl)amino]-5H,6H,7H,8H-pyrido[3,4-d]pyrimidine-7-carboxylate To a stirred solution of tert-butyl 4-[[4-fluoro-2-(trifluoromethyl)phenyl](2-methoxy-2-oxoethyl)amino]-5H,6H,7H,8H-pyrido[3,4-d]pyrimidine-7-carboxylate (500 mg, 1.032 mmol, 1 equiv.) in THF (50 mL) was added LiAlH$_4$ (78.34 mg, 2.064 mmol, 2.00 equiv.) in portions at −30° C. under nitrogen atmosphere. The reaction mixture was stirred for 16 hours at rt. The reaction was monitored by LCMS. The reaction was quenched by the addition of Water (1 mL) at −30° C. The precipitated solids were collected by filtration and washed with MeOH (3×30 mL).

The resulting mixture was concentrated under vacuum. The residue was purified by Prep-TLC (PE/EA=1/1) to afford tert-butyl 4-[[4-fluoro-2-(trifluoromethyl)phenyl](2-hydroxyethyl)amino]-5H,6H,7H,8H-pyrido[3,4-d]pyrimidine-7-carboxylate (100 mg, 21.23%) as a yellow oil.

4-[1-[4-Fluoro-2-(trifluoromethyl)phenyl]ethyl]-5H,6H,7H,8H-pyrido[3,4-d]pyrimidine To a stirred solution of tert-butyl 4-[1-[4-fluoro-2-(trifluoromethyl)phenyl]ethyl]-5H,6H,7H,8H-pyrido[3,4-d]pyrimidine-7-carboxylate (150 mg) in DCM (10 mL) was added TFA (1 mL) dropwise at rt. The reaction mixture was stirred for 2 hours at rt. The reaction was monitored by LCMS. The resulting mixture was concentrated under reduced pressure. The residue was basified to pH=8 with saturated NH$_4$HCO$_3$ (aq.). The resulting mixture was extracted with DCM (3×50 mL). The combined organic layers were washed with brine (1×30 mL), dried over anhydrous Na$_2$SO$_4$. After filtration, the filtrate was concentrated under reduced pressure. The residue was purified by reverse phase flash chromatography with the following conditions: Column: Spherical C18, 20-40 um, 120 g; Mobile Phase A: Water (plus 5 mM NH$_4$HCO$_3$); Mobile Phase B: acetonitrile; Flow rate: 80 mL/min; Gradient: 5%-5% B, 10 min, 40% B-58% B gradient in 15 min; Detector: 220 nm. The fractions containing the desired product were collected at 53% B and concentrated under reduced pressure to afford 4-[1-[4-fluoro-2-(trifluoromethyl)phenyl]ethyl]-5H,6H,7H,8H-pyrido[3,4-d]pyrimidine (100 mg) as a yellow oil.

4-Chloro-5-(4-[[4-fluoro-2-(trifluoromethyl)phenyl](2-hydroxyethyl)amino]-5H,6H,7H,8H-pyrido[3,4-d]pyrimidin-7-yl)-2-(oxan-2-yl)-2,3-dihydropyridazin-3-one Into a 50 mL round-bottom flask were added 2-[[4-fluoro-2-(trifluoromethyl)phenyl]([5H,6H,7H,8H-pyrido[3,4-d]pyrimidin-4-yl])amino]ethan-1-ol (40 mg, 0.112 mmol, 1 equiv), 4,5-dichloro-2-(oxan-2-yl)-2,3-dihydropyridazin-3-one (55.92 mg, 0.224 mmol, 2.00 equiv.) and DIEA (43.53 mg, 0.337 mmol, 3.00 equiv.) at rt under nitrogen atmosphere. The resulting mixture was stirred for 2 hours at 90° C. under nitrogen atmosphere. The reaction was monitored by LCMS. The mixture was allowed to cool down to rt. The residue was purified by reverse phase flash chromatography with the following conditions: Column: Spherical C18, 20-40 um, 120 g; Mobile Phase A: Water (plus 5 mM NH$_4$HCO3); Mobile Phase B: acetonitrile; Flow rate: 45 mL/min; Gradient: 5%-5% B, 10 min, 40% B-60% B gradient in 15 min; Detector: 220 nm. The fractions containing the desired product were collected at 55% B and concentrated under reduced pressure to afford 4-chloro-5-(4-[[4-fluoro-2-(trifluoromethyl)phenyl](2-hydroxyethyl)amino]-5H,6H,7H,8H-pyrido[3,4-d]pyrimidin-7-yl)-2-(oxan-2-yl)-2,3-dihydropyridazin-3-one (50 mg, 78.28%) as a yellow oil.

4-Chloro-5-(4-[[4-fluoro-2-(trifluoromethyl)phenyl] (2-hydroxyethyl)amino]-5H,6H,7H,8H-pyrido[3,4-d] pyrimidin-7-yl)-2,3-dihydropyridazin-3-one To a stirred solution of 4-chloro-5-(4-[[4-fluoro-2-(trifluoromethyl)phenyl](2-hydroxyethyl)amino]-5H,6H,7H,8H-pyrido[3,4-d]pyrimidin-7-yl)-2-(oxan-2-yl)-2,3-dihydropyridazin-3-one (50 mg) in DCM (10 mL) was added TFA (1 mL) dropwise at rt. The reaction mixture was stirred for 2 hours at rt. The reaction was monitored by LCMS. The resulting mixture was concentrated under reduced pressure. The residue was basified to pH=8 with saturated NH$_4$HCO$_3$ (aq.). The resulting mixture was extracted with EtOAc (2×50 mL). The combined organic layers were washed with brine (1×100 mL), dried over anhydrous Na$_2$SO$_4$. After filtration, the filtrate was concentrated under reduced pressure. The residue was purified by Prep-HPLC with the following conditions (Column: XBridge Prep OBD C18 Column 30×150 mm 5 um; Mobile Phase A: undefined, Mobile Phase B: undefined; Flow rate: 60 mL/min; Gradient: 30% B to 45% B in 8 min; 220 nm; Rt: 7.6 min) to afford 4-chloro-5-(4-[[4-fluoro-2-(trifluoromethyl)phenyl](2-hydroxyethyl)amino]-5H,6H,7H,8H-pyrido[3,4-d]pyrimidin-7-yl)-2,3-dihydropyridazin-3-one (6.2 mg) as a white solid.

Example 18. Synthesis of Compound 132

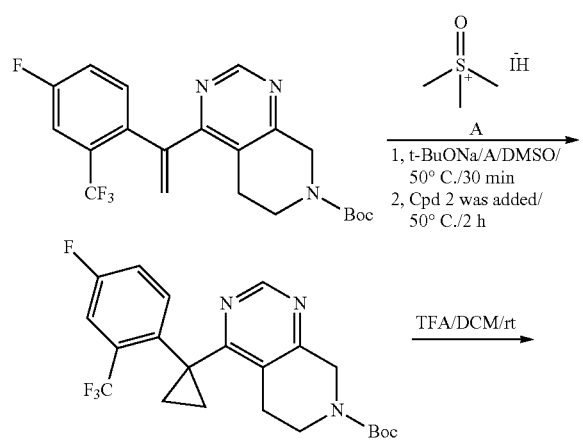

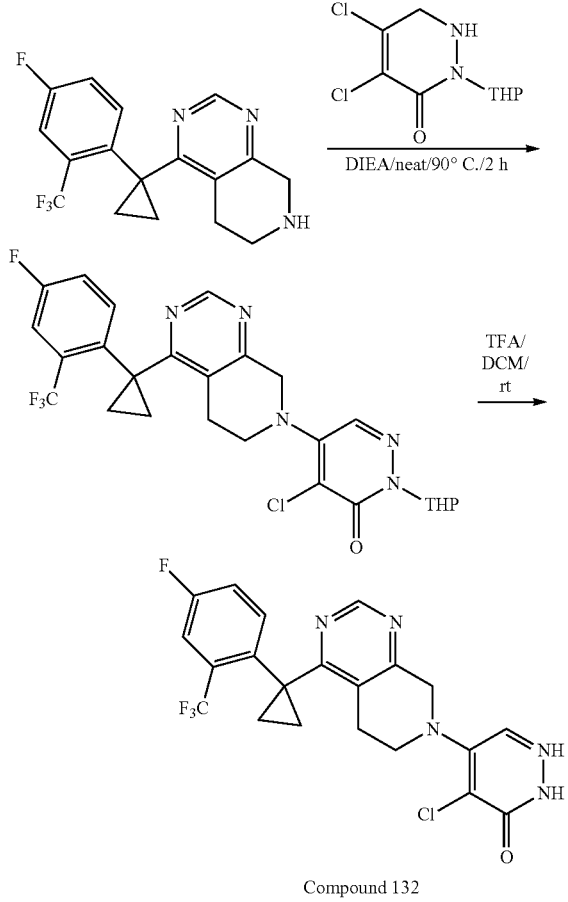

Compound 132

Tert-Butyl 4-[1-[4-fluoro-2-(trifluoromethyl)phenyl] cyclopropyl]-5H,6H,7H,8H-pyrido[3,4-d]pyrimidine-7-carboxylate To a stirred solution of t-BuONa (226.97 mg, 2.362 mmol, 2.00 equiv.) in DMSO (20 mL) was added Me3SiI (472.57 mg, 2.362 mmol, 2.00 equiv.) in portions at 40° C. under nitrogen atmosphere. The resulting mixture was stirred for 0.5 hours at 40° C. under nitrogen atmosphere. Then tert-butyl 4-[1-[4-fluoro-2-(trifluoromethyl)phenyl]ethenyl]-5H,6H,7H,8H-pyrido[3,4-d]pyrimidine-7-carboxylate (500 mg, 1.181 mmol, 1 equiv.) in DMSO (5 mL) was dropwise at rt under nitrogen atmosphere. The resulting mixture was stirred for 1 hours at rt under nitrogen atmosphere. The reaction was monitored by LCMS. The mixture was allowed to cool down to rt. The resulting mixture was extracted with EtOAc (3×100 mL). The combined organic layers were washed with brine (2×100 mL), dried over anhydrous Na$_2$SO$_4$. After filtration, the filtrate was concentrated under reduced pressure. The residue was purified by reverse phase flash chromatography with the following conditions: Column: Spherical C18, 20-40 um, 330 g; Mobile Phase A: Water (plus 5 mM NH$_4$HCO3); Mobile Phase B: acetonitrile; Flow rate: 80 mL/min; Gradient: 5%-5% B, 10 min, 55% B-80% B gradient in 25 min; Detector: 220 nm. The fractions containing the desired product were collected at 73% B and concentrated under reduced pressure to afford tert-butyl 4-[1-[4-fluoro-2-(trifluoromethyl)phenyl]cyclopropyl]-5H,6H,7H,8H-pyrido[3,4-d]pyrimidine-7-carboxylate (240 mg, 46.46%) as a yellow oil.

4-[1-[4-Fluoro-2-(trifluoromethyl)phenyl]cyclopropyl]-5H,6H,7H,8H-pyrido[3,4-d]pyrimidine To a stirred solution of tert-butyl 4-[1-[4-fluoro-2-(trifluoromethyl)phenyl]cyclopropyl]-5H,6H,7H,8H-pyrido[3,4-d]pyrimidine-7-carboxylate (240 mg, 0.549 mmol, 1 equiv.) in DCM (10 mL) was added TFA (1 mL, 13.463 mmol, 24.54 equiv.) dropwise at rt. The reaction mixture was stirred for 2 hours at rt. The reaction was monitored by LCMS. The resulting mixture was concentrated under reduced pressure. The residue was basified to pH=8 with saturated NH₄HCO₃ (aq.). The resulting mixture was extracted with EtOAc (2×100 mL). The combined organic layers were washed with brine (1×100 mL), dried over anhydrous Na₂SO₄. After filtration, the filtrate was concentrated under reduced pressure. The residue was purified by reverse phase flash chromatography with the following conditions: Column: Spherical C18, 20-40 um, 120 g; Mobile Phase A: Water (plus 5 mM AcOH); Mobile Phase B: acetonitrile; Flow rate: 45 mL/min; Gradient: 5%-5% B, 10 min, 33% B-45% B gradient in 20 min; Detector: 254 nm. The fractions containing the desired product were collected at 40% B and concentrated under reduced pressure to afford 4-[1-[4-fluoro-2-(trifluoromethyl)phenyl]cyclopropyl]-5H,6H,7H,8H-pyrido[3,4-d]pyrimidine (150 mg, 81.05%) as a yellow oil.

4-Chloro-5-(4-[1-[4-fluoro-2-(trifluoromethyl)phenyl]cyclopropyl]-5H,6H,7H,8H-pyrido[3,4-d]pyrimidin-7-yl)-2-(oxan-2-yl)-2,3-dihydropyridazin-3-one Into a 50 mL round-bottom flask were added 4-[1-[4-fluoro-2-(trifluoromethyl)phenyl]cyclopropyl]-5H,6H,7H,8H-pyrido[3,4-d]pyrimidine (150 mg, 0.445 mmol, 1 equiv), 4,5-dichloro-2-(oxan-2-yl)-1,2,3,6-tetrahydropyridazin-3-one (134.00 mg, 0.534 mmol, 1.20 equiv.) and DIEA (172.42 mg, 1.334 mmol, 3.00 equiv.) at rt under nitrogen atmosphere. The resulting mixture was stirred for 2 hours at 90° C. under nitrogen atmosphere. The reaction was monitored by LCMS. The mixture was allowed to cool down to rt. The residue was purified by reverse phase flash chromatography with the following conditions: Column: Spherical C18, 20-40 um, 330 g; Mobile Phase A: Water (plus 5 mM NH₄HCO3); Mobile Phase B: acetonitrile; Flow rate: 80 mL/min; Gradient: 5%-5% B, 10 min, 40% B-60% B gradient in 15 min; Detector: 220 nm. The fractions containing the desired product were collected at 54% B and concentrated under reduced pressure to afford 4-chloro-5-(4-[1-[4-fluoro-2-(trifluoromethyl)phenyl]cyclopropyl]-5H,6H,7H,8H-pyrido[3,4-d]pyrimidin-7-yl)-2-(oxan-2-yl)-2,3-dihydropyridazin-3-one (200 mg, 81.78%) as a yellow oil.

4-Chloro-5-(4-[1-[4-fluoro-2-(trifluoromethyl)phenyl]cyclopropyl]-5H,6H,7H,8H-pyrido[3,4-d]pyrimidin-7-yl)-2,3-dihydropyridazin-3-one To a stirred solution of 4-chloro-5-(4-[1-[4-fluoro-2-(trifluoromethyl)phenyl]cyclopropyl]-5H,6H,7H,8H-pyrido[3,4-d]pyrimidin-7-yl)-2-(oxan-2-yl)-2,3-dihydropyridazin-3-one (200 mg) in DCM (10 mL) was added TFA (2 mL) dropwise at rt. The reaction mixture was stirred for 2 hours at rt. The reaction was monitored by LCMS. The resulting mixture was concentrated under reduced pressure. The residue was basified to pH=8 with saturated NH₄HCO₃ (aq.). The resulting mixture was extracted with EtOAc (2×100 mL). The combined organic layers were washed with brine (1×100 mL), dried over anhydrous Na₂SO₄. After filtration, the filtrate was concentrated under reduced pressure. The residue was purified by Prep-HPLC with the following conditions (Column: XBridge Prep OBD C18 Column 30×150 mm 5 um; Mobile Phase A: undefined, Mobile Phase B: undefined; Flow rate: 60 mL/min; Gradient: 30% B to 55% B in 8 min; 220 nm; Rt: 7.232 min) to afford 4-chloro-5-(4-[1-[4-fluoro-2-(trifluoromethyl)phenyl]cyclopropyl]-5H,6H,7H,8H-pyrido[3,4-d]pyrimidin-7-yl)-2,3-dihydropyridazin-3-one (39.2 mg) as an off-white solid.

Example 19. Synthesis of Compound 109

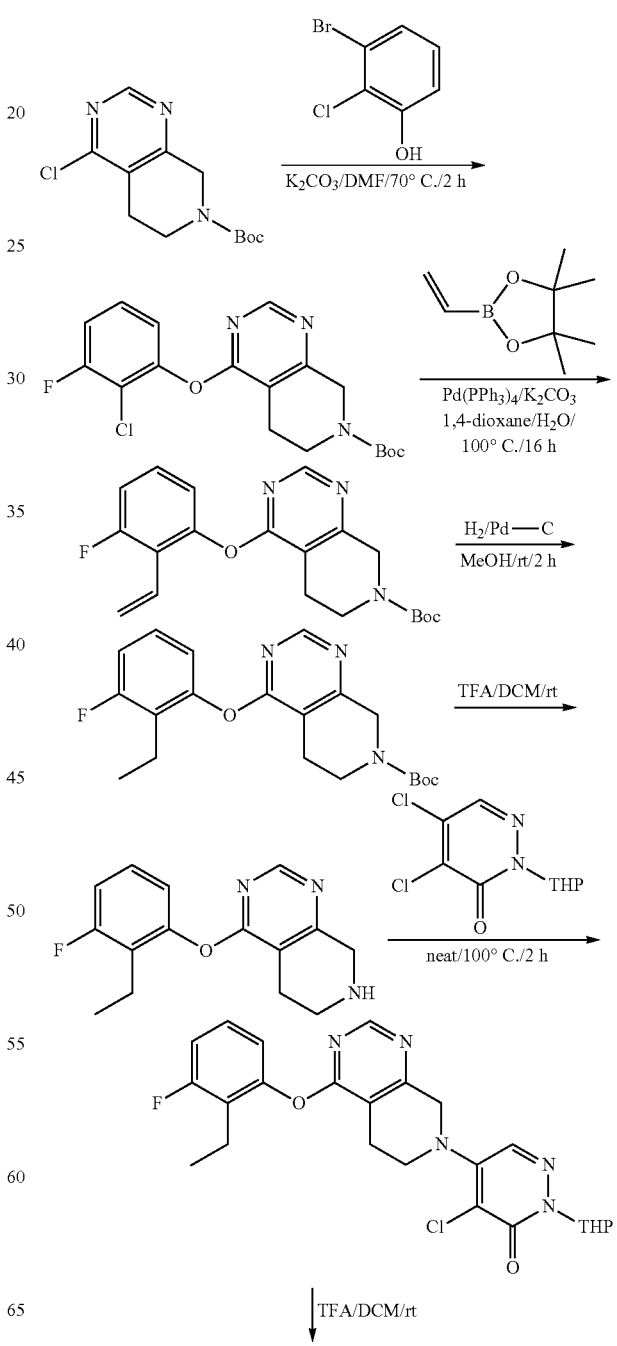

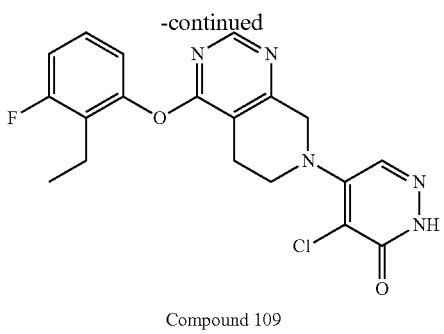

Compound 109

Tert-Butyl 4-(2-bromo-3-fluorophenoxy)-5H,6H,7H,8H-pyrido[3,4-d]pyrimidine-7-carboxylate To a stirred solution of tert-butyl 4-chloro-5H,6H,7H,8H-pyrido[3,4-d]pyrimidine-7-carboxylate (500 mg, 1.854 mmol, 1 equiv.) and 2-bromo-3-fluorophenol (424.87 mg, 2.224 mmol, 1.20 equiv.) in DMF (10 mL) was added K$_2$CO$_3$ (512.38 mg, 3.707 mmol, 2 equiv). The resulting mixture was stirred for 0.5 hours at 70° C. The mixture was allowed to cool down to room temperature. The reaction was quenched with Water at room temperature. The resulting mixture was extracted with EtOAc (2×100 mL). The combined organic layers were washed with brine (2×100 mL), dried over anhydrous Na$_2$SO$_4$. After filtration, the filtrate was concentrated under reduced pressure. The residue was purified by silica gel column chromatography, eluted with PE/EtOAc (5:1) to afford tert-butyl 4-(2-bromo-3-fluorophenoxy)-5H,6H,7H,8H-pyrido[3,4-d]pyrimidine-7-carboxylate (500 mg, 63.58%) as a white solid.

Tert-Butyl 4-(2-ethenyl-3-fluorophenoxy)-5H,6H,7H,8H-pyrido[3,4-d]pyrimidine-7-carboxylate To a solution of tert-butyl 4-(2-bromo-3-fluorophenoxy)-5H,6H,7H,8H-pyrido[3,4-d]pyrimidine-7-carboxylate (500 mg, 1.178 mmol, 1 equiv.) and pentamethyl-1,3,2-dioxaborolane (334.72 mg, 2.357 mmol, 2.00 equiv.) in H2O (2 mL) and 1,4-dioxane (16 mL) were added K$_2$CO$_3$ (325.75 mg, 2.357 mmol, 2 equiv.) and Pd(PPh$_3$)$_4$ (68.09 mg, 0.059 mmol, 0.05 equiv). After stirring for overnight at 90° C. under a nitrogen atmosphere, the resulting mixture was concentrated under reduced pressure. The residue was purified by silica gel column chromatography, eluted with PE/EtOAc (5:1) to afford tert-butyl 4-(2-ethenyl-3-fluorophenoxy)-5H,6H,7H,8H-pyrido[3,4-d]pyrimidine-7-carboxylate (250 mg, 57.12%) as a yellow oil.

Tert-Butyl 4-(2-ethyl-3-fluorophenoxy)-5H,6H,7H,8H-pyrido[3,4-d]pyrimidine-7-carboxylate To a stirred solution of tert-butyl 4-(2-ethenyl-3-fluorophenoxy)-5H,6H,7H,8H-pyrido[3,4-d]pyrimidine-7-carboxylate (250 mg, 0.673 mmol, 1 equiv.) in MeOH (10 mL) was added Pd/C (100 mg, 0.940 mmol, 1.40 equiv). The resulting mixture was stirred for 2 hours at RT under hydrogen atmosphere. The resulting mixture was filtered, the filter cake was washed with MeOH (2×10 mL). The filtrate was concentrated under reduced pressure. The resulting mixture was concentrated under reduced pressure. This resulted in tert-butyl 4-(2-ethyl-3-fluorophenoxy)-5H,6H,7H,8H-pyrido[3,4-d]pyrimidine-7-carboxylate (210 mg, 0.08%) as a black oil.

4-(2-Ethyl-3-fluorophenoxy)-5H,6H,7H,8H-pyrido[3,4-d]pyrimidine

To a stirred solution of tert-butyl 4-(2-ethyl-3-fluorophenoxy)-5H,6H,7H,8H-pyrido[3,4-d]pyrimidine-7-carboxylate (210 mg, 0.562 mmol, 1 equiv.) in DCM (3 mL) was added TFA (1 mL). The resulting mixture was stirred for 2 hours at room temperature under air atmosphere. The resulting mixture was concentrated under reduced pressure. The mixture was basified to pH 8 with saturated NH$_4$HCO3 (aq.). The mixture was purified by reverse flash chromatography with the following conditions: Column: spherical C18, 20-40 um, 180 g; Mobile Phase A: Water (5 mM NH$_4$HCO$_3$), Mobile Phase B: acetonitrile; Flow rate: 45 mL/min; Gradient: 25% B to 60% B in 40 min; 254 nm). The fractions containing the desired product were collected at 40% B and concentrated under reduced pressure. This resulted in 4-(2-ethyl-3-fluorophenoxy)-5H,6H,7H,8H-pyrido[3,4-d]pyrimidine (120 mg, 78.07%) as a light yellow oil.

4-Chloro-5-[4-(2-ethyl-3-fluorophenoxy)-5H,6H,7H,8H-pyrido[3,4-d]pyrimidin-7-yl]-2-(oxan-2-yl)-2,3-dihydropyridazin-3-one To a stirred solution of 4-(2-ethyl-3-fluorophenoxy)-5H,6H,7H,8H-pyrido[3,4-d]pyrimidine (120 mg, 0.439 mmol, 1 equiv.) and 4,5-dichloro-2-(oxan-2-yl)-2,3-dihydropyridazin-3-one (109.37 mg, 0.439 mmol, 1.00 equiv.) in DIEA (113.49 mg, 0.878 mmol, 2 equiv). The resulting mixture was stirred for 2 hours at 100° C. under air atmosphere. The residue was purified by Prep-TLC (PE/EtOAc 1:1) to afford 4-chloro-5-[4-(2-ethyl-3-fluorophenoxy)-5H,6H,7H,8H-pyrido[3,4-d]pyrimidin-7-yl]-2-(oxan-2-yl)-2,3-dihydropyridazin-3-one (100 mg, 46.87%) as a light yellow solid.

4-Chloro-5-[4-(2-ethyl-3-fluorophenoxy)-5H,6H,7H,8H-pyrido[3,4-d]pyrimidin-7-yl]-2,3-dihydropyridazin-3-one To a stirred solution of 4-chloro-5-[4-(2-ethyl-3-fluorophenoxy)-5H,6H,7H,8H-pyrido[3,4-d]pyrimidin-7-yl]-2-(oxan-2-yl)-2,3-dihydropyridazin-3-one (100 mg, 0.206 mmol, 1 equiv.) in DCM (3 mL) was added TFA (1 mL). The resulting mixture was stirred for 2 hours at room temperature. The resulting mixture was concentrated under reduced pressure. The mixture was basified to pH 7 with saturated NH$_4$HCO$_3$ (aq.). The crude product was purified by Prep-HPLC with the following conditions (Column: XBridge Prep OBD C18 Column 30×150 mm 5 um; Mobile Phase A: Water (10 mM NH$_4$HCO$_3$), Mobile Phase B: acetonitrile; Flow rate: 60 mL/min; Gradient: 30% B to 50% B in 8 min; 220 nm; Rt: 7.27 min) to afford 4-chloro-5-[4-(2-ethyl-3-fluorophenoxy)-5H,6H,7H,8H-pyrido[3,4-d]pyrimidin-7-yl]-2,3-dihydropyridazin-3-one (41.6 mg, 50.31%) as a white solid.

Example 20. Synthesis of Compound 127

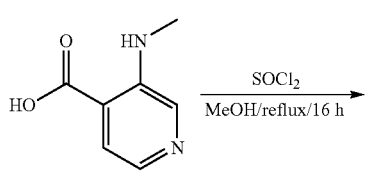

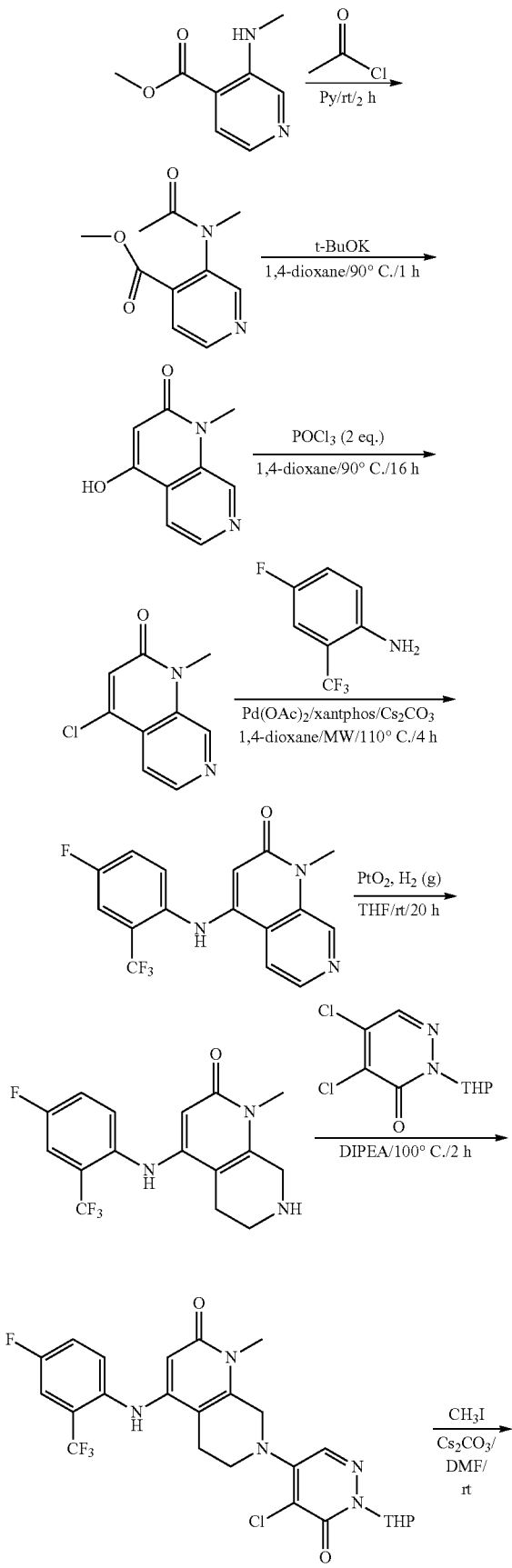

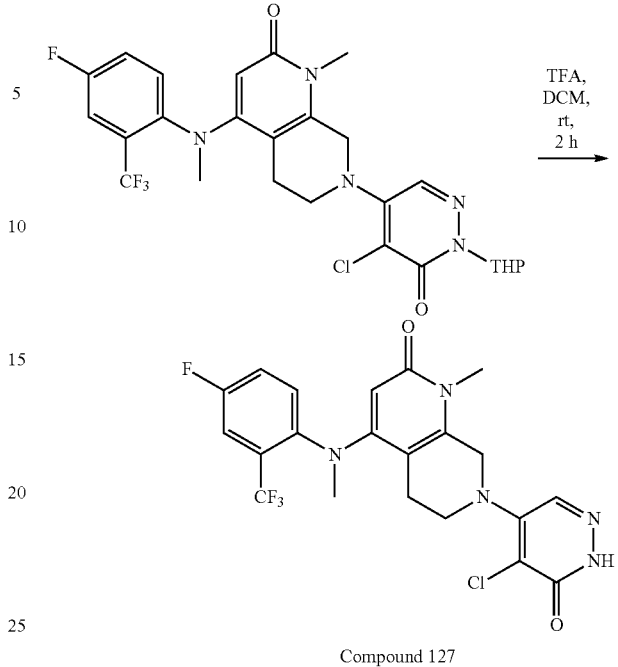

Compound 127

Methyl 3-(methylamino)pyridine-4-carboxylate

To a stirred solution of 3-(methylamino)pyridine-4-carboxylic acid (11 g, 72.296 mmol, 1 equiv.) in MeOH (500 mL, 12349.455 mmol, 170.82 equiv.) was added SOCl₂ (43.01 g, 361.478 mmol, 5 equiv.) dropwise at 0° C. The resulting mixture was stirred for 30 hours at 70° C. The reaction was monitored by LCMS. The mixture was allowed to cool down to room temperature. The resulting mixture was concentrated under reduced pressure. The residue was dissolved in ethyl acetate (50 mL). The mixture basified to pH 8 with saturated NaHCO3 (aq.). The resulting mixture was extracted with EtOAc (2×20 mL). The combined organic layers were washed with brine (1×30 mL), dried over anhydrous Na₂SO₄. After filtration, the filtrate was concentrated under reduced pressure to afford methyl 3-(methylamino)pyridine-4-carboxylate (9 g, crude) as a yellow solid.

Methyl 3-(N-methylacetamido)pyridine-4-carboxylate

To a stirred solution of methyl 3-(methylamino)pyridine-4-carboxylate (9 g, 54.158 mmol, 1 equiv.) in DCM (100 mL) were added Pyridine (21.42 g, 270.791 mmol, 5 equiv.) and acetyl chloride (6.38 g, 81.237 mmol, 1.5 equiv.) dropwise at room temperature. The resulting mixture was stirred for 2 hours at room temperature. The reaction was monitored by LCMS. The solution was basified to pH 8 with saturated NaHCO3 (aq.). The resulting mixture was concentrated under reduced pressure. The residue was purified by reverse phase flash with the following conditions (Column: C18 Column 330 g; Mobile Phase A: Water (10 mM NH₄HCO₃), Mobile Phase B: acetonitrile; Flow rate: 80 mL/min; Gradient: 10% B to 30% B in 25 min; 254/220 nm) to afford methyl 3-(N-methylacetamido)pyridine-4-carboxylate (8 g, 70.94%) as a brown liquid.

4-Hydroxy-1-methyl-1,2-dihydro-1,7-naphthyridin-2-one

To a stirred solution of methyl 3-(N-methylacetamido)pyridine-4-carboxylate (6 g, 28.816 mmol, 1 equiv.) in dry 1,4-dioxane (100 mL) was added t-BuOK (6.47 g, 57.632 mmol, 2 equiv.) at room temperature under nitrogen atmosphere. The resulting mixture was stirred for 1 hours at 90° C. under nitrogen atmosphere. The reaction was monitored by LCMS. The mixture was allowed to cool down to room temperature. The resulting mixture was concentrated under vacuum. The residue was purified by silica gel column chromatography, eluted with DCM/MeOH (10:1) to afford 4-hydroxy-1-methyl-1,2-dihydro-1,7-naphthyridin-2-one (4.5 g, 88.64%) as a orange solid.

4-Chloro-1-methyl-1,2-dihydro-1,7-naphthyridin-2-one

To a stirred solution of 4-hydroxy-1-methyl-1,2-dihydro-1,7-naphthyridin-2-one (4.5 g, 25.543 mmol, 1 equiv.) in dry 1,4-dioxane (100 mL) was added POCl3 (3.92 g, 25.543 mmol, 1 equiv.) dropwise at room temperature. The resulting mixture was stirred for 16 hours at 90° C. The mixture was allowed to cool down to room temperature. The resulting mixture was concentrated under reduced pressure. The residue was purified by silica gel column chromatography, eluted with DCM/MeOH (10:1) to afford 4-chloro-1-methyl-1,2-dihydro-1,7-naphthyridin-2-one (2 g, 40.23%) as a red solid.

4-[[4-Fluoro-2-(trifluoromethyl)phenyl]amino]-1-methyl-1,2-dihydro-1,7-naphthyridin-2-one To a stirred solution of 4-chloro-1-methyl-1,2-dihydro-1,7-naphthyridin-2-one (0.8 g, 4.111 mmol, 1 equiv.) in dry 1,4-dioxane (15 mL) were added Cs2CO3 (2.68 g, 8.221 mmol, 2 equiv), 4-fluoro-2-(trifluoromethyl)aniline (1.47 g, 8.221 mmol, 2.00 equiv), XantPhos (0.95 g, 1.644 mmol, 0.4 equiv.) and Pd(AcO)$_2$ (0.18 g, 0.822 mmol, 0.2 equiv.) at room temperature under nitrogen atmosphere. The final reaction mixture was irradiated with microwave radiation for 4 hours at 110° C. The reaction was monitored by LCMS. The resulting mixture was extracted with EtOAc (3×50 mL). The combined organic layers were washed with brine (1×100 mL), dried over anhydrous Na$_2$SO$_4$. After filtration, the filtrate was concentrated under reduced pressure. The residue was purified by reverse phase flash with the following conditions (Column: C18 Column 330 g; Mobile Phase A: Water (10 mM AcOH), Mobile Phase B: acetonitrile; Flow rate: 50 mL/min; Gradient: 20% B to 40% B in 40 min; 254/220 nm) to afford 4-[[4-fluoro-2-(trifluoromethyl)phenyl]amino]-1-methyl-1,2-dihydro-1,7-naphthyridin-2-one (1.1 g, 79.34%) as an off-white solid.

4-[[4-Fluoro-2-(trifluormethyl)phenyl]amino]-1-methyl-1,2,5,6,7,8-hexahydro-1,7-naphthyridin-2-one To a stirred solution of 4-[[4-fluoro-2-(trifluoromethyl)phenyl]amino]-1-methyl-1,2-dihydro-1,7-naphthyridin-2-one (1 g, 2.965 mmol, 1 equiv.) in THF (20 mL) was added PtO$_2$ (67.33 mg, 0.296 mmol, 0.10 equiv.) at room temperature under nitrogen atmosphere. The resulting mixture was stirred for 16 hours at room temperature under hydrogen atmosphere. The reaction was monitored by LCMS. The resulting mixture was filtered, the filter cake was washed with EtOAc (3×20 mL). The filtrate was concentrated under reduced pressure. The resulting mixture was concentrated under reduced pressure. The residue was purified by reverse phase flash with the following conditions (Column: C18 Column 330 g; Mobile Phase A: Water (10 mM AcOH), Mobile Phase B: acetonitrile; Flow rate: 80 mL/min; Gradient: 5% B to 20% B in 40 min; 254/220 nm) The fractions containing the desired product were collected at 16% B and concentrated under reduced pressure to afford 4-[[4-fluoro-2-(trifluoromethyl)phenyl]amino]-1-methyl-1,2,5,6,7,8-hexahydro-1,7-naphthyridin-2-one (750 mg, 74.11%) as an off-white solid.

7-[5-chloro-1-(oxan-2-yl)-6-oxo-1,6-dihydro-pyridazin-4-yl]-4-[[4-fluoro-2-(trifluoromethyl)phenyl]amino]-1-methyl-1,2,5,6,7,8-hexahydro-1,7-naphthyridin-2-one To a stirred mixture of 4-[[4-fluoro-2-(trifluoromethyl)phenyl]amino]-1-methyl-1,2,5,6,7,8-hexahydro-1,7-naphthyridin-2-one (750 mg, 2.197 mmol, 1 equiv.) and 4,5-dichloro-2-(oxan-2-yl)-2,3-dihydropyridazin-3-one (1.09 g, 4.395 mmol, 2 equiv.) was added DIPEA (568.00 mg, 4.395 mmol, 2 equiv.) at room temperature. The resulting mixture was stirred for 2 hours at 100° C. The reaction was monitored by LCMS. The residue was dissolved in DMF (10 mL). The solution was purified by reverse phase flash with the following conditions (Column: C18 Column 330 g; Mobile Phase A: Water (10 mM FA), Mobile Phase B: acetonitrile; Flow rate: 80 mL/min; Gradient: 30% B to 50% B in 40 min; 254/220 nm). The fractions containing the desired product were collected at 44% B and concentrated under reduced pressure to afford 7-[5-chloro-1-(oxan-2-yl)-6-oxo-1,6-dihydropyridazin-4-yl]-4-[[4-fluoro-2-(trifluoromethyl)phenyl]amino]-1-methyl-1,2,5,6,7,8-hexahydro-1,7-naphthyridin-2-one (1 g, 82.15%) as a yellow oil.

7-[5-Chloro-1-(oxan-2-yl)-6-oxo-1,6-dihydro-pyridazin-4-yl]-4-[[4-fluoro-2-(trifluoromethyl)phenyl](methyl)amino]-1-methyl-1,2,5,6,7,8-hexahydro-1,7-naphthyridin-2-one To a stirred solution of 7-[5-chloro-1-(oxan-2-yl)-6-oxo-1,6-dihydropyridazin-4-yl]-4-[[4-fluoro-2-(trifluoromethyl)phenyl]amino]-1-methyl-1,2,5,6,7,8-hexahydro-1,7-naphthyridin-2-one (800 mg, 1.444 mmol, 1 equiv.) in DMF (20 mL) were added Cs$_2$CO$_3$ (0.94 g, 2.888 mmol, 2 equiv.) and MeI (614.96 mg, 4.333 mmol, 3 equiv.) at room temperature. The resulting mixture was stirred for 16 hours at room temperature. The reaction was monitored by LCMS. The mixture was purified by reverse phase flash with the following conditions (Column: C18 Column 120 g; Mobile Phase A: Water (10 mM AcOH), Mobile Phase B: acetonitrile; Flow rate: 60 mL/min; Gradient: 40% B to 60% B in 40 min; 254/220 nm). The fractions containing the desired product were collected at 49% B and concentrated under reduced pressure to afford 7-[5-chloro-1-(oxan-2-yl)-6-oxo-1,6-dihydropyridazin-4-yl]-4-[[4-fluoro-2-(trifluoromethyl)phenyl](methyl)amino]-1-methyl-1,2,5,6,7,8-hexahydro-1,7-naphthyridin-2-one (80 mg, 9.75%) as a yellow oil.

7-(5-Chloro-6-oxo-1,6-dihydropyridazin-4-yl)-4-[[4-fluoro-2-(trifluoromethyl)phenyl](methyl)amino]-1-methyl-1,2,5,6,7,8-hexahydro-1,7-naphthyridin-2-one To a stirred solution of 7-[5-chloro-1-(oxan-2-yl)-6-oxo-1,6-dihydropyridazin-4-yl]-4-[[4-fluoro-2-(trifluoromethyl)

phenyl](methyl)amino]-1-methyl-1,2,5,6,7,8-hexahydro-1,7-naphthyridin-2-one (80 mg, 0.141 mmol, 1 equiv.) in DCM (4.5 mL) was added TFA (0.5 mL, 6.732 mmol, 31.07 equiv.) dropwise at room temperature. The resulting mixture was stirred for 2 hours at room temperature. The reaction was monitored by LCMS. The resulting mixture was concentrated under reduced pressure. The residue was basified to pH 8 with saturated NaHCO3 (aq.). The solution was purified by reverse phase flash to afford 7-(5-chloro-6-oxo-1,6-dihydropyridazin-4-yl)-4-[[4-fluoro-2-(trifluoromethyl)phenyl](methyl)amino]-1-methyl-1,2,5,6,7,8-hexahydro-1,7-naphthyridin-2-one (40 mg, 58.69%) as a white solid.

Example 21. Synthesis of Compounds 135 and 137

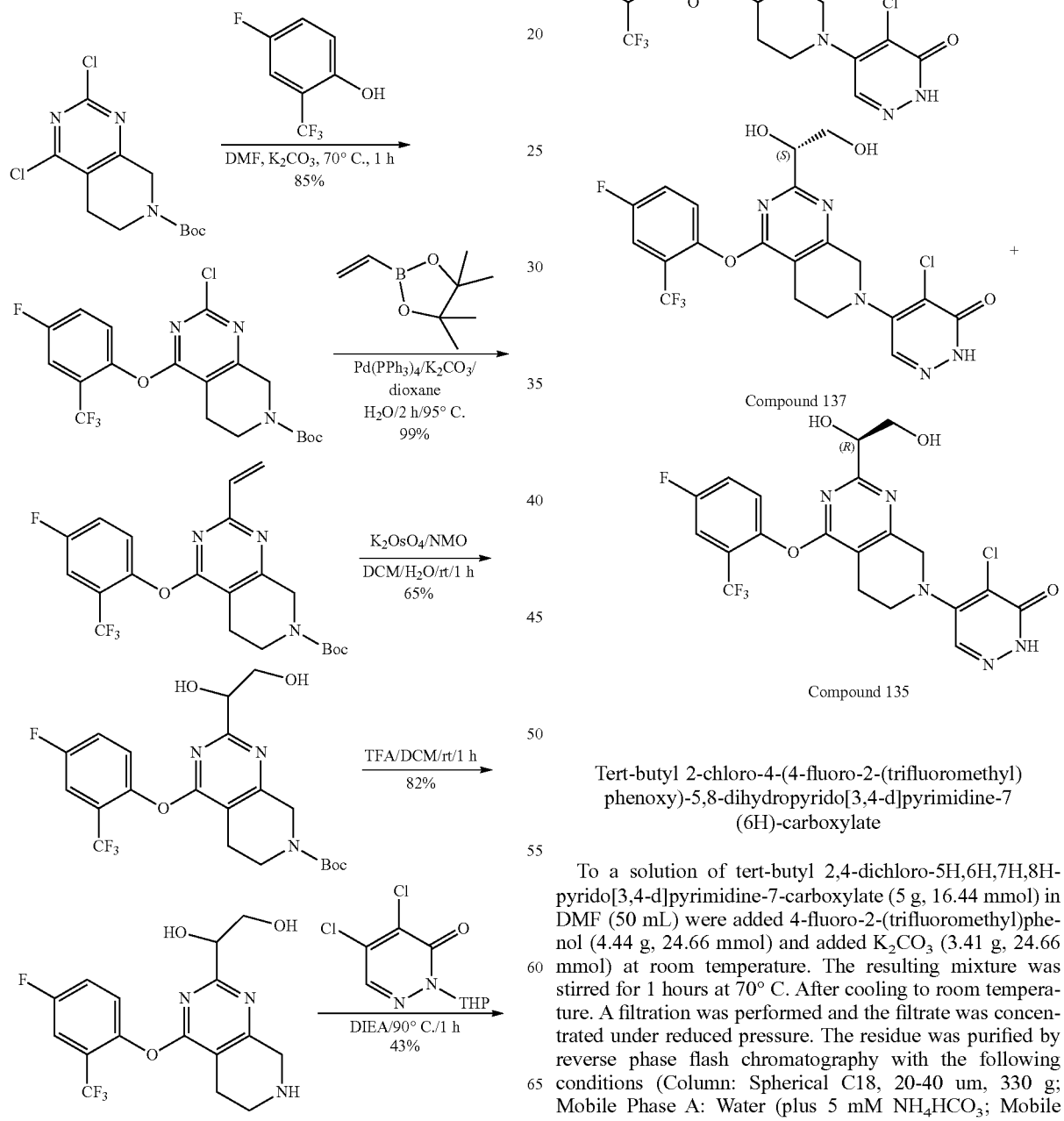

Compound 137

Compound 135

Tert-butyl 2-chloro-4-(4-fluoro-2-(trifluoromethyl)phenoxy)-5,8-dihydropyrido[3,4-d]pyrimidine-7(6H)-carboxylate To a solution of tert-butyl 2,4-dichloro-5H,6H,7H,8H-pyrido[3,4-d]pyrimidine-7-carboxylate (5 g, 16.44 mmol) in DMF (50 mL) were added 4-fluoro-2-(trifluoromethyl)phenol (4.44 g, 24.66 mmol) and added K$_2$CO$_3$ (3.41 g, 24.66 mmol) at room temperature. The resulting mixture was stirred for 1 hours at 70° C. After cooling to room temperature. A filtration was performed and the filtrate was concentrated under reduced pressure. The residue was purified by reverse phase flash chromatography with the following conditions (Column: Spherical C18, 20-40 um, 330 g; Mobile Phase A: Water (plus 5 mM NH$_4$HCO$_3$; Mobile Phase B: acetonitrile; Flow rate: 80 mL/min; Gradient: 5% in 10 min, 35% B to 45% B in 10 min; Detector: 254 nm/220 nm. The fractions containing desired product were collected at 44% B and concentrated under reduced pressure to afford tert-butyl 2-chloro-4-[4-fluoro-2-(trifluoromethyl)phenoxy]-5H,6H,7H,8H-pyrido[3,4-d]pyrimidine-7-carboxylate (6.2 g, 85%) as a white solid.

Tert-butyl 4-(4-fluoro-2-(trifluoromethyl)phenoxy)-2-vinyl-5,8-dihydropyrido[3,4-d]pyrimidine-7(6H)-carboxylate To a solution of tert-butyl 2-chloro-4-[4-fluoro-2-(trifluoromethyl)phenoxy]-5H,6H,7H,8H-pyrido[3,4-d]pyrimidine-7-carboxylate (500 mg, 1.12 mmol) in dioxane (10 mL) were added 2-ethenyl-4,4,5,5-tetramethyl-1,3,2-dioxaborolane (344 mg, 2.23 mmol) and $H_2O$ (0.5 mL, 27.75 mmol) $K_2CO_3$ (309 mg, 2.23 mmol) and $Pd(PPh_3)_4$ (129 mg, 0.11 mmol). After stirring for 2 hours at 95° C. under a nitrogen atmosphere, the resulting mixture was concentrated under reduced pressure. The residue was purified by Prep-TLC, eluted with 17% ethyl acetate in petroleum ether to afford tert-butyl 2-ethenyl-4-[4-fluoro-2-(trifluoromethyl)phenoxy]-5H,6H,7H,8H-pyrido[3,4-d]pyrimidine-7-carboxylate (490 mg, 99%) as a light yellow solid.

Tert-butyl 2-(1,2-dihydroxyethyl)-4-(4-fluoro-2-(trifluoromethyl)phenoxy)-5,8-dihydropyrido[3,4-d]pyrimidine-7(6H)-carboxylate To a solution of tert-butyl 2-ethenyl-4-[4-fluoro-2-(trifluoromethyl)phenoxy]-5H,6H,7H,8H-pyrido[3,4-d]pyrimidine-7-carboxylate (400 mg, 0.91 mmol) in DCM (20 mL) were added 4-hydroxy-4-methylmorpholin-4-ium (323 mg, 2.73 mmol) and $K_2OsO_4.2H_2O$ (34 mg, 0.091 mmol) at room temperature. After stirring for additional 1 hour, the resulting mixture was concentrated under reduced pressure and the residue was purified by reverse phase flash chromatography with the following conditions: Column: Spherical C18, 20~40 um, 120 g; Mobile Phase A: Water (plus 5 mM $NH_4HCO_3$; Mobile Phase B: acetonitrile; Flow rate: 45 mL/min; Gradient: 5% B in 10 min, 45% B to 65% B in 15 min; Detector: 254 nm and 220 nm. The fractions containing desired product were collected at 64% B and concentrated under reduced pressure to afford tert-butyl 2-(1,2-dihydroxyethyl)-4-[4-fluoro-2-(trifluoromethyl)phenoxy]-5H,6H,7H,8H-pyrido[3,4-d]pyrimidine-7-carboxylate (280 mg, 65%) as a white solid.

1-(4-(4-fluoro-2-(trifluoromethyl)phenoxy)-5,6,7,8-tetrahydropyrido[3,4-d]pyrimidin-2-yl)ethane-1,2-diol To a stirred solution of tert-butyl 2-(1,2-dihydroxyethyl)-4-[4-fluoro-2-(trifluoromethyl)phenoxy]-5H,6H,7H,8H-pyrido[3,4-d]pyrimidine-7-carboxylate (280 mg, 0.59 mmol) in DCM (4 mL) was added TFA (1 mL) at room temperature. The resulting mixture was stirred for 1 hours at room temperature. The resulting mixture was concentrated under vacuum. The residue was dissolved into DCM (50 mL) and washed with saturated aqueous NaHCO3 (20 mL). the organic layer was separated out and dried over anhydrous sodium sulfate. After filtration, the filtrate was concentrated under reduced pressure and the residue was purified by Prep-TLC with 8% methanol in dichloromethane to afford 1-[4-[4-fluoro-2-(trifluoromethyl)phenoxy]-5H,6H,7H,8H-pyrido[3,4-d]pyrimidin-2-yl]ethane-1,2-diol (180 mg, 82%) as a brown solid.

4-chloro-5-(2-(1,2-dihydroxyethyl)-4-(4-fluoro-2-(trifluoromethyl)phenoxy)-5,8-dihydropyrido[3,4-d]pyrimidin-7(6H)-yl)-2-(tetrahydro-2H-pyran-2-yl)pyridazin-3(2H)-one To a stirred solution of 2-[5H,6H,7H,8H-pyrido[3,4-d]pyrimidin-4-yloxy]benzaldehyde (180 mg, 0.71 mmol) in DIEA (0.5 mL) was added 4,5-dichloro-2-(oxan-2-yl)-2,3-dihydropyridazin-3-one (176 mg, 0.71 mmol) at room temperature. The resulting mixture was stirred for 1 hours at 90° C. After cooling to ambient temperature, the resulting mixture was concentrated under reduced pressure. The residue was purified by Prep-TLC, eluted with 8% methanol in dichloromethane to afford 4-chloro-5-(2-(1,2-dihydroxyethyl)-4-(4-fluoro-2-(trifluoromethyl)phenoxy)-5,8-dihydropyrido[3,4-d]pyrimidin-7(6H)-yl)-2-(tetrahydro-2H-pyran-2-yl)pyridazin-3(2H)-one (140 mg, 43%) as a brown solid.

(S)-4-chloro-5-(2-(1,2-dihydroxyethyl)-4-(4-fluoro-2-(trifluoromethyl)phenoxy)-5,8-dihydropyrido[3,4-d]pyrimidin-7(6H)-yl)pyridazin-3(2H)-one and (R)-4-chloro-5-(2-(1,2-dihydroxyethyl)-4-(4-fluoro-2-(trifluoromethyl)phenoxy)-5,8-dihydropyrido[3,4-d]pyrimidin-7(6H)-yl)pyridazin-3(2H)-one To a solution of 4-chloro-5-[2-(1,2-dihydroxyethyl)-4-[4-fluoro-2-(trifluoromethyl)phenoxy]-5H,6H,7H,8H-pyrido[3,4-d]pyrimidin-7-yl]-2-(oxan-2-yl)-2,3-dihydropyridazin-3-one (150 mg, 0.27 mmol) in DCM (4 mL) was added TFA (1 mL) at room temperature. The resulting mixture was stirred for 1 hours at room temperature. The resulting mixture was concentrated under reduced pressure. The residue was purified by reverse phase flash chromatography with the following conditions: Column: Spherical C18, 20-40 um, 120 g; Mobile Phase A: Water (plus 5 mM $NH_4HCO_3$); Mobile Phase B: acetonitrile; Flow rate: 45 mL/min; Gradient: 5% B in 10 min, 45% B to 65% B in 15 min; Detector: 254 nm and 220 nm. The fractions containing desired product were collected at 64% B and concentrated under reduced pressure to afford the racemic product (130 mg) which was separated by Prep-Chiral-HPLC with the following conditions: Column: XBridge Prep OBD C18 Column 30×150 mm, 5 um; Mobile Phase A: Hexane, Mobile Phase B: EtOH; Flow rate: 20 mL/min; Gradient: 35% B in 10 min; Detector: 254/220 nm). Although the two isomers were separated by this technique, the absolute orientation was not determined. The fractions containing desired product were collected and concentrated under reduced pressure to afford the product: The compound designated as (S)-4-chloro-5-(2-(1,2-dihydroxyethyl)-4-(4-fluoro-2-(trifluoromethyl)phenoxy)-5,8-dihydropyrido[3,4-d]pyrimidin-7(6H)-yl)pyridazin-3(2H)-one: retention time (4.97 min) (49.5 mg, 39%) as a white solid and The compound designated as (R)-4-chloro-5-(2-(1,2-dihydroxyethyl)-4-(4-fluoro-2-(trifluoromethyl)phenoxy)-5,8-dihydropyrido[3,4-d]pyrimidin-7(6H)-yl)pyridazin-3(2H)-one: retention time (8.05 min) (45.7 mg, 36%) as a white solid.

Example 22. Synthesis of Compound 131

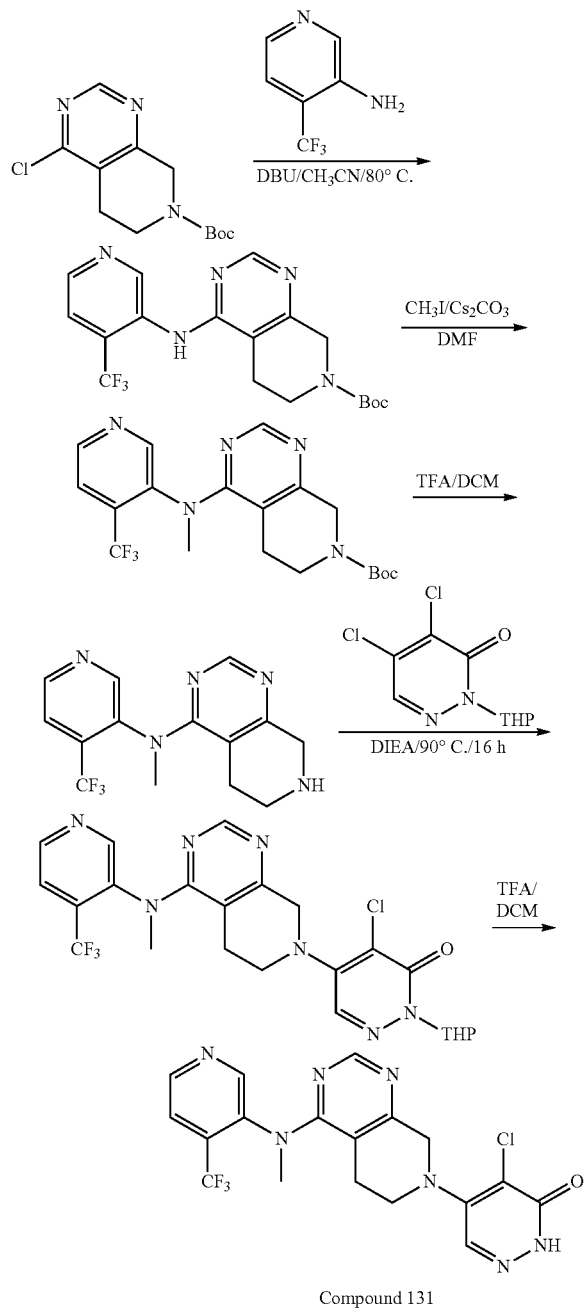

Compound 131

Tert-butyl 4-[[4-(trifluoromethyl)pyridin-3-yl]amino]-5H,6H,7H,8H-pyrido[3,4-d]pyrimidine-7-carboxylate To a stirred mixture of tert-butyl 4-chloro-5H,6H,7H,8H-pyrido[3,4-d]pyrimidine-7-carboxylate (500 mg, 1.854 mmol, 1 equiv.) and 4-(trifluoromethyl)pyridin-3-amine (601.03 mg, 3.707 mmol, 2.0 equiv.) in 1,4-dioxane (5 mL) were added Pd(AcO)$_2$ (83.24 mg, 0.371 mmol, 0.2 equiv.) and Cs$_2$CO$_3$ (1207.95 mg, 3.707 mmol, 2.0 equiv.) and XantPhos (429.04 mg, 0.741 mmol, 0.4 equiv.) at room temperature under nitrogen atmosphere. The resulting mixture was stirred for 2 h at 110 degrees C. under nitrogen atmosphere. The reaction was monitored by LCMS. The mixture was allowed to cool down to room temperature. The resulting mixture was filtered, the filter cake was washed with DCM (3×2 mL). The filtrate was concentrated under reduced pressure. The resulting mixture was concentrated under reduced pressure. The crude product was purified by reverse phase flash with the following conditions (Column: C18,120 g; Mobile Phase A: Water/0.05% NH$_4$HCO$_3$, Mobile Phase B: ACN; Flow rate: 45 mL/min; Gradient: 45% B to 65% B in 15 min; Detector, 254 nm and 220 nm, the desired product were collected at 64% B) to afford tert-butyl 4-[[4-(trifluoromethyl)pyridin-3-yl]amino]-5H,6H,7H,8H-pyrido[3,4-d]pyrimidine-7-carboxylate (600 mg, 81.86%) as a white solid.

Tert-butyl 4-[methyl[4-(trifluoromethyl)pyridin-3-yl]amino]-5H,6H,7H,8H-pyrido[3,4-d]pyrimidine-7-carboxylate To a stirred mixture of tert-butyl 4-[[4-(trifluoromethyl)pyridin-3-yl]amino]-5H,6H,7H,8H-pyrido[3,4-d]pyrimidine-7-carboxylate (1.32 g, 3.339 mmol, 1 equiv.) and Cs$_2$CO$_3$ (2.18 g, 6.677 mmol, 2.0 equiv.) in DMF (10 mL) was added CH3I (0.95 g, 6.677 mmol, 2.0 equiv.) at 0° C. under nitrogen atmosphere. The resulting mixture was stirred for 2 h at room temperature under nitrogen atmosphere. The reaction was monitored by LCMS. The crude product was purified by reverse phase flash with the following conditions (Column: C18,120 g; Mobile Phase A: Water/0.05% NH$_4$HCO$_3$, Mobile Phase B: ACN; Flow rate: 45 mL/min; Gradient: 45% B to 65% B in 15 min; Detector, 254 nm and 220 nm, the desired product were collected at 64% B) to afford tert-butyl 4-[methyl[4-(trifluoromethyl)pyridin-3-yl]amino]-5H,6H,7H,8H-pyrido[3,4-d]pyrimidine-7-carboxylate (400 mg, 29.26%) as a brown solid.

N-methyl-N-[5H,6H,7H,8H-pyrido[3,4-d]pyrimidin-4-yl]-4-(trifluoromethyl)pyridin-3-amine To a stirred solution of tert-butyl 4-[methyl[4-(trifluoromethyl)pyridin-3-yl]amino]-5H,6H,7H,8H-pyrido[3,4-d]pyrimidine-7-carboxylate (220 mg, 0.537 mmol, 1 equiv.) in DCM (4 mL) was added TFA (1 mL) at room temperature under nitrogen atmosphere. The resulting mixture was stirred for 1 h at room temperature. The reaction was monitored by LCMS. The resulting mixture was concentrated under reduced pressure. The mixture was basified to pH 8 with saturated NaHCO$_3$ (aq.). The resulting mixture was concentrated under reduced pressure. The residue was purified by Prep-TLC (DCM/MeOH 12:1) to afford N-methyl-N-[5H,6H,7H,8H-pyrido[3,4-d]pyrimidin-4-yl]-4-(trifluoromethyl)pyridin-3-amine (130 mg, 78.22%) as a brown solid.

4-chloro-5-(4-[methyl[4-(trifluoromethyl)pyridin-3-yl]amino]-5H,6H,7H,8H-pyrido[3,4-d]pyrimidin-7-yl)-2-(oxan-2-yl)-2,3-dihydropyridazin-3-one To a stirred solution of N-methyl-N-[5H,6H,7H,8H-pyrido[3,4-d]pyrimidin-4-yl]-4-(trifluoromethyl)pyridin-3-amine (130 mg, 0.420 mmol, 1 equiv.) in DIEA (0.5 mg) was added 4,5-dichloro-2-(oxan-2-yl)-2,3-dihydropyridazin-3-one (104.69 mg, 0.420 mmol, 1.0 equiv.) at room temperature. The resulting mixture was stirred for 1 h at 90° C. The reaction was monitored by LCMS. The mixture was allowed to cool down to room temperature. The resulting mixture was concentrated under reduced pressure. The residue was purified by Prep-TLC (DCM/MeOH 12:1) to afford 4-chloro-5-(4-[methyl[4-(trifluoromethyl)pyridin-3-yl]amino]-5H,6H,7H,8H-pyrido[3,4-d]pyrimidin-7-yl)-2-(oxan-2-yl)-2,3-dihydropyridazin-3-one (100 mg, 45.58%) as a brown solid.

4-chloro-5-(4-[methyl[4-(trifluoromethyl)pyridin-3-yl]amino]-5H,6H,7H,8H-pyrido[3,4-d]pyrimidin-7-yl)-2,3-dihydropyridazin-3-one To a stirred solution of 4-chloro-5-(4-[methyl[4-(trifluoromethyl)pyridin-3-yl]amino]-5H,6H,7H,8H-pyrido[3,4-d]pyrimidin-7-yl)-2-(oxan-2-yl)-2,3-dihydropyridazin-3-one (100 mg, 0.192 mmol, 1 equiv.) in DCM (4 mL) was added TFA (1 mL) at room temperature. The resulting mixture was stirred for 1 h at room temperature. The reaction was monitored by LCMS. The resulting mixture was concentrated under reduced pressure. The mixture was basified to pH 8 with saturated NaHCO₃ (aq.). The resulting mixture was concentrated under reduced pressure. The crude product (100 mg) was purified by Prep-HPLC with the following conditions (Column: XBridge Prep Phenyl OBD Column 19×150 mm 5 um 13 nm; Mobile phase A: water, 5 mM NH₄HCO₃, Mobile phase B: Acetonitrile; Flow rate: 60 mL/min; Gradient: 35% B to 55% B in 8 min; 220 nm; Rt: 7.13 min) to afford 4-chloro-5-(4-[methyl[4-(trifluoromethyl)pyridin-3-yl]amino]-5H,6H,7H,8H-pyrido[3,4-d]pyrimidin-7-yl)-2,3-dihydropyridazin-3-one (52 mg, 61.99%) as a white solid.

Example 23. Synthesis of Intermediates

A. 2-(Difluoromethyl)-4-fluorophenyl acetate

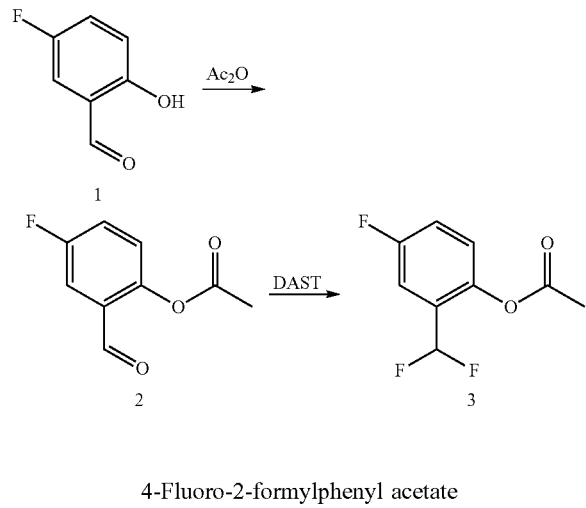

4-Fluoro-2-formylphenyl acetate

To a solution of 5-fluoro-2-hydroxybenzaldehyde (10 g, 71.371 mmol, 1 equiv.) in Pyridine (100 mL, 1242.353 mmol, 17.41 equiv.) was added acetyl acetate (14.57 g, 0.143 mmol, 2 equiv.) at 25° C. The solution was stirred at 25° C. for 30 min. The resulting solution was concentrated under reduced pressure. The residue was purified by silica gel column chromatography, eluted with PE/EA (100/1 to 20/1) to afford 4-fluoro-2-formylphenyl acetate (12 g, 92.31%) as a light yellow oil.

2-(Difluoromethyl)-4-fluorophenyl acetate

To a solution of 4-fluoro-2-formylphenyl acetate (12 g, 65.880 mmol, 1 equiv.) in DCM (200 mL, 3146.009 mmol, 47.75 equiv.) was added DAST (21.24 g, 131.760 mmol, 2 equiv.) at 0° C. The solution was stirred at 25° C. for 4 hours. The resulting solution was quenched with water (100 mL). The resulting mixture was extracted with DCM (100 mL×2). The combined organic layers were washed with saturated NaCl aq. (100 mL×2) dried over anhydrous Na₂SO₄. After filtration, the filtrate was concentrated under reduced pressure. The residue was purified by silica gel column chromatography, eluted with PE/EA (10/1 to 5/1) to afford 2-(difluoromethyl)-4-fluorophenyl acetate (10 g, 74.35%) as a light yellow oil.

B. 2-(Difluoromethyl)-4-fluorophenol

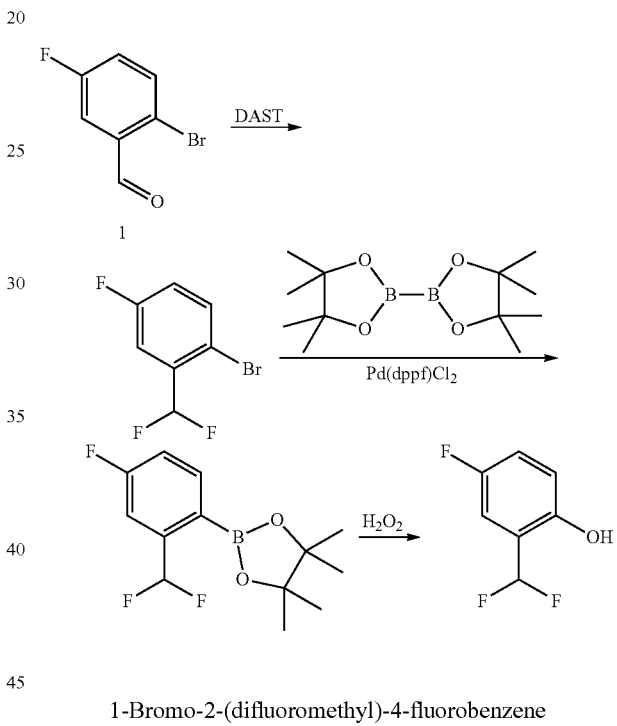

1-Bromo-2-(difluoromethyl)-4-fluorobenzene

To a stirred solution of 2-bromo-5-fluorobenzaldehyde (10 g, 49.26 mmol, 1 equiv.) in DCM (60 mL) was added DAST (15.9 g, 98.52 mmol, 2 equiv). The resulting mixture was stirred for 2 hours at −10° C. The reaction was quenched with Water at −10° C. The resulting mixture was extracted with EtOAc (4×30 mL). The combined organic layers were washed with brine (2×40 mL), dried over anhydrous Na₂SO₄. After filtration, the filtrate was concentrated under reduced pressure. The residue was purified by silica gel column chromatography, eluted with PE/EtOAc (6:1) to afford 1-bromo-2-(difluoromethyl)-4-fluorobenzene (8 g, 72.18%) as a light yellow oil.

2-[2-(Difluoromethyl)-4-fluorophenyl]-4,4,5,5-tetramethyl-1,3,2-dioxaborolane

To a solution of 1-bromo-2-(difluoromethyl)-4-fluorobenzene (31 g, 137.773 mmol, 1 equiv.) and BPD (52.48 g, 206.664 mmol, 1.50 equiv.) in 1,4-dioxane (300 mL, 3541.225 mmol, 25.70 equiv.) were added AcOK (27.04 g, 275.546 mmol, 2 equiv.) and Pd(dppf)Cl$_2$.CH$_2$Cl$_2$ (5.63 g, 6.889 mmol, 0.05 equiv.) at 25° C. under nitrogen atmosphere. The mixture was stirred at 90° C. for 2 hours. The resulting mixture was concentrated under reduced pressure. The residue was purified by silica gel column chromatography, eluted with PE/EA (10/1) to afford 2-[2-(difluoromethyl)-4-fluorophenyl]-4,4,5,5-tetramethyl-1,3,2-dioxaborolane (30 g, 80.03%) as a light yellow oil. The reaction was monitored by TLC. The crude was used the next step directly.

2-(Difluoromethyl)-4-fluorophenol

To a solution of 2-[2-(difluoromethyl)-4-fluorophenyl]-4,4,5,5-tetramethyl-1,3,2-dioxaborolane (50 g, 183.776 mmol, 1 equiv.) in MeOH (300 mL, 7409.673 mmol, 40.32 equiv.) and H$_2$O (100 mL, 5550.837 mmol, 30.20 equiv.) was added H$_2$O$_2$ (30%) (50 mL, 2146.131 mmol, 11.68 equiv.) dropwise at 0° C. The solution was stirred at 25° C. for 3 hours. The resulting solution was concentrated under reduced pressure. The residue was diluted with EA (500 mL), The organic layer was washed with 3×200 mL of saturated NaCl (aq.). Combined organic layers was dried with anhydrous Na$_2$SO$_4$, concentrated under reduced pressure to afford 2-(difluoromethyl)-4-fluorophenol (25 g, 83.91%) as a light yellow oil.

Example 24. TRPC4 Activity Assay

ICLN-1694 cells (HEK-TREx hTRPC4) expressing TRPC4 were generated as follows. Commercially available HekTrex-293 cells were seeded at 0.7×10$^6$ cells/well in a 1×6-well plate 24 hrs prior to transfection using 2 mL cell growth media containing no antibiotics (lx DMEM/high glucose (Hyclone # SH30022.02); 10% fetal bovine serum (Sigma) 2 mM sodium pyruvate, 10 mM HEPES). The human codon-optimized TRPC4 coding sequence was cloned into pcDNA5/TO (Invitrogen; Cat No. V103320) using hygromycin as the resistance gene and the plasmid (SEQ ID NO: 1) propagated using T-Rex-293 cells (Invitrogen; Cat No. R71007) following manufacturer's directions. On day 2, 2 μg of plasmid DNA plus 6 μl of Xtreme-GENE HP reagent in Optimem (200 μl total volume) was prepared and incubated for 15 min at room temperature. This plasmid solution was then gently overlayed dropwise onto each well and the plate was gently swirled to mix complex with the media for approximately 30 seconds. Transfected cells were incubated at 37° C. in a 10% CO$_2$ incubator for 24 hrs. The transfected cells were harvested and transferred into 2×150 mm dishes containing cell growth media with no antibiotics at 37° C.

The next day selection was initiated to generate a stable pool by adding cell growth media containing 150 μg/mL Hygromycin and 5 μg/mL Blasticidin and cells were allowed to grow. Media with the selection agent was changed every 1-2 days as needed to remove dead cells. After 7 days, the hygromycin concentration was reduced to 75 μg/mL and cells growth was allowed to continue.

Single clones were selected as follows. The stable pool was diluted to 10 cells/mL and seeded (100 μl/well) into 24×96 well plates (~1 cell/well) and allowed to grow for 7 days in cell growth media. Fresh media (100 μl) was added and the cells allowed to grow for another 1-2 weeks and then stored frozen or used immediately.

Compounds were made up to, or supplied as, a 10 mM stock solution generally using DMSO as the vehicle. 10-point dose response curves were generated using the Echo-550 acoustic dispenser. Compound source plates were made by serially diluting compound stocks to create 10 mM, 1 mM, and 0.1 mM solutions in DMSO into Echo-certified LDV plates. The Echo then serially spotted 100% DMSO stock solutions into source dose response plates to generate a 4-fold dilution scheme. 100% DMSO was added to the spotted dose response plates to bring the final volume to 5 μl. 300 nl of the dose response stock plate was then spotted into pre-incubation and stimulation assay plates. 50 μl of pre-incubation buffer and 100 μl of stimulation buffer was then added to the plates resulting in a final assay test concentration range of 30 μM to 0.0001 μM with a final DMSO concentration of 0.3%.

ICLN-1694 cells (HEK-TREx hTRPC4) were plated onto 384 well, black pdl-coated microplates and maintained in cell growth media supplemented with 1 μg/mL tetracycline the day prior to use for experiments. TRPC4 expression was induced by the application of 1 μg/mL tetracycline at the time of plating. Media was removed from the plates and 10 μl of 4 μM of Fluo-4 AM (mixed with equal volume of Pluronic F-127) in EBSS (NaCl (142 mM), KCl (5.4 mM), glucose (10 mM), CaCl$_2$) (1.8 mM), MgCl2 (0.8 mM), HEPES (10 mM), pH 7.4) is added to the cells. Cells were incubated at room temperature, protected from light, for 60-90 minutes. After the incubation period, the dye was removed and replaced with 10 μl of EBSS. Cell, pre-incubation and stimulation plates were loaded onto the FLIPR-II and the assay was initiated. The FLIPR measured a 10 second baseline and then added 10 μl of 2× compounds (or controls). Changes in fluorescence were monitored for an additional 5 minutes. After a 5 minute pre-incubation, 20 μl of 2× Englerin A (with 1× compound or controls) was added to the cell plate. The final Engerlin A stimulation concentration in the assay was 100 nM. After the Englerin A addition, changes in fluorescence were monitored for an additional 5 minutes.

Compound modulation of TRPC4 calcium response was determined as follows. After the Englerin A, fluorescence was monitored for a 5-minute period. The maximum relative fluorescence response (minus the control response of 1 μM of an internal control compound known to maximally block TRPC4 calcium response, the "REF INHIB" in the formula below) was captured and exported from the FLIPR.

Compound effect is calculated as % inhibition using the following formula:

$$\% \text{ inhibition} = \frac{RFU \text{ TEST AGENT} - \text{Plate Average } RFU \text{ REF INHIB}}{\text{Plate Average } RFU \text{ CONTROL} - \text{Plate Average } RFU \text{ REF INHIB}} \times 100$$

wherein "RFU" is the relative fluorescent units.

The results of these assays are shown in Table 2, below, wherein "A" indicates an IC$_{50}$ of less than or equal to 50 nM; "B" an IC$_{50}$ of greater than 50 nM and less than or equal to 500 nM; "C" an IC$_{50}$ of greater than 500 nM and less than 1 μM; "D" an IC$_{50}$ of 1 μM or greater; and "NT" indicates that the compound was not tested.

Example 25. TRPC5 Activity Assay

ICLN-1633 cells (HEK-TREx hTRPC5) expressing TRPC5 were generated as follows. Commercially available HekTrex-293 cells were seeded at 0.7×10$^6$ cells/well in a 1×6-well plate 24 hrs prior to transfection using 2 mL cell growth media containing no antibiotics (lx DMEM/high glucose (Hyclone # SH30022.02); 10% fetal bovine serum (Sigma) 2 mM sodium pyruvate, 10 mM HEPES). The human TRPC5 coding sequence (NM_012471 with a silent T478C mutation) was cloned into pcDNA5/TO (Invitrogen; Cat No. V103320) using hygromycin as the resistance gene and the plasmid (SEQ ID NO:2) propagated using T-Rex-293 cells (Invitrogen; Cat No. R71007) following manufacturer's directions. On day 2, 2 µg of plasmid DNA plus 6 µl of Xtreme-GENE HP reagent in Optimem (200 µl total volume) was prepared and incubated for 15 min at room temperature. This plasmid solution was then gently overlayed dropwise onto each well and the plate was gently swirled to mix complex with the media for approximately 30 seconds. Transfected cells were incubated at 37° C. in a 10% $CO_2$ incubator for 24 hrs. The transfected cells were harvested and transferred into 2×150 mm dishes containing cell growth media with no antibiotics at 37° C.

The next day selection was initiated to generate a stable pool by adding cell growth media containing 150 µg/mL Hygromycin and 5 µg/mL Blasticidin and cells were allowed to grow. Media with the selection agent was changed every 1-2 days as needed to remove dead cells. After 7 days, the hygromycin concentration was reduced to 75 µg/mL and cells growth was allowed to continue.

Single clones were selected as follows. The stable pool was diluted to 10 cells/mL and seeded (100 µl/well) into 24×96 well plates (~1 cell/well) and allowed to grow for 7 days in cell growth media. Fresh media (100 µl) was added and the cells allowed to grow for another 1-2 weeks and then stored frozen or used immediately.

Compounds were made up to, or supplied as a 10 mM stock solution generally using DMSO as the vehicle. 10-point dose response curves were generated using the Echo-550 acoustic dispenser. Compound source plates were made by serially diluting compound stocks to create 10 mM, 1 mM, and 0.1 mM solutions in DMSO into Echo certified LDV plates. The Echo then serially spotted 100% DMSO stock solutions into source dose response plates to generate a 4-fold dilution scheme. 100% DMSO was added to the spotted dose response plates to bring the final volume to 5 µl. 300 nl of the dose response stock plate was then spotted into pre-incubation and stimulation assay plates. 50 µl of pre-incubation buffer and 100 µl of stimulation buffer was then added to the plates resulting in a final assay test concentration range of 30 µM to 0.0001 µM with a final DMSO concentration of 0.3%.

Human ICLN-1633 cells expressing were plated onto 384 well, black PDL-coated microplates and maintained in TRPC5 growth media the day prior to use for experiments. TRPC5 expression was induced by the application of 1 µg/mL tetracycline at the time of plating. Media is removed from the plates and 10 µl of 4 µM of Fluo-4 AM (mixed with equal volume of Pluronic F-127) in EBSS is added to the cells. Cells are incubated at room temperature, protected from light, for 60-90 minutes. After the incubation period, the dye is removed and replaced with 10 µl of EBSS. Cell, pre-incubation and stimulation plates are loaded onto the FLIPR-II and the assay is initiated. The FLIPR measures a 10 second baseline and then adds 10 µl of 2× compounds (or controls). Changes in fluorescence are monitored for an additional 5 minutes. After the 5 minute pre-incubation, 20 µl of 2× Riluzole (with 1× compound or controls) is added to the cell plate. The final Riluzole stimulation concentration in the assay is 30 µM. After the Riluzole addition, changes in fluorescence are monitored for an additional 5 minutes.

Compound modulation of TRPC5 calcium response was determined as follows. After the Englerin A, fluorescence was monitored for a 5-minute period. The maximum relative fluorescence response (minus the control response of 1 µM of an internal control compound known to maximally block TRPC5 calcium response, the "REF INHIB" in the formula below) was captured and exported from the FLIPR.

Compound effect is calculated as % inhibition using the following formula:

% inhibition=

$$\frac{RFU \text{ TEST AGENT} - \text{Plate Average } RFU\ REF\ INHIB}{\text{Plate Average } RFU \text{ CONTROL} - \text{Plate Average } RFU\ REF\ INHIB} \times 100$$

wherein "RFU" is the relative fluorescent units.

The results of these assays are shown in Table 2, below, wherein "A" indicates an $IC_{50}$ of less than or equal to 50 nM; "B" an $IC_{50}$ of greater than 50 nM and less than or equal to 500 nM; "C" an $IC_{50}$ of greater than 500 nM and less than 1 µM; "D" an $IC_{50}$ of 1 µM or greater; and "NT" indicates that the compound was not tested.

TABLE 2

TRPC4 and TRPC5 Activities of Exemplary Compounds

| Compound | TRPC5 | TRPC4 |
|---|---|---|
| 100 | A | A |
| 101 | A | A |
| 102 | A | A |
| 103 | A | A |
| 104 | A | A |
| 105 | A | A |
| 106 | A | B |
| 107 | A | B |
| 108 | B | C |
| 109 | A | B |
| 110 | B | A |
| 111 | B | NT |
| 112 | A | B |
| 113 | A | B |
| 114 | A | A |
| 115 | B | B |
| 116 | A | A |
| 117 | A | B |
| 117a | D | NT |
| 118 | B | B |
| 119 | A | A |
| 120 | A | A |
| 121 | A | NT |
| 122 | A | NT |
| 123 | B | NT |
| 124 | A | NT |
| 125 | A | NT |
| 126 | A | NT |
| 126a | B | NT |
| 127 | B | NT |
| 128 | A | NT |
| 129 | A | NT |
| 130 | A | NT |
| 131 | A | NT |
| 132 | B | NT |
| 133 | B | NT |
| 133a | C | NT |
| 134 | A | NT |
| 135 | A | NT |
| 136 | A | NT |
| 137 | A | NT |
| 138 | B | NT |
| 139 | B | NT |
| 140 | B | NT |

$^1$H NMR and MS data for selected compounds is provided in the table below:

| Compound | Structure | NMR | MS |
|---|---|---|---|
| 100 | 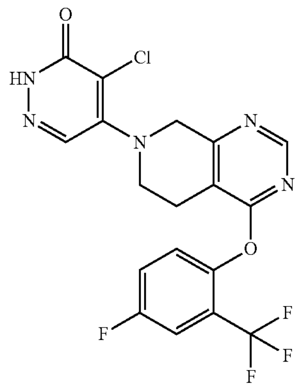 [SMILES: O=c1[nH]ncc(N2CCc3c(ncnc3Oc3ccc(F)cc3C(F)(F)F)C2)c1Cl] | 1H NMR (400 MHz, DMSO-d6) chemical shifts 13.00 (s, 1H), 8.57 (s, 1H), 8.04 (s, 1H), 7.79 (dd, J = 8.4, 3.0 Hz, 1H), 7.70 (s, 1H), 7.70-7.59 (m, 1H), 4.68 (s, 2H), 3.79 (t, J = 5.6 Hz, 2H), 2.98 (s, 2H). | 442 |
| 101 | 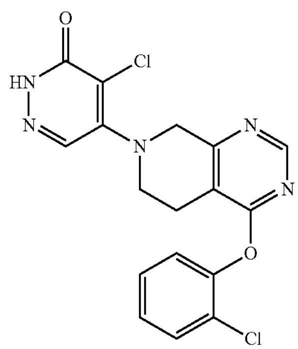 [SMILES: O=c1[nH]ncc(N2CCc3c(ncnc3Oc3ccccc3Cl)C2)c1Cl] | 1H NMR (400 MHz, DMSO-d6) chemical shifts 13.00 (s, 1H), 8.54 (s, 1H), 8.03 (s, 1H), 7.63 (dd, J = 8.0, 1.4 Hz, 1H), 7.51-7.40 (m, 2H), 7.36 (td, J = 7.4, 2.2 Hz, 1H), 4.67 (s, 2H), 3.80 (t, J = 5.7 Hz, 2H), 3.03 (t, J = 5.7 Hz, 2H). | 390 |
| 102 | 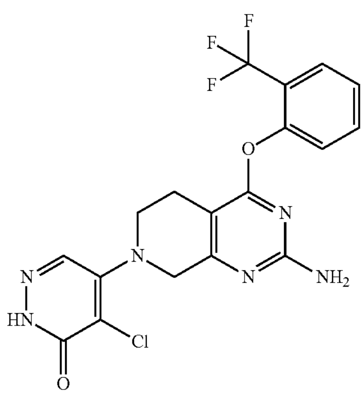 [SMILES: Nc1nc2c(c(Oc3ccccc3C(F)(F)F)n1)CCN(c1cn[nH]c(=O)c1Cl)C2] | 1H NMR (400 MHz, Methanol-d4) chemical shifts 8.00 (s, 1H), 7.79-7.67 (m, 2H), 7.44 (dd, J = 13.1, 7.9 Hz, 2H), 4.51 (s, 2H), 3.87 (t, J = 5.8 Hz, 2H), 2.93 (t, J = 5.6 Hz, 2H). | 439 |
| 103 | 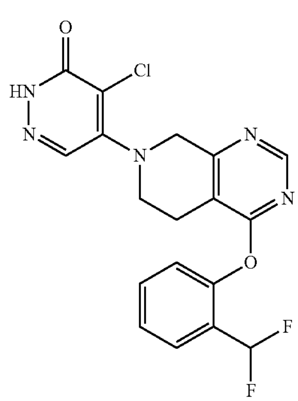 [SMILES: O=c1[nH]ncc(N2CCc3c(ncnc3Oc3ccccc3C(F)F)C2)c1Cl] | 1H NMR (400 MHz, DMSO-d6) chemical shifts 13.00 (s, 1H), 8.54 (s, 1H), 8.04 (s, 1H), 7.71 (d, J = 7.7 Hz, 1H), 7.65 (t, J = 7.9 Hz, 1H), 7.46 (t, J = 7.6 Hz, 1H), 7.40 (d, J = 8.2 Hz, 1H), 7.13 (t, J = 54.3 Hz, 1H), 4.67 (s, 2H), 3.79 (t, J = 5.7 Hz, 2H), 3.03 (t, J = 5.7 Hz, 2H). | 406 |

| Compound | Structure | NMR | MS |
|---|---|---|---|
| 104 | 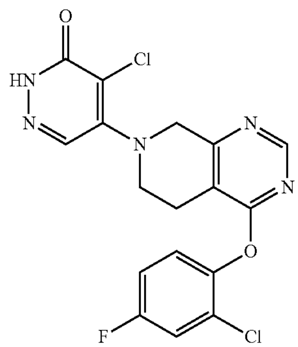 [SMILES: O=c1[nH]ncc(N2CCc3c(ncnc3Oc3ccc(F)cc3Cl)C2)c1Cl] | 1H NMR (400 MHz, DMSO-d6) chemical shifts 12.97 (s, 1H), 8.55 (s, 1H), 8.03 (s, 1H), 7.66 (dd, J = 8.3, 3.0 Hz, 1H), 7.51 (dd, J = 8.9, 5.3 Hz, 1H), 7.42-7.24 (m, 1H), 4.67 (s, 2H), 3.80 (t, J = 5.9 Hz, 2H), 3.02 (s, 2H). | 407 |
| 105 | 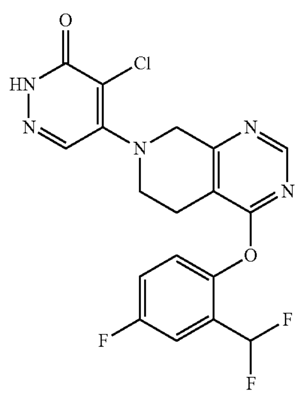 [SMILES: O=c1[nH]ncc(N2CCc3c(ncnc3Oc3ccc(F)cc3C(F)F)C2)c1Cl] | 1H NMR (400 MHz, DMSO-d6) chemical shifts 13.00 (s, 1H), 8.55 (s, 1H), 8.04 (s, 1H), 7.51 (ddd, J = 14.3, 10.8, 6.8 Hz, 3H), 7.13 (t, J = 53.9 Hz, 1H), 4.67 (s, 2H), 3.79 (t, J = 5.7 Hz, 2H), 3.03 (t, J = 5.8 Hz, 2H). | 424 |
| 106 | 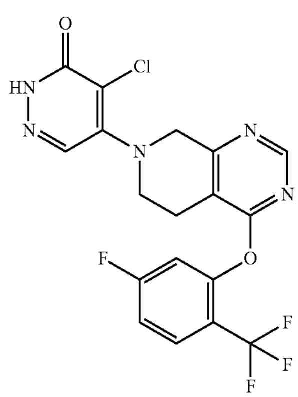 [SMILES: O=c1[nH]ncc(N2CCc3c(ncnc3Oc3cc(F)ccc3C(F)(F)F)C2)c1Cl] | 1H NMR (400 MHz, DMSO-d6) chemical shifts 13.00 (s, 1H), 8.61 (s, 1H), 8.03 (s, 1H), 7.95 (d, J = 8.4 Hz, 1H), 7.62 (d, J = 9.7 Hz, 1H), 7.41 (s, 1H), 4.69 (s, 2H), 3.80 (s, 2H), 2.98 (s, 2H). | 442 |
| 107 | 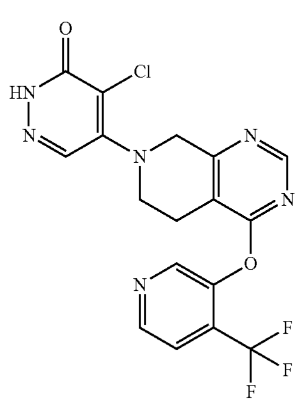 [SMILES: O=c1[nH]ncc(N2CCc3c(ncnc3Oc3cnccc3C(F)(F)F)C2)c1Cl] | 1H NMR (400 MHz, DMSO-d6) chemical shifts 13.00 (s, 1H), 8.91 (s, 1H), 8.79 (d, J = 4.9 Hz, 1H), 8.59 (s, 1H), 8.04 (s, 1H), 7.92 (d, J = 5.0 Hz, 1H), 4.70 (s, 2H), 3.81 (t, J = 5.7 Hz, 2H), 3.02 (s, 2H). | 425 |

| Compound | Structure | NMR | MS |
|---|---|---|---|
| 108 | 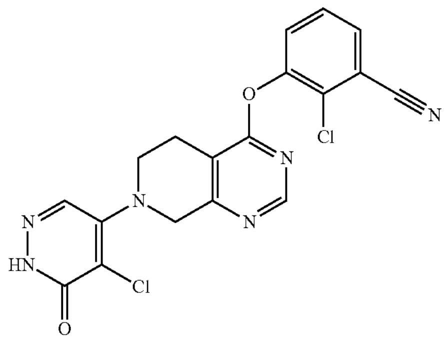 [SMILES: N#Cc1cccc(Oc2ncnc3c2CCN(c2cn[nH]c(=O)c2Cl)C3)c1Cl] | 1H NMR (400 MHz, DMSO-d6) chemical shifts 13.00 (s, 1H), 8.57 (s, 1H), 8.04 (s, 1H), 7.99 (dd, J = 7.8, 1.5 Hz, 1H), 7.86 (dd, J = 8.3, 1.5 Hz, 1H), 7.69 (t, J = 8.0 Hz, 1H), 4.69 (s, 2H), 3.81 (t, J = 5.7 Hz, 2H), 3.08-3.01 (m, 2H). | 415 |
| 109 | 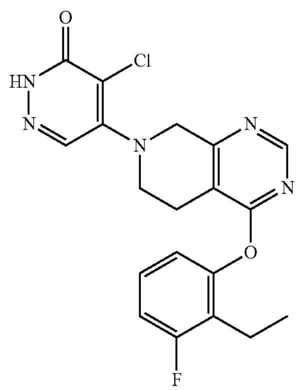 [SMILES: CCc1c(F)cccc1Oc1ncnc2c1CCN(c1cn[nH]c(=O)c1Cl)C2] | 1H NMR (400 MHz, DMSO-d6) chemical shifts 13.01 (s, 1H), 8.54 (s, 1H), 8.04 (s, 1H), 7.38-7.28 (m, 1H), 7.15 (t, J = 8.9 Hz, 1H), 7.06 (d, J = 8.2 Hz, 1H), 4.67 (s, 2H), 3.80 (t, J = 5.8 Hz, 2H), 3.03 (d, J = 5.8 Hz, 2H), 2.48 (d, J = 7.4 Hz, 2H), 1.05 (t, J = 7.5 Hz, 3H). | 402 |
| 110 | 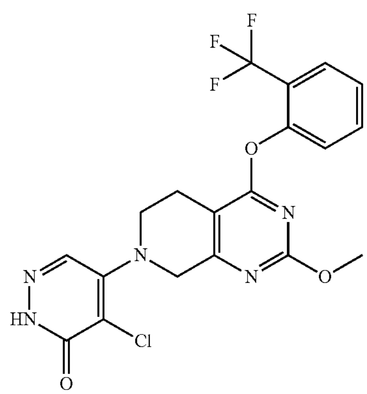 [SMILES: COc1nc2c(c(Oc3ccccc3C(F)(F)F)n1)CCN(c1cn[nH]c(=O)c1Cl)C2] | 1H NMR (400 MHz, DMSO-d6) chemical shifts 12.98 (s, 1H), 8.02 (s, 1H), 7.88-7.75 (m, 2H), 7.59-7.48 (m, 2H), 4.60 (s, 2H), 3.77 (t, J = 5.7 Hz, 2H), 3.74 (s, 3H), 2.89 (t, J = 5.6 Hz, 2H). | 454 |
| 111 | 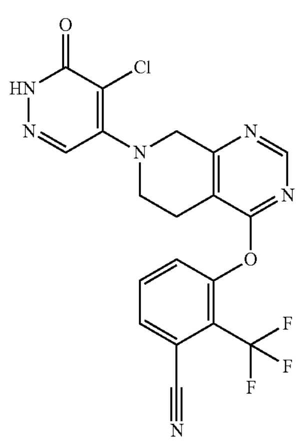 [SMILES: N#Cc1cccc(Oc2ncnc3c2CCN(c2cn[nH]c(=O)c2Cl)C3)c1C(F)(F)F] | 1H NMR (400 MHz, DMSO-d6) chemical shifts 13.01 (s, 1H), 8.60 (s, 1H), 8.13 (d, J = 7.4 Hz, 1H), 8.07-7.99 (m, 2H), 7.96 (d, J = 8.4 Hz, 1H), 4.70 (s, 2H), 3.81 (t, J = 5.6 Hz, 2H), 3.01 (s, 2H). | 449 |

-continued

| Compound | Structure | NMR | MS |
|---|---|---|---|
| 112 | 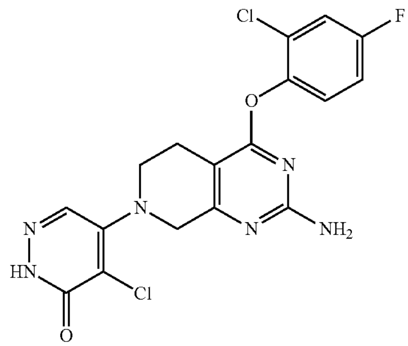 [SMILES: Nc1nc2c(c(Oc3ccc(F)cc3Cl)n1)CCN(c1cn[nH]c(=O)c1Cl)C2] | 1H NMR (400 MHz, DMSO-d6) chemical shifts 12.95 (s, 1H), 7.97 (s, 1H), 7.62 (dd, J = 8.5, 3.1 Hz, 1H), 7.45 (dd, J = 9.0, 5.3 Hz, 1H), 7.31 (td, J = 8.5, 2.9 Hz, 1H), 6.50 (s, 2H), 4.41 (s, 2H), 3.72 (d, J = 6.0 Hz, 2H), 2.80 (s, 2H). | 423 |
| 113 | 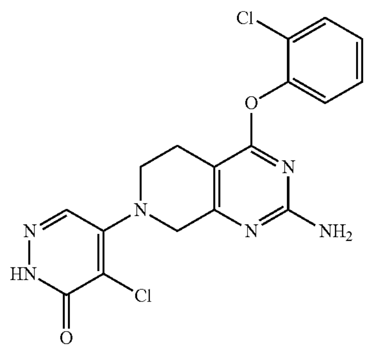 [SMILES: Nc1nc2c(c(Oc3ccccc3Cl)n1)CCN(c1cn[nH]c(=O)c1Cl)C2] | 1H NMR (400 MHz, DMSO-d6) chemical shifts 12.95 (s, 1H), 7.97 (s, 1H), 7.58 (dd, J = 7.9, 1.5 Hz, 1H), 7.47-7.38 (m, 1H), 7.41-7.34 (m, 1H), 7.34-7.25 (m, 1H), 6.48 (s, 2H), 4.41 (s, 2H), 3.73 (t, J = 5.8 Hz, 2H), 2.81 (d, J = 5.7 Hz, 2H). | 405 |
| 114 | 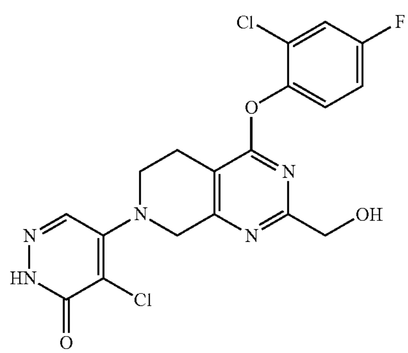 [SMILES: O=c1[nH]ncc(N2CCc3c(nc(CO)nc3Oc3ccc(F)cc3Cl)C2)c1Cl] | 1H NMR (400 MHz, DMSO-d6) chemical shifts 13.00 (s, 1H), 8.03 (s, 1H), 7.66 (dd, J = 8.4, 3.0 Hz, 1H), 7.51 (dd, J = 9.0, 5.3 Hz, 1H), 7.35 (td, J = 8.6, 3.0 Hz, 1H), 5.17 (t, J = 6.3 Hz, 1H), 4.67 (s, 2H), 4.32 (d, J = 6.3 Hz, 2H), 3.80 (t, J = 5.7 Hz, 2H), 3.00 (d, J = 6.4 Hz, 2H). | 438 |
| 115 | 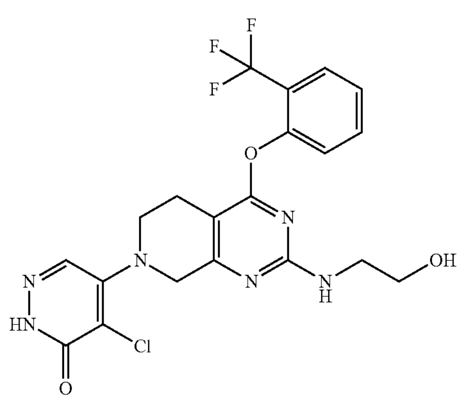 [SMILES: O=c1[nH]ncc(N2CCc3c(nc(NCCO)nc3Oc3ccccc3C(F)(F)F)C2)c1Cl] | 1H NMR (400 MHz, DMSO-d6) chemical shifts 12.95 (s, 1H), 7.98 (s, 1H), 7.83-7.72 (m, 2H), 7.48 (dd, J = 18.0, 8.2 Hz, 2H), 6.82 (s, 1H), 4.54 (s, 1H), 4.44 (s, 2H), 3.73 (t, J = 5.6 Hz, 2H), 3.33 (m, 4H), 2.78 (s, 2H). | 483 |

-continued

| Compound | Structure | NMR | MS |
|---|---|---|---|
| 116 | 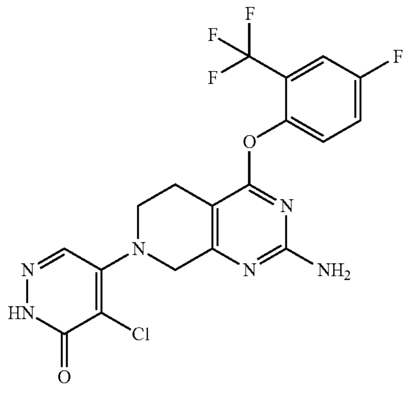 [SMILES: Nc1nc2c(c(Oc3ccc(F)cc3C(F)(F)F)n1)CCN(c1cn[nH]c(=O)c1Cl)C2] | 1H NMR (400 MHz, DMSO-d6) chemical shifts 12.96 (s, 1H), 7.97 (s, 1H), 7.79-7.71 (m, 1H), 7.66 (td, J = 8.5, 3.0 Hz, 1H), 7.56 (dd, J = 9.2, 4.6 Hz, 1H), 6.54 (s, 2H), 4.41 (s, 2H), 3.72 (t, J = 5.8 Hz, 2H), 2.76 (t, J = 5.7 Hz, 2H). | 457 |
| 117* | 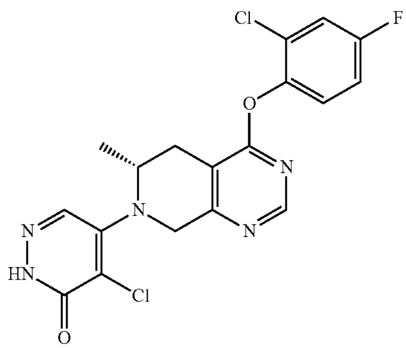 [SMILES: C[C@@H]1Cc2c(ncnc2Oc2ccc(F)cc2Cl)CN1c1cn[nH]c(=O)c1Cl] | 1H NMR (400 MHz, DMSO-d6) chemical shifts 13.04 (s, 1H), 8.56 (s, 1H), 8.02 (s, 1H), 7.67 (dd, J = 8.4, 2.5 Hz, 1H), 7.53 (dd, J = 9.2, 5.3 Hz, 1H), 7.41-7.31 (m, 1H), 4.75 (d, J = 18.1 Hz, 1H), 4.62-4.34 (m, 2H), 3.23 (dd, J = 17.0, 6.0 Hz, 1H), 2.81 (d, J = 17.1 Hz, 1H), 1.20 (d, J = 6.6 Hz, 3H). | 422 |
| 117a* | 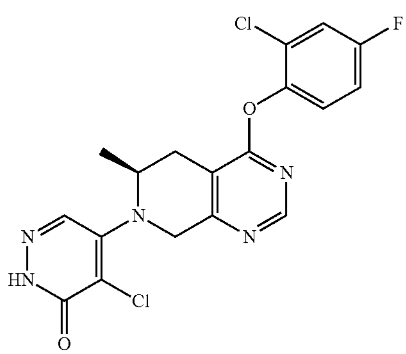 [SMILES: C[C@H]1Cc2c(ncnc2Oc2ccc(F)cc2Cl)CN1c1cn[nH]c(=O)c1Cl] | 1H NMR (400 MHz, DMSO-d6) chemical shifts 13.04 (s, 1H), 8.56 (s, 1H), 8.02 (s, 1H), 7.67 (dd, J = 8.6, 2.5 Hz, 1H), 7.58-7.50 (m, 1H), 7.36 (dd, J = 9.9, 7.3 Hz, 1H), 4.76 (d, J = 18.1 Hz, 1H), 4.63-4.40 (m, 2H), 3.23 (dd, J = 17.3, 5.9 Hz, 1H), 2.81 (d, J = 17.0 Hz, 1H), 1.20 (d, J = 6.7 Hz, 3H). | 422 |
| 118 | 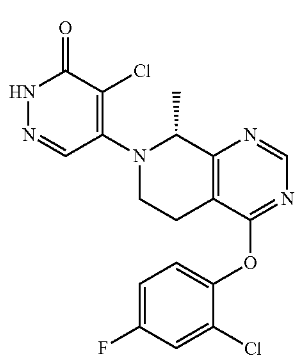 [SMILES: C[C@@H]1c2ncnc(Oc3ccc(F)cc3Cl)c2CCN1c1cn[nH]c(=O)c1Cl] | 1H NMR (400 MHz, DMSO-d6) chemical shifts 12.96 (s, 1H), 8.55 (s, 1H), 8.02 (s, 1H), 7.66 (dd, J = 8.4, 3.0 Hz, 1H), 7.50 (dd, J = 9.0, 5.3 Hz, 1H), 7.35 (td, J = 8.5, 3.0 Hz, 1H), 5.06 (q, J = 6.7 Hz, 1H), 4.00 (dd, J = 14.1, 5.7 Hz, 1H), 3.68 (ddd, J = 14.4, 11.1, 4.2 Hz, 1H), 3.06 (ddd, J = 17.1, 11.2, 6.0 Hz, 1H), 2.98-2.88 (m, 1H), 1.60 (d, J = 6.8 Hz, 3H). | 422 |

-continued

| Compound | Structure | NMR | MS |
|---|---|---|---|
| 119 | 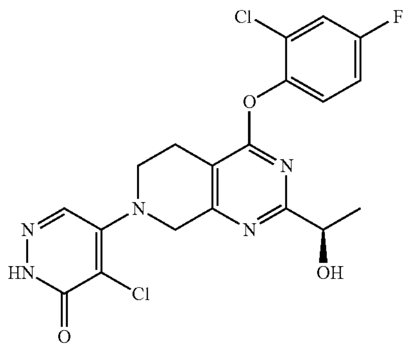 [SMILES: C[C@@H](O)c1nc2c(c(Oc3ccc(F)cc3Cl)n1)CCN(c1cn[nH]c(=O)c1Cl)C2] | 1H NMR (400 MHz, DMSO-d6) chemical shifts 12.98 (s, 1H), 8.03 (s, 1H), 7.66 (dd, J = 8.4, 3.0 Hz, 1H), 7.51 (dd, J = 9.1, 5.3 Hz, 1H), 7.35 (td, J = 8.5, 3.0 Hz, 1H), 5.06 (d, J = 5.3 Hz, 1H), 4.67 (s, 2H), 4.48 (p, J = 6.4 Hz, 1H), 3.80 (t, J = 5.5 Hz, 2H), 2.99 (s, 2H), 1.22 (t, J = 6.4 Hz, 3H). | 452 |
| 120 | 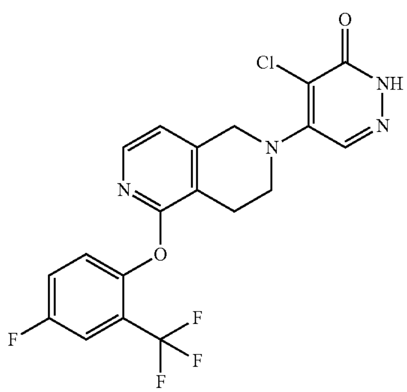 [SMILES: O=c1[nH]ncc(N2CCc3c(ccnc3Oc3ccc(F)cc3C(F)(F)F)C2)c1Cl] | 1H NMR (400 MHz, DMSO-d6) chemical shifts 13.00 (s, 1H), 7.98 (s, 1H), 7.90 (d, J = 5.2 Hz, 1H), 7.72 (dd, J = 8.6, 3.1 Hz, 1H), 7.63 (td, J = 8.6, 3.1 Hz, 1H), 7.49 (dd, J = 9.1, 4.6 Hz, 1H), 7.00 (d, J = 5.2 Hz, 1H), 4.69 (s, 2H), 3.78 (t, J = 5.8 Hz, 2H), 2.95 (t, J = 5.9 Hz, 2H). | 441 |
| 121 | 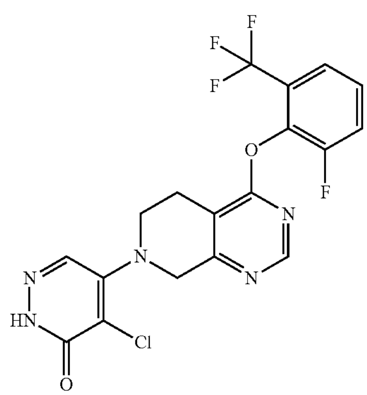 [SMILES: O=c1[nH]ncc(N2CCc3c(ncnc3Oc3c(F)cccc3C(F)(F)F)C2)c1Cl] | 1H NMR (400 MHz, DMSO-d6) chemical shifts 13.01 (s, 1H), 8.60 (s, 1H), 8.04 (s, 1H), 7.83 (t, J = 9.2 Hz, 1H), 7.73 (d, J = 7.9 Hz, 1H), 7.67-7.57 (m, 1H), 4.71 (s, 2H), 3.81 (t, J = 5.8 Hz, 2H), 3.01 (s, 2H). | 442 |
| 122 | 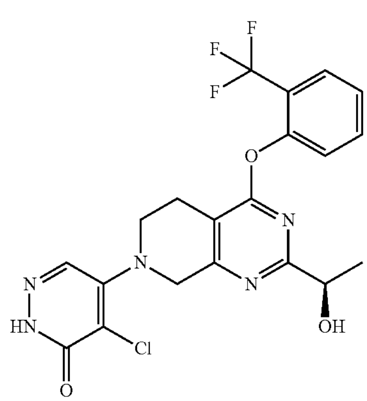 [SMILES: C[C@@H](O)c1nc2c(c(Oc3ccccc3C(F)(F)F)n1)CCN(c1cn[nH]c(=O)c1Cl)C2] | 1H NMR (400 MHz, DMSO-d6) chemical shifts 13.00 (s, 1H), 8.03 (s, 1H), 7.88-7.75 (m, 2H), 7.57 (d, J = 8.2 Hz, 1H), 7.51 (t, J = 7.6 Hz, 1H), 5.07 (d, J = 5.3 Hz, 1H), 4.67 (s, 2H), 4.50 (p, J = 6.2 Hz, 1H), 3.80 (t, J = 5.6 Hz, 2H), 2.96 (s, 2H), 1.23 (d, J = 6.5 Hz, 3H). | 468 |

-continued

| Compound | Structure | NMR | MS |
|---|---|---|---|
| 123 | 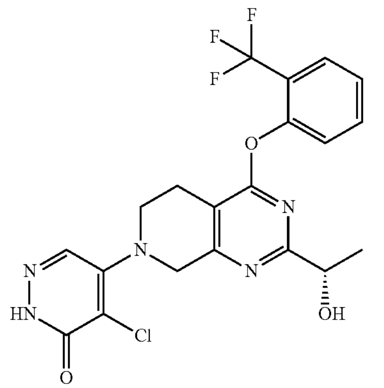 [SMILES: C[C@H](O)c1nc2c(c(Oc3ccccc3C(F)(F)F)n1)CCN(c1cn[nH]c(=O)c1Cl)C2] | 1H NMR (400 MHz, DMSO-d6) chemical shifts 13.00 (s, 1H), 8.03 (s, 1H), 7.88-7.75 (m, 2H), 7.57 (d, J = 8.3 Hz, 1H), 7.51 (t, J = 7.7 Hz, 1H), 5.07 (d, J = 5.2 Hz, 1H), 4.67 (s, 2H), 4.50 (p, J = 6.4 Hz, 1H), 3.80 (t, J = 5.6 Hz, 2H), 2.96 (s, 2H), 1.23 (d, J = 6.6 Hz, 3H). | 468 |
| 124 | 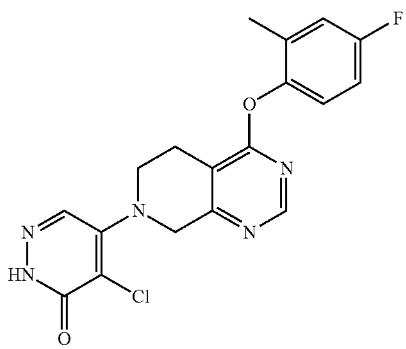 [SMILES: Cc1cc(F)ccc1Oc1ncnc2c1CCN(c1cn[nH]c(=O)c1Cl)C2] | 1H NMR (DMSO-d6) δ: 12.97 (br s, 1H), 8.49 (s, 1H), 8.01 (s, 1H), 7.15-7.24 (m, 2H), 7.05-7.12 (m, 1H), 4.63 (s, 2H), 3.78 (t, J = 5.7 Hz, 2H), 3.00 (s, 2H), 2.06 (s, 3H) | 388.3 |
| 125 | 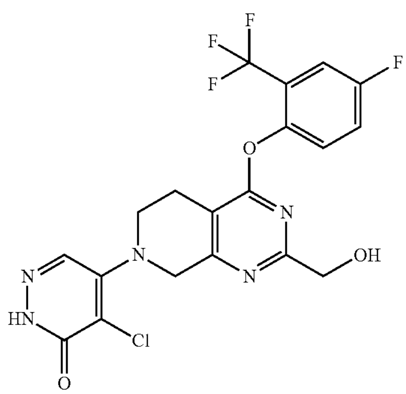 [SMILES: O=c1[nH]ncc(N2CCc3c(nc(CO)nc3Oc3ccc(F)cc3C(F)(F)F)C2)c1Cl] | 1H NMR (400 MHz, DMSO-d6) chemical shifts 13.00 (s, 1H), 8.03 (s, 1H), 7.81-7.74 (m, 1H), 7.74-7.60 (m, 2H), 5.19 (t, J = 6.3 Hz, 1H), 4.67 (s, 2H), 4.34 (d, J = 6.3 Hz, 2H), 3.79 (t, J = 5.6 Hz, 2H), 2.95 (s, 2H). | 472 |
| 126* | 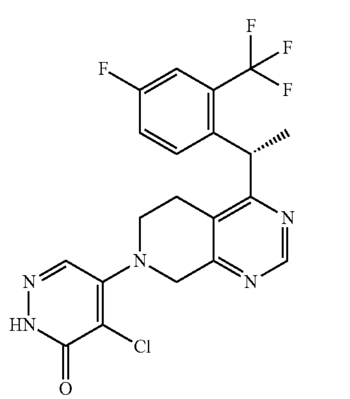 [SMILES: C[C@@H](c1ccc(F)cc1C(F)(F)F)c1ncnc2c1CCN(c1cn[nH]c(=O)c1Cl)C2] | 1H NMR (400 MHz, DMSO-d6) chemical shifts 12.98 (s, 1H), 9.02 (s, 1H), 7.97 (s, 1H), 7.63 (dd, J = 9.4, 2.6 Hz, 1H), 7.53 (p, J = 8.7 Hz, 2H), 4.71 (t, J = 7.1 Hz, 1H), 4.65 (s, 2H), 3.68 (t, J = 5.7 Hz, 2H), 3.08 (d, J = 16.5 Hz, 1H), 2.57 (s, 1H), 1.60 (d, J = 6.8 Hz, 3H). | 454 |

-continued

| Compound | Structure | NMR | MS |
|---|---|---|---|
| 126a* | 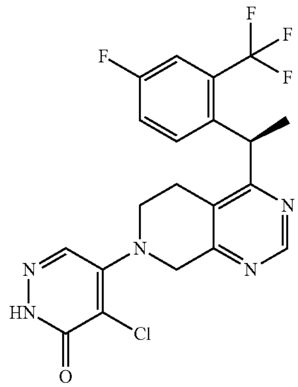 [SMILES: C[C@H](c1ccc(F)cc1C(F)(F)F)c1ncnc2c1CCN(c1cn[nH]c(=O)c1Cl)C2] | 1H NMR (400 MHz, DMSO-d6) chemical shifts 12.97 (s, 1H), 9.02 (s, 1H), 7.97 (s, 1H), 7.63 (d, J = 7.9 Hz, 1H), 7.60-7.49 (m, 2H), 4.72 (d, J = 6.9 Hz, 1H), 4.65 (s, 2H), 3.68 (s, 2H), 3.08 (d, J = 16.3 Hz, 1H), 2.58 (s, 1H), 1.60 (d, J = 6.8 Hz, 3H). | 454 |
| 127 | 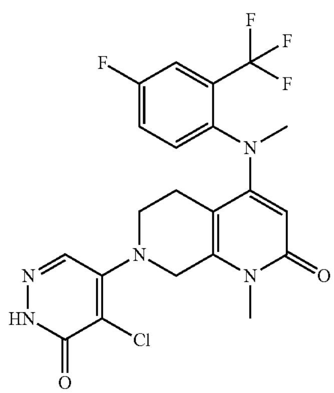 [SMILES: CN(c1ccc(F)cc1C(F)(F)F)c1cc(=O)n(C)c2c1CCN(c1cn[nH]c(=O)c1Cl)C2] | 1H NMR (400 MHz, DMSO-d6) chemical shifts 12.98 (s, 1H), 7.96 (s, 1H), 7.81-7.74 (m, 1H), 7.55 (d, J = 8.8 Hz, 1H), 7.35-7.27 (m, 1H), 5.85 (s, 1H), 4.52 (s, 2H), 3.39 (s, 3H), 3.39-3.34 (m, 2H), 3.09 (s, 3H), 1.95 (s, 2H). | 484 |
| 128 | 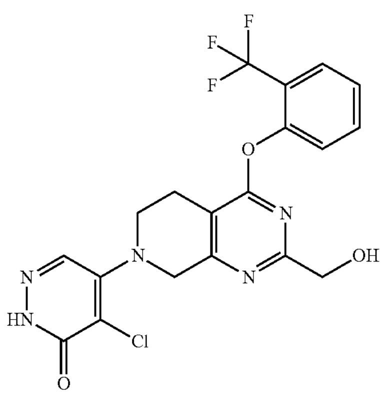 [SMILES: O=c1[nH]ncc(N2CCc3c(nc(CO)nc3Oc3ccccc3C(F)(F)F)C2)c1Cl] | 1H NMR (400 MHz, DMSO-d6) chemical shifts 13.01 (s, 1H), 8.03 (s, 1H), 7.88-7.75 (m, 2H), 7.56 (d, J = 8.3 Hz, 1H), 7.51 (t, J = 7.7 Hz, 1H), 5.19 (t, J = 6.3 Hz, 1H), 4.68 (s, 2H), 4.34 (d, J = 6.3 Hz, 2H), 3.80 (t, J = 5.7 Hz, 2H), 2.96 (s, 2H). | 454 |
| 129* | 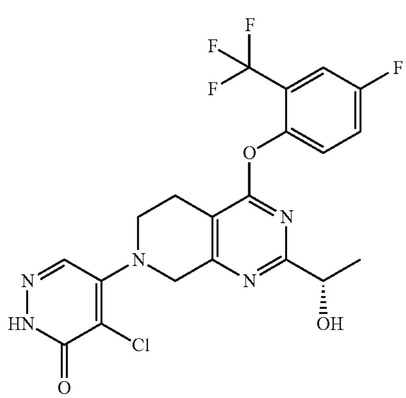 [SMILES: C[C@H](O)c1nc2c(c(Oc3ccc(F)cc3C(F)(F)F)n1)CCN(c1cn[nH]c(=O)c1Cl)C2] | 1H NMR (400 MHz, DMSO-d6) chemical shifts 13.00 (s, 1H), 8.03 (s, 1H), 7.78 (dd, J = 8.6, 2.9 Hz, 1H), 7.75-7.61 (m, 2H), 5.08 (d, J = 5.3 Hz, 1H), 4.67 (s, 2H), 4.50 (p, J = 6.5 Hz, 1H), 3.79 (t, J = 5.7 Hz, 2H), 2.94 (d, J = 6.1 Hz, 2H), 1.23 (d, J = 6.5 Hz, 3H). | 486 |

| Compound | Structure | NMR | MS |
|---|---|---|---|
| 130* | 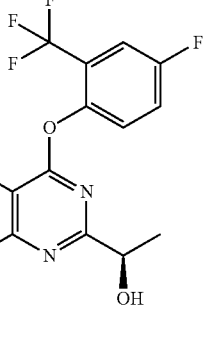 | 1H NMR (400 MHz, DMSO-d6) chemical shifts 13.00 (s, 1H), 8.03 (s, 1H), 7.78 (dd, J = 8.6, 3.0 Hz, 1H), 7.67 (ddd, J = 19.1, 8.6, 3.8 Hz, 2H), 5.08 (d, J = 5.3 Hz, 1H), 4.67 (s, 2H), 4.50 (p, J = 6.5 Hz, 1H), 3.79 (t, J = 5.5 Hz, 2H), 2.95 (s, 2H), 1.23 (d, J = 6.6 Hz, 3H). | 486 |
| 131 | 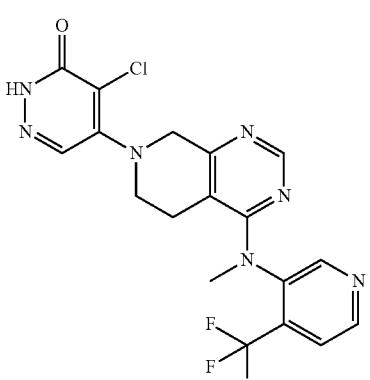 | 1H NMR (400 MHz, DMSO-d6) chemical shifts 12.07 (s, 1H), 8.89-8.79 (m, 2H), 8.59 (s, 1H), 7.94-7.84 (m, 2H), 4.53 (s, 2H), 3.44 (d, J = 11.0 Hz, 2H), 3.41 (s, 3H), 1.96 (t, J = 5.6 Hz, 2H). | 438 |
| 132 | 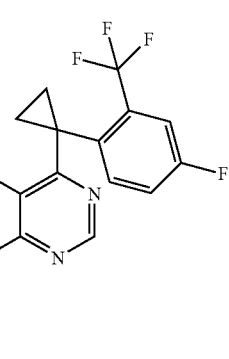 | 1H NMR (400 MHz, DMSO-d6) chemical shifts 12.94 (s, 1H), 8.89 (s, 1H), 8.00 (d, J = 8.8 Hz, 1H), 7.87 (s, 1H), 7.62 (d, J = 8.6 Hz, 2H), 4.58 (s, 2H), 3.48 (s, 2H), 2.27 (s, 2H), 1.84 (s, 2H), 1.47 (s, 2H). | 466 |
| 133 | 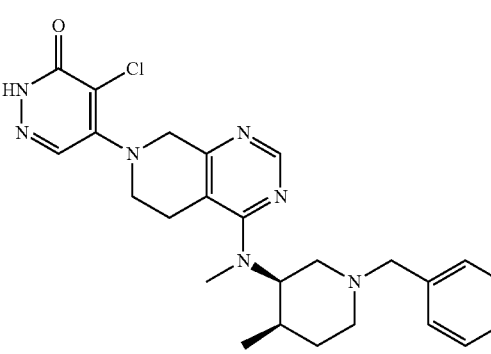 | 1H NMR (400 MHz, Methanol-d4) chemical shifts 8.34 (s, 1H), 8.02 (s, 1H), 7.33 (q, J = 7.8 Hz, 4H), 7.25 (t, J = 7.0 Hz, 1H), 4.67 (d, J = 17.3 Hz, 1H), 4.58 (d, J = 17.2 Hz, 2H), 3.97 (d, J = 13.9 Hz, 1H), 3.55 (s, 2H), 3.47 (s, 1H), 3.39 (s, 3H), 2.94 (s, 1H), 2.81 (d, J = 15.8 Hz, 1H), 2.74-2.53 (m, 3H), 2.35 (s, 1H), 2.15 (s, 1H), 1.76 (s, 2H), 1.01 (d, J = 7.0 Hz, 3H). | 480 |

-continued

| Compound | Structure | NMR | MS |
|---|---|---|---|
| 133a | 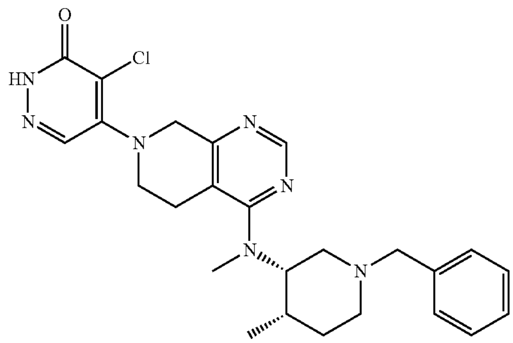 [SMILES: C[C@H]1CCN(Cc2ccccc2)C[C@H]1N(C)c1ncnc2c1CCN(c1cn[nH]c(=O)c1Cl)C2] | 1H NMR (400 MHz, Methanol-d4) chemical shifts 8.34 (s, 1H), 8.02 (s, 1H), 7.42-7.21 (m, 5H), 4.62 (q, J = 17.5 Hz, 3H), 3.97 (d, J = 13.3 Hz, 1H), 3.55 (s, 2H), 3.47 (s, 1H), 3.39 (s, 3H), 3.15 (s, 1H), 2.94 (s, 1H), 2.87-2.61 (m, 3H), 2.35 (s, 1H), 2.15 (s, 1H), 1.76 (s, 2H), 1.01 (d, J = 7.0 Hz, 3H). | 480 |
| 134 | 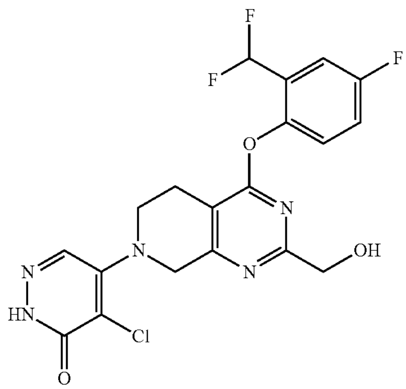 [SMILES: O=c1[nH]ncc(N2CCc3c(nc(CO)nc3Oc3ccc(F)cc3C(F)F)C2)c1Cl] | 1H NMR (400 MHz, DMSO-d6) chemical shifts 13.01 (s, 1H), 8.03 (s, 1H), 7.58-7.49 (m, 3H), 7.27-7.00 (m, 1H), 5.17 (t, J = 6.3 Hz, 1H), 4.66 (s, 2H), 4.34 (d, J = 6.3 Hz, 2H), 3.79 (t, J = 5.7 Hz, 2H), 2.99 (s, 2H). | 454 |
| 135* | 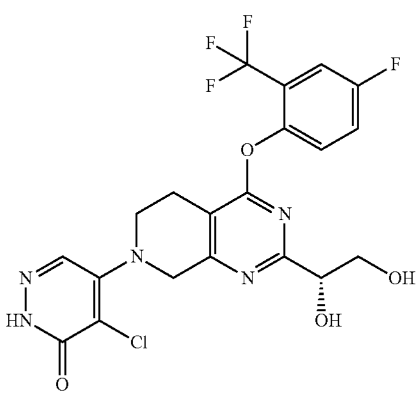 [SMILES: O=c1[nH]ncc(N2CCc3c(nc([C@@H](O)CO)nc3Oc3ccc(F)cc3C(F)(F)F)C2)c1Cl] | 1H NMR (400 MHz, DMSO-d6) chemical shifts 12.97 (s, 1H), 8.03 (s, 1H), 7.78 (dd, J = 8.5, 3.0 Hz, 1H), 7.75-7.61 (m, 2H), 5.12 (d, J = 5.7 Hz, 1H), 4.67 (s, 2H), 4.57 (t, J = 6.0 Hz, 1H), 4.37 (q, J = 5.8 Hz, 1H), 3.79 (t, J = 5.7 Hz, 2H), 3.57 (dt, J = 11.2, 5.7 Hz, 1H), 3.46 (dt, J = 10.8, 6.1 Hz, 1H), 2.96 (t, J = 5.6 Hz, 2H). | 502 |
| 136 | 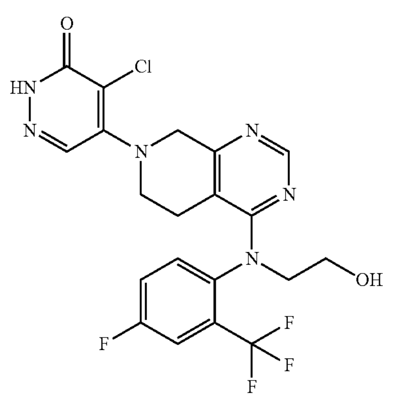 [SMILES: O=c1[nH]ncc(N2CCc3c(ncnc3N(CCO)c3ccc(F)cc3C(F)(F)F)C2)c1Cl] | 1H NMR (400 MHz, Methanol-d4) chemical shifts 8.54 (s, 1H), 7.87 (s, 1H), 7.75 (s, 1H), 7.63 (dd, J = 8.8, 3.0 Hz, 1H), 7.54 (s, 1H), 4.57 (m, 3H), 3.88 (s, 2H), 3.51 (m, 3H), 2.05 (s, 1H), 1.98 (s, 1H). | 485 |

-continued

| Compound | Structure | NMR | MS |
|---|---|---|---|
| 137* | 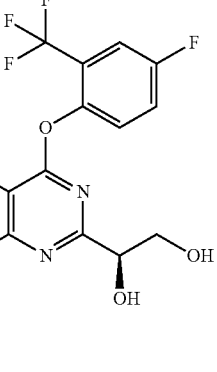 | 1H NMR (400 MHz, DMSO-d6) chemical shifts 12.94 (s, 1H), 8.03 (s, 1H), 7.78 (dd, J = 8.5, 3.0 Hz, 1H), 7.75-7.61 (m, 2H), 5.12 (d, J = 5.7 Hz, 1H), 4.67 (s, 2H), 4.57 (t, J = 6.0 Hz, 1H), 4.37 (q, J = 5.7 Hz, 1H), 3.79 (t, J = 5.7 Hz, 2H), 3.57 (dt, J = 11.2, 5.7 Hz, 1H), 3.52-3.43 (m, 1H), 2.96 (t, J = 5.6 Hz, 2H). | 502 |
| 138 | 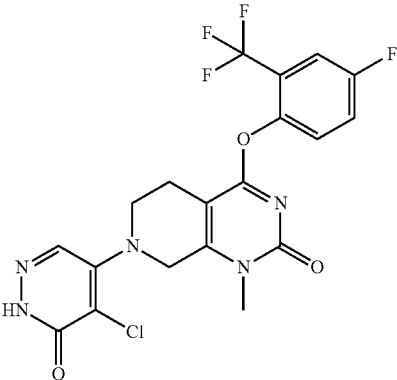 [SMILES: Cn1c2c(c(Oc3ccc(F)cc3C(F)(F)F)nc1=O)CCN(c1cn[nH]c(=O)c1Cl)C2] | 1H NMR (400 MHz, DMSO-d6) chemical shifts 13.05 (s, 1H), 8.11 (s, 1H), 7.78 (dd, J = 8.5, 3.1 Hz, 1H), 7.70 (td, J = 8.5, 3.2 Hz, 1H), 7.57 (dd, J = 9.1, 4.6 Hz, 1H), 4.65 (s, 2H), 3.66 (t, J = 5.7 Hz, 2H), 3.38 (s, 3H), 2.74 (t, J = 5.4 Hz, 2H). | 472 |
| 139 | 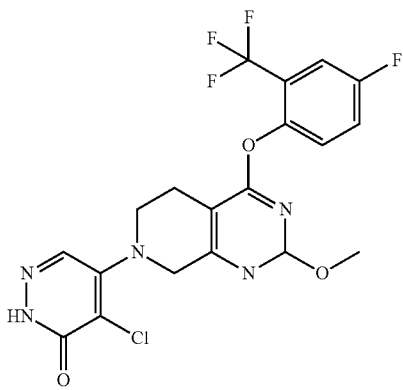 [SMILES: COC1N=C(Oc2ccc(F)cc2C(F)(F)F)C2=C(CN(c3cn[nH]c(=O)c3Cl)CC2)N1] | 1H NMR (400 MHz, DMSO-d6) chemical shifts 12.84 (s, 1H), 8.02 (s, 1H), 7.79 (dd, J = 8.6, 2.9 Hz, 1H), 7.68 (dtd, J = 18.8, 9.0, 3.8 Hz, 2H), 4.60 (s, 2H), 3.77 (d, J = 5.6 Hz, 2H), 3.75 (s, 3H), 2.88 (t, J = 5.7 Hz, 2H) | 472 |
| 140 | 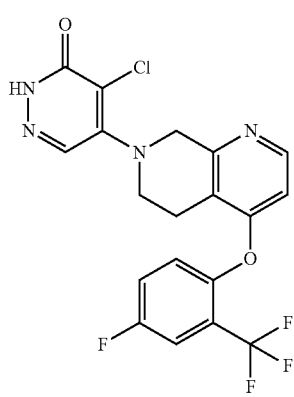 [SMILES: O=c1[nH]ncc(N2CCc3c(Oc4ccc(F)cc4C(F)(F)F)ccnc3C2)c1Cl] | 1H NMR (400 MHz, DMSO-d6) chemical shifts 12.97 (s, 1H), 8.30 (d, J = 5.6 Hz, 1H), 8.02 (s, 1H), 7.83 (dd, J = 8.5, 3.2 Hz, 1H), 7.68 (td, J = 8.6, 3.1 Hz, 1H), 7.50 (dd, J = 9.1, 4.5 Hz, 1H), 6.58 (d, J = 5.6 Hz, 1H), 4.69 (s, 2H), 3.77 (t, J = 5.7 Hz, 2H), 2.98 (t, J = 5.8 Hz, 2H). | 441 |

*Compound is a pure isomer separated from its opposite isomer by HPLC of the corresponding racemic mixture. Absolute orientation has not been determined and therefore designation of the specific orientation around a chiral center is arbitrary.

Example 26. Effect of Compound 100 on Puromycin Aminonucleoside (PAN)-Induced Glomerular Injury in Rats Objective:

The objective of this study is to evaluate the dose-dependent effects of compound 100 on PAN induced glomerular kidney injury as indexed by albuminuria.

Methods:

Eighty (80), male Sprague-Dawley rats weighing approximately 125-150 g and approximately 5-6 weeks of age were acquired from Charles River. They were fed a standard chow diet (Harlan 8640), housed under standard conditions, and allowed to acclimate for at least 5 days prior to study inception.

On D-2, rats were placed into weight-matched treatment groups and were placed, individually housed, into metabolic cages for the balance of the study.

A 24 hour baseline (Day 0) urine was collected followed by a baseline blood collection via conscious tail venous puncture. Rats were then administered vehicle or test article.

Two (2) hours following administration of vehicle or test agent on Day 0, rats received an administration of (5 ml/kg, s.c.) vehicle (sterile saline) or puromycin aminonucleoside (PAN; challenge agent; 75 mg/kg) dissolved in vehicle.

Intermittent (Day 4, 7 and 10) 24 hour urine volumes were determined and samples (4 samples/animal/time point; 0.5 ml/sample) were obtained. Additionally, intermittent (Day 4, 7 and 10) blood samples were collected via conscious tail venous puncture 2 hours±1 minute post-AM dose.

Immediately following the last blood collection, rats were anesthetized with isoflurane, tissues harvested, and animals sacrificed. Endpoint kidney weights and indices were obtained.

Urine samples were immediately flash-frozen in liquid $N_2$ and stored at −80° C. until analyzed.

Whole blood samples collected on $K_3$EDTA were processed appropriately for the production of plasma for PK measurements.

Results:

As shown in FIG. 1, treatment with compound 100 at 30 mg/kg once- (QD) or twice- (BID) daily resulted in reduced urinary albumin excretion on following injury with PAN. Significant reductions were seen at 7 and 10 days with BID dosing, and at 10 days with QD dosing of compound 100. Mizoribine, the positive control compound, was also efficacious in reducing albuminuria.

Conclusion:

Compound 100 is effective in reducing albuminuria in the PAN model of glomerular injury in rats.

Example 27. Compound 100 is Efficacious in the AT1R Transgenic Rat Model of FSGS The AT1R transgenic rat model of FSGS is characterized by podocyte-specific expression of human AT1R. Males have been shown to have substantially worse pathology compared to females. The efficacy of TRPC5 inhibitors in the AT1R model has been demonstrated with a tool compound. See Zhou et al., Science (2017), vol. 358 (6368), 1332-1336.

Figure 2:
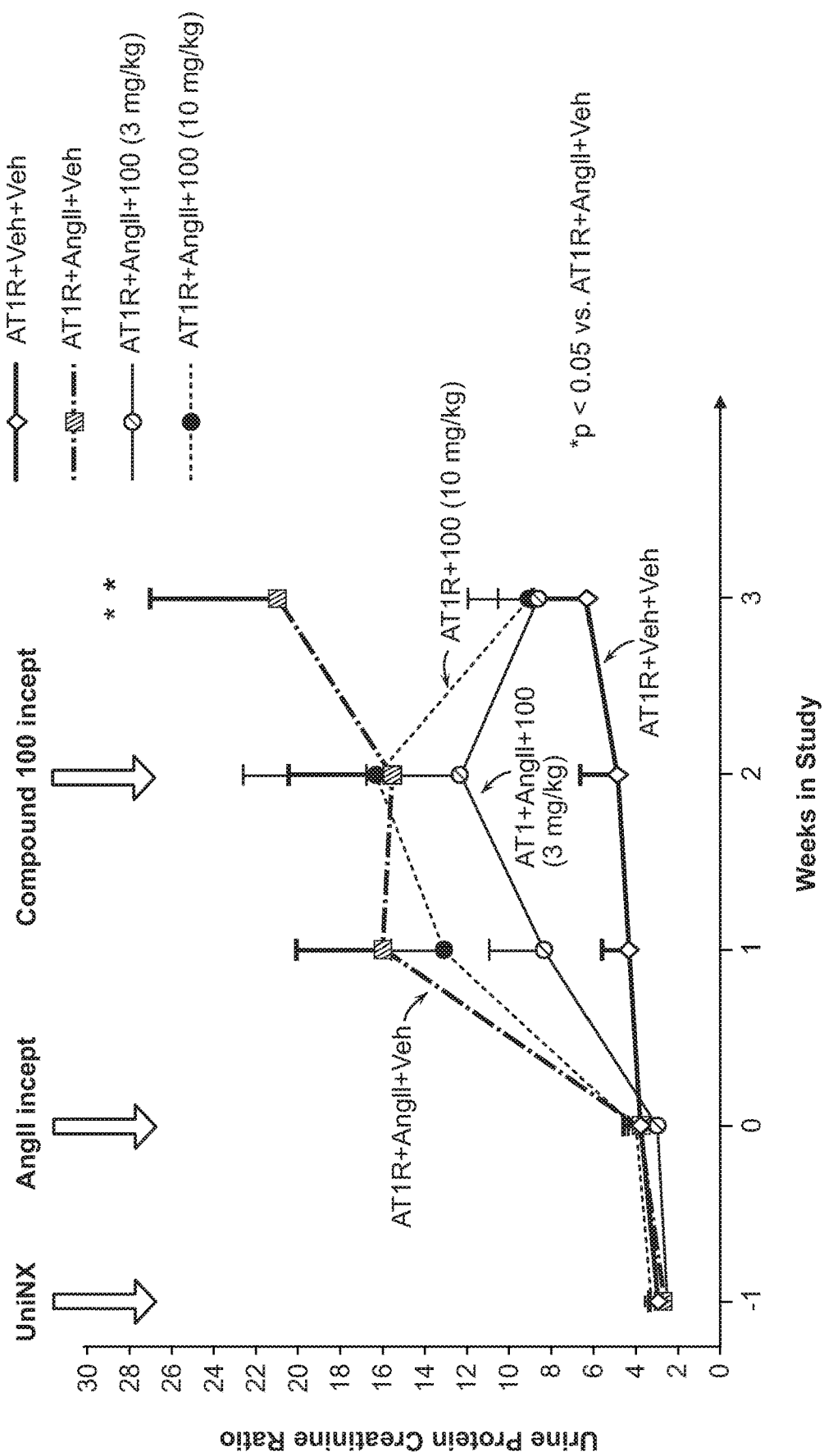
FIG. 2 shows urine protein creatinine ratio data in AT1R transgenic rats treated with compound 100 compared to vehicle, with AngII infusion.
Figure 3:
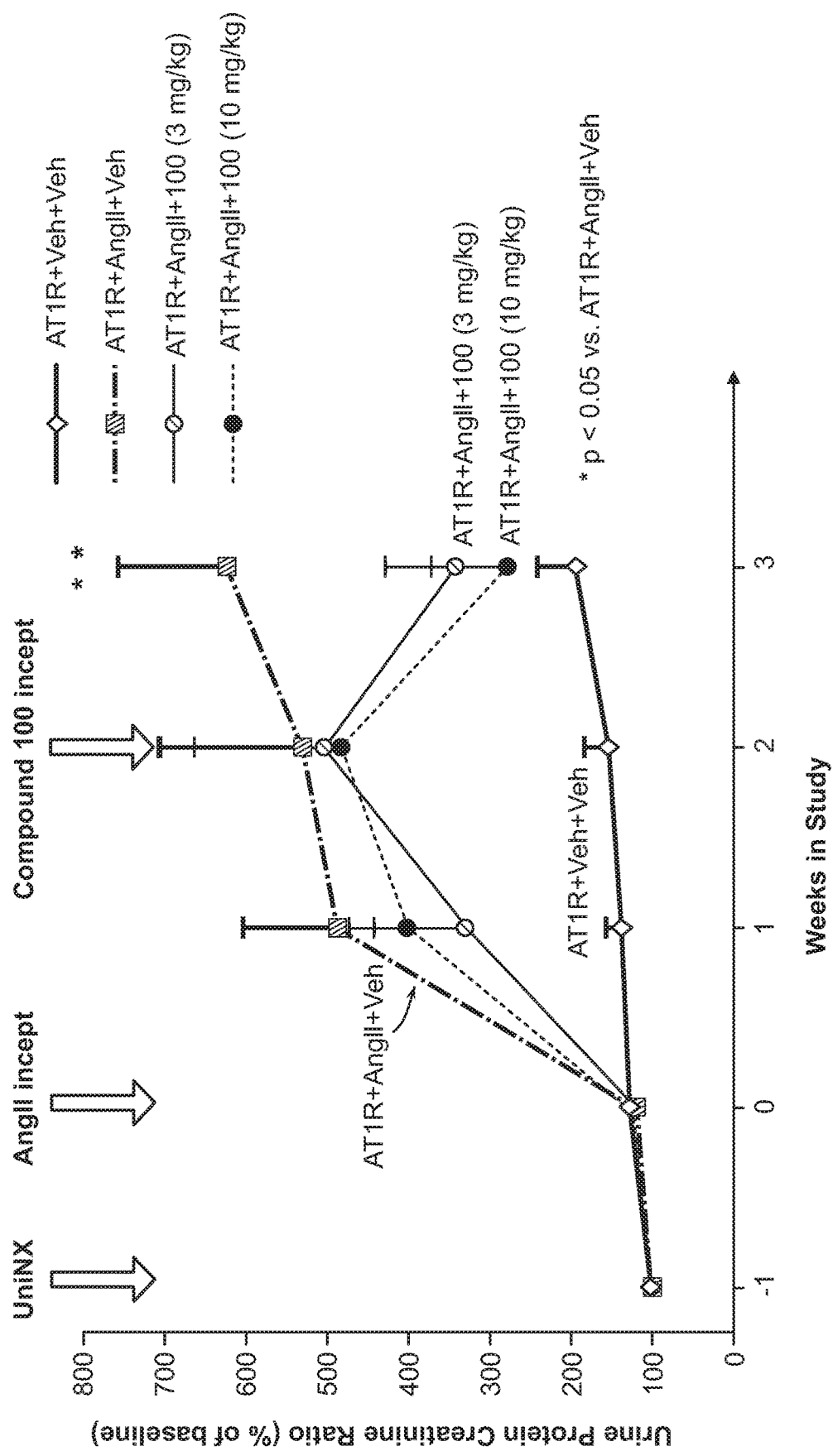
FIG. 3 shows the urine protein creatinine ratio data presented in FIG. 2 expressed as percent of baseline.

In the present study, pathophysiology in AT1R transgenic rats was accelerated with unilateral nephrectomy (UniNX) and minipump AngII infusion. Compound 100 was dosed orally once daily at 3 mg/kg or 10 mg/kg, and the urine protein creatinine ratio was determined at −1, 0, 1, 2, and 3 weeks of treatment. FIG. 2 shows the urine protein creatinine ratio over the course of the study for rats treated with compound 100 or those treated with vehicle. UniNX, AngII incept, and compound 100 incept occurred at the time points indicated. FIG. 3 shows the same data presented as % of baseline.

The results show that compound 100 is efficacious in the AT1R transgenic rat model of FSGS.

INCORPORATION BY REFERENCE

All of the U.S. patents and U.S. and PCT published patent applications cited herein are hereby incorporated by reference.

EQUIVALENTS

The foregoing written specification is sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

```
SEQ ID NO: 1 TRPC4 Plasmid Sequence
The DNA sequence of the TRPC4 plasmid used in Example 24 is
included below. Underlined nucleic acids represent those
encoding human TRPC4.
GACGGATCGGGAGATCTCCCGATCCCCTATGGTGCACTCTCAGTACAATCTGCTCTG

ATGCCGCATAGTTAAGCCAGTATCTGCTCCCTGCTTGTGTGTTGGAGGTCGCTGAGT

AGTGCGCGAGCAAAATTTAAGCTACAACAAGGCAAGGCTTGACCGACAATTGCATG

AAGAATCTGCTTAGGGTTAGGCGTTTTGCGCTGCTTCGCGATGTACGGGCCAGATAT

ACGCGTTGACATTGATTATTGACTAGTTATTAATAGTAATCAATTACGGGGTCATTA

GTTCATAGCCCATATATGGAGTTCCGCGTTACATAACTTACGGTAAATGGCCCGCCT

GGCTGACCGCCCAACGACCCCCGCCCATTGACGTCAATAATGACGTATGTTCCCATA

GTAACGCCAATAGGGACTTTCCATTGACGTCAATGGGTGGAGTATTTACGGTAAACT

GCCCACTTGGCAGTACATCAAGTGTATCATATGCCAAGTACGCCCCCTATTGACGTC
```

```
AATGACGGTAAATGGCCCGCCTGGCATTATGCCCAGTACATGACCTTATGGGACTTT

CCTACTTGGCAGTACATCTACGTATTAGTCATCGCTATTACCATGGTGATGCGGTTTT

GGCAGTACATCAATGGGCGTGGATAGCGGTTTGACTCACGGGGATTTCCAAGTCTCC

ACCCCATTGACGTCAATGGGAGTTTGTTTTGGCACCAAAATCAACGGGACTTTCCAA

AATGTCGTAACAACTCCGCCCCATTGACGCAAATGGGCGGTAGGCGTGTACGGTGG

GAGGTCTATATAAGCAGAGCTCTCCCTATCAGTGATAGAGATCTCCCTATCAGTGAT

AGAGATCGTCGACGAGCTCGTTTAGTGAACCGTCAGATCGCCTGGAGACGCCATCC

ACGCTGTTTTGACCTCCATAGAAGACACCGGGACCGATCCAGCCTCCGGACTCTAGC

GTTTAAACTTAAGCTTGGTACCGAGCTCGGATCCGCCACCATGGCCCAGTTCTACTA

TAAGAGAAACGTGAATGCCCCTTACCGCGACAGAATCCCCCTGAGAATCGTGAGGG

CAGAGTCCGAGCTGAGCCCATCCGAGAAGGCCTACCTGAACGCCGTGGAGAAGGGC

GACTATGCCAGCGTGAAGAAGTCCCTGGAGGAGGCCGAGATCTACTTTAAGATCAA

CATCAATTGCATCGATCCTCTGGGCAGAACCGCCCTGCTGATCGCCATCGAGAACGA

GAATCTGGAGCTGATCGAGCTGCTGCTGAGCTTCAACGTGTATGTGGGCGATGCCCT

GCTGCACGCCATCAGGAAGGAGGTGGTGGGAGCAGTGGAGCTGCTGCTGAATCACA

AGAAGCCAAGCGGAGAGAAGCAGGTGCCACCTATCCTGCTGGACAAGCAGTTCTCC

GAGTTTACCCCAGATATCACACCCATCATCCTGGCCGCCCACACCAACAATTACGAG

ATCATCAAGCTGCTGGTGCAGAAGGGCGTGTCCGTGCCTCGCCCACACGAGGTGCG

GTGCAACTGCGTGGAGTGCGTGAGCTCCTCTGACGTGGATTCTCTGAGGCACAGCCG

GAGCCGGCTGAACATCTATAAGGCCCTGGCCTCCCCATCTCTGATCGCCCTGAGCTC

CGAGGACCCCTTCCTGACCGCCTTTCAGCTGTCTTGGGAGCTGCAGGAGCTGAGCAA

GGTGGAGAACGAGTTTAAGAGCGAGTACGAGGAGCTGTCCAGACAGTGCAAGCAGT

TCGCCAAGGACCTGCTGGATCAGACACGCTCTAGCCGGGAGCTGGAGATCATCCTG

AACTATAGGGACGATAATTCTCTGATCGAGGAGCAGAGCGGAAACGACCTGGCACG

CCTGAAGCTGGCCATCAAGTACCGGCAGAAGGAGTTCGTGGCCCAGCCTAATTGTC

AGCAGCTGCTGGCCTCCCGCTGGTATGATGAGTTTCCAGGATGGCGGAGAAGGCAC

TGGGCAGTGAAGATGGTGACCTGCTTCATCATCGGCCTGCTGTTCCCCGTGTTCAGC

GTGTGCTACCTGATCGCCCCTAAGTCTCCACTGGGCCTGTTTATCCGGAAGCCTTTCA

TCAAGTTTATCTGCCACACCGCCAGCTATCTGACATTCCTGTTTCTGCTGCTGCTGGC

CTCCCAGCACATCGACAGATCTGATCTGAACAGGCAGGGCCCACCCCCTACCATCGT

GGAGTGGATGATCCTGCCATGGGTGCTGGGCTTCATCTGGGGCGAGATCAAGCAGA

TGTGGGACGGCGGCCTGCAGGACTACATCCACGATTGGTGGAACCTGATGGATTTTG

TGATGAATTCCCTGTACCTGGCCACAATCTCTCTGAAGATCGTGGCCTTCGTGAAGT

ATAGCGCCCTGAATCCCAGAGAGTCCTGGGACATGTGGCACCCTACCCTGGTGGCA

GAGGCCCTGTTCGCAATCGCCAACATCTTTTCCTCTCTGCGCCTGATCAGCCTGTTTA

CAGCCAATTCCCACCTGGGACCACTGCAGATCTCCCTGGGACGGATGCTGCTGGATA

TCCTGAAGTTCCTGTTTATCTACTGCCTGGTGCTGCTGGCCTTCGCCAACGGCCTGAA

TCAGCTGTACTTCTACTATGAGGAGACCAAGGGCCTGACATGCAAGGGCATCCGCTG

TGAGAAGCAGAACAATGCCTTCAGCACCCTGTTCGAGACACTGCAGTCTCTGTTCTG

GAGCATCTTTGGCCTGATCAACCTGTACGTGACCAATGTGAAGGCCCAGCACGAGTT
```

CACAGAGTTTGTGGGCGCCACCATGTTCGGCACATACAACGTGATCTCTCTGGTGGT

GCTGCTGAATATGCTGATCGCCATGATGAACAATAGCTATCAGCTGATCGCCGACCA

CGCCGATATCGAGTGGAAGTTCGCCCGGACCAAGCTGTGGATGTCCTACTTTGAGGA

GGGCGGCACCCTGCCCACACCTTTCAACGTGATCCCATCCCCCAAGTCTCTGTGGTA

TCTGATCAAGTGGATCTGGACACACCTGTGCAAGAAGAAGATGCGCCGGAAGCCTG

AGAGCTTTGGCACCATCGGCGTGCGCACACAGCACAGAAGGGCAGCAGACAACCTG

CGCCGGCACCACCAGTACCAGGAAGTGATGCGCAATCTGGTGAAGCGGTATGTGGC

CGCCATGATCAGGGACGCAAAGACCGAGGAGGGACTGACAGAGGAGAACTTCAAG

GAGCTGAAGCAGGATATCAGCTCCTTCAGATTTGAGGTGCTGGGCCTGCTGAGGGG

CAGCAAGCTGTCCACCATCCAGTCCGCCAACGCCTCTAAGGAGTCTAGCAATTCTGC

CGACAGCGATGAGAAGAGCGACTCCGAGGGCAACTCTAAGGATAAGAAGAAGAAC

TTCAGCCTGTTTGACCTGACCACACTGATCCACCCACGCAGCGCCGCAATCGCATCC

GAGCGGCACAACATCTCCAATGGCTCTGCCCTGGTGGTGCAGGAGCCACCAAGAGA

GAAGCAGAGGAAGGTGAACTTTGTGACAGATATCAAGAATTTCGGCCTGTTTCACA

GAAGGAGCAAGCAGAACGCCGCCGAGCAGAACGCCAATCAGATCTTCTCTGTGAGC

GAGGAGGTGGCAAGACAGCAGGCAGCAGGACCACTGGAGAGGAATATCCAGCTGG

AGAGCCGGGACTGGCAAGCAGGGGCGACCTGTCCATCCCAGGACTGTCTGAGCAG

TGCGTGCTGGTGGACCACAGGGAGCGGAACACCGATACACTGGGACTGCAAGTGGG

CAAGCGGGTGTGCCCTTTCAAGAGCGAGAAGGTCGTGGTGGAGGACACCGTGCCCA

TCATCCCTAAGGAGAAGCACGCCAAGGAGGAGGATTCCTCTATCGACTACGATCTG

AATCTGCCAGACACCGTGACACACGAGGATTATGTGACCACAAGGCTGTGAGCGGC

CGCTCTAGAGGGCCCGTTTAAACCCGCTGATCAGCCTCGACTGTGCCTTCTAGTTGC

CAGCCATCTGTTGTTTGCCCCTCCCCCGTGCCTTCCTTGACCCTGGAAGGTGCCACTC

CCACTGTCCTTTCCTAATAAAATGAGGAAATTGCATCGCATTGTCTGAGTAGGTGTC

ATTCTATTCTGGGGGGTGGGGTGGGGCAGGACAGCAAGGGGGAGGATTGGGAAGAC

AATAGCAGGCATGCTGGGGATGCGGTGGGCTCTATGGCTTCTGAGGCGGAAAGAAC

CAGCTGGGGCTCTAGGGGGTATCCCCACGCGCCCTGTAGCGGCGCATTAAGCGCGG

CGGGTGTGGTGGTTACGCGCAGCGTGACCGCTACACTTGCCAGCGCCCTAGCGCCCG

CTCCTTTCGCTTTCTTCCCTTCCTTTCTCGCCACGTTCGCCGGCTTTCCCCGTCAAGCT

CTAAATCGGGGGCTCCCTTTAGGGTTCCGATTTAGTGCTTTACGGCACCTCGACCCC

AAAAAACTTGATTAGGGTGATGGTTCACGTAGTGGGCCATCGCCCTGATAGACGGTT

TTTCGCCCTTTGACGTTGGAGTCCACGTTCTTTAATAGTGGACTCTTGTTCCAAACTG

GAACAACACTCAACCCTATCTCGGTCTATTCTTTTGATTTATAAGGGATTTTGCCGAT

TTCGGCCTATTGGTTAAAAAATGAGCTGATTTAACAAAAATTTAACGCGAATTAATT

CTGTGGAATGTGTGTCAGTTAGGGTGTGGAAAGTCCCCAGGCTCCCCAGCAGGCAG

AAGTATGCAAAGCATGCATCTCAATTAGTCAGCAACCAGGTGTGGAAAGTCCCCAG

GCTCCCCAGCAGGCAGAAGTATGCAAAGCATGCATCTCAATTAGTCAGCAACCATA

GTCCCGCCCCTAACTCCGCCCATCCCGCCCCTAACTCCGCCCAGTTCCGCCCATTCTC

CGCCCCATGGCTGACTAATTTTTTTTATTTATGCAGAGGCCGAGGCCGCCTCTGCCTC

TGAGCTATTCCAGAAGTAGTGAGGAGGCTTTTTTGGAGGCCTAGGCTTTTGCAAAAA

GCTCCCGGGAGCTTGTATATCCATTTTCGGATCTGATCAGCACGTGATGAAAAGCC

-continued

```
TGAACTCACCGCGACGTCTGTCGAGAAGTTTCTGATCGAAAAGTTCGACAGCGTCTC

CGACCTGATGCAGCTCTCGGAGGGCGAAGAATCTCGTGCTTTCAGCTTCGATGTAGG

AGGGCGTGGATATGTCCTGCGGGTAAATAGCTGCGCCGATGGTTTCTACAAAGATCG

TTATGTTTATCGGCACTTTGCATCGGCCGCGCTCCCGATTCCGGAAGTGCTTGACATT

GGGGAATTCAGCGAGAGCCTGACCTATTGCATCTCCCGCCGTGCACAGGGTGTCAC

GTTGCAAGACCTGCCTGAAACCGAACTGCCCGCTGTTCTGCAGCCGGTCGCGGAGG

CCATGGATGCGATCGCTGCGGCCGATCTTAGCCAGACGAGCGGGTTCGGCCCATTCG

GACCGCAAGGAATCGGTCAATACACTACATGGCGTGATTTCATATGCGCGATTGCTG

ATCCCCATGTGTATCACTGGCAAACTGTGATGGACGACACCGTCAGTGCGTCCGTCG

CGCAGGCTCTCGATGAGCTGATGCTTTGGGCCGAGGACTGCCCCGAAGTCCGGCAC

CTCGTGCACGCGGATTTCGGCTCCAACAATGTCCTGACGGACAATGGCCGCATAACA

GCGGTCATTGACTGGAGCGAGGCGATGTTCGGGGATTCCCAATACGAGGTCGCCAA

CATCTTCTTCTGGAGGCCGTGGTTGGCTTGTATGGAGCAGCAGACGCGCTACTTCGA

GCGGAGGCATCCGGAGCTTGCAGGATCGCCGCGGCTCCGGGCGTATATGCTCCGCA

TTGGTCTTGACCAACTCTATCAGAGCTTGGTTGACGGCAATTTCGATGATGCAGCTT

GGGCGCAGGGTCGATGCGACGCAATCGTCCGATCCGGAGCCGGGACTGTCGGGCGT

ACACAAATCGCCCGCAGAAGCGCGGCCGTCTGGACCGATGGCTGTGTAGAAGTACT

CGCCGATAGTGGAAACCGACGCCCAGCACTCGTCCGAGGGCAAAGGAATAGCACG

TGCTACGAGATTTCGATTCCACCGCCGCCTTCTATGAAAGGTTGGGCTTCGGAATCG

TTTTCCGGGACGCCGGCTGGATGATCCTCCAGCGCGGGGATCTCATGCTGGAGTTCT

TCGCCCACCCCAACTTGTTTATTGCAGCTTATAATGGTTACAAATAAAGCAATAGCA

TCACAAATTTCACAAATAAAGCATTTTTTTCACTGCATTCTAGTTGTGGTTTGTCCAA

ACTCATCAATGTATCTTATCATGTCTGTATACCGTCGACCTCTAGCTAGAGCTTGGCG

TAATCATGGTCATAGCTGTTTCCTGTGTGAAATTGTTATCCGCTCACAATTCCACACA

ACATACGAGCCGGAAGCATAAAGTGTAAAGCCTGGGGTGCCTAATGAGTGAGCTAA

CTCACATTAATTGCGTTGCGCTCACTGCCCGCTTTCCAGTCGGGAAACCTGTCGTGC

CAGCTGCATTAATGAATCGGCCAACGCGCGGGGAGAGGCGGTTTGCGTATTGGGCG

CTCTTCCGCTTCCTCGCTCACTGACTCGCTGCGCTCGGTCGTTCGGCTGCGGCGAGCG

GTATCAGCTCACTCAAAGGCGGTAATACGGTTATCCACAGAATCAGGGGATAACGC

AGGAAAGAACATGTGAGCAAAAGGCCAGCAAAAGGCCAGGAACCGTAAAAAGGCC

GCGTTGCTGGCGTTTTTCCATAGGCTCCGCCCCCCTGACGAGCATCACAAAAATCGA

CGCTCAAGTCAGAGGTGGCGAAACCCGACAGGACTATAAAGATACCAGGCGTTTCC

CCCTGGAAGCTCCCTCGTGCGCTCTCCTGTTCCGACCCTGCCGCTTACCGGATACCTG

TCCGCCTTTCTCCCTTCGGGAAGCGTGGCGCTTTCTCATAGCTCACGCTGTAGGTATC

TCAGTTCGGTGTAGGTCGTTCGCTCCAAGCTGGGCTGTGTGCACGAACCCCCCGTTC

AGCCCGACCGCTGCGCCTTATCCGGTAACTATCGTCTTGAGTCCAACCCGGTAAGAC

ACGACTTATCGCCACTGGCAGCAGCCACTGGTAACAGGATTAGCAGAGCGAGGTAT

GTAGGCGGTGCTACAGAGTTCTTGAAGTGGTGGCCTAACTACGGCTACACTAGAAG

AACAGTATTTGGTATCTGCGCTCTGCTGAAGCCAGTTACCTTCGGAAAAAGAGTTGG

TAGCTCTTGATCCGGCAAACAAACCACCGCTGGTAGCGGTTGGTTTTTTGTTTGCAA
```

```
GCAGCAGATTACGCGCAGAAAAAAAGGATCTCAAGAAGATCCTTTGATCTTTTCTAC

GGGGTCTGACGCTCAGTGGAACGAAAACTCACGTTAAGGGATTTTGGTCATGAGATT

ATCAAAAAGGATCTTCACCTAGATCCTTTTAAATTAAAAATGAAGTTTTAAATCAAT

CTAAAGTATATATGAGTAAACTTGGTCTGACAGTTACCAATGCTTAATCAGTGAGGC

ACCTATCTCAGCGATCTGTCTATTTCGTTCATCCATAGTTGCCTGACTCCCCGTCGTG

TAGATAACTACGATACGGGAGGGCTTACCATCTGGCCCCAGTGCTGCAATGATACCG

CGAGACCCACGCTCACCGGCTCCAGATTTATCAGCAATAAACCAGCCAGCCGGAAG

GGCCGAGCGCAGAAGTGGTCCTGCAACTTTATCCGCCTCCATCCAGTCTATTAATTG

TTGCCGGGAAGCTAGAGTAAGTAGTTCGCCAGTTAATAGTTTGCGCAACGTTGTTGC

CATTGCTACAGGCATCGTGGTGTCACGCTCGTCGTTTGGTATGGCTTCATTCAGCTCC

GGTTCCCAACGATCAAGGCGAGTTACATGATCCCCCATGTTGTGCAAAAAAGCGGTT

AGCTCCTTCGGTCCTCCGATCGTTGTCAGAAGTAAGTTGGCCGCAGTGTTATCACTC

ATGGTTATGGCAGCACTGCATAATTCTCTTACTGTCATGCCATCCGTAAGATGCTTTT

CTGTGACTGGTGAGTACTCAACCAAGTCATTCTGAGAATAGTGTATGCGGCGACCGA

GTTGCTCTTGCCCGGCGTCAATACGGGATAATACCGCGCCACATAGCAGAACTTTAA

AAGTGCTCATCATTGGAAAACGTTCTTCGGGGCGAAAACTCTCAAGGATCTTACCGC

TGTTGAGATCCAGTTCGATGTAACCCACTCGTGCACCCAACTGATCTTCAGCATCTTT

TACTTTCACCAGCGTTTCTGGGTGAGCAAAAACAGGAAGGCAAAATGCCGCAAAAA

AGGGAATAAGGGCGACACGGAAATGTTGAATACTCATACTCTTCCTTTTTCAATATT

ATTGAAGCATTTATCAGGGTTATTGTCTCATGAGCGGATACATATTTGAATGTATTTA

GAAAAATAAACAAATAGGGGTTCCGCGCACATTTCCCCGAAAAGTGCCACCTGACGTC
```

SEQ ID NO: 2 TRPC5 Plasmid Sequence
The DNA sequence of the TRPC5 plasmid used in Example 25
is included below. Underlined nucleic acids represent those
encoding human TRPC5.

```
GACGGATCGGGAGATCTCCCGATCCCCTATGGTGCACTCTCAGTACAATCTGCTCTG

ATGCCGCATAGTTAAGCCAGTATCTGCTCCCTGCTTGTGTGTTGGAGGTCGCTGAGT

AGTGCGCGAGCAAAATTTAAGCTACAACAAGGCAAGGCTTGACCGACAATTGCATG

AAGAATCTGCTTAGGGTTAGGCGTTTTGCGCTGCTTCGCGATGTACGGGCCAGATAT

ACGCGTTGACATTGATTATTGACTAGTTATTAATAGTAATCAATTACGGGGTCATTA

GTTCATAGCCCATATATGGAGTTCCGCGTTACATAACTTACGGTAAATGGCCCGCCT

GGCTGACCGCCCAACGACCCCCGCCCATTGACGTCAATAATGACGTATGTTCCCATA

GTAACGCCAATAGGGACTTTCCATTGACGTCAATGGGTGGAGTATTTACGGTAAACT

GCCCACTTGGCAGTACATCAAGTGTATCATATGCCAAGTACGCCCCCTATTGACGTC

AATGACGGTAAATGGCCCGCCTGGCATTATGCCCAGTACATGACCTTATGGGACTTT

CCTACTTGGCAGTACATCTACGTATTAGTCATCGCTATTACCATGGTGATGCGGTTTT

GGCAGTACATCAATGGGCGTGGATAGCGGTTTGACTCACGGGGATTTCCAAGTCTCC

ACCCCATTGACGTCAATGGGAGTTTGTTTTGGCACCAAAATCAACGGGACTTTCCAA

AATGTCGTAACAACTCCGCCCCATTGACGCAAATGGGCGGTAGGCGTGTACGGTGG

GAGGTCTATATAAGCAGAGCTCTCCCTATCAGTGATAGAGATCTCCCTATCAGTGAT

AGAGATCGTCGACGAGCTCGTTTAGTGAACCGTCAGATCGCCTGGAGACGCCATCC

ACGCTGTTTTGACCTCCATAGAAGACACCGGGACCGATCCAGCCTCCGGACTCTAGC

GTTTAAACTTAAGCCCAAGCTGGCTAGACCGCCATGGCCCAACTGTACTACAAAAA
```

-continued

```
GGTCAACTACTCACCGTACAGAGACCGCATCCCCCTGCAAATTGTGAGGGCTGAGA

CAGAGCTCTCTGCAGAGGAGAAGGCCTTCCTCAATGCTGTGGAGAAGGGGGACTAT

GCCACTGTGAAGCAGGCCCTTCAGGAGGCTGAGATCTACTATAATGTTAACATCAAC

TGCATGGACCCCTTGGGCCGGAGTGCCCTGCTCATTGCCATTGAGAACGAGAACCTG

GAGATCATGGAGCTACTGCTGAACCACAGCGTGTATGTGGGTGATGCATTGCTCTAT

GCCATACGCAAGGAAGTGGTGGGCGCTGTGGAGCTTCTGCTCAGCTACAGGCGGCC

CAGCGGAGAGAAGCAGGTCCCCACTCTGATGATGGACACGCAGTTCTCTGAATTCA

CACCGGACATCACTCCCATCATGCTGGCTGCCCACACCAACAACTACGAAATCATCA

AACTGCTTGTCCAAAAACGGGTCACTATCCCACGGCCCCACCAGATCCGCTGCAACT

GTGTGGAGTGTGTGTCTAGTTCAGAGGTAGACAGCCTGCGCCACTCTCGCTCCCGAC

TGAACATCTATAAGGCTCTGGCAAGCCCCTCACTCATTGCCTTATCAAGTGAGGACC

CCATCCTAACTGCCTTCCGTCTGGGCTGGGAGCTCAAGGAGCTCAGCAAGGTGGAG

AATGAGTTCAAGGCCGAGTATGAGGAGCTCTCTCAGCAGTGCAAGCTCTTTGCCAAA

GACCTGCTGGACCAAGCTCGGAGCTCCAGGGAACTGGAGATCATCCTCAACCATCG

AGATGACCACAGTGAAGAGCTTGACCCTCAGAAGTACCATGACCTGGCCAAGTTGA

AGGTGGCAATCAAATACCACCAGAAAGAGTTTGTTGCTCAGCCCAACTGCCAACAG

TTGCTTGCCACCCTGTGGTATGATGGCTTCCCTGGATGGCGGCGGAAACACTGGGTA

GTCAAGCTTCTAACCTGCATGACCATTGGGTTCCTGTTTCCCATGCTGTCTATAGCCT

ACCTGATCTCACCCAGGAGCAACCTTGGGCTGTTCATCAAGAAACCCTTTATCAAGT

TTATCTGCCACACAGCATCCTATTTGACCTTCCTCTTTATGCTTCTCCTGGCTTCTCAG

CACATTGTCAGGACAGACCTTCATGTACAGGGGCCTCCCCCAACTGTCGTGGAATGG

ATGATATTGCCTTGGGTTCTAGGTTTCATTTGGGGTGAGATTAAGGAAATGTGGGAT

GGTGGATTTACTGAATACATCCATGACTGGTGGAACCTGATGGATTTTGCAATGAAC

TCCCTCTACCTGGCAACTATTTCCCTGAAGATTGTGGCCTATGTCAAGTATAATGGTT

CTCGTCCAAGGGAGGAATGGGAAATGTGGCACCCGACTCTGATTGCGGAAGCACTC

TTCGCAATATCCAACATTTTAAGTTCGTTGCGTCTCATATCCCTGTTCACAGCCAACT

CCCACTTAGGACCTCTGCAGATCTCTTTGGGACGCATGCTGCTTGATATCCTCAAATT

CCTCTTTATCTACTGCCTGGTACTACTAGCTTTTGCCAATGGACTGAACCAGCTTTAC

TTCTATTATGAAACCAGAGCTATCGATGAGCCTAACAACTGCAAGGGGATCCGATGT

GAGAAACAGAACAATGCCTTCTCCACGCTCTTTGAGACTCTTCAGTCACTCTTCTGG

TCTGTATTTGGCCTTTTAAATCTATATGTCACCAATGTGAAAGCCAGACACGAATTC

ACCGAGTTTGTAGGAGCTACCATGTTTGGAACATACAATGTCATCTCCCTGGTAGTG

CTGCTGAACATGCTGATTGCTATGATGAACAACTCCTATCAGCTTATTGCCGATCAT

GCTGATATCGAGTGGAAGTTTGCAAGGACGAAGCTCTGGATGAGTTACTTTGATGAA

GGTGGCACCTTGCCACCTCCTTTCAACATCATCCCCAGCCCCAAGTCATTTCTATACC

TTGGTAACTGGTTCAACAACACCTTCTGCCCCAAAAGAGACCCTGACGGTAGACGG

AGAAGGCGCAACTTGAGAAGTTTCACAGAACGCAATGCTGACAGCCTGATACAAAA

TCAACATTATCAGGAAGTTATCAGGAATTTAGTCAAAAGATATGTGGCTGCTATGAT

AAGAAATTCCAAAACACATGAGGGACTTACAGAAGAAAATTTTAAGGAATTAAAGC

AAGACATCTCCAGCTTTCGGTATGAAGTGCTTGACCTCTTGGGAAATAGAAAACATC
```

-continued

```
CAAGGAGCTTTTCCACTAGCAGCACTGAACTGTCTCAGAGAGACGATAATAATGAT
GGCAGTGGTGGGGCTCGGGCCAAATCCAAGAGTGTCTCTTTTAATTTAGGCTGCAAG
AAAAAGACTTGCCATGGGCCACCTCTCATCAGAACCATGCCAAGGTCCAGTGGTGC
CCAAGGAAAGTCAAAAGCTGAGTCATCAAGCAAACGCTCCTTCATGGGTCCTTCTCT
CAAGAAACTGGGTCTCCTATTCTCCAAATTTAATGGTCATATGTCTGAACCCAGTTC
AGAGCCAATGTACACAATTTCTGATGGAATTGTTCAGCAGCACTGTATGTGGCAGGA
CATCAGATATTCTCAGATGGAGAAAGGGAAAGCAGAGGCCTGTTCTCAAAGTGAAA
TTAACCTCAGTGAGGTAGAATTAGGTGAAGTCCAGGGCGCTGCTCAGAGCAGTGAA
TGCCCTCTAGCCTGTTCCAGCTCTCTTCACTGTGCATCCAGCATCTGCTCCTCAAATT
CTAAACTTTTAGACTCCTCAGAGGATGTATTTGAAACTTGGGGAGAGGCTTGTGACT
TGCTCATGCACAAATGGGGTGATGGACAGGAAGAACAAGTTACAACTCGCCTCTAA
TGACTCGAGTCTAGAGGGCCCGTTTAAACCCGCTGATCAGCCTCGACTGTGCCTTCT
AGTTGCCAGCCATCTGTTGTTTGCCCCTCCCCCGTGCCTTCCTTGACCCTGGAAGGTG
CCACTCCCACTGTCCTTTCCTAATAAAATGAGGAAATTGCATCGCATTGTCTGAGTA
GGTGTCATTCTATTCTGGGGGGTGGGGTGGGGCAGGACAGCAAGGGGGAGGATTGG
GAAGACAATAGCAGGCATGCTGGGGATGCGGTGGGCTCTATGGCTTCTGAGGCGGA
AAGAACCAGCTGGGGCTCTAGGGGGTATCCCCACGCGCCCTGTAGCGGCGCATTAA
GCGCGGCGGGTGTGGTGGTTACGCGCAGCGTGACCGCTACACTTGCCAGCGCCCTA
GCGCCCGCTCCTTTCGCTTTCTTCCCTTCCTTTCTCGCCACGTTCGCCGGCTTTCCCCG
TCAAGCTCTAAATCGGGGGCTCCCTTTAGGGTTCCGATTTAGTGCTTTACGGCACCTC
GACCCCAAAAAACTTGATTAGGGTGATGGTTCACGTAGTGGGCCATCGCCCTGATAG
ACGGTTTTTCGCCCTTTGACGTTGGAGTCCACGTTCTTTAATAGTGGACTCTTGTTCC
AAACTGGAACAACACTCAACCCTATCTCGGTCTATTCTTTTGATTTATAAGGGATTTT
GCCGATTTCGGCCTATTGGTTAAAAAATGAGCTGATTTAACAAAAATTTAACGCGAA
TTAATTCTGTGGAATGTGTGTCAGTTAGGGTGTGGAAAGTCCCCAGGCTCCCCAGCA
GGCAGAAGTATGCAAAGCATGCATCTCAATTAGTCAGCAACCAGGTGTGGAAAGTC
CCCAGGCTCCCCAGCAGGCAGAAGTATGCAAAGCATGCATCTCAATTAGTCAGCAA
CCATAGTCCCGCCCCTAACTCCGCCCATCCCGCCCCTAACTCCGCCCAGTTCCGCCC
ATTCTCCGCCCCATGGCTGACTAATTTTTTTATTTATGCAGAGGCCGAGGCCGCCTC
TGCCTCTGAGCTATTCCAGAAGTAGTGAGGAGGCTTTTTTGGAGGCCTAGGCTTTTG
CAAAAAGCTCCCGGGAGCTTGTATATCCATTTTCGGATCTGATCAGCACGTGATGAA
AAAGCCTGAACTCACCGCGACGTCTGTCGAGAAGTTTCTGATCGAAAAGTTCGACA
GCGTCTCCGACCTGATGCAGCTCTCGGAGGGCGAAGAATCTCGTGCTTTCAGCTTCG
ATGTAGGAGGGCGTGGATATGTCCTGCGGGTAAATAGCTGCGCCGATGGTTTCTACA
AAGATCGTTATGTTTATCGGCACTTTGCATCGGCCGCGCTCCCGATTCCGGAAGTGC
TTGACATTGGGGAATTCAGCGAGAGCCTGACCTATTGCATCTCCCGCCGTGCACAGG
GTGTCACGTTGCAAGACCTGCCTGAAACCGAACTGCCCGCTGTTCTGCAGCCGGTCG
CGGAGGCCATGGATGCGATCGCTGCGGCCGATCTTAGCCAGACGAGCGGGTTCGGC
CCATTCGGACCGCAAGGAATCGGTCAATACACTACATGGCGTGATTTCATATGCGCG
ATTGCTGATCCCCATGTGTATCACTGGCAAACTGTGATGGACGACACCGTCAGTGCG
TCCGTCGCGCAGGCTCTCGATGAGCTGATGCTTTGGGCCGAGGACTGCCCCGAAGTC
```

-continued

```
CGGCACCTCGTGCACGCGGATTTCGGCTCCAACAATGTCCTGACGGACAATGGCCGC

ATAACAGCGGTCATTGACTGGAGCGAGGCGATGTTCGGGGATTCCCAATACGAGGT

CGCCAACATCTTCTTCTGGAGGCCGTGGTTGGCTTGTATGGAGCAGCAGACGCGCTA

CTTCGAGCGGAGGCATCCGGAGCTTGCAGGATCGCCGCGGCTCCGGGCGTATATGC

TCCGCATTGGTCTTGACCAACTCTATCAGAGCTTGGTTGACGGCAATTTCGATGATG

CAGCTTGGGCGCAGGGTCGATGCGACGCAATCGTCCGATCCGGAGCCGGGACTGTC

GGGCGTACACAAATCGCCCGCAGAAGCGCGGCCGTCTGGACCGATGGCTGTGTAGA

AGTACTCGCCGATAGTGGAAACCGACGCCCCAGCACTCGTCCGAGGGCAAAGGAAT

AGCACGTGCTACGAGATTTCGATTCCACCGCCGCCTTCTATGAAAGGTTGGGCTTCG

GAATCGTTTTCCGGGACGCCGGCTGGATGATCCTCCAGCGCGGGGATCTCATGCTGG

AGTTCTTCGCCCACCCCAACTTGTTTATTGCAGCTTATAATGGTTACAAATAAGCA

ATAGCATCACAAATTTCACAAATAAAGCATTTTTTTCACTGCATTCTAGTTGTGGTTT

GTCCAAACTCATCAATGTATCTTATCATGTCTGTATACCGTCGACCTCTAGCTAGAGC

TTGGCGTAATCATGGTCATAGCTGTTTCCTGTGTGAAATTGTTATCCGCTCACAATTC

CACACAACATACGAGCCGGAAGCATAAAGTGTAAAGCCTGGGGTGCCTAATGAGTG

AGCTAACTCACATTAATTGCGTTGCGCTCACTGCCCGCTTTCCAGTCGGGAAACCTG

TCGTGCCAGCTGCATTAATGAATCGGCCAACGCGCGGGGAGAGGCGGTTTGCGTATT

GGGCGCTCTTCCGCTTCCTCGCTCACTGACTCGCTGCGCTCGGTCGTTCGGCTGCGGC

GAGCGGTATCAGCTCACTCAAAGGCGGTAATACGGTTATCCACAGAATCAGGGGAT

AACGCAGGAAAGAACATGTGAGCAAAAGGCCAGCAAAAGGCCAGGAACCGTAAAA

AGGCCGCGTTGCTGGCGTTTTTCCATAGGCTCCGCCCCCCTGACGAGCATCACAAAA

ATCGACGCTCAAGTCAGAGGTGGCGAAACCCGACAGGACTATAAAGATACCAGGCG

TTTCCCCCTGGAAGCTCCCTCGTGCGCTCTCCTGTTCCGACCCTGCCGCTTACCGGAT

ACCTGTCCGCCTTTCTCCCTTCGGGAAGCGTGGCGCTTTCTCATAGCTCACGCTGTAG

GTATCTCAGTTCGGTGTAGGTCGTTCGCTCCAAGCTGGGCTGTGTGCACGAACCCCC

CGTTCAGCCCGACCGCTGCGCCTTATCCGGTAACTATCGTCTTGAGTCCAACCCGGT

AAGACACGACTTATCGCCACTGGCAGCAGCCACTGGTAACAGGATTAGCAGAGCGA

GGTATGTAGGCGGTGCTACAGAGTTCTTGAAGTGGTGGCCTAACTACGGCTACACTA

GAAGAACAGTATTTGGTATCTGCGCTCTGCTGAAGCCAGTTACCTTCGGAAAAAGAG

TTGGTAGCTCTTGATCCGGCAAACAAACCACCGCTGGTAGCGGTTGGTTTTTTGTTTG

CAAGCAGCAGATTACGCGCAGAAAAAAAGGATCTCAAGAAGATCCTTTGATCTTTT

CTACGGGGTCTGACGCTCAGTGGAACGAAAACTCACGTTAAGGGATTTTGGTCATGA

GATTATCAAAAGGATCTTCACCTAGATCCTTTTAAATTAAAAATGAAGTTTTAAAT

CAATCTAAAGTATATATGAGTAAACTTGGTCTGACAGTTACCAATGCTTAATCAGTG

AGGCACCTATCTCAGCGATCTGTCTATTTCGTTCATCCATAGTTGCCTGACTCCCCGT

CGTGTAGATAACTACGATACGGGAGGGCTTACCATCTGGCCCCAGTGCTGCAATGAT

ACCGCGAGACCCACGCTCACCGGCTCCAGATTTATCAGCAATAAACCAGCCAGCCG

GAAGGGCCGAGCGCAGAAGTGGTCCTGCAACTTTATCCGCCTCCATCCAGTCTATTA

ATTGTTGCCGGGAAGCTAGAGTAAGTAGTTCGCCAGTTAATAGTTTGCGCAACGTTG

TTGCCATTGCTACAGGCATCGTGGTGTCACGCTCGTCGTTTGGTATGGCTTCATTCAG
```

```
CTCCGGTTCCCAACGATCAAGGCGAGTTACATGATCCCCCATGTTGTGCAAAAAGC

GGTTAGCTCCTTCGGTCCTCCGATCGTTGTCAGAAGTAAGTTGGCCGCAGTGTTATC

ACTCATGGTTATGGCAGCACTGCATAATTCTCTTACTGTCATGCCATCCGTAAGATG

CTTTTCTGTGACTGGTGAGTACTCAACCAAGTCATTCTGAGAATAGTGTATGCGGCG

ACCGAGTTGCTCTTGCCCGGCGTCAATACGGGATAATACCGCGCCACATAGCAGAA

CTTTAAAAGTGCTCATCATTGGAAAACGTTCTTCGGGGCGAAAACTCTCAAGGATCT

TACCGCTGTTGAGATCCAGTTCGATGTAACCCACTCGTGCACCCAACTGATCTTCAG

CATCTTTTACTTTCACCAGCGTTTCTGGGTGAGCAAAAACAGGAAGGCAAAATGCCG

CAAAAAAGGGAATAAGGGCGACACGGAAATGTTGAATACTCATACTCTTCCTTTTTC

AATATTATTGAAGCATTTATCAGGGTTATTGTCTCATGAGCGGATACATATTTGAAT

GTATTTAGAAAAATAAACAATAGGGGTTCCGCGCACATTTCCCCGAAAAGTGCCACCTG

ACGTC
```

---

What is claimed is:
1. A compound represented by:

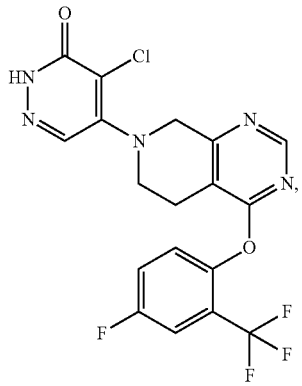

or a pharmaceutically acceptable salt thereof.

2. The compound of claim 1, wherein the compound is represented by:

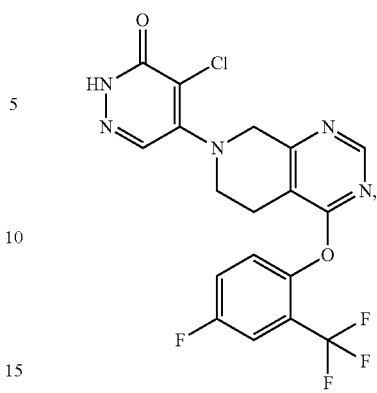

3. A pharmaceutical composition, comprising the compound of claim 1; and a pharmaceutically acceptable carrier.

4. A pharmaceutical composition, comprising the compound of claim 2; and a pharmaceutically acceptable carrier.

* * * * *

UNITED STATES PATENT AND TRADEMARK OFFICE
CERTIFICATE OF CORRECTION

Page 1 of 4

PATENT NO. : 10,654,850 B2
APPLICATION NO. : 16/575161
DATED : May 19, 2020
INVENTOR(S) : Mark W. Ledeboer et al.

It is certified that error appears in the above-identified patent and that said Letters Patent is hereby corrected as shown below:

On the Title Page

In the Abstract (57), please replace:

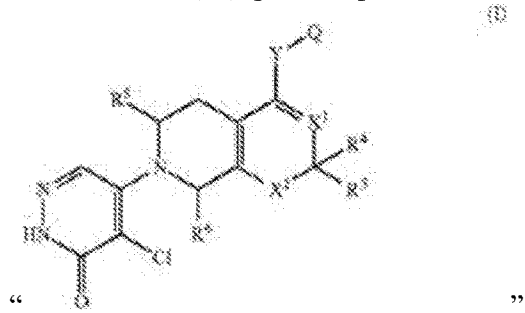

"                              "

With:

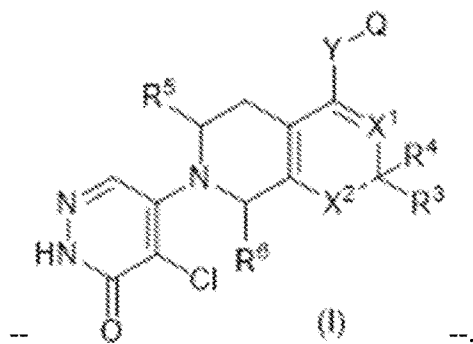

--                              --.

Signed and Sealed this
Fourteenth Day of July, 2020

Andrei Iancu
*Director of the United States Patent and Trademark Office*

CERTIFICATE OF CORRECTION (continued)
U.S. Pat. No. 10,654,850 B2

Page 2 of 4

In the Specification

At Column 2, Lines 8-21, please replace:

"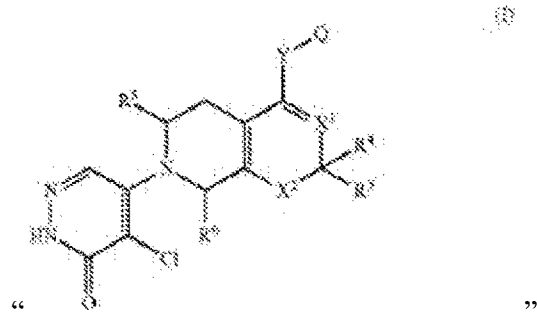"

With:

--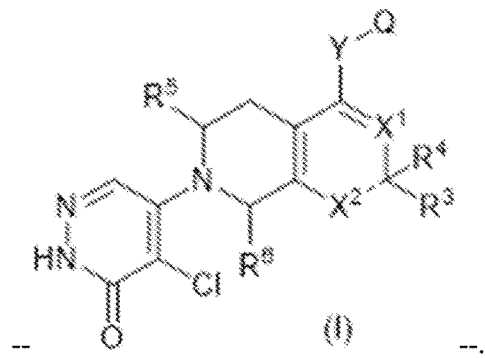--.

At Column 12, Lines 25-35, please replace:

"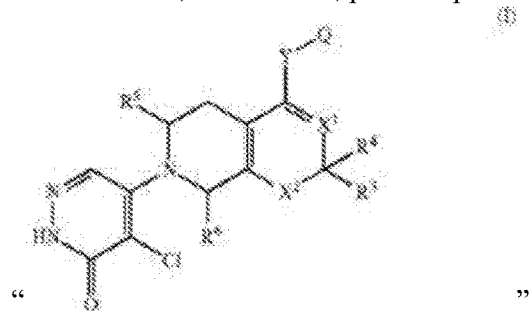"

With:

--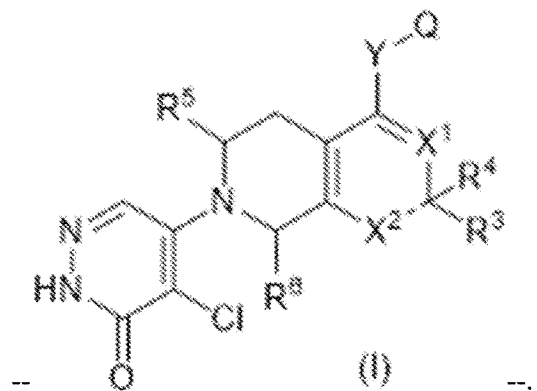--.

CERTIFICATE OF CORRECTION (continued)
U.S. Pat. No. 10,654,850 B2

In the Claims

In Claim 1, at Column 163, Lines 5-19, please replace:

"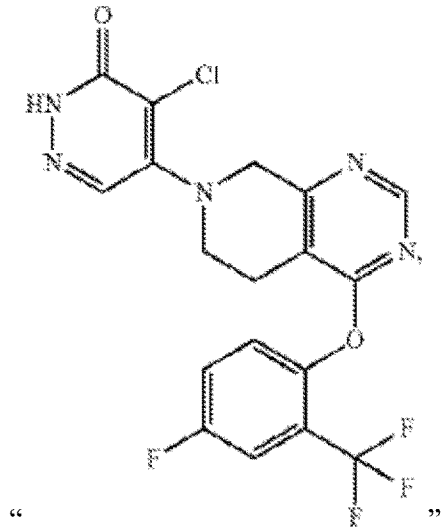"

With:

--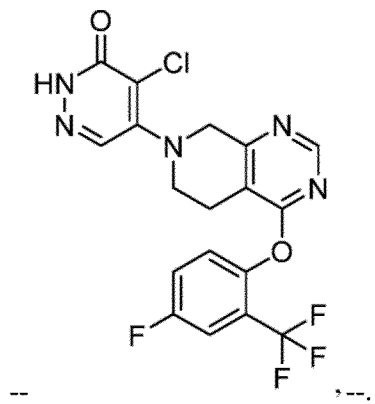,--.

In Claim 2, at Column 164, Lines 1-16, please replace:

"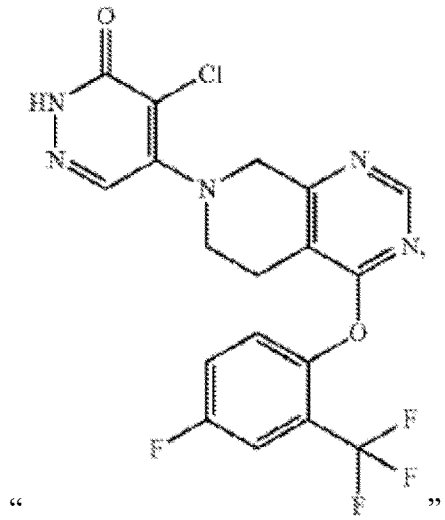"

CERTIFICATE OF CORRECTION (continued)
U.S. Pat. No. 10,654,850 B2

With:

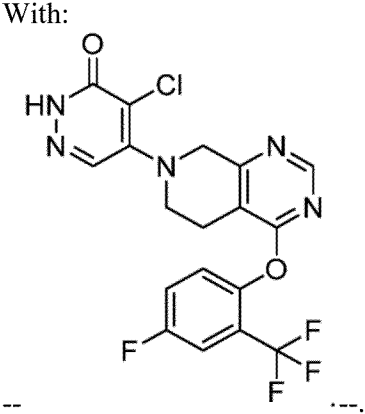

-- .--.

SEQUENCE LISTING

<160> NUMBER OF SEQ ID NOS: 2

<210> SEQ ID NO 1
<211> LENGTH: 8574
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ccctatcagt gatagagatc     840
tccctatcag tgatagagat cgtcgacgag ctcgtttagt gaaccgtcag atcgcctgga     900
gacgccatcc acgctgtttt gacctccata gaagacaccg gaccgatcca gcctccgga     960 ctctagcgtt taaacttaag cttggtaccg agctcggatc cgccaccatg gcccagttct    1020
actataagag aaacgtgaat gccccttacc gcgacagaat cccctgaga atcgtgaggg    1080 cagagtccga gctgagccca tccgagaagg cctacctgaa cgccgtggag aagggcgact    1140
atgccagcgt gaagaagtcc ctggaggagg ccgagatcta ctttaagatc aacatcaatt    1200
```

-continued

```
gcatcgatcc tctgggcaga accgccctgc tgatcgccat cgagaacgag aatctggagc    1260
tgatcgagct gctgctgagc ttcaacgtgt atgtgggcga tgccctgctg cacgccatca    1320
ggaaggaggt ggtgggagca gtggagctgc tgctgaatca caagaagcca agcggagaga    1380
agcaggtgcc acctatcctg ctggacaagc agttctccga gtttacccca gatatcacac    1440
ccatcatcct ggccgcccac accaacaatt acgagatcat caagctgctg gtgcagaagg    1500
gcgtgtccgt gcctcgccca cacgaggtgc ggtgcaactg cgtggagtgc gtgagctcct    1560
ctgacgtgga ttctctgagg cacagccgga gccggctgaa catctataag gccctggcct    1620
ccccatctct gatcgccctg agctccgagg accccttcct gaccgccttt cagctgtctt    1680
gggagctgca ggagctgagc aaggtggaga cgagtttaa gagcgagtac gaggagctgt    1740
ccagacagtg caagcagttc gccaaggacc tgctggatca gacacgctct agccgggagc    1800
tggagatcat cctgaactat agggacgata attctctgat cgaggagcag agcggaaacg    1860
acctggcacg cctgaagctg gccatcaagt accggcagaa ggagttcgtg gcccagccta    1920
attgtcagca gctgctggcc tcccgctggt atgatgagtt tccaggatgg cggagaaggc    1980
actgggcagt gaagatggtg acctgcttca tcatcggcct gctgttcccc gtgttcagcg    2040
tgtgctacct gatcgcccct aagtctccac tgggcctgtt tatccggaag cctttcatca    2100
agtttatctg ccacaccgcc agctatctga cattcctgtt tctgctgctg ctggcctccc    2160
agcacatcga cagatctgat ctgaacaggc agggcccacc cctaccatc gtggagtgga    2220
tgatcctgcc atgggtgctg gcttcatct ggggcgagat caagcagatg tgggacggcg    2280
gcctgcagga ctacatccac gattggtgga acctgatgga ttttgtgatg aattccctgt    2340
acctggccac aatctctctg aagatcgtgg ccttcgtgaa gtatagcgcc ctgaatccca    2400
gagagtcctg ggacatgtgg caccctaccc tggtggcaga ggccctgttc gcaatcgcca    2460
acatcttttc ctctctgcgc ctgatcagcc tgtttacagc caattcccac ctgggaccac    2520
tgcagatctc cctgggacgg atgctgctgg atatcctgaa gttcctgttt atctactgcc    2580
tggtgctgct ggccttcgcc aacggccctg atcagctgta cttctactat gaggagacca    2640
agggcctgac atgcaagggc atccgctgtg agaagcagaa caatgccttc agcaccctgt    2700
tcgagacact gcagtctctg ttctggagca tctttggcct gatcaacctg tacgtgacca    2760
atgtgaaggc ccagcacgag ttcacagagt ttgtgggcgc caccatgttc ggcacataca    2820
acgtgatctc tctggtggtg ctgctgaata tgctgatcgc catgatgaac aatagctatc    2880
agctgatcgc cgaccacgcc gatatcgagt ggaagttcgc ccggaccaag ctgtggatgt    2940
cctactttga ggagggcggc accctgccca cctttcaa cgtgatccca tcccccaagt    3000
ctctgtggta tctgatcaag tggatctgga cacacctgtg caagaagaag atgcgccgga    3060
agcctgagag ctttggcacc atcggcgtgc gcacacagca cagaagggca gcagacaacc    3120
tgcgccggca ccaccagtac caggaagtga tgcgcaatct ggtgaagcgg tatgtggccg    3180
ccatgatcag ggacgcaaag accgaggagg gactgacaga ggagaacttc aaggagctga    3240
agcaggatat cagctccttc agatttgagg tgctgggcct gctgagggcc agcaagctgt    3300
ccaccatcca gtccgccaac gcctctaagg agtctagcaa ttctgccgac agcgatgaga    3360
agagcgactc cgagggcaac tctaaggata agaagaagaa cttcagcctg tttgacctga    3420
ccacactgat ccaccacgc agcgccgcaa tcgcatccga gcggcacaac atctccaatg    3480
gctctgccct ggtggtgcag gagccaccaa gagagaagca gaggaaggtg aactttgtga    3540
```

```
cagatatcaa gaatttcggc ctgtttcaca gaaggagcaa gcagaacgcc gccgagcaga   3600
acgccaatca gatcttctct gtgagcgagg aggtggcaag acagcaggca gcaggaccac   3660
tggagaggaa tatccagctg gagagccggg gactggcaag caggggcgac ctgtccatcc   3720
caggactgtc tgagcagtgc gtgctggtgg accacaggga gcggaacacc gatacactgg   3780
gactgcaagt gggcaagcgg gtgtgccctt caagagcga gaaggtcgtg gtggaggaca    3840
ccgtgcccat catccctaag gagaagcacg ccaaggagga ggattcctct atcgactacg   3900
atctgaatct gccagacacc gtgacacacg aggattatgt gaccacaagg ctgtgagcgg   3960
ccgctctaga gggcccgttt aaacccgctg atcagcctcg actgtgcctt ctagttgcca   4020
gccatctgtt gtttgcccct cccccgtgcc ttccttgacc ctggaaggtg ccactcccac   4080
tgtcctttcc taataaaatg aggaaattgc atcgcattgt ctgagtaggt gtcattctat   4140
tctgggggt ggggtggggc aggacagcaa ggggaggat tggaagaca atagcaggca     4200
tgctggggat gcggtgggct ctatggcttc tgaggcggaa agaaccagct ggggctctag   4260
ggggtatccc cacgcgccct gtagcggcgc attaagcgcg gcgggtgtgg tggttacgcg   4320
cagcgtgacc gctacacttg ccagcgccct agcgcccgct cctttcgctt tcttcccttc   4380
ctttctcgcc acgttcgccg gctttccccg tcaagctcta atcggggc tccctttagg     4440
gttccgattt agtgctttac ggcacctcga ccccaaaaaa cttgattagg gtgatggttc   4500
acgtagtggg ccatcgccct gatagacggt ttttcgccct tgacgttgg agtccacgtt    4560
ctttaatagt ggactcttgt tccaaactgg aacaacactc aaccctatct cggtctattc   4620
ttttgattta aagggatt tgccgatttc ggcctattgg ttaaaaatg agctgattta      4680
acaaaattt aacgcgaatt aattctgtgg aatgtgtgtc agttagggtg tggaaagtcc    4740
ccaggctccc cagcaggcag aagtatgcaa agcatgcatc tcaattagtc agcaaccagg   4800
tgtggaaagt ccccaggctc cccagcaggc agaagtatgc aaagcatgca tctcaattag   4860
tcagcaacca tagtcccgcc cctaactccg cccatcccgc ccctaactcc gcccagttcc   4920
gcccattctc cgccccatgg ctgactaatt ttttttattt atgcagaggc cgaggccgcc   4980
tctgcctctg agctattcca gaagtagtga ggaggctttt ttggaggcct aggcttttgc   5040
aaaaagctcc cgggagcttg tatatccatt ttcggatctg atcagcacgt gatgaaaaag   5100
cctgaactca ccgcgacgtc tgtcgagaag tttctgatcg aaaagttcga cagcgtctcc   5160
gacctgatgc agctctcgga gggcgaagaa tctcgtgctt tcagcttcga gtaggaggg    5220
cgtggatatg tcctgcgggt aaatagctgc gccgatggtt tctacaaaga tcgttatgtt   5280
tatcggcact ttgcatcggc cgcgctcccg attccggaag tgcttgacat tggggaattc   5340
agcgagagcc tgacctattg catctcccgc cgtgcacagg tgtcacgtt gcaagacctg    5400
cctgaaaccg aactgcccgc tgttctgcag ccggtcgcgg aggccatgga tgcgatcgct   5460
gcggccgatc ttagccagac gagcgggttc ggcccattcg accgcaagg aatcggtcaa   5520
tacactacat ggcgtgattt catatgcgcg attgctgatc cccatgtgta tcactggcaa   5580
actgtgatgg acgacaccgt cagtgcgtcc gtcgcgcagg ctctcgatga gctgatgctt   5640
tgggccgagg actgccccga agtccggcac ctcgtgcacg cggatttcgg ctccaacaat   5700
gtcctgacgg acaatggccg cataacagcg gtcattgact ggagcgaggc gatgttcggg   5760
gattcccaat acgaggtcgc caacatcttc ttctggaggc cgtggttggc ttgtatggag   5820
cagcagacgc gctacttcga gcggaggcat ccggagcttg caggatcgcc gcggctccgg   5880
gcgtatatgc tccgcattgg tcttgaccaa ctctatcaga gcttggttga cggcaatttc   5940
```

```
gatgatgcag cttgggcgca gggtcgatgc gacgcaatcg tccgatccgg agccgggact   6000
gtcgggcgta cacaaatcgc ccgcagaagc gcggccgtct ggaccgatgg ctgtgtagaa   6060
gtactcgccg atagtggaaa ccgacgcccc agcactcgtc cgagggcaaa ggaatagcac   6120
gtgctacgag atttcgattc caccgccgcc ttctatgaaa ggttgggctt cggaatcgtt   6180
ttccgggacg ccggctggat gatcctccag cgcgggatc tcatgctgga gttcttcgcc    6240
caccccaact tgtttattgc agcttataat ggttacaaat aaagcaatag catcacaaat   6300
ttcacaaata aagcattttt ttcactgcat tctagttgtg gtttgtccaa actcatcaat   6360
gtatcttatc atgtctgtat accgtcgacc tctagctaga gcttggcgta atcatggtca   6420
tagctgtttc ctgtgtgaaa ttgttatccg ctcacaattc cacacaacat acgagccgga   6480
agcataaagt gtaaagcctg gggtgcctaa tgagtgagct aactcacatt aattgcgttg   6540
cgctcactgc ccgctttcca gtcgggaaac ctgtcgtgcc agctgcatta atgaatcggc   6600
caacgcgcgg ggagaggcgg tttgcgtatt gggcgctctt ccgcttcctc gctcactgac   6660
tcgctgcgct cggtcgttcg gctgcggcga gcggtatcag ctcactcaaa ggcggtaata   6720
cggttatcca cagaatcagg ggataacgca ggaaagaaca tgtgagcaaa aggccagcaa   6780
aaggccagga accgtaaaaa ggccgcgttg ctggcgtttt tccataggct ccgcccccct   6840
gacgagcatc acaaaaatcg acgctcaagt cagaggtggc gaaacccgac aggactataa   6900
agataccagg cgtttccccc tggaagctcc ctcgtgcgct ctcctgttcc gaccctgccg   6960
cttaccggat acctgtccgc ctttctccct tcgggaagcg tggcgctttc tcatagctca   7020
cgctgtaggt atctcagttc ggtgtaggtc gttcgctcca agctgggctg tgtgcacgaa   7080
ccccccgttc agcccgaccg ctgcgcctta tccggtaact atcgtcttga gtccaacccg   7140
gtaagacacg acttatcgcc actggcagca gccactggta acaggattag cagagcgagg   7200
tatgtaggcg gtgctacaga gttcttgaag tggtggccta actacggcta cactagaaga   7260
acagtatttg gtatctgcgc tctgctgaag ccagttacct tcggaaaaag agttggtagc   7320
tcttgatccg gcaaacaaac caccgctggt agcggttggt ttttgtttg caagcagcag   7380 attacgcgca gaaaaaaagg atctcaagaa gatcctttga tcttttctac ggggtctgac   7440
gctcagtgga acgaaaactc acgttaaggg attttggtca tgagattatc aaaaaggatc   7500
ttcacctaga tccttttaaa ttaaaaatga agttttaaat caatctaaag tatatatgag   7560
taaacttggt ctgacagtta ccaatgctta atcagtgagg cacctatctc agcgatctgt   7620
ctatttcgtt catccatagt tgcctgactc cccgtcgtgt agataactac gatacgggag   7680
ggcttaccat ctggccccag tgctgcaatg ataccgcgag acccacgctc accggctcca   7740
gatttatcag caataaacca gccagccgga agggccgagc gcagaagtgg tcctgcaact   7800
ttatccgcct ccatccagtc tattaattgt tgccgggaag ctagagtaag tagttcgcca   7860
gttaatagtt tgcgcaacgt tgttgccatt gctacaggca tcgtggtgtc acgctcgtcg   7920
tttggtatgg cttcattcag ctccggttcc caacgatcaa ggcgagttac atgatccccc   7980
atgttgtgca aaaaagcggt tagctccttc ggtcctccga tcgttgtcag aagtaagttg   8040
gccgcagtgt tatcactcat ggttatggca gcactgcata attctcttac tgtcatgcca   8100
tccgtaagat gcttttctgt gactggtgag tactcaacca agtcattctg agaatagtgt   8160
atgcggcgac cgagttgctc ttgcccggcg tcaatacggg ataataccgc gccacatagc   8220
agaactttaa aagtgctcat cattggaaaa cgttcttcgg ggcgaaaact ctcaaggatc   8280
```

| | |
|---|---:|
| ttaccgctgt tgagatccag ttcgatgtaa cccactcgtg cacccaactg atcttcagca | 8340 |
| tcttttactt tcaccagcgt ttctgggtga gcaaaaacag gaaggcaaaa tgccgcaaaa | 8400 |
| aagggaataa gggcgacacg gaaatgttga atactcatac tcttcctttt tcaatattat | 8460 |
| tgaagcattt atcagggtta ttgtctcatg agcggataca tatttgaatg tatttagaaa | 8520 |
| aataaacaaa taggggttcc gcgcacattt ccccgaaaag tgccacctga cgtc | 8574 |

<210> SEQ ID NO 2
<211> LENGTH: 8541
<212> TYPE: DNA
<213> ORGANISM: Artificial Sequence
<220> FEATURE:
<223> OTHER INFORMATION: Description of Artificial Sequence: Synthetic
  polynucleotide

<400> SEQUENCE: 2

| | |
|---|---:|
| gacggatcgg gagatctccc gatcccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacgggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ccctatcagt gatagagatc | 840 |
| tccctatcag tgatagagat cgtcgacgag ctcgtttagt gaaccgtcag atcgcctgga | 900 |
| gacgccatcc acgctgtttt gacctccata agagacaccg ggaccgatcc agcctccgga | 960 |
| ctctagcgtt taaacttaag cccaagctgg ctagaccgcc atgggcccaac tgtactacaa | 1020 |
| aaaggtcaac tactcaccgt acagagaccg catcccctg caaattgtga gggctgagac | 1080 |
| agagctctct gcagaggaga aggccttcct caatgctgtg gagaagggg actatgccac | 1140 |
| tgtgaagcag gcccttcagg aggctgagat ctactataat gttaacatca actgcatgga | 1200 |
| ccccttgggc cggagtgccc tgctcattgc cattgagaac gagaacctgg agatcatgga | 1260 |
| gctactgctg aaccacagcg tgtatgtggg tgatgcattg ctctatgcca tacgcaagga | 1320 |
| agtggtgggc gctgtggagc ttctgctcag ctacaggcgg cccagcggag agaagcaggt | 1380 |
| ccccactctg atgatggaca cgcagttctc tgaattcaca ccggacatca ctcccatcat | 1440 |
| gctggctgcc cacaccaaca actacgaaat catcaaactg cttgtccaaa acgggtcac | 1500 |
| tatcccacgg ccccaccaga tccgctgcaa ctgtgtggag tgtgtgtcta gttcagaggt | 1560 |
| agacagcctg cgccactctc gctcccgact gaacatctat aaggctctgg caagcccctc | 1620 |
| actcattgcc ttatcaagtg aggacccat cctaactgcc ttccgtctgg gctgggagct | 1680 |
| caaggagctc agcaaggtgg agaatgagtt caaggccgag tatgaggagc tctctcagca | 1740 |

```
gtgcaagctc tttgccaaag acctgctgga ccaagctcgg agctccaggg aactggagat    1800
catcctcaac catcgagatg accacagtga agagcttgac cctcagaagt accatgacct    1860
ggccaagttg aaggtggcaa tcaaatacca ccagaaagag tttgttgctc agcccaactg    1920
ccaacagttg cttgccaccc tgtggtatga tggcttccct ggatggcggc ggaaacactg    1980
ggtagtcaag cttctaacct gcatgaccat tgggttcctg tttcccatgc tgtctatagc    2040
ctacctgatc tcacccagga gcaaccttgg gctgttcatc aagaaaccct ttatcaagtt    2100
tatctgccac acagcatcct atttgacctt cctctttatg cttctcctgg cttctcagca    2160
cattgtcagg acagaccttc atgtacaggg gcctccccca actgtcgtgg aatggatgat    2220
attgccttgg gttctaggtt tcatttgggg tgagattaag gaaatgtggg atggtggatt    2280
tactgaatac atccatgact ggtggaacct gatggatttt gcaatgaact ccctctacct    2340
ggcaactatt tccctgaaga ttgtggccta tgtcaagtat aatggttctc gtccaaggga    2400
ggaatgggaa atgtgcacc cgactctgat tgcggaagca ctcttcgcaa tatccaacat    2460
tttaagttcg ttgcgtctca tatccctgtt cacagccaac tcccacttag acctctgca    2520
gatctctttg ggacgcatgc tgcttgatat cctcaaattc ctctttatct actgcctggt    2580
actactagct tttgccaatg gactgaacca gctttacttc tattatgaaa ccagagctat    2640
cgatgagcct aacaactgca aggggatccg atgtgagaaa cagaacaatg ccttctccac    2700
gctctttgag actcttcagt cactcttctg gtctgtattt ggccttttaa atctatatgt    2760
caccaatgtg aaagccagac acgaattcac cgagtttgta ggagctacca tgtttggaac    2820
atacaatgtc atctccctgg tagtgctgct gaacatgctg attgctatga tgaacaactc    2880
ctatcagctt attgccgatc atgctgatat cgagtggaag tttgcaagga cgaagctctg    2940
gatgagttac tttgatgaag gtggcacctt gccacctcct ttcaacatca tccccagccc    3000
caagtcattt ctataccttg gtaactggtt caacaacacc ttctgcccca aagagaccc    3060
tgacggtaga cggagaaggc gcaacttgag aagtttcaca gaacgcaatg ctgacagcct    3120
gatacaaaat caacattatc aggaagttat caggaattta gtcaaaagat atgtggctgc    3180
tatgataaga aattccaaaa cacatgaggg acttacagaa gaaattttta aggaattaaa    3240
gcaagacatc tccagctttc ggtatgaagt gcttgacctc ttgggaaata gaaaacatcc    3300
aaggagcttt tccactagca gcactgaact gtctcagaga gacgataata atgatggcag    3360
tggtgggget cgggccaaat ccaagagtgt ctcttttaat ttaggctgca agaaaaagac    3420
ttgccatggg ccacctctca tcagaaccat gccaaggtcc agtggtgccc aaggaaagtc    3480
aaaagctgag tcatcaagca acgctccctt catgggtcct tctctcaaga aactgggtct    3540
cctattctcc aaatttaatg gtcatatgtc tgaacccagt tcagagccaa tgtacacaat    3600
ttctgatgga attgttcagc agcactgtat gtggcaggac atcagatatt ctcagatgga    3660
gaaagggaaa gcagaggcct gttctcaaag tgaaattaac ctcagtgagg tagaattagg    3720
tgaagtccag ggcgctgctc agagcagtga atgccctcta gcctgttcca gctctcttca    3780
ctgtgcatcc agcatctgct cctcaaattc taaacttta gactcctcag aggatgtatt    3840
tgaaacttgg ggagaggctt gtgacttgct catgcacaaa tggggtgatg acaggaaga    3900
acaagttaca actcgcctct aatgactcga gtctagaggg cccgtttaaa cccgctgatc    3960
agcctcgact gtgccttcta gttgccagcc atctgttgtt tgcccctccc ccgtgccttc    4020
cttgaccctg gaaggtgcca ctcccactgt ccttttcctaa taaaatgagg aaattgcatc    4080
gcattgtctg agtaggtgtc attctattct gggggggtggg gtggggcagg acagcaaggg    4140
```

```
ggaggattgg gaagacaata gcaggcatgc tggggatgcg gtgggctcta tggcttctga    4200
ggcggaaaga accagctggg gctctagggg gtatccccac gcgccctgta gcggcgcatt    4260
aagcgcggcg ggtgtggtgg ttacgcgcag cgtgaccgct acacttgcca gcgccctagc    4320
gcccgctcct ttcgctttct tcccttcctt tctcgccacg ttcgccggct ttccccgtca    4380
agctctaaat cggggggctcc ctttaggggtt ccgatttagt gctttacggc acctcgaccc    4440
caaaaaactt gattagggtg atggttcacg tagtgggcca tcgccctgat agacggtttt    4500
tcgccctttg acgttggagt ccacgttctt taatagtgga ctcttgttcc aaactggaac    4560
aacactcaac cctatctcgg tctattcttt tgatttataa gggattttgc cgatttcggc    4620
ctattggtta aaaaatgagc tgatttaaca aaaatttaac gcgaattaat tctgtggaat    4680
gtgtgtcagt tagggtgtgg aaagtcccca ggctccccag caggcagaag tatgcaaagc    4740
atgcatctca attagtcagc aaccaggtgt ggaaagtccc caggctcccc agcaggcaga    4800
agtatgcaaa gcatgcatct caattagtca gcaaccatag tcccgcccct aactccgccc    4860
atcccgcccc taactccgcc cagttccgcc cattctccgc cccatggctg actaattttt    4920
tttatttatg cagaggccga ggccgcctct gcctctgagc tattccagaa gtagtgagga    4980
ggcttttttg gaggcctagg cttttgcaaa aagctcccgg gagcttgtat atccattttc    5040
ggatctgatc agcacgtgat gaaaaagcct gaactcaccg cgacgtctgt cgagaagttt    5100
ctgatcgaaa agttcgacag cgtctccgac ctgatgcagc tctcggaggg cgaagaatct    5160
cgtgctttca gcttcgatgt aggagggcgt ggatatgtcc tgcgggtaaa tagctgcgcc    5220
gatggtttct acaaagatcg ttatgtttat cggcactttg catcggccgc gctcccgatt    5280
ccggaagtgc ttgacattgg ggaattcagc gagagcctga cctattgcat ctcccgccgt    5340
gcacagggtg tcacgttgca agacctgcct gaaaccgaac tgcccgctgt tctgcagccg    5400
gtcgcggagg ccatgatgc gatcgctgcg gccgatctta gccagacgag cgggttcggc    5460
ccattcggac cgcaaggaat cggtcaatac actacatggc gtgatttcat atgcgcgatt    5520
gctgatcccc atgtgtatca ctggcaaact gtgatggacg acaccgtcag tgcgtccgtc    5580
gcgcaggctc tcgatgagct gatgctttgg gccgaggact gccccgaagt ccggcacctc    5640
gtgcacgcgg atttcggctc caacaatgtc ctgacggaca atggccgcat aacagcggtc    5700
attgactgga gcgaggcgat gttcggggat tcccaatacg aggtcgccaa catcttcttc    5760
tggaggccgt ggttggcttg tatggagcag cagacgcgct acttcgagcg gaggcatccg    5820
gagcttgcag atcgccgcg gctccgggcg tatatgctcc gcattggtct tgaccaactc    5880
tatcagagct tggttgacgg caatttcgat gatgcagctt gggcgcaggg tcgatgcgac    5940
gcaatcgtcc gatccggagc cgggactgtc ggcgtacac aaatcgcccg cagaagcgcg    6000
gccgtctgga ccgatggctg tgtagaagta ctcgccgata gtggaaaccg acgccccagc    6060
actcgtccga gggcaaagga atagcacgtg ctacgagatt tcgattccac cgccgccttc    6120
tatgaaaggt tgggcttcgg aatcgttttc cgggacgccg gctggatgat cctccagcgc    6180
ggggatctca tgctggagtt cttcgcccac cccaacttgt ttattgcagc ttataatggt    6240
tacaaataaa gcaatagcat cacaaatttc acaaataaag catttttttc actgcattct    6300
agttgtggtt tgtccaaact catcaatgta tcttatcatg tctgtatacc gtcgacctct    6360
agctagagct tggcgtaatc atggtcatag ctgtttcctg tgtgaaattg ttatccgctc    6420
acaattccac acaacatacg agccggaagc ataaagtgta aagcctgggg tgcctaatga    6480
```

```
gtgagctaac tcacattaat tgcgttgcgc tcactgcccg ctttccagtc gggaaacctg      6540
tcgtgccagc tgcattaatg aatcggccaa cgcgcgggga gaggcggttt gcgtattggg      6600
cgctcttccg cttcctcgct cactgactcg ctgcgctcgg tcgttcggct gcggcgagcg      6660
gtatcagctc actcaaaggc ggtaatacgg ttatccacag aatcagggga taacgcagga      6720
aagaacatgt gagcaaaagg ccagcaaaag gccaggaacc gtaaaaaggc cgcgttgctg      6780
gcgtttttcc ataggctccg ccccctgac gagcatcaca aaaatcgacg ctcaagtcag       6840
aggtggcgaa acccgacagg actataaaga taccaggcgt ttccccctgg aagctccctc      6900
gtgcgctctc ctgttccgac cctgccgctt accggatacc tgtccgcctt tctcccttcg      6960
ggaagcgtgg cgctttctca tagctcacgc tgtaggtatc tcagttcggt gtaggtcgtt      7020
cgctccaagc tgggctgtgt gcacgaaccc cccgttcagc ccgaccgctg cgccttatcc      7080
ggtaactatc gtcttgagtc caacccggta agacacgact tatcgccact ggcagcagcc      7140
actggtaaca ggattagcag agcgaggtat gtaggcggtg ctacagagtt cttgaagtgg      7200
tggcctaact acggctacac tagaagaaca gtatttggta tctgcgctct gctgaagcca      7260
gttaccttcg gaaaaagagt tggtagctct tgatccggca acaaaccac cgctggtagc       7320 ggttggtttt ttgtttgcaa gcagcagatt acgcgcagaa aaaaggatc tcaagaagat       7380 cctttgatct tttctacggg gtctgacgct cagtggaacg aaaactcacg ttaagggatt      7440
ttggtcatga gattatcaaa aaggatcttc acctagatcc ttttaaatta aaaatgaagt      7500
tttaaatcaa tctaaagtat atatgagtaa acttggtctg acagttacca atgcttaatc      7560
agtgaggcac ctatctcagc gatctgtcta tttcgttcat ccatagttgc ctgactcccc      7620
gtcgtgtaga taactacgat acgggagggc ttaccatctg gccccagtgc tgcaatgata      7680
ccgcgagacc cacgctcacc ggctccagat ttatcagcaa taaaccagcc agccggaagg      7740
gccgagcgca gaagtggtcc tgcaacttta tccgcctcca tccagtctat taattgttgc      7800
cgggaagcta gagtaagtag ttcgccagtt aatagtttgc gcaacgttgt tgccattgct      7860
acaggcatcg tggtgtcacg ctcgtcgttt ggtatggctt cattcagctc cggttcccaa      7920
cgatcaaggc gagttacatg atcccccatg ttgtgcaaaa aagcggttag ctccttcggt      7980
cctccgatcg ttgtcagaag taagttggcc gcagtgttat cactcatggt tatggcagca      8040
ctgcataatt ctcttactgt catgccatcc gtaagatgct tttctgtgac tggtgagtac      8100
tcaaccaagt cattctgaga atagtgtatg cggcgaccga gttgctcttg cccggcgtca      8160
atacgggata ataccgcgcc acatagcaga actttaaaag tgctcatcat tggaaaacgt      8220 tcttcgggc gaaaactctc aaggatctta ccgctgttga tccagttc gatgtaaccc         8280 actcgtgcac ccaactgatc ttcagcatct tttactttca ccagcgtttc tgggtgagca      8340
aaaacaggaa ggcaaaatgc cgcaaaaaag ggaataaggg cgacacggaa atgttgaata      8400
ctcatactct tcctttttca atattattga agcatttatc agggttattg tctcatgagc      8460
ggatacatat ttgaatgtat ttagaaaaat aaacaaatag gggttccgcg cacatttccc      8520
cgaaaagtgc cacctgacgt c                                                8541
```